(12) United States Patent
Soliman

(10) Patent No.: US 11,319,379 B2
(45) Date of Patent: *May 3, 2022

(54) AFFINITY MATURATED TAG72 SPECIFIC SINGLE CHAIN ANTIBODIES

(71) Applicant: H. Lee Moffitt Cancer Center and Research Institute, Inc., Tampa, FL (US)

(72) Inventor: Hatem Soliman, Tampa, FL (US)

(73) Assignee: H. Lee Moffitt Cancer Center and Research Institute, Inc., Tampa, FL (US)

(*) Notice: Subject to any disclaimer, the term of this patent is extended or adjusted under 35 U.S.C. 154(b) by 271 days.

This patent is subject to a terminal disclaimer.

(21) Appl. No.: 16/318,589

(22) PCT Filed: Aug. 4, 2017

(86) PCT No.: PCT/US2017/045533
§ 371 (c)(1),
(2) Date: Jan. 17, 2019

(87) PCT Pub. No.: WO2018/027147
PCT Pub. Date: Feb. 8, 2018

(65) Prior Publication Data
US 2019/0315882 A1   Oct. 17, 2019

Related U.S. Application Data

(60) Provisional application No. 62/449,892, filed on Jan. 24, 2017, provisional application No. 62/371,018, filed on Aug. 4, 2016.

(51) Int. Cl.
*C07K 16/30* (2006.01)
*A61P 35/00* (2006.01)
*C07K 16/28* (2006.01)
*C07K 16/46* (2006.01)

(52) U.S. Cl.
CPC .......... *C07K 16/3092* (2013.01); *A61P 35/00* (2018.01); *C07K 16/283* (2013.01); *C07K 16/2818* (2013.01); *C07K 16/2827* (2013.01); *C07K 16/468* (2013.01); *C07K 2317/31* (2013.01); *C07K 2317/565* (2013.01); *C07K 2317/622* (2013.01); *C07K 2317/73* (2013.01); *C07K 2317/76* (2013.01); *C07K 2317/92* (2013.01)

(58) Field of Classification Search
CPC ............ C07K 16/3092; C07K 16/2818; C07K 16/2827; A61P 35/00
See application file for complete search history.

(56) References Cited

U.S. PATENT DOCUMENTS

| 5,877,291 A * | 3/1999 | Mezes ................... C07K 16/30 |
| | | 530/387.3 |
| 2008/0241884 A1 | 10/2008 | Shitara et al. |
| 2009/0311780 A1 | 12/2009 | Kashmiri et al. |
| 2010/0303720 A1 | 12/2010 | Kashmiri et al. |
| 2016/0176979 A1 | 6/2016 | Magliery et al. |
| 2019/0276555 A1* | 9/2019 | Solimam ............ C07K 16/3092 |

FOREIGN PATENT DOCUMENTS

WO   2016089610 A1   6/2016

OTHER PUBLICATIONS

Almagro et al., Humanization of antibodies, Frontiers in Bioscience, 13, 1619-1633, Publication Date: Jan. 1, 2008 (Year: 2008).*
Rudikoff et al., Single amino acid substitution altering antigen-binding specificity, Proc. Natl. Acad. Sci. USA, 79, 1979-1983, Publication Date: Mar. 1982 (Year: 1982).*
Riemer et al., Matching of trastuzumab (Herceptin®) epitope mimics onto the surface of Her-2/neu—a new method of epitope definition, Molecular Immunology, 42, 1121-1124, Publication Date: Jan. 8, 2005. (Year: 2005).*
Gura, T., Systems for identifying new drugs are often faulty, Science, 1997, 278, 5340, 1041-1042 (Year: 1997).*
Chames et al., Therapeutic antibodies: successes, limitations and hopes for the future, British Journal of Pharmacology, 2009, 157, 220-233 (Year: 2009).*
Kaiser, J., First pass at cancer genome reveals complex landscape, Science, 2006, 313 (5792), 1370 (Year: 2006).*
International Search Report for PCT/US2017/045533, dated Oct. 27, 2017.

* cited by examiner

*Primary Examiner* — Peter J Reddig
*Assistant Examiner* — Cheng Lu
(74) *Attorney, Agent, or Firm* — Thomas|Horstemeyer, LLP

(57) ABSTRACT

Disclosed are compositions and methods for targeted treatment of TAG-72-expressing cancers. In particular, affinity maturated single chain variable fragment (scFv) antibodies that bind TAG-72 on cancer cells are disclosed.

17 Claims, 116 Drawing Sheets

Specification includes a Sequence Listing.

SEQUENCE LISTING

<160> NUMBER OF SEQ ID NOS: 47

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Asp His Ala Ile His
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Construct

<400> SEQUENCE: 2

Leu Asn Met Ala Tyr
1               5

<210> SEQ ID NO 3
<211> LENGTH: 20
<212> TYPE: PRT
<213> ORGANISM: Artificial Sequence
<220> FEATURE:
<223> OTHER INFORMATION: Synthetic Construct

<400> SEQUENCE: 3

Trp Ile Gly Tyr Phe Ser Pro Gly Asn Asp Asp Phe Arg Tyr Asn Glu
1               5                   10                  15

Arg Phe Lys Gly
            20

<210> SEQ ID NO 4
<211> LENGTH: 20
<212> TYPE: PRT
<213> ORGANISM: Artificial Sequence
<220> FEATURE:
<223> OTHER INFORMATION: Synthetic Construct

<400> SEQUENCE: 4

Trp Ile Gly Tyr Phe Ser Pro Gly Asn Asp Asp Phe Lys Tyr Asn Glu
1               5                   10                  15

Arg Tyr Lys Gly
            20

<210> SEQ ID NO 5
<211> LENGTH: 20
<212> TYPE: PRT
<213> ORGANISM: Artificial Sequence
<220> FEATURE:
<223> OTHER INFORMATION: Synthetic Construct

<400> SEQUENCE: 5

Trp Ile Gly Tyr Phe Ser Pro Gly Asn Asn Asp Phe Lys Tyr Asn Glu
1               5                   10                  15

Arg Phe Lys Gly
            20

<210> SEQ ID NO 6
<211> LENGTH: 115
<212> TYPE: PRT
<213> ORGANISM: Artificial Sequence
<220> FEATURE:
<223> OTHER INFORMATION: Synthetic Construct

<400> SEQUENCE: 6

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Arg Tyr Asn Glu Arg Phe
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser
        115
```

<210> SEQ ID NO 7
<211> LENGTH: 115
<212> TYPE: PRT
<213> ORGANISM: Artificial Sequence
<220> FEATURE:
<223> OTHER INFORMATION: Synthetic Construct

<400> SEQUENCE: 7

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asp Asp Phe Lys Tyr Asn Glu Arg Tyr
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser
        115
```

<210> SEQ ID NO 8
<211> LENGTH: 115
<212> TYPE: PRT
<213> ORGANISM: Artificial Sequence
<220> FEATURE:
<223> OTHER INFORMATION: Synthetic Construct

<400> SEQUENCE: 8

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Asn Asp Phe Lys Tyr Asn Glu Arg Phe
    50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
            100                 105                 110

Val Ser Ser
        115

<210> SEQ ID NO 9
<211> LENGTH: 17
<212> TYPE: PRT
<213> ORGANISM: Artificial Sequence
<220> FEATURE:
<223> OTHER INFORMATION: Synthetic Construct

<400> SEQUENCE: 9

Lys Ser Ser Gln Ser Leu Leu Tyr Ser Gly Asn Gln Lys Asn Tyr Leu
1               5                   10                  15

Ala

<210> SEQ ID NO 10
<211> LENGTH: 7
<212> TYPE: PRT
<213> ORGANISM: Artificial Sequence
<220> FEATURE:
<223> OTHER INFORMATION: Synthetic Construct

<400> SEQUENCE: 10

Trp Ala Ser Ala Arg Glu Ser
1               5

<210> SEQ ID NO 11
<211> LENGTH: 9
<212> TYPE: PRT
<213> ORGANISM: Artificial Sequence
<220> FEATURE:
<223> OTHER INFORMATION: Synthetic Construct

<400> SEQUENCE: 11

Gln Gln Tyr Tyr Ser Tyr Pro Leu Thr
1               5

<210> SEQ ID NO 12
<211> LENGTH: 17
<212> TYPE: PRT
<213> ORGANISM: Artificial Sequence
<220> FEATURE:
<223> OTHER INFORMATION: Synthetic Construct

<400> SEQUENCE: 12

Lys Ser Ser Gln Ser Leu Leu Tyr Ser Gly Asn His Lys Asn Tyr Leu
1               5                   10                  15
Ala

<210> SEQ ID NO 13
<211> LENGTH: 113
<212> TYPE: PRT
<213> ORGANISM: Artificial Sequence
<220> FEATURE:
<223> OTHER INFORMATION: Synthetic Construct

<400> SEQUENCE: 13

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn His Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys

<210> SEQ ID NO 14
<211> LENGTH: 113
<212> TYPE: PRT
<213> ORGANISM: Artificial Sequence
<220> FEATURE:
<223> OTHER INFORMATION: Synthetic Construct

<400> SEQUENCE: 14

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys

<210> SEQ ID NO 15
<211> LENGTH: 25
<212> TYPE: PRT
<213> ORGANISM: Artificial Sequence
<220> FEATURE:
<223> OTHER INFORMATION: Synthetic Construct

<400> SEQUENCE: 15

Leu Ser Ala Asp Asp Ala Lys Lys Asp Ala Lys Lys Asp Ala
1               5                   10                  15

Lys Lys Asp Asp Ala Lys Lys Asp Leu
            20                  25

<210> SEQ ID NO 16
<211> LENGTH: 253
<212> TYPE: PRT
<213> ORGANISM: Artificial Sequence
<220> FEATURE:
<223> OTHER INFORMATION: Synthetic Construct

<400> SEQUENCE: 16

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn His Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Leu Ser Ala Asp Asp Ala Lys Lys Asp Ala Ala Lys Lys Asp Asp
        115                 120                 125

Ala Lys Lys Asp Asp Ala Lys Lys Asp Leu Gln Val Gln Leu Gln Gln
    130                 135                 140

Ser Asp Ala Glu Leu Val Lys Pro Gly Ala Ser Val Lys Ile Ser Cys
145                 150                 155                 160

Lys Ala Ser Gly Tyr Thr Phe Thr Asp His Ala Ile His Trp Val Lys
                165                 170                 175

Gln Asn Pro Glu Gln Gly Leu Glu Trp Ile Gly Tyr Phe Ser Pro Gly
            180                 185                 190

Asn Asp Asp Phe Arg Tyr Asn Glu Arg Phe Lys Gly Lys Ala Thr Leu
        195                 200                 205

Thr Ala Asp Lys Ser Ser Ser Thr Ala Tyr Val Gln Leu Asn Ser Leu
    210                 215                 220

Thr Ser Glu Asp Ser Ala Val Tyr Phe Cys Thr Arg Ser Leu Asn Met
225                 230                 235                 240

Ala Tyr Trp Gly Gln Gly Thr Ser Val Thr Val Ser Ser
                245                 250

<210> SEQ ID NO 17
<211> LENGTH: 253
<212> TYPE: PRT
<213> ORGANISM: Artificial Sequence
<220> FEATURE:
<223> OTHER INFORMATION: Synthetic Construct

<400> SEQUENCE: 17

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Leu Ser Ala Asp Asp Ala Lys Lys Asp Ala Ala Lys Lys Asp Asp
        115                 120                 125

Ala Lys Lys Asp Asp Ala Lys Lys Gly Leu Gln Val Gln Leu Gln Gln
    130                 135                 140

Ser Asp Ala Glu Leu Val Lys Pro Gly Ala Ser Val Lys Ile Ser Cys
145                 150                 155                 160

Lys Ala Ser Gly Tyr Thr Phe Thr Asp His Ala Ile His Trp Val Lys
                165                 170                 175

Gln Asn Pro Glu Gln Gly Leu Glu Trp Ile Gly Tyr Phe Ser Pro Gly
            180                 185                 190

Asn Asp Asp Phe Lys Tyr Asn Glu Arg Tyr Lys Gly Lys Ala Thr Leu
        195                 200                 205

Thr Ala Asp Lys Ser Ser Thr Ala Tyr Val Gln Leu Asn Ser Leu
    210                 215                 220

Thr Ser Glu Asp Ser Ala Val Tyr Phe Cys Thr Arg Ser Leu Asn Met
225                 230                 235                 240

Ala Tyr Trp Gly Gln Gly Thr Ser Val Thr Val Ser Ser
                245                 250

<210> SEQ ID NO 18
<211> LENGTH: 253
<212> TYPE: PRT
<213> ORGANISM: Artificial Sequence
<220> FEATURE:
<223> OTHER INFORMATION: Synthetic Construct

<400> SEQUENCE: 18

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Leu Ser Ala Asp Asp Ala Lys Lys Asp Ala Lys Lys Asp
        115                 120                 125

Ala Lys Lys Asp Asp Ala Lys Lys Asp Leu Gln Val Gln Leu Gln Gln
        130                 135                 140

Ser Asp Ala Glu Leu Val Lys Pro Gly Ala Ser Val Lys Ile Ser Cys
145                 150                 155                 160

Lys Ala Ser Gly Tyr Thr Phe Thr Asp His Ala Ile His Trp Val Lys
                165                 170                 175

Gln Asn Pro Glu Gln Gly Leu Glu Trp Ile Gly Tyr Phe Ser Pro Gly
            180                 185                 190

Asn Asn Asp Phe Lys Tyr Asn Glu Arg Phe Lys Gly Lys Ala Thr Leu
        195                 200                 205

Thr Ala Asp Lys Ser Ser Thr Ala Tyr Val Gln Leu Asn Ser Leu
        210                 215                 220

Thr Ser Glu Asp Ser Ala Val Tyr Phe Cys Thr Arg Ser Leu Asn Met
225                 230                 235                 240

Ala Tyr Trp Gly Gln Gly Thr Ser Val Thr Val Ser Ser
                245                 250

<210> SEQ ID NO 19
<211> LENGTH: 5
<212> TYPE: PRT
<213> ORGANISM: Artificial Sequence
<220> FEATURE:
<223> OTHER INFORMATION: Synthetic Construct

<400> SEQUENCE: 19

Gly Gly Gly Gly Ser
1               5

<210> SEQ ID NO 20
<211> LENGTH: 249
<212> TYPE: PRT
<213> ORGANISM: Artificial Sequence
<220> FEATURE:
<223> OTHER INFORMATION: Synthetic Construct

<400> SEQUENCE: 20

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser Val Glu Gly Gly Ser Gly Gly Ser Gly
        115                 120                 125

Gly Ser Gly Gly Ser Gly Gly Val Asp Asp Ile Gln Leu Thr Gln Ser
    130                 135                 140

```
Pro Ala Ile Met Ser Ala Ser Pro Gly Glu Lys Val Thr Met Thr Cys
145                 150                 155                 160

Arg Ala Ser Ser Val Ser Tyr Met Asn Trp Tyr Gln Gln Lys Ser
                165                 170                 175

Gly Thr Ser Pro Lys Arg Trp Ile Tyr Asp Thr Ser Lys Val Ala Ser
                180                 185                 190

Gly Val Pro Tyr Arg Phe Ser Gly Ser Gly Ser Gly Thr Ser Tyr Ser
                195                 200                 205

Leu Thr Ile Ser Ser Met Glu Ala Glu Asp Ala Ala Thr Tyr Tyr Cys
                210                 215                 220

Gln Gln Trp Ser Ser Asn Pro Leu Thr Phe Gly Ala Gly Thr Lys Leu
225                 230                 235                 240

Glu Leu Lys His His His His His His
                245
```

<210> SEQ ID NO 21
<211> LENGTH: 253
<212> TYPE: PRT
<213> ORGANISM: Artificial Sequence
<220> FEATURE:
<223> OTHER INFORMATION: Synthetic Construct

<400> SEQUENCE: 21

```
Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Asn Pro Glu Gln Gly Leu Glu Trp Ile
            35                  40                  45

Gly Tyr Phe Ser Pro Gly Asn Asp Asp Phe Lys Tyr Asn Glu Arg Phe
        50                  55                  60

Lys Gly Lys Ala Thr Leu Thr Ala Asp Lys Ser Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Ser Val Thr
                100                 105                 110

Val Ser Ser Leu Ser Ala Asp Asp Ala Lys Lys Asp Ala Ala Lys Lys
            115                 120                 125

Asp Asp Ala Lys Lys Asp Asp Ala Lys Lys Asp Leu Asp Ile Val Met
130                 135                 140

Ser Gln Ser Pro Ser Ser Leu Pro Val Ser Val Gly Glu Lys Val Thr
145                 150                 155                 160

Leu Ser Cys Lys Ser Ser Gln Ser Leu Leu Tyr Ser Gly Asn Gln Lys
                165                 170                 175

Asn Tyr Leu Ala Trp Tyr Gln Gln Lys Pro Gly Gln Ser Pro Lys Leu
            180                 185                 190

Leu Ile Tyr Trp Ala Ser Ala Arg Glu Ser Gly Val Pro Asp Arg Phe
        195                 200                 205

Thr Gly Ser Gly Ser Gly Thr Asp Phe Thr Leu Ser Ile Ser Ser Val
        210                 215                 220

Lys Thr Glu Asp Leu Ala Val Tyr Tyr Cys Gln Gln Tyr Tyr Ser Tyr
225                 230                 235                 240

Pro Leu Thr Phe Gly Ala Gly Thr Lys Leu Val Leu Lys
                245                 250
```

```
<210> SEQ ID NO 22
<211> LENGTH: 253
<212> TYPE: PRT
<213> ORGANISM: Artificial Sequence
<220> FEATURE:
<223> OTHER INFORMATION: Synthetic Construct

<400> SEQUENCE: 22

Asp Ile Val Met Ser Gln Ser Pro Ser Ser Leu Pro Val Ser Val Gly
1               5                   10                  15

Glu Lys Val Thr Leu Ser Cys Lys Ser Ser Gln Ser Leu Leu Tyr Ser
            20                  25                  30

Gly Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Leu
            100                 105                 110

Lys Leu Ser Ala Asp Ala Lys Lys Asp Ala Ala Lys Lys Asp Asp
        115                 120                 125

Ala Lys Lys Asp Asp Ala Lys Lys Asp Leu Gln Val Gln Leu Gln Gln
    130                 135                 140

Ser Asp Ala Glu Leu Val Lys Pro Gly Ala Ser Val Lys Ile Ser Cys
145                 150                 155                 160

Lys Ala Ser Gly Tyr Thr Phe Thr Asp His Ala Ile His Trp Val Lys
                165                 170                 175

Gln Asn Pro Glu Gln Gly Leu Glu Trp Ile Gly Tyr Phe Ser Pro Gly
            180                 185                 190

Asn Asp Asp Phe Lys Tyr Asn Glu Arg Phe Lys Gly Lys Ala Thr Leu
        195                 200                 205

Thr Ala Asp Lys Ser Ser Ser Thr Ala Tyr Val Gln Leu Asn Ser Leu
    210                 215                 220

Thr Ser Glu Asp Ser Ala Val Tyr Phe Cys Thr Arg Ser Leu Asn Met
225                 230                 235                 240

Ala Tyr Trp Gly Gln Gly Thr Ser Val Thr Val Ser Ser
                245                 250

<210> SEQ ID NO 23
<211> LENGTH: 20
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is Ile or Met
<220> FEATURE:
<221> NAME/KEY: MISC_FEATURE
<222> LOCATION: (5)..(5)
<223> OTHER INFORMATION: Xaa is Phe or Ile
<220> FEATURE:
<221> NAME/KEY: MISC_FEATURE
<222> LOCATION: (8)..(8)
<223> OTHER INFORMATION: Xaa is Gly or Gln
```

```
<220> FEATURE:
<221> NAME/KEY: MISC_FEATURE
<222> LOCATION: (10)..(10)
<223> OTHER INFORMATION: Xaa is Asp or Asn
<220> FEATURE:
<221> NAME/KEY: MISC_FEATURE
<222> LOCATION: (12)..(1)
<223> OTHER INFORMATION: Xaa is Phe or Ile
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: MISC_FEATURE
<222> LOCATION: (13)..(13)
<223> OTHER INFORMATION: Xaa is Lys or Arg
<220> FEATURE:
<221> NAME/KEY: MISC_FEATURE
<222> LOCATION: (15)..(15)
<223> OTHER INFORMATION: Xaa is Asn or Ser
<220> FEATURE:
<221> NAME/KEY: MISC_FEATURE
<222> LOCATION: (16)..(16)
<223> OTHER INFORMATION: Xaa is Glu or Gln
<220> FEATURE:
<221> NAME/KEY: MISC_FEATURE
<222> LOCATION: (17)..(17)
<223> OTHER INFORMATION: Xaa is Arg or Lys
<220> FEATURE:
<221> NAME/KEY: MISC_FEATURE
<222> LOCATION: (18)..(18)
<223> OTHER INFORMATION: Xaa is Phe or Tyr
<220> FEATURE:
<221> NAME/KEY: MISC_FEATURE
<222> LOCATION: (19)..(19)
<223> OTHER INFORMATION: Xaa is Lys or Gln

<400> SEQUENCE: 23

Trp Xaa Gly Tyr Xaa Ser Pro Xaa Asn Xaa Asp Xaa Xaa Tyr Xaa Xaa
1               5                   10                  15

Xaa Xaa Xaa Gly
            20

<210> SEQ ID NO 24
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Lys or Arg
<220> FEATURE:
<221> NAME/KEY: MISC_FEATURE
<222> LOCATION: (64)..(64)
<223> OTHER INFORMATION: Xaa is Phe or Tyr

<400> SEQUENCE: 24

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Xaa Asp Phe Xaa Tyr Asn Glu Arg Xaa
    50                  55                  60
```

```
Lys Gly Lys Ala Thr Leu Thr Ala Asp Lys Ser Ser Thr Ala Tyr
 65                  70                  75                  80

Val Gln Leu Asn Ser Leu Thr Ser Glu Asp Ser Ala Val Tyr Phe Cys
                 85                  90                  95

Thr Arg Ser Leu Asn Met Ala Tyr Trp Gly Gln Gly Thr Ser Val Thr
            100                 105                 110

Val Ser Ser
        115

<210> SEQ ID NO 25
<211> LENGTH: 116
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (57)..(57)
<223> OTHER INFORMATION: Xaa is Asp or Asn
<220> FEATURE:
<221> NAME/KEY: MISC_FEATURE
<222> LOCATION: (60)..(60)
<223> OTHER INFORMATION: Xaa is Lys or Arg
<220> FEATURE:
<221> NAME/KEY: MISC_FEATURE
<222> LOCATION: (65)..(65)
<223> OTHER INFORMATION: Xaa is Phe or Tyr

<400> SEQUENCE: 25

Gln Val Gln Leu Gln Gln Ser Asp Ala Glu Leu Val Lys Pro Gly Ala
 1               5                  10                  15

Ser Val Lys Ile Ser Cys Lys Ala Ser Gly Tyr Thr Phe Thr Thr Asp
            20                  25                  30

His Ala Ile His Trp Val Lys Gln Asn Pro Glu Gln Gly Leu Glu Trp
        35                  40                  45

Ile Gly Tyr Phe Ser Pro Gln Asn Xaa Asp Phe Xaa Tyr Asn Glu Arg
    50                  55                  60

Xaa Lys Gly Lys Ala Thr Leu Thr Ala Asp Lys Ser Ser Thr Ala
 65                  70                  75                  80

Tyr Val Gln Leu Asn Ser Leu Thr Ser Asn Asp Ser Ala Val Tyr Phe
                 85                  90                  95

Cys Thr Arg Ser Leu Asn Met Ala Tyr Trp Gly Gln Gly Thr Ser Val
            100                 105                 110

Thr Val Ser Ser
        115

<210> SEQ ID NO 26
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (57)..(57)
<223> OTHER INFORMATION: Xaa is Asp or Asn
<220> FEATURE:
<221> NAME/KEY: MISC_FEATURE
<222> LOCATION: (60)..(60)
<223> OTHER INFORMATION: Xaa is Lys or Arg
<220> FEATURE:
<221> NAME/KEY: MISC_FEATURE
<222> LOCATION: (65)..(65)
<223> OTHER INFORMATION: Xaa is Phe or Tyr
```

```
<400> SEQUENCE: 26

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Thr Asp
            20                  25                  30

His Ala Ile His Trp Val Lys Gln Asn Pro Glu Gln Gly Leu Glu Trp
        35                  40                  45

Ile Gly Tyr Ile Ser Pro Gln Asn Xaa Asp Ile Xaa Tyr Asn Glu Lys
    50                  55                  60

Xaa Lys Gly Lys Ala Thr Leu Thr Ala Asp Lys Ser Ser Ser Thr Ala
65                  70                  75                  80

Tyr Met Gln Leu Asn Ser Leu Thr Ser Asn Asp Ser Ala Val Tyr Phe
                85                  90                  95

Cys Arg Arg Ser Phe Tyr Gly Asn Trp Gly Gln Gly Thr Thr Leu Thr
                100                 105                 110

Val Ser Ser
        115

<210> SEQ ID NO 27
<211> LENGTH: 116
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (57)..(57)
<223> OTHER INFORMATION: Xaa is Asp or Asn
<220> FEATURE:
<221> NAME/KEY: MISC_FEATURE
<222> LOCATION: (60)..(60)
<223> OTHER INFORMATION: Xaa is Lys or Arg
<220> FEATURE:
<221> NAME/KEY: MISC_FEATURE
<222> LOCATION: (65)..(65)
<223> OTHER INFORMATION: Xaa is Phe or Tyr

<400> SEQUENCE: 27

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Thr Asp
            20                  25                  30

His Ala Ile His Trp Val Lys Gln Lys Pro Glu Gln Gly Leu Glu Trp
        35                  40                  45

Ile Gly Tyr Ile Ser Pro Gln Asn Xaa Asp Ile Xaa Tyr Asn Glu Lys
    50                  55                  60

Xaa Lys Gly Lys Ala Thr Leu Thr Ala Asp Lys Pro Ser Asn Thr Val
65                  70                  75                  80

Tyr Met Gln Leu Asn Ser Leu Thr Ser Asn Asp Ser Ala Val Tyr Phe
                85                  90                  95

Cys Thr Arg Ser Leu Ser Gly Asp Ser Trp Gly Gln Gly Thr Thr Leu
                100                 105                 110

Thr Val Ser Ser
        115

<210> SEQ ID NO 28
<211> LENGTH: 115
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (56)..(56)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Lys or Arg
<220> FEATURE:
<221> NAME/KEY: MISC_FEATURE
<222> LOCATION: (64)..(64)
<223> OTHER INFORMATION: Xaa is Lys or Arg

<400> SEQUENCE: 28

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Asn Pro Gly Gln Arg Leu Glu Trp Ile
            35                  40                  45

Gly Tyr Phe Ser Pro Gly Asn Xaa Asp Phe Xaa Tyr Asn Glu Arg Xaa
        50                  55                  60

Lys Gly Lys Ala Thr Leu Thr Ala Asp Thr Ser Ala Ser Thr Ala Tyr
65                  70                  75                  80

Val Glu Leu Ser Ser Leu Pro Ser Glu Asp Thr Ala Val Tyr Phe Cys
                85                  90                  95

Thr Arg Ser Leu Asn Met Ala Tyr Trp Gly Gln Gly Thr Leu Val Thr
                100                 105                 110

Val Ser Ser
        115

<210> SEQ ID NO 29
<211> LENGTH: 114
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Lys or Arg
<220> FEATURE:
<221> NAME/KEY: MISC_FEATURE
<222> LOCATION: (64)..(64)
<223> OTHER INFORMATION: Xaa is Phe or Tyr

<400> SEQUENCE: 29

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Thr Phe Thr Asp His
                20                  25                  30

Ala Ile His Trp Val Arg Gln Pro Pro Gly Arg Gly Leu Glu Trp Ile
            35                  40                  45

Gly Tyr Ile Ser Pro Gly Asn Xaa Asp Ile Xaa Tyr Asn Glu Lys Xaa
        50                  55                  60

Lys Gly Arg Val Thr Met Leu Val Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95
```

```
Ala Arg Ser Tyr Tyr Gly His Trp Gly Gln Gly Ser Leu Val Thr Val
                100                 105                 110

Ser Ser

<210> SEQ ID NO 30
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Lys or Arg
<220> FEATURE:
<221> NAME/KEY: MISC_FEATURE
<222> LOCATION: (64)..(64)
<223> OTHER INFORMATION: Xaa is Phe or Tyr

<400> SEQUENCE: 30

Gln Val Gln Leu Val Gln Ser Gly Ala Glu Val Val Lys Pro Gly Ala
1               5                   10                  15

Ser Val Lys Ile Ser Cys Lys Ala Ser Gly Tyr Thr Phe Thr Asp His
                20                  25                  30

Ala Ile His Trp Val Lys Gln Asn Pro Gly Gln Arg Leu Glu Trp Ile
            35                  40                  45

Gly Tyr Phe Ser Pro Gly Asn Xaa Asp Phe Xaa Tyr Ser Gln Lys Xaa
        50                  55                  60

Gln Gly Lys Ala Thr Leu Thr Ala Asp Thr Ser Ala Ser Thr Ala Tyr
65                  70                  75                  80

Val Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
                100                 105                 110

Val Ser Ser
        115

<210> SEQ ID NO 31
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Lys or Arg
<220> FEATURE:
<221> NAME/KEY: MISC_FEATURE
<222> LOCATION: (64)..(64)
<223> OTHER INFORMATION: Xaa is Phe or Tyr

<400> SEQUENCE: 31

Gln Val Gln Leu Val Gln Ser Gly Ala Glu Val Val Lys Pro Gly Ala
1               5                   10                  15

Ser Val Lys Val Ser Cys Lys Ala Ser Gly Tyr Thr Phe Thr Asp His
                20                  25                  30
```

Ala Ile His Trp Val Arg Gln Asn Pro Gly Gln Arg Leu Glu Trp Met
            35                  40                  45

Gly Tyr Phe Ser Pro Gly Asn Xaa Asp Phe Xaa Tyr Ser Gln Lys Xaa
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser
    115

<210> SEQ ID NO 32
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Lys or Arg
<220> FEATURE:
<221> NAME/KEY: MISC_FEATURE
<222> LOCATION: (64)..(64)
<223> OTHER INFORMATION: Xaa is Phe or Tyr

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
            35                  40                  45

Gly Tyr Phe Ser Pro Gly Asn Xaa Asp Phe Xaa Tyr Ser Gln Lys Xaa
    50                  55                  60

Gln Gly Arg Val Thr Ile Thr Ala Asp Thr Ser Ala Ser Thr Ala Tyr
65                  70                  75                  80

Met Glu Leu Ser Ser Leu Arg Ser Glu Asp Thr Ala Val Tyr Phe Cys
                85                  90                  95

Thr Arg Ser Leu Asn Met Ala Tyr Trp Gly Gln Gly Thr Leu Val Thr
            100                 105                 110

Val Ser Ser
    115

<210> SEQ ID NO 33
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Lys or Arg

```
<220> FEATURE:
<221> NAME/KEY: MISC_FEATURE
<222> LOCATION: (64)..(64)
<223> OTHER INFORMATION: Xaa is Phe or Tyr

<400> SEQUENCE: 33

Gln Val Gln Leu Gln Gln Ser Asp Ala Glu Leu Val Lys Pro Gly Ala
1               5                   10                  15

Ser Val Lys Ile Ser Cys Lys Ala Ser Gly Tyr Thr Phe Thr Asp His
            20                  25                  30

Ala Ile His Trp Val Lys Gln Asn Pro Glu Gln Gly Leu Glu Trp Ile
        35                  40                  45

Gly Tyr Phe Ser Pro Gly Asn Xaa Asp Phe Xaa Tyr Asn Glu Arg Xaa
    50                  55                  60

Lys Gly Lys Ala Thr Leu Thr Ala Asp Lys Ser Ser Thr Ala Tyr
65                  70                  75                  80

Val Gln Leu Asn Ser Leu Thr Ser Glu Asp Ser Ala Val Tyr Phe Cys
                85                  90                  95

Thr Arg Ser Leu Asn Met Ala Tyr Trp Gly Gln Gly Thr Thr Leu Thr
            100                 105                 110

Val Ser Ser
        115

<210> SEQ ID NO 34
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Lys or Arg
<220> FEATURE:
<221> NAME/KEY: MISC_FEATURE
<222> LOCATION: (64)..(64)
<223> OTHER INFORMATION: Xaa is Phe or Tyr

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
            20                  25                  30

Ala Ile His Trp Val Arg Gln Ala Pro Gly Gln Arg Leu Glu Trp Met
        35                  40                  45

Gly Tyr Phe Ser Pro Gly Asn Xaa Asp Phe Xaa Tyr Ser Gln Lys Xaa
    50                  55                  60

Gln Gly Arg Val Thr Ile Thr Ala Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Asn Met Ala Tyr Trp Gly Gln Gly Thr Leu Val Thr
            100                 105                 110

Val Ser Ser
        115
```

```
<210> SEQ ID NO 35
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Lys or Arg
<220> FEATURE:
<221> NAME/KEY: MISC_FEATURE
<222> LOCATION: (64)..(64)
<223> OTHER INFORMATION: Xaa is Phe or Tyr

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Arg Leu Glu Trp Met
            35                  40                  45

Gly Tyr Phe Ser Pro Gly Asn Xaa Asp Phe Xaa Tyr Ser Gln Lys Xaa
50                  55                  60

Gln Gly Arg Val Thr Ile Thr Arg Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Leu Asn Met Ala Tyr Trp Gly Gln Gly Thr Leu Val Thr
            100                 105                 110

Val Ser Ser
        115

<210> SEQ ID NO 36
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Lys or Arg
<220> FEATURE:
<221> NAME/KEY: MISC_FEATURE
<222> LOCATION: (64)..(64)
<223> OTHER INFORMATION: Xaa is Phe or Tyr

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Arg Leu Glu Trp Met
            35                  40                  45

Gly Tyr Phe Ser Pro Gly Asn Xaa Asp Phe Xaa Tyr Ser Gln Lys Xaa
50                  55                  60
```

```
Gln Gly Arg Val Thr Ile Thr Ala Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Leu Asn Met Ala Tyr Trp Gly Gln Gly Thr Leu Val Thr
            100                 105                 110

Val Ser Ser
        115

<210> SEQ ID NO 37
<211> LENGTH: 115
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (56)..(56)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Lys or Arg
<220> FEATURE:
<221> NAME/KEY: MISC_FEATURE
<222> LOCATION: (64)..(64)
<223> OTHER INFORMATION: Xaa is Phe or Tyr

<400> SEQUENCE: 37

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp His
                20                  25                  30

Ala Ile His Trp Val Arg Gln Ala Pro Gly Gln Arg Leu Glu Trp Met
            35                  40                  45

Gly Tyr Phe Ser Pro Gly Asn Xaa Asp Phe Xaa Tyr Ser Gln Lys Xaa
        50                  55                  60

Gln Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Leu Asn Met Ala Tyr Trp Gly Gln Gly Thr Leu Val Thr
            100                 105                 110

Val Ser Ser
        115

<210> SEQ ID NO 38
<211> LENGTH: 113
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Ser or Thr
<220> FEATURE:
<221> NAME/KEY: MISC_FEATURE
<222> LOCATION: (9)..(9)
<223> OTHER INFORMATION: Xaa is Ser or Asp
<220> FEATURE:
<221> NAME/KEY: MISC_FEATURE
<222> LOCATION: (12)..(12)
<223> OTHER INFORMATION: Xaa is Pro or Ala
```

```
<220> FEATURE:
<221> NAME/KEY: MISC_FEATURE
<222> LOCATION: (15)..(15)
<223> OTHER INFORMATION: Xaa is Leu or Val
<220> FEATURE:
<221> NAME/KEY: MISC_FEATURE
<222> LOCATION: (17)..(17)
<223> OTHER INFORMATION: Xaa is E or Asp
<220> FEATURE:
<221> NAME/KEY: misc_feature
<222> LOCATION: (19)..(19)
<223> OTHER INFORMATION: Xaa can be any naturally occurring amino acid
<220> FEATURE:
<221> NAME/KEY: MISC_FEATURE
<222> LOCATION: (21)..(21)
<223> OTHER INFORMATION: Xaa is Leu or Ile
<220> FEATURE:
<221> NAME/KEY: MISC_FEATURE
<222> LOCATION: (22)..(22)
<223> OTHER INFORMATION: Xaa is Ser or Asn
<220> FEATURE:
<221> NAME/KEY: MISC_FEATURE
<222> LOCATION: (29)..(29)
<223> OTHER INFORMATION: Xaa is Leu or Val
<220> FEATURE:
<221> NAME/KEY: MISC_FEATURE
<222> LOCATION: (33)..(33)
<223> OTHER INFORMATION: Xaa is Gly or Ser
<220> FEATURE:
<221> NAME/KEY: MISC_FEATURE
<222> LOCATION: (49)..(49)
<223> OTHER INFORMATION: Xaa is Ser or Pro
<220> FEATURE:
<221> NAME/KEY: MISC_FEATURE
<222> LOCATION: (59)..(59)
<223> OTHER INFORMATION: Xaa is Ala or Thr
<220> FEATURE:
<221> NAME/KEY: MISC_FEATURE
<222> LOCATION: (69)..(69)
<223> OTHER INFORMATION: Xaa is Thr or Ser
<220> FEATURE:
<221> NAME/KEY: MISC_FEATURE
<222> LOCATION: (80)..(80)
<223> OTHER INFORMATION: Xaa is Ser or Thr
<220> FEATURE:
<221> NAME/KEY: MISC_FEATURE
<222> LOCATION: (84)..(84)
<223> OTHER INFORMATION: Xaa is Val or Leu
<220> FEATURE:
<221> NAME/KEY: MISC_FEATURE
<222> LOCATION: (85)..(85)
<223> OTHER INFORMATION: Xaa is Lys or Gln
<220> FEATURE:
<221> NAME/KEY: MISC_FEATURE
<222> LOCATION: (86)..(86)
<223> OTHER INFORMATION: Xaa is Thr or Ala
<220> FEATURE:
<221> NAME/KEY: MISC_FEATURE
<222> LOCATION: (89)..(89)
<223> OTHER INFORMATION: Xaa is Leu or Val
<220> FEATURE:
<221> NAME/KEY: MISC_FEATURE
<222> LOCATION: (106)..(106)
<223> OTHER INFORMATION: Xaa is Ala or Gln
<220> FEATURE:
<221> NAME/KEY: MISC_FEATURE
<222> LOCATION: (110)..(110)
<223> OTHER INFORMATION: Xaa is Leu or Val
<220> FEATURE:
<221> NAME/KEY: MISC_FEATURE
<222> LOCATION: (111)..(111)
<223> OTHER INFORMATION: Xaa is Val or Glu
<220> FEATURE:
<221> NAME/KEY: MISC_FEATURE
<222> LOCATION: (112)..(112)
<223> OTHER INFORMATION: Xaa is Leu or Ile
```

```
<400> SEQUENCE: 38

Asp Ile Val Met Xaa Gln Ser Pro Xaa Ser Leu Xaa Val Ser Xaa Gly
1               5                   10                  15

Xaa Lys Xaa Thr Xaa Xaa Cys Lys Ser Ser Gln Ser Xaa Leu Tyr Ser
            20                  25                  30

Xaa Asn His Lys Asn Tyr Leu Ala Trp Tyr Gln Gln Lys Pro Gly Gln
        35                  40                  45

Xaa Pro Lys Leu Leu Ile Tyr Trp Ala Ser Xaa Arg Glu Ser Gly Val
    50                  55                  60

Pro Asp Arg Phe Xaa Gly Ser Gly Ser Gly Thr Asp Phe Thr Leu Xaa
65                  70                  75                  80

Ile Ser Ser Xaa Xaa Xaa Glu Asp Xaa Ala Val Tyr Tyr Cys Gln Gln
                85                  90                  95

Tyr Tyr Ser Tyr Pro Leu Thr Phe Gly Xaa Gly Thr Lys Xaa Xaa Xaa
            100                 105                 110

Lys

<210> SEQ ID NO 39
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Leu or Val
<220> FEATURE:
<221> NAME/KEY: MISC_FEATURE
<222> LOCATION: (10)..(10)
<223> OTHER INFORMATION: Xaa is Gly or Ser

<400> SEQUENCE: 39

Lys Ser Ser Gln Ser Xaa Leu Tyr Ser Xaa Asn His Lys Asn Tyr Leu
1               5                   10                  15

Ala

<210> SEQ ID NO 40
<211> LENGTH: 113
<212> TYPE: PRT
<213> ORGANISM: Artificial Sequence
<220> FEATURE:
<223> OTHER INFORMATION: Synthetic Construct

<400> SEQUENCE: 40

Asp Ile Val Met Ser Gln Ser Pro Asp Ser Leu Ala Val Ser Leu Gly
1               5                   10                  15

Glu Arg Val Thr Leu Asn Cys Lys Ser Ser Gln Ser Leu Leu Tyr Ser
            20                  25                  30

Gly Asn His Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95
```

Tyr Tyr Ser Tyr Pro Leu Thr Phe Gly Ala Gly Thr Lys Leu Glu Leu
                100                 105                 110
Lys

<210> SEQ ID NO 41
<211> LENGTH: 113
<212> TYPE: PRT
<213> ORGANISM: Artificial Sequence
<220> FEATURE:
<223> OTHER INFORMATION: Synthetic Construct

<400> SEQUENCE: 41

Asp Ile Val Met Ser Gln Ser Pro Asp Ser Leu Ala Val Ser Leu Gly
1               5                   10                  15

Glu Arg Val Thr Leu Asn Cys Lys Ser Ser Gln Ser Val Leu Tyr Ser
            20                  25                  30

Gly Asn His Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Gln Ala Glu Asp Val Ala Val Tyr Tyr Cys Gln Gln
                85                  90                  95

Tyr Tyr Ser Tyr Pro Leu Thr Phe Gly Ala Gly Thr Lys Leu Glu Leu
                100                 105                 110
Lys

<210> SEQ ID NO 42
<211> LENGTH: 113
<212> TYPE: PRT
<213> ORGANISM: Artificial Sequence
<220> FEATURE:
<223> OTHER INFORMATION: Synthetic Construct

<400> SEQUENCE: 42

Asp Ile Val Met Ser Gln Thr Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Gly Asn His Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Leu Thr Phe Gly Ala Gly Thr Lys Leu Glu Ile
                100                 105                 110
Lys

<210> SEQ ID NO 43
<211> LENGTH: 113
<212> TYPE: PRT
<213> ORGANISM: Artificial Sequence
<220> FEATURE:
<223> OTHER INFORMATION: Synthetic Construct

<400> SEQUENCE: 43

Asp Ile Val Met Ser Gln Thr Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Gly Asn His Lys Asn Tyr Leu Ala Trp Tyr Gln Gln Lys Pro Gly Gln
        35                  40                  45

Pro Pro Lys Leu Leu Ile Tyr Trp Ala Ser Ala Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Leu Thr Phe Gly Gln Gly Thr Lys Leu Glu Ile
            100                 105                 110

Lys

<210> SEQ ID NO 44
<211> LENGTH: 113
<212> TYPE: PRT
<213> ORGANISM: Artificial Sequence
<220> FEATURE:
<223> OTHER INFORMATION: Synthetic Construct

<400> SEQUENCE: 44

Asp Ile Val Met Ser Gln Ser Pro Ser Ser Leu Pro Val Ser Val Gly
1               5                   10                  15

Asp Lys Val Thr Leu Ser Cys Lys Ser Ser Gln Ser Leu Leu Tyr Ser
            20                  25                  30

Gly Asn His Lys Asn Tyr Leu Ala Trp Tyr Gln Gln Lys Pro Gly Gln
        35                  40                  45

Ser Pro Lys Leu Leu Ile Tyr Trp Ala Ser Ala Arg Glu Ser Gly Val
50                  55                  60

Pro Asp Arg Phe Thr Gly Ser Gly Ser Gly Thr Asp Phe Thr Leu Ser
65                  70                  75                  80

Ile Ser Ser Val Lys Thr Glu Asp Leu Ala Val Tyr Tyr Cys Gln Gln
                85                  90                  95

Tyr Tyr Ser Tyr Pro Leu Thr Phe Gly Ala Gly Thr Lys Leu Val Ile
            100                 105                 110

Lys

<210> SEQ ID NO 45
<211> LENGTH: 113
<212> TYPE: PRT
<213> ORGANISM: Artificial Sequence
<220> FEATURE:
<223> OTHER INFORMATION: Synthetic Construct

<400> SEQUENCE: 45

Asp Ile Val Met Thr Gln Ser Pro Asp Ser Leu Ala Val Ser Leu Gly
1               5                   10                  15

Glu Arg Ala Thr Ile Asn Cys Ser Ser Gln Ser Val Leu Tyr Ser
            20                  25                  30

Ser Asn His Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Leu Thr Phe Gly Gly Gly Thr Lys Val Glu Ile
            100                 105                 110

Lys

<210> SEQ ID NO 46
<211> LENGTH: 113
<212> TYPE: PRT
<213> ORGANISM: Artificial Sequence
<220> FEATURE:
<223> OTHER INFORMATION: Synthetic Construct

<400> SEQUENCE: 46

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Gly Asn His Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Tyr Pro Leu Thr Phe Gly Gly Gly Thr Lys Val Glu Ile
            100                 105                 110

Lys

<210> SEQ ID NO 47
<211> LENGTH: 116
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is Val or Gln
<220> FEATURE:
<221> NAME/KEY: MISC_FEATURE
<222> LOCATION: (6)..(6)
<223> OTHER INFORMATION: Xaa is Gln or Glu
<220> FEATURE:
<221> NAME/KEY: MISC_FEATURE
<222> LOCATION: (8)..(8)
<223> OTHER INFORMATION: Xaa is Asp or Gly
<220> FEATURE:
<221> NAME/KEY: MISC_FEATURE
<222> LOCATION: (9)..(9)
<223> OTHER INFORMATION: Xaa is Ala or Pro
<220> FEATURE:
<221> NAME/KEY: MISC_FEATURE
<222> LOCATION: (10)..(10)
<223> OTHER INFORMATION: Xaa is Glu or Gly
<220> FEATURE:
<221> NAME/KEY: MISC_FEATURE
<222> LOCATION: (11)..(11)
<223> OTHER INFORMATION: Xaa is Leu or Val
<220> FEATURE:
<221> NAME/KEY: MISC_FEATURE
<222> LOCATION: (12)..(12)
<223> OTHER INFORMATION: Xaa is Val or Lys

```
<220> FEATURE:
<221> NAME/KEY: MISC_FEATURE
<222> LOCATION: (13)..(13)
<223> OTHER INFORMATION: Xaa is Lys or Arg
<220> FEATURE:
<221> NAME/KEY: MISC_FEATURE
<222> LOCATION: (15)..(15)
<223> OTHER INFORMATION: Xaa is Gly or Ser
<220> FEATURE:
<221> NAME/KEY: MISC_FEATURE
<222> LOCATION: (16)..(16)
<223> OTHER INFORMATION: Xaa is Ala or Gln
<220> FEATURE:
<221> NAME/KEY: MISC_FEATURE
<222> LOCATION: (17)..(17)
<223> OTHER INFORMATION: Xaa is Ser or Thr
<220> FEATURE:
<221> NAME/KEY: MISC_FEATURE
<222> LOCATION: (18)..(18)
<223> OTHER INFORMATION: Xaa is Val or Leu
<220> FEATURE:
<221> NAME/KEY: MISC_FEATURE
<222> LOCATION: (19)..(19)
<223> OTHER INFORMATION: Xaa is Lys or Ser
<220> FEATURE:
<221> NAME/KEY: MISC_FEATURE
<222> LOCATION: (20)..(20)
<223> OTHER INFORMATION: Xaa is Ile, Leu or Val
<220> FEATURE:
<221> NAME/KEY: MISC_FEATURE
<222> LOCATION: (21)..(21)
<223> OTHER INFORMATION: Xaa is Ser or Thr
<220> FEATURE:
<221> NAME/KEY: MISC_FEATURE
<222> LOCATION: (23)..(23)
<223> OTHER INFORMATION: Xaa is Lys or Thr
<220> FEATURE:
<221> NAME/KEY: MISC_FEATURE
<222> LOCATION: (24)..(24)
<223> OTHER INFORMATION: Xaa is Ala or Val
<220> FEATURE:
<221> NAME/KEY: MISC_FEATURE
<222> LOCATION: (31)..(31)
<223> OTHER INFORMATION: Xaa is Thr or nothing
<220> FEATURE:
<221> NAME/KEY: MISC_FEATURE
<222> LOCATION: (39)..(39)
<223> OTHER INFORMATION: Xaa is Lys or Arg
<220> FEATURE:
<221> NAME/KEY: MISC_FEATURE
<222> LOCATION: (41)..(41)
<223> OTHER INFORMATION: Xaa is Asn, Lys, Pro, or Ala
<220> FEATURE:
<221> NAME/KEY: MISC_FEATURE
<222> LOCATION: (43)..(43)
<223> OTHER INFORMATION: Xaa is Glu or Gly
<220> FEATURE:
<221> NAME/KEY: MISC_FEATURE
<222> LOCATION: (44)..(44)
<223> OTHER INFORMATION: Xaa is Gln or Arg
<220> FEATURE:
<221> NAME/KEY: MISC_FEATURE
<222> LOCATION: (45)..(45)
<223> OTHER INFORMATION: Xaa is Gly or Arg
<220> FEATURE:
<221> NAME/KEY: MISC_FEATURE
<222> LOCATION: (49)..(49)
<223> OTHER INFORMATION: Xaa is Ile or Met
<220> FEATURE:
<221> NAME/KEY: MISC_FEATURE
<222> LOCATION: (52)..(52)
<223> OTHER INFORMATION: Xaa is Phe or Ile
<220> FEATURE:
<221> NAME/KEY: MISC_FEATURE
<222> LOCATION: (55)..(55)
<223> OTHER INFORMATION: Xaa is Gly or Gln
```

```
<220> FEATURE:
<221> NAME/KEY: MISC_FEATURE
<222> LOCATION: (57)..(57)
<223> OTHER INFORMATION: Xaa is Asp or Asn
<220> FEATURE:
<221> NAME/KEY: MISC_FEATURE
<222> LOCATION: (59)..(59)
<223> OTHER INFORMATION: Xaa is Phe or Ile
<220> FEATURE:
<221> NAME/KEY: MISC_FEATURE
<222> LOCATION: (60)..(60)
<223> OTHER INFORMATION: Xaa is Lys or Arg
<220> FEATURE:
<221> NAME/KEY: MISC_FEATURE
<222> LOCATION: (62)..(62)
<223> OTHER INFORMATION: Xaa is Asn or Ser
<220> FEATURE:
<221> NAME/KEY: MISC_FEATURE
<222> LOCATION: (63)..(63)
<223> OTHER INFORMATION: Xaa is Glu or Gln
<220> FEATURE:
<221> NAME/KEY: MISC_FEATURE
<222> LOCATION: (64)..(64)
<223> OTHER INFORMATION: Xaa is Arg or Lys
<220> FEATURE:
<221> NAME/KEY: MISC_FEATURE
<222> LOCATION: (65)..(65)
<223> OTHER INFORMATION: Xaa is Phe or Tyr
<220> FEATURE:
<221> NAME/KEY: MISC_FEATURE
<222> LOCATION: (66)..(66)
<223> OTHER INFORMATION: Xaa is Lys or Gln
<220> FEATURE:
<221> NAME/KEY: MISC_FEATURE
<222> LOCATION: (68)..(68)
<223> OTHER INFORMATION: Xaa is Lys or Arg
<220> FEATURE:
<221> NAME/KEY: MISC_FEATURE
<222> LOCATION: (69)..(69)
<223> OTHER INFORMATION: Xaa is Ala or Val
<220> FEATURE:
<221> NAME/KEY: MISC_FEATURE
<222> LOCATION: (71)..(71)
<223> OTHER INFORMATION: Xaa is Leu, Met, or Ile
<220> FEATURE:
<221> NAME/KEY: MISC_FEATURE
<222> LOCATION: (72)..(72)
<223> OTHER INFORMATION: Xaa is Thr or Leu
<220> FEATURE:
<221> NAME/KEY: MISC_FEATURE
<222> LOCATION: (73)..(73)
<223> OTHER INFORMATION: Xaa is Ala, Val, or Arg
<220> FEATURE:
<221> NAME/KEY: MISC_FEATURE
<222> LOCATION: (75)..(75)
<223> OTHER INFORMATION: Xaa is Lys or Thr
<220> FEATURE:
<221> NAME/KEY: MISC_FEATURE
<222> LOCATION: (76)..(76)
<223> OTHER INFORMATION: Xaa is Ser or Pro
<220> FEATURE:
<221> NAME/KEY: MISC_FEATURE
<222> LOCATION: (77)..(77)
<223> OTHER INFORMATION: Xaa is Ser, Ala, or Lys
<220> FEATURE:
<221> NAME/KEY: MISC_FEATURE
<222> LOCATION: (78)..(78)
<223> OTHER INFORMATION: Xaa is Ser or Asn
<220> FEATURE:
<221> NAME/KEY: MISC_FEATURE
<222> LOCATION: (79)..(79)
<223> OTHER INFORMATION: Xaa is Thr or Gln
<220> FEATURE:
<221> NAME/KEY: MISC_FEATURE
<222> LOCATION: (80)..(80)
<223> OTHER INFORMATION: Xaa is Ala, Val, or Phe
```

```
<220> FEATURE:
<221> NAME/KEY: MISC_FEATURE
<222> LOCATION: (81)..(81)
<223> OTHER INFORMATION: Xaa is Tyr or Ser
<220> FEATURE:
<221> NAME/KEY: MISC_FEATURE
<222> LOCATION: (82)..(82)
<223> OTHER INFORMATION: Xaa is Val, Met, or Leu
<220> FEATURE:
<221> NAME/KEY: MISC_FEATURE
<222> LOCATION: (83)..(83)
<223> OTHER INFORMATION: Xaa is Gln, Glu, or Arg
<220> FEATURE:
<221> NAME/KEY: MISC_FEATURE
<222> LOCATION: (85)..(85)
<223> OTHER INFORMATION: Xaa is Asn or Ser
<220> FEATURE:
<221> NAME/KEY: MISC_FEATURE
<222> LOCATION: (87)..(87)
<223> OTHER INFORMATION: Xaa is Leu or Val
<220> FEATURE:
<221> NAME/KEY: MISC_FEATURE
<222> LOCATION: (88)..(88)
<223> OTHER INFORMATION: Xaa is Thr, Pro, or Arg
<220> FEATURE:
<221> NAME/KEY: MISC_FEATURE
<222> LOCATION: (89)..(89)
<223> OTHER INFORMATION: Xaa is Ser or Ala
<220> FEATURE:
<221> NAME/KEY: MISC_FEATURE
<222> LOCATION: (90)..(90)
<223> OTHER INFORMATION: Xaa is Glu, Asn, or Ala
<220> FEATURE:
<221> NAME/KEY: MISC_FEATURE
<222> LOCATION: (92)..(92)
<223> OTHER INFORMATION: Xaa is Ser or Thr
<220> FEATURE:
<221> NAME/KEY: MISC_FEATURE
<222> LOCATION: (96)..(96)
<223> OTHER INFORMATION: Xaa is Phe or Tyr
<220> FEATURE:
<221> NAME/KEY: MISC_FEATURE
<222> LOCATION: (98)..(98)
<223> OTHER INFORMATION: Xaa is Thr, Arg, or Ala
<220> FEATURE:
<221> NAME/KEY: MISC_FEATURE
<222> LOCATION: (101)..(101)
<223> OTHER INFORMATION: Xaa is Lys, Phe, or Tyr
<220> FEATURE:
<221> NAME/KEY: MISC_FEATURE
<222> LOCATION: (102)..(102)
<223> OTHER INFORMATION: Xaa is Asn, Tyr, or Ser
<220> FEATURE:
<221> NAME/KEY: MISC_FEATURE
<222> LOCATION: (103)..(103)
<223> OTHER INFORMATION: Xaa is Met or Gly
<220> FEATURE:
<221> NAME/KEY: MISC_FEATURE
<222> LOCATION: (104)..(104)
<223> OTHER INFORMATION: Xaa is Ala, Asn, Asp, or His
<220> FEATURE:
<221> NAME/KEY: MISC_FEATURE
<222> LOCATION: (105)..(105)
<223> OTHER INFORMATION: Xaa is Tyr, Ser, or nothing
<220> FEATURE:
<221> NAME/KEY: MISC_FEATURE
<222> LOCATION: (110)..(110)
<223> OTHER INFORMATION: Xaa is Thr or Ser
<220> FEATURE:
<221> NAME/KEY: MISC_FEATURE
<222> LOCATION: (111)..(111)
<223> OTHER INFORMATION: Xaa is Ser, Thr, or Leu
<220> FEATURE:
<221> NAME/KEY: MISC_FEATURE
<222> LOCATION: (112)..(112)
<223> OTHER INFORMATION: Xaa is Val or Leu
```

-continued

```
<400> SEQUENCE: 47

Gln Val Gln Leu Xaa Xaa Ser Xaa Xaa Xaa Xaa Xaa Pro Xaa Xaa
1               5                   10                  15

Xaa Xaa Xaa Xaa Xaa Cys Xaa Xaa Ser Gly Tyr Thr Phe Thr Xaa Asp
            20                  25                  30

His Ala Ile His Trp Val Xaa Gln Xaa Pro Xaa Xaa Xaa Leu Trp Glu
        35                  40                  45

Xaa Gly Tyr Xaa Ser Pro Xaa Asn Xaa Asp Xaa Xaa Tyr Xaa Xaa Xaa
    50                  55                  60

Xaa Xaa Gly Xaa Xaa Thr Xaa Xaa Xaa Asp Xaa Xaa Xaa Xaa Xaa
65                  70                  75                  80

Xaa Xaa Xaa Leu Xaa Ser Xaa Xaa Xaa Xaa Asp Xaa Ala Val Tyr Xaa
                85                  90                  95

Cys Xaa Arg Ser Xaa Xaa Xaa Xaa Xaa Trp Gly Gln Gly Xaa Xaa Xaa
            100                 105                 110

Thr Val Ser Ser
            115
```

AFFINITY MATURATED TAG72 SPECIFIC SINGLE CHAIN ANTIBODIES

CROSS-REFERENCE TO RELATED APPLICATIONS

This application claims benefit of U.S. Provisional Application No. 62/371,018, filed Aug. 4, 2016, and Application No. 62/449,892, filed Jan. 24, 2017, which are hereby incorporated herein by reference in their entirety.

BACKGROUND

Surgery, radiation therapy, and chemotherapy have been the standard accepted approaches for treatment of cancers including leukemia, solid tumors, and metastases. Immunotherapy (sometimes called biological therapy, biotherapy, or biological response modifier therapy), which uses the body's immune system, either directly or indirectly, to shrink or eradicate cancer has been studied for many years as an adjunct to conventional cancer therapy. It is believed that the human immune system is an untapped resource for cancer therapy and that effective treatment can be developed once the components of the immune system are property harnessed.

SUMMARY

Disclosed herein are affinity maturated single chain variable fragment (scFv) antibodies that bind TAG-72 on cancer cells with higher affinity than prior TAG-72 scFv antibodies. In some cases, the bispecific antibody has a dissociation constant ($K_D$) for TAG-72 that is less than 50 nM, 40 nM, 30 nM, 25 nM, 20 nM, 15 nM, or 10 nM.

The affinity/specificity of the binding construct is driven in large part by specific sequences within complementarity determining regions (CDRs) in the heavy ($V_H$) and light ($V_L$) chain. Each $V_H$ and $V_L$ sequence will have three CDRs (CDR1, CDR2, CDR3). In some embodiments, the TAG-72 $V_H$ domain comprises the following CDR domains: CDR1: DHAIH (SEQ ID NO:1), and CDR3: LNMAY (SEQ ID NO:2). In some cases, the CDR2 domain is selected from the group consisting of WIGYFSPGNDDF$\underline{R}$YNERFKG (SEQ ID NO:3), WIGYFSPGNDDFKYNER$\underline{Y}$KG (SEQ ID NO:4), and WIGYFSPGN$\underline{N}$DFKYNERFKG (SEQ ID NO:5).

In some embodiments, the $V_H$ domain of the disclosed TAG-72 scFv antibodies comprises the amino acid sequence: QVQLX$_1$X$_2$SX$_3$X$_4$X$_5$X$_6$X$_7$X$_8$PX$_9$X$_{10}$X$_{11}$X$_{12}$X$_{13}$X$_{14}$X$_{15}$CX$_{16}$X$_{17}$SGYTFTX$_{18}$DHAIHWVX$_{19}$QX$_{20}$PX$_{21}$X$_{22}$X$_{23}$LWEX$_{24}$GYX$_{25}$SPX$_{26}$NX$_{27}$DX$_{28}$X$_{29}$YX$_{30}$X$_{31}$X$_{32}$X$_{33}$X$_{34}$GX$_{35}$X$_{36}$TX$_{37}$X$_{38}$X$_{39}$D X$_{40}$X$_{41}$X$_{42}$X$_{43}$X$_{44}$X$_{45}$X$_{46}$X$_{47}$X$_{48}$LX$_{49}$SX$_{50}$X$_{51}$X$_{52}$X$_{53}$DX$_{54}$AVYX$_{55}$CX$_{56}$RS X$_{57}$X$_{58}$X$_{59}$X$_{60}$X$_{61}$WGQGX$_{62}$ X$_{63}$X$_{64}$TVSS (SEQ ID NO:47), wherein at least one of X$_{27}$=D or N, X$_{29}$=K or R, X$_{33}$=F or Y, or any combination thereof; and wherein X$_1$=V or Q; X$_2$=Q or E; X$_3$=D or G; X$_4$=A or P; X$_5$=E or G; X$_6$=L or V; X$_7$=V or K; X$_8$=K or R; X$_9$=G or S; X$_{10}$=A or Q; X$_{11}$=S or T; X$_{12}$=V or L; X$_{13}$=K or S; X$_{14}$=I, L or V; X$_{15}$=S or T; X$_{16}$=K or T; X$_{17}$=A or V; X$_{18}$=T or nothing; X$_{19}$=K or R; X$_{20}$=N, K, P, or A; X$_{21}$=E or G; X$_{22}$=Q or R; X$_{23}$=G or R; X$_{24}$=I or M; X$_{25}$=F or I; X$_{26}$=G or Q; X$_{28}$=F or I; X$_{30}$=N or S; X$_{31}$=E or Q; X$_{32}$=R or K; X$_{34}$=K or Q; X$_{35}$=K or R; X$_{36}$=A or V; X$_{37}$=L, M, or I; X$_{38}$=T or L; X$_{39}$=A, V, or R; X$_{40}$=K or T; X$_{41}$=S or P; X$_{42}$=S, A, or K; X$_{43}$=S or N; X$_{44}$=T or Q; X$_{45}$=A, V, or F; X$_{46}$=Y or S; X$_{47}$=V M, or L; X$_{48}$=Q, E, or R; X$_{49}$=N or S; X$_{50}$=L or V; X$_{51}$=T, P, or R; X$_{52}$=S or A; X$_{53}$=E, N, or A; X$_{54}$=S or T; X$_{55}$=F or Y; X$_{56}$=T, R. or A; X$_{57}$=L, F, or Y; X$_{58}$=N, Y, or S; X$_{59}$=M or G; X$_{60}$=A, N, D or H: X$_{61}$=Y, S, or nothing; X$_{62}$=T or S; X$_{63}$=S, T, or L; and X$_{64}$=V or L.

Therefore, in some cases, the CDR2 domain comprises the amino acid sequence WX$_{24}$GYX$_{25}$SPX$_{26}$NX$_{27}$DX$_{28}$X$_{29}$YX$_{30}$X$_{31}$X$_{32}$X$_{33}$X$_{34}$G (SEQ ID NO:23), wherein at least one of X$_{27}$=D or N, X$_{29}$=K or R, X$_{33}$=F or Y, or any combination thereof; and wherein X$_{24}$=I or M; X$_{25}$=F or I; X$_{26}$=G or Q; X$_{28}$e=F or I; X$_{30}$=N or S; X$_{31}$=E or Q; X$_{32}$=R or K; X$_{34}$=K or Q.

In some cases, the TAG-72 $V_H$ domain is selected from the group consisting of:

```
                                          (SEQ ID NO: 24)
QVQLQQSDAELVKPGASVKISCKASGYTFTDHAIHWVKQNPEQGLEWIGY

FSPGNX₁DFX₂YNERX₃KGKATLTADKSSSTAYVQLNSLTSEDSAVYFCT

RSLNMAYWGQGTSVTVSS;

(SEQ ID NO: 25)
QVQLQQSDAELVKPGASVKISCKASGYTFTTDHAIHWVKQNPEQGLEWIG

YFSPQNX₁DFX₂YNERX₃KGKATLTADKSSSTAYVQLNSLTSNDSAVYFC

TRSLNMAYWGQGTSVTVSS;

(SEQ ID NO: 26)
QVQLQQSDAELVKPGASVKISCKASGYTFTTDHAIHWVKQNPEQGLEWIG

YISPQNX₁DIX₂YNEKX₃KGKATLTADKSSSTAYMQLNSLTSNDSAVYFC

RRSFYGN-WGQGTTLTVSS;

(SEQ ID NO: 27)
QVQLQQSDAELVKPGASVKISCKASGYTFTTDHAIHWVKQKPEQGLEWIG

YISPQNX₁DIX₂YNEKX₃KGKATLTADKPSNTVYMQLNSLTSNDSAVYFC

TRSLSGDSWGQGTTLTVSS;

(SEQ ID NO: 28)
QVQLVQSGAEVVKPGASVKISCKASGYTFTDHAIHWVKQNPGQRLEWIGY

FSPGNX₁DFX₂YNERX₃KGKATLTADTSASTAYVELSSLPSEDTAVYFCT

RSLNMAYWGQGTLVTVSS;

(SEQ ID NO: 29)
QVQLQESGPGLVRPSQTLSLTCTVSGYTFTDHAIHWVRQPPGRGLEWIGY

ISPGNX₁DIX₂YNEKX₃KGRVTMLVDTSKNQFSLRLSSVTAADTAVYYCA

RSYYGH-WGQGSLVTVSS;

(SEQ ID NO: 30)
QVQLVQSGAEVVKPGASVKISCKASGYTFTDHAIHWVKQNPGQRLEWIGY

FSPGNX₁DFX₂YSQKX₃QGKATLTADTSASTAYVELSSLRSEDTAVYFCT

RSLNMAYWGQGTLVTVSS;

(SEQ ID NO: 31)
QVQLVQSGAEVVKPGASVKVSCKASGYTFTDHAIHWVRQNPGQRLEWMG

YFSPGNX₁DFX₂YSQKX₃QGRVTITADTSASTAYMELSSLRSEDTAVYFC

TRSLNMAYWGQGTLVTVSS;

(SEQ ID NO: 32)
QVQLVQSGAEVKKPGASVKVSCKASGYTFTDHAIHWVRQAPGQRLEWMG

YFSPGNX₁DFX₂YSQKX₃QGRVTITADTSASTAYMELSSLRSEDTAVYFC

TRSLNMAYWGQGTLVTVSS;
```

-continued

```
                                       (SEQ ID NO: 33)
QVQLQQSDAELVKPGASVKISCKASGYTFTDHAIHWVKQNPEQGLEWIGY

FSPGNX1DFX2YNERX3KGKATLTADKSSSTAYVQLNSLTSEDSAVYFCT

RSLNMAYWGQGTTLTVSS;

(SEQ ID NO: 34)
QVQLVQSGAEVKKPGASVKVSCKASGYTFTDHAIHWVRQAPGQRLEWMG

YFSPGNX1DFX2YSQKX3QGRVTITADKSASTAYMELSSLRSEDTAVYYC

ARSLNMAYWGQGTLVTVSS;

(SEQ ID NO: 35)
QVQLVQSGAEVKKPGASVKVSCKASGYTFTDHAIHWVRQAPGQRLEWMG

YFSPGNX1DFX2YSQKX3QGRVTITRDKSASTAYMELSSLRSEDTAVYYC

ARSLNMAYWGQGTLVTVSS;

(SEQ ID NO: 36)
QVQLVQSGAEVKKPGASVKVSCKASGYTFTDHAIHWVRQAPGQRLEWMG

YFSPGNX1DFX2YSQKX3QGRVTITADTSASTAYMELSSLRSEDTAVYYC

ARSLNMAYWGQGTLVTVSS;
and (SEQ ID NO: 37)
QVQLVQSGAEVKKPGASVKVSCKASGYTFTDHAIHWVRQAPGQRLEWMG

YFSPGNX1DFX2YSQKX3QGRVTITRDTSASTAYMELSSLRSEDTAVYYC

ARSLNMAYWGQGTLVTVSS;
``` wherein at least one of $X_1$=D or N, $X_2$=K or R, $X_3$=F or Y, or any combination thereof.

In some cases, the TAG-72 $V_H$ domain is selected from the group consisting of:

```
                                        (SEQ ID NO: 6)
QVQLQQSDAELVKPGASVKISCKASGYTFTDHAIHWVKQNPEQGLEWIGY

FSPGNDDFRYNERFKGKATLTADKSSSTAYVQLNSLTSEDSAVYECTRSL

NMAYWGQGTSVTVSS;

(SEQ ID NO: 7)
QVQLQQSDAELVKPGASVKISCKASGYTFTDHAIHWVKQNPEQGLEWIGY

FSPGNDDFKYNERYKGKATLTADKSSSTAYVQLNSLTSEDSAVYFCTRSL

NMAYWGQGTSVTVSS;
and (SEQ ID NO: 8)
QVQLQQSDAELVKPGASVKISCKASGYTFTDHAIHWVKQNPEQGLEWIGY

FSPGNNDFKYNERFKGKATLTADKSSSTAYVQLNSLTSEDSAVYFCTRSL

NMAYWGQGTSVTVSS.
```

In some embodiments, the TAG-72 $V_L$ domain comprises the following CDR domains: CDR1: KSSQSLLYSGNQKNYLA (SEQ ID NO:9), CDR2: WASARES (SEQ ID NO:10), and CDR3: QQYYSYPLT (SEQ ID NO:11). In some embodiments, the TAG-72 $V_L$ domain comprises the CDR1 domain KSSQSLLYSGNHKNYLA (SEQ ID NO:12). In some embodiments, when the CDR2 sequence of the TAG-72 $V_H$ domain has the amino acid sequence SEQ ID NO:3, the CDR1 sequence of the TAG-72 $V_L$ domain has the amino acid sequence SEQ ID NO:12.

In some cases, the TAG-72 $V_L$ domain comprises the amino acid sequence DIVMX$_1$QSPX$_2$SLX$_3$VSX$_4$GX$_5$KX$_6$TX$_7$X$_8$CKSSQSX$_9$LYSX$_{10}$NHKNYLAWYQQKPGQX$_{11}$PKLLIYWASX$_{12}$RESGVPDRFX$_{13}$GSGSGTDFTLX$_{14}$ISSX$_{15}$X$_{16}$X$_{17}$EDX$_{18}$AVYYCQQYYSYPLTFGX$_{19}$GTK X$_{20}$X$_{21}$X$_{22}$K (SEQ ID NO:38), wherein $X_1$=S or T; $X_2$=S or D; $X_3$=P or A; $X_4$=L or V; $X_5$=E or D; $X_6$=V or A; $X_7$=L or I; $X_8$=S or N; $X_9$=L or V; $X_{10}$=G or S; $X_{11}$=S or P; $X_{12}$=A or T; $X_{13}$=T or S; $X_{14}$=S or T; $X_{15}$=V or L; $X_{16}$=K or Q; $X_{17}$=T or A; $X_{18}$=L or V; $X_{19}$=A or Q; $X_{20}$=L or V; $X_{21}$=V or E; and $X_{22}$=L or I.

Therefore, in some cases, the the TAG-72 $V_L$ domain comprises the CDR1 domain KSSQSX$_1$LYSX$_2$NHKNYLA (SEQ ID NO: 39), wherein $X_1$=L or V, and $X_2$=G or S.

In some cases, the TAG-72 $V_L$ domain is selected from the group consisting of:

```
                                       (SEQ ID NO: 13)
DIVMSQSPSSLPVSVGEKVTLSCKSSQSLLYSGNHKNYLAWYQQKPGQSP

KLLIYWASARESGVPDRFTGSGSGTDFTLSISSVKTEDLAVYYCQQYYSY

PLTFGAGTKLVLK,
and (SEQ ID NO: 14)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLK.
```

In some cases, the TAG-72 $V_L$ domain is selected from the group consisting of:

```
                                       (SEQ ID NO: 40)
DIVMSQSPDSLAVSLGERVTLNCKSSQSLLYSGNHKNYLAWYQQKPGQSP

KLLIYWASARESGVPDRFSGSGSGTDFTLTISSVQAEDVAVYYCQQYYSY

PLTFGAGTKLELK;

(SEQ ID NO: 41)
DIVMSQSPDSLAVSLGERVTLNCKSSQSVLYSGNHKNYLAWYQQKPGQSP

KLLIYWASARESGVPDRFSGSGSGTDFTLTISSVQAEDVAVYYCQQYYSY

PLTFGAGTKLELK;

(SEQ ID NO: 42)
DIVMSQTPDSLAVSLGERATINCKSSQSVLYSGNHKNYLAWYQQKPGQSP

KLLIYWASARESGVPDRFSGSGSGTDFTLTISSLQAEDVAVYYCQQYYSY

PLTFGAGTKLEIK;

(SEQ ID NO: 43)
DIVMSQTPDSLAVSLGERATINCKSSQSVLYSGNHKNYLAWYQQKPGQPP

KLLIYWASARESGVPDRFSGSGSGTDFTLTISSLQAEDVAVYYCQQYYSY

PLTFGQGTKLEIK;

(SEQ ID NO: 44)
DIVMSQSPSSLPVSVGDKVTLSCKSSQSLLYSGNHKNYLAWYQQKPGQSP

KLLIYWASARESGVPDRFTGSGSGTDFTLSISSVKTEDLAVYYCQQYYSY

PLTFGAGTKLVIK;

(SEQ ID NO: 45)
DIVMTQSPDSLAVSLGERATINCKSSQSVLYSSNHKNYLAWYQQKPGQPP

KLLIYWASTRESGVPDRFSGSGSGTDFTLTISSLQAEDVAVYYCQQYYSY

PLTFGGGTKVEIK;
and (SEQ ID NO: 46)
DIVMTQSPDSLAVSLGERATINCKSSQSVLYSGNHKNYLAWYQQKPGQPP

KLLIYWASTRESGVPDRFSGSGSGTDFTLTISSLQAEDVAVYYCQQYYSY

PLTFGGGTKVEIK.
```

The $V_H$ and $V_L$ domains of the TAG-72 scFv antibodies are preferably separated by a peptide linker. In some embodiments, the peptide linker comprises the amino acid sequence LSADDAKKDAAKKDDAKKDDAKKDL (SEQ ID NO: 15).

Therefore, in some embodiments, the disclosed TAG-72 scFv antibodies have an amino acid sequence selected from the group consisting of:

```
                                          (SEQ ID NO: 16)
DIVMSQSPSSLPVSVGEKVTLSCKSSQSLLYSGNHKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNDDFRYNE

RFKGKATLTADKSSSTAYVQLNSLTSEDSAVYFCTRSLNMAYWGQGTSVT

VSS,
                                          (SEQ ID NO: 17)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKGLQVQLQQSDAELV

KPGASVKISCKASGYTFTDHAIHWVKQNPEQGLEWIGYFSPGNDDFKYNE

RYKGKATLTADKSSSTAYVQLNSLTSEDSAVYFCTRSLNMAYWGQGTSVT

VSS,
                                          (SEQ ID NO: 18)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNNDFKYNE

RFKGKATLTADKSSSTAYVQLNSLTSEDSAVYFCTRSLNMAYWGQGTSVT

VSS.
```

Also disclosed are bispecific antibodies that are able to engage T-cells to destroy TAG-72-expressing malignant cells. The antibodies can be engineered from fusion polypeptides comprising 1) variable domains of antibodies that specifically bind an immune cell antigen and 2) the disclosed variable domains that specifically bind TAG-72. In some embodiments, the antibody is a diabody (fusion polypeptide) having, for example, the following formula:

$V_L I$-$V_H T$ & $V_L T$-$V_H I$, or $V_H I$-$V_L T$ & $V_H T$-$V_L I$, wherein "$V_L I$" is a light chain variable domain specific for an immune cell antigen;
wherein "$V_H T$" is a heavy chain variable domain specific for TAG-72 disclosed herein;
wherein "$V_L T$" is a light chain variable domain specific for TAG-72 disclosed herein;
wherein "$V_H I$" is a heavy chain variable domain specific for the immune cell antigen; and
wherein "-" consists of a peptide linker or a peptide bond.

In some embodiments, the antibody is a Bispecific T-Cell Engaging (BiTE) antibody (fusion polypeptide) having, for example, the following formula:

$V_L I$-$V_H I$-$V_L T$-$V_H T$, $V_H I$-$V_L I$-$V_H T$-$V_L T$, $V_L I$-$V_H I$-$V_H T$-$V_L T$, or $V_H I$-$V_L I$-$V_L T$-$V_H T$, wherein "$V_L I$" is a light chain variable domain specific for an immune cell antigen;
wherein "$V_H T$" is a heavy chain variable domain specific for TAG-72;
wherein "$V_L T$" is a light chain variable domain specific for TAG-72;
wherein "$V_H I$" is a heavy chain variable domain specific for the immune cell antigen;
wherein "-" consists of a peptide linker or a peptide bond; and
wherein "--" consists of a peptide linker or a peptide bond.

The immune cell antigen can be a cell surface molecule that is expressed on human NK cells, T cells, monocytes, macrophages or granulocytes. For example, the cell surface molecule can be antigen CD2, CD3, CD16, CD64, CD89; NKp30, NKp44, NKp46, NKp80 (KLR-F1), NKG2C or NKG2D.

Also disclosed is an isolated nucleic acid encoding the disclosed fusion polypeptide, as well as nucleic acid vectors containing this isolated nucleic acid operably linked to an expression control sequence. Also disclosed are cells transfected with these vectors and the use of these cells to produce the disclosed fusion polypeptides.

A bi-specific antigen binding molecule can be formed from dimerization of heavy and light chains. In these embodiments, the $V_L I$ dimerizes with $V_H I$ to form an antigen binding site for an immune cell antigen (e.g., CD3) and the $V_H T$ dimerizes with $V_L T$ to form an antigen binding site for TAG-72.

Also disclosed is a bispecific antibody that is a single polypeptide chain comprising a bispecific antibody having a first antigen-binding region and a second antigen-binding region. In some cases, the first antigen-binding region is capable of recruiting the activity of a human immune effector cell by specifically binding to an immune cell antigen located on the human immune effector cell; and the second antigen-binding region is capable of specifically binding to TAG-72 on a target cell.

Each of the first and second portions can comprise 1, 2, 3, or more antibody variable domains. In particular embodiments, each of the first and second portions contains two variable domains, a variable heavy ($V_H$) domain and a variable light ($V_L$) domain.

Each of the first and second portions can be derived from natural antibodies, such as monoclonal antibodies. In some cases, the antibody is human. In some cases, the bispecific antibody has undergone an alteration to render it less immunogenic when administered to humans. For example, the alteration comprises one or more techniques selected from the group consisting of chimerization, humanization, CDR-grafting, deimmunization, and mutation of framework amino acids to correspond to the closest human germline sequence.

Currently, the most widely used technique for antibody human adaptation is known as "CDR grafting." The scientific basis of this technology is that the binding specificity of an antibody resides primarily within the three hypervariable loops known as the complementarity determining regions (CDRs) of its light and heavy chain variable regions (V-regions), whereas the more conserved framework regions (framework, FW; framework region, FR) provide structure support function. By grafting the CDRs to an appropriately selected FW, some or all of the antibody-binding activity can be transferred to the resulting recombinant antibody.

CDR grafting is the selection of a most appropriate human antibody acceptor for the graft. Various strategies have been developed to select human antibody acceptors with the highest similarities to the amino acid sequences of donor CDRs or donor FW, or to the donor structures. All these "best fit" strategies, while appearing very rational, are in fact based on one assumption, i.e., a resulting recombinant antibody that is most similar (in amino acid sequence or in structure) to the original antibody will best preserve the original antigen binding activity.

Not all amino acids in the CDRs are involved in antigen binding. Thus, it has been proposed that the grafting of only those residues that are critical in antigen-antibody interaction—the so-called specificity determining residues grafting (SDR-grafting)-will further increase the content of human antibody sequences in the resulting recombinant antibody. The application of this strategy requires information on the antibody structure as well as antibody-antigen contact residues, which are quite often unavailable. Even when such information is available, there is no systematic method to reliably identify the SDRs, and SDR-grafting remains so far mostly at the basic research level.

Recently, a strategy called "human framework shuffling" has been developed. This technique works by ligating DNA fragments encoding CDRs to DNA fragments encoding human FR1, FR2, FR3, and FR4, thus generating a library of all combinations between donor CDRs and human FRs. Methods for making human-adapted antibodies based on molecular structures, modeling and sequences for human engineering of antibody molecules are disclosed in U.S. Pat. No. 8,748,356, which is incorporated by reference for these methods.

The effector cell recruited by the bispecific antibody is one capable of exerting a cytotoxic or an apoptotic effect on a target cell. In some embodiments, the human effector cell can in some embodiments be a member of the human lymphoid lineage or myeloid lineage. As an example, for lymphoid cells, the immune cell antigen can be selected from the group consisting of human CD3 antigen, human CD16 antigen, human NKG2D antigen, human CD2 antigen, human CD28 antigen, and human CD25 antigen. Similarly, for myeloid cells, the immune cell antigen can be human CD64 antigen or human CD89 antigen.

Also disclosed is a pharmaceutical composition comprising a molecule disclosed herein in a pharmaceutically acceptable carrier. Also disclosed is a method for treating cancer in a subject that involves administering to the subject a therapeutically effective amount of a disclosed pharmaceutical composition. Also disclosed is a kit comprising an antibody disclosed herein.

Also disclosed is an expression vector comprising an isolated nucleic acid encoding an antibody disclosed herein operably linked to an expression control sequence. Also disclosed is a cell comprising the disclosed expression vector. The cell can be a primary cell, transformed cell, cell line, or the like. In some cases, the cell is a mammalian cell line. In some cases, the cell is a non-mammalian cell line. For example, the cell can be a bacteria or insect cell line.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 21A to 12C are flow cytometry plots showing MDA-231 (target) cells treated with normal human CD8 T (effector) cells at 1:5 of T to E ratio+bispecific antibody (pilot) at conc of 10 ug/m.

FISG. 33 are flow cytometry plots showing MCF-7 (target) cells treated with normal human CD8 T (effector) cells at 1:5 T to E ratio+Pembro (5 μM).

Figure 34B:
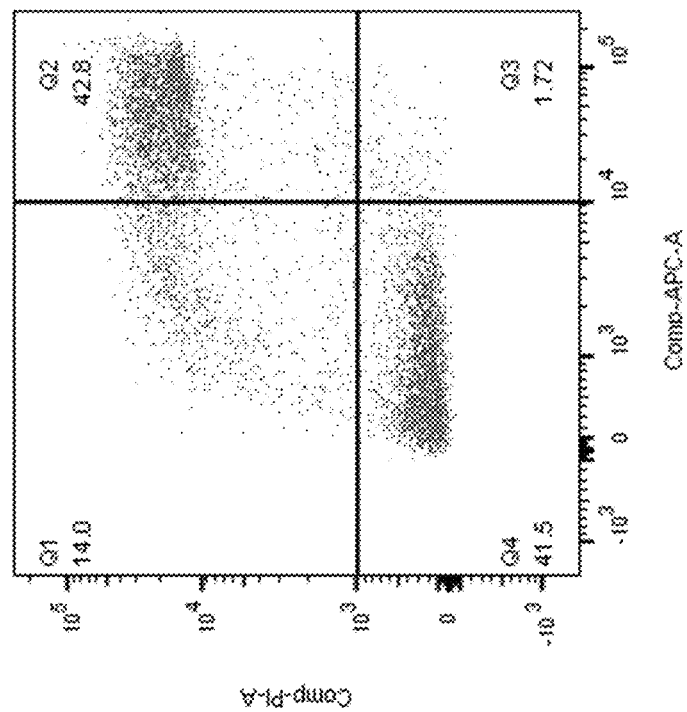
Figure 34A:
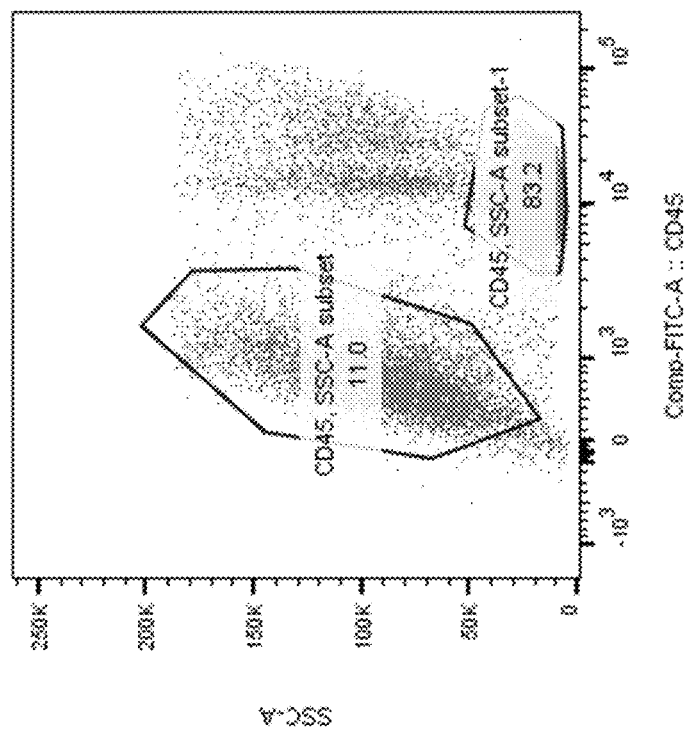
Figure 34C:
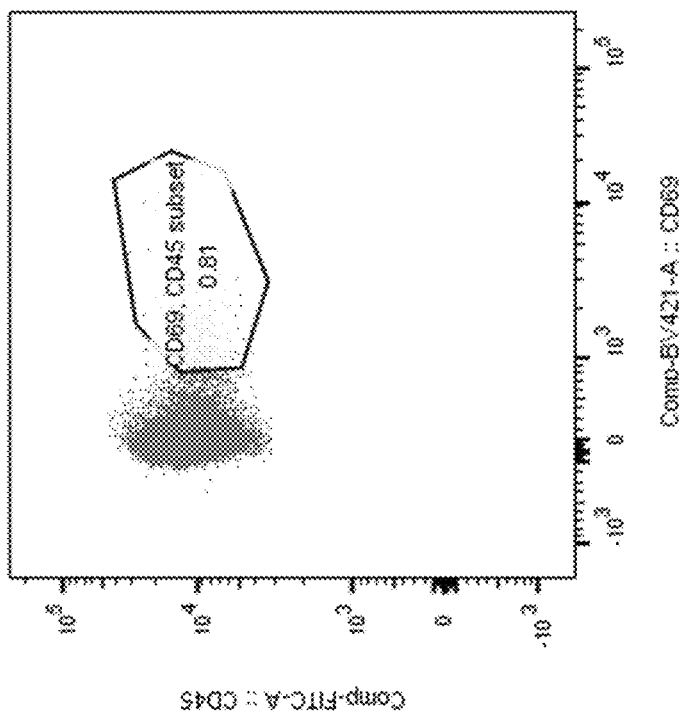

FIGS. 34 are flow cytometry plots showing MCF-7 (target) cells treated with normal human CD8 T (effector) cells at 1:5 T to E ratio+Nivo (5 μM).

Figure 35A:
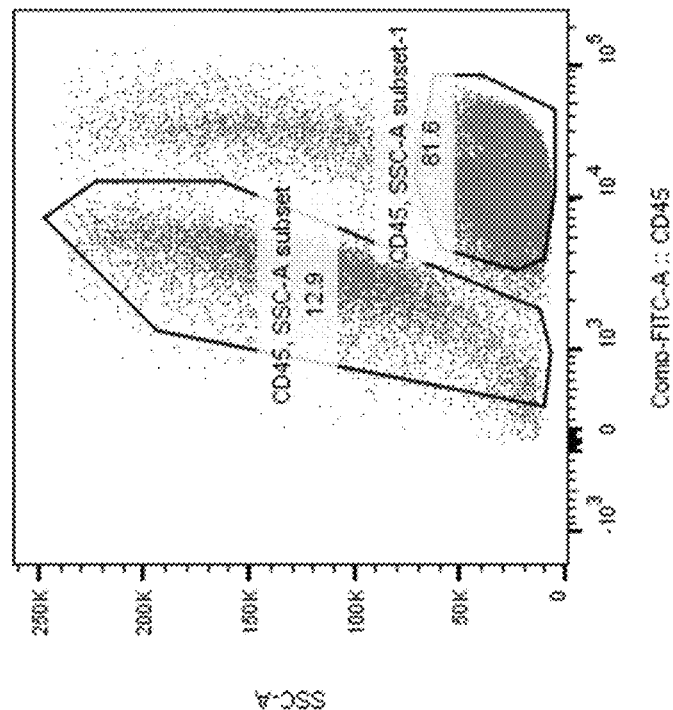
Figure 35C:
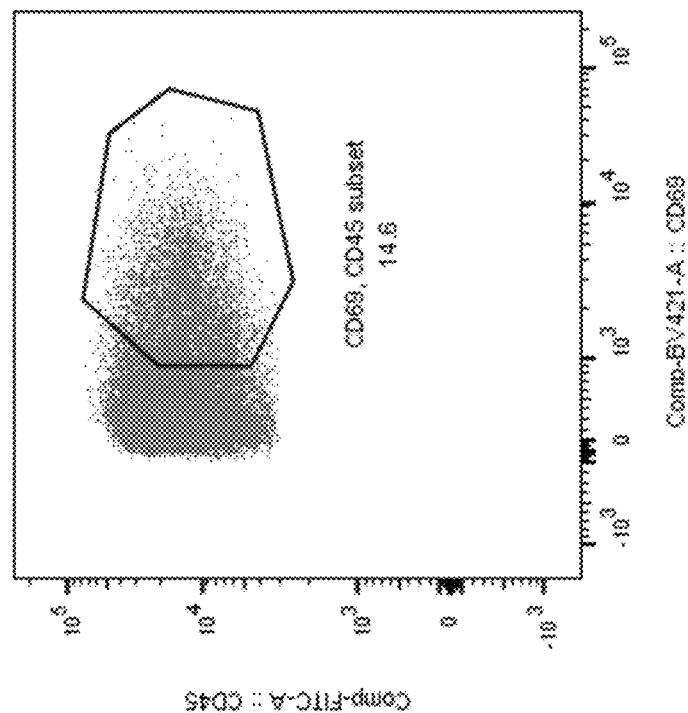
Figure 35B:
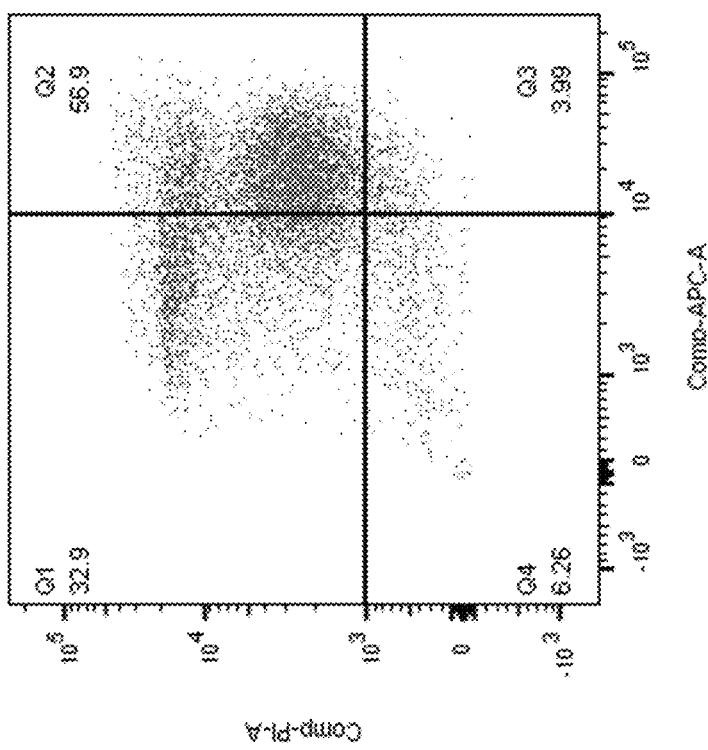

FIGS. 35A to 35C are flow cytometry plots showing MCF-7 (target) cells treated with normal human CD8 T (effector) cells at 1:5 of T to E ratio+bispecific antibody at conc of 5 ug/ml.

Figure 36B:
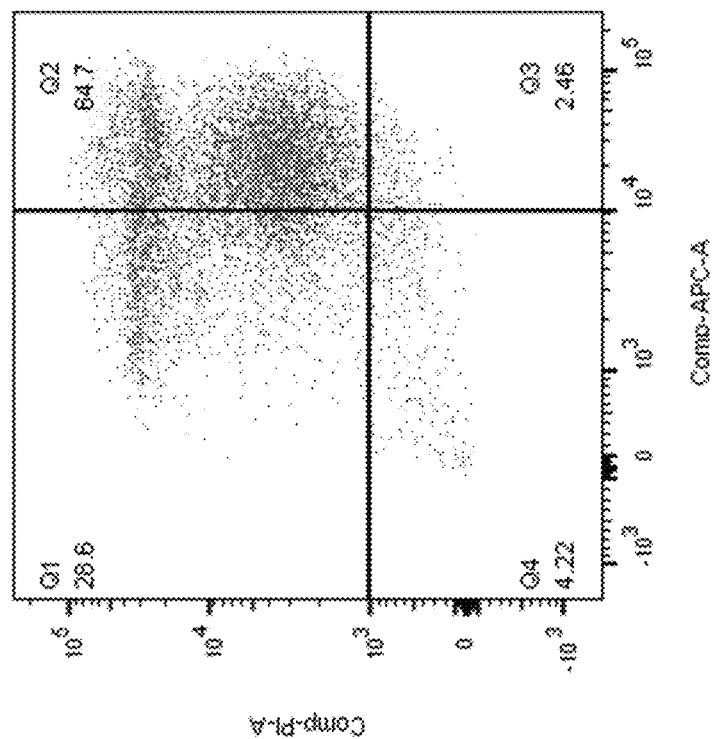
Figure 36A:
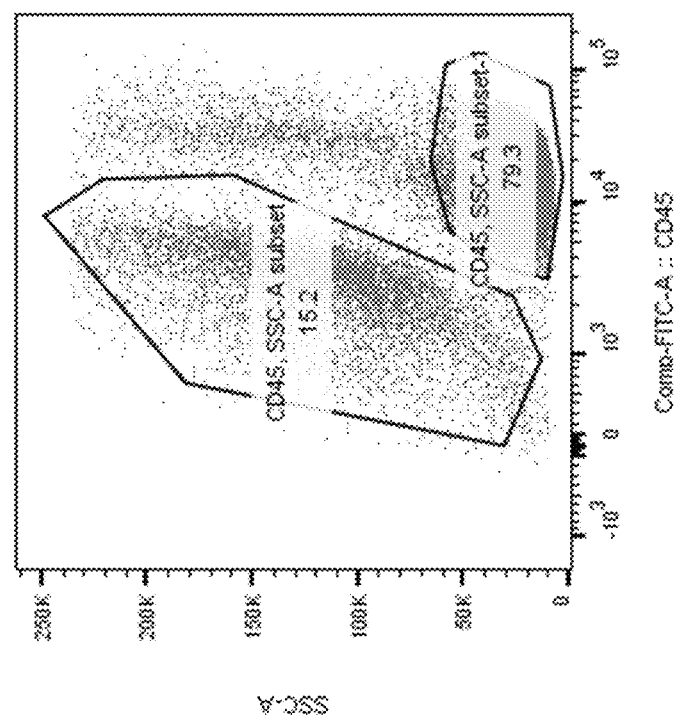
Figure 36C:
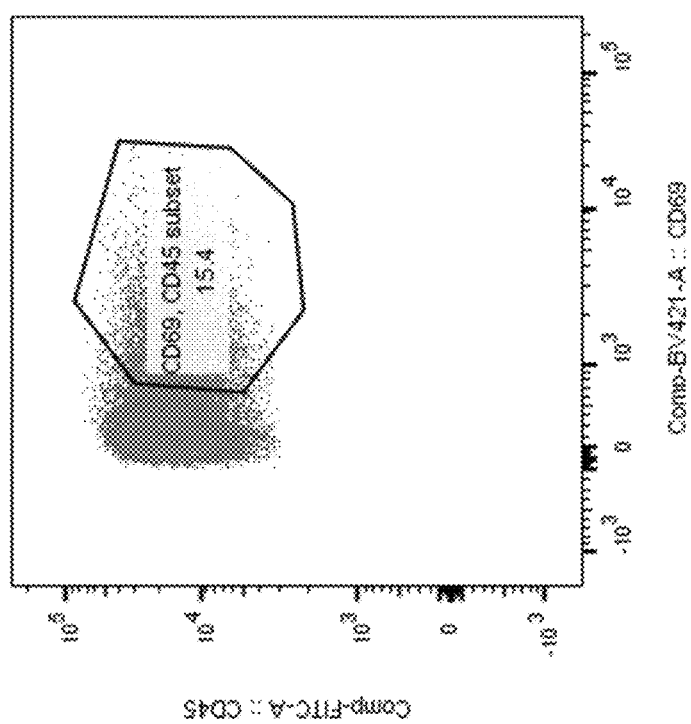

FIGS. 36A to 36C are flow cytometry plots showing MCF-7 (target) cells treated with normal human CD8 T (effector) cells at 1:5 of T to E ratio+bispecific antibody at conc of 5 ug/ml+Pembro (5 μM).

Figure 37A:
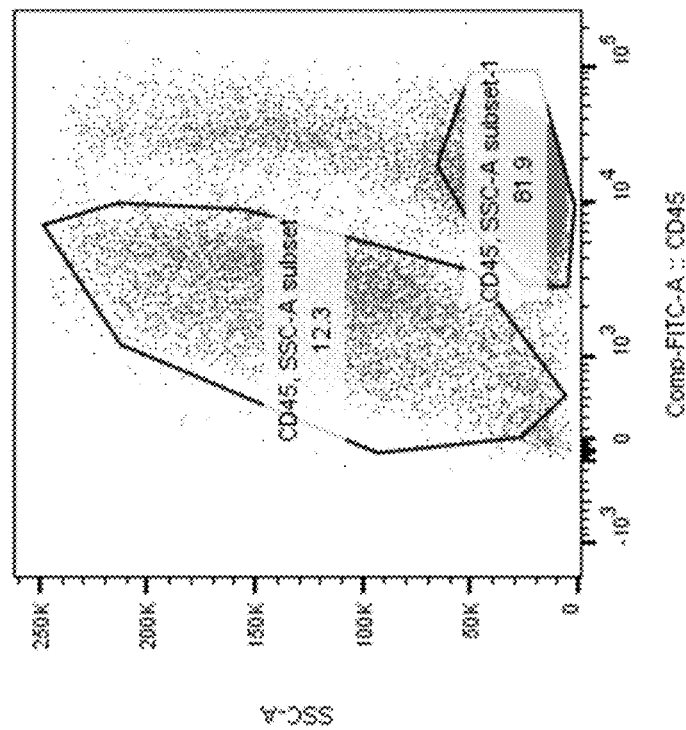
Figure 37C:
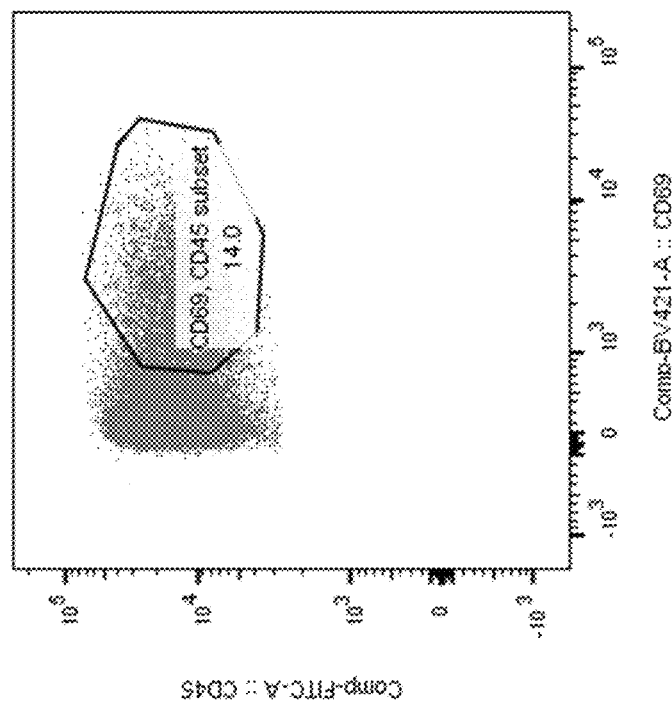
Figure 37B:
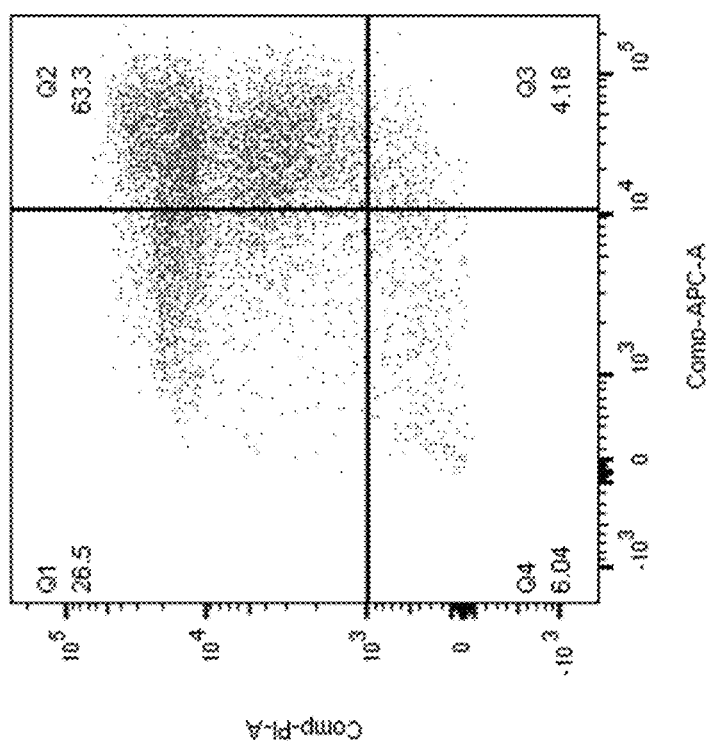

FIGS. 37A to 37C are flow cytometry plots showing MCF-7 (target) cells treated with normal human CD8 T (effector) cells at 1:5 of T to E ratio+bispecific antibody at conc of 5 ug/ml+Nivo (5 μM).

Figure 38:
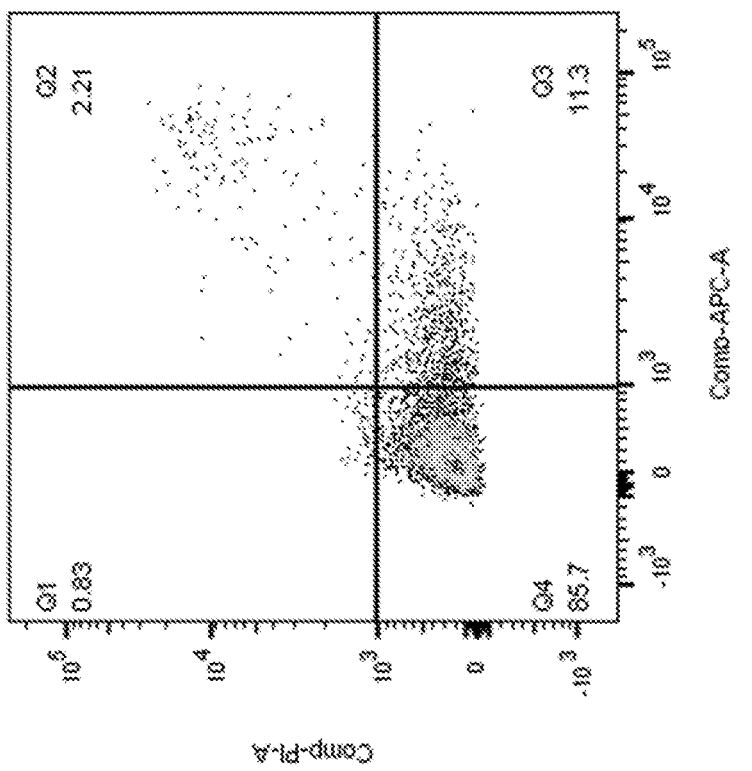

FIG. 38 is a flow cytometry plot showing untreated MDA-231 (target) cells as negative control.

Figure 39:
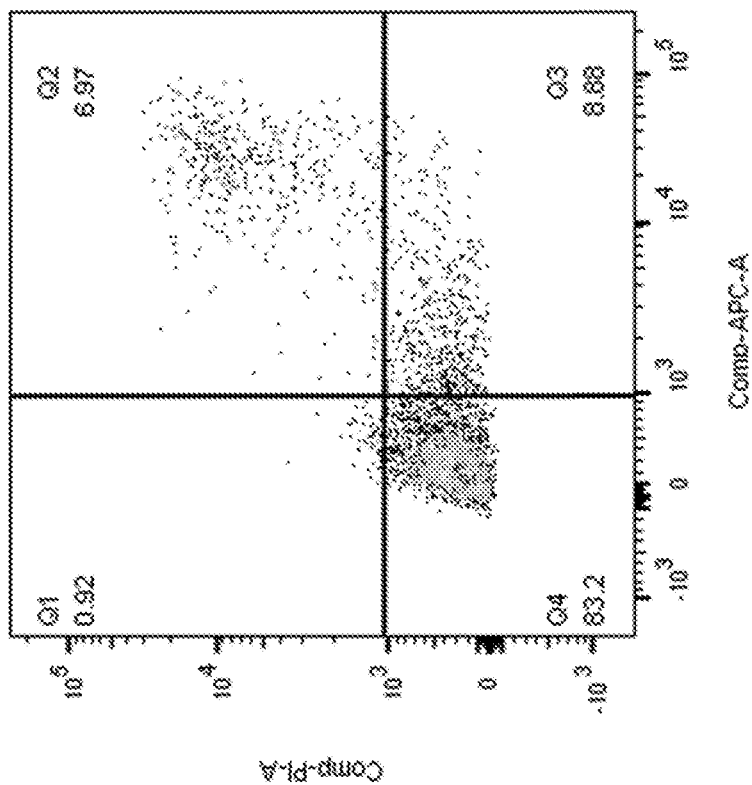

FIG. 39 is a flow cytometry plot showing MDA-231 cells treated with bispecific antibody at conc of 5 μg/ml.

Figure 40:
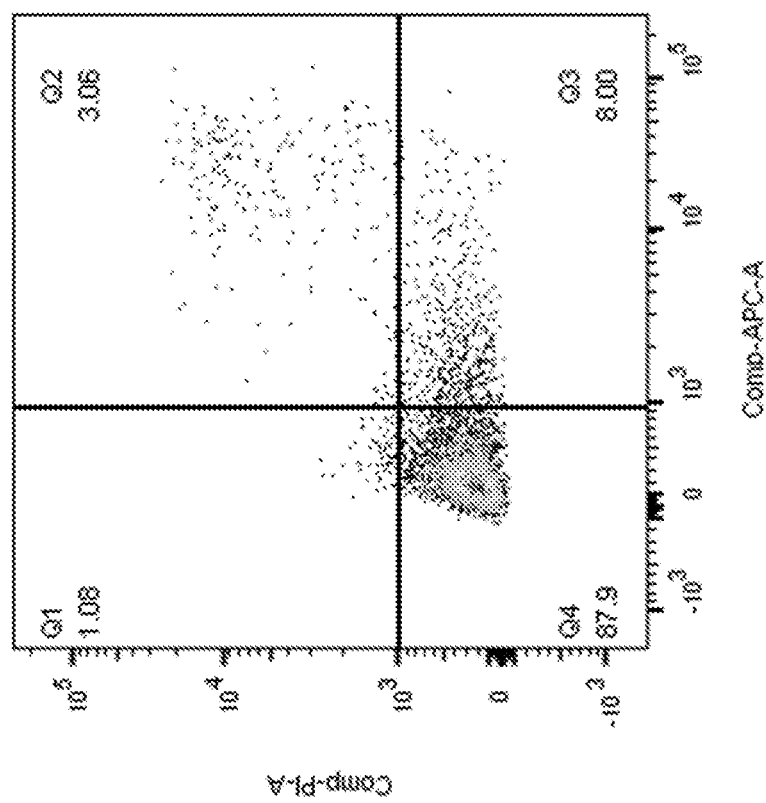

FIG. 40 is a flow cytometry plot showing MDA-231 (target) cells treated with Pembro (5 μM).

Figure 41:
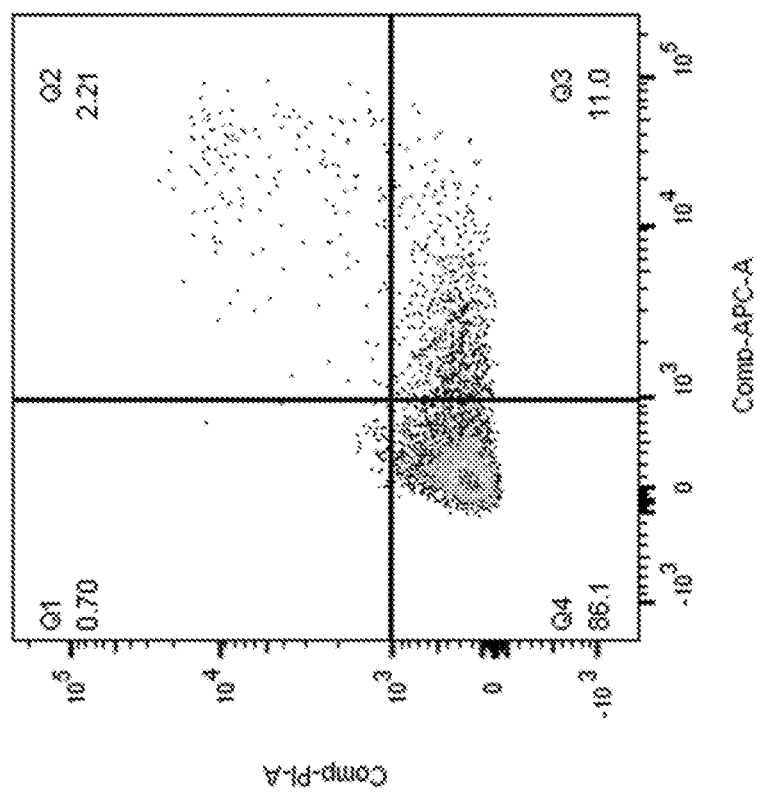

FIG. 41 is a flow cytometry plot showing MDA-231 (target) cells treated with Nivo (5 μM).

Figure 42B:
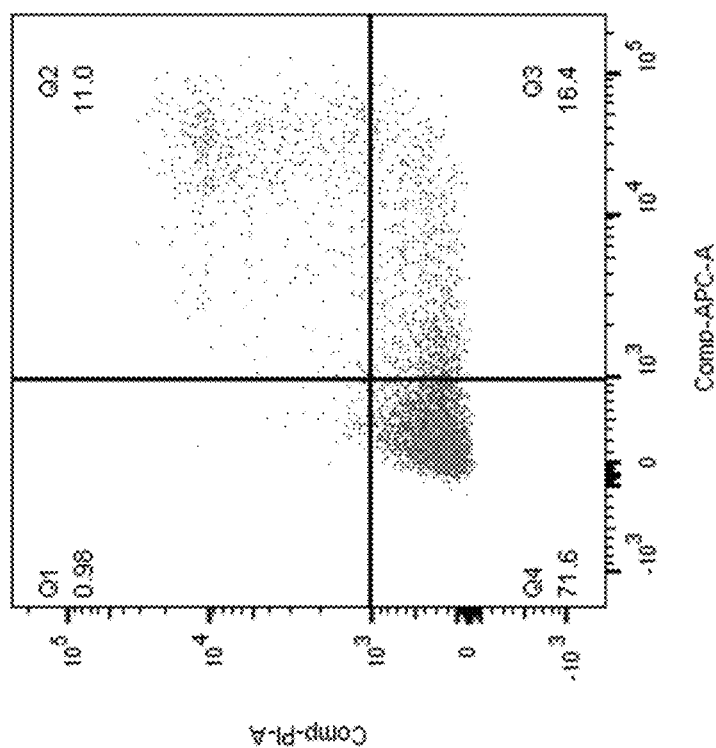
Figure 42A:
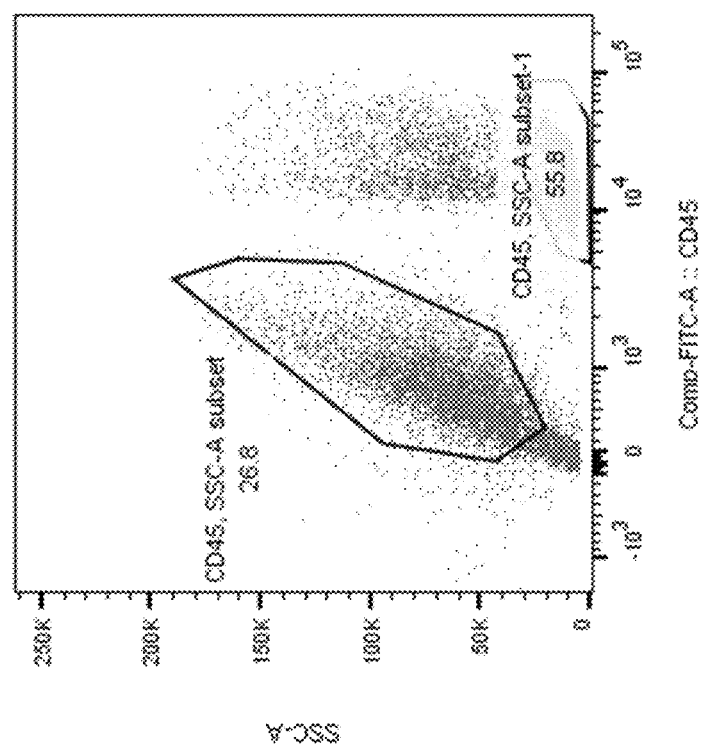
Figure 42C:
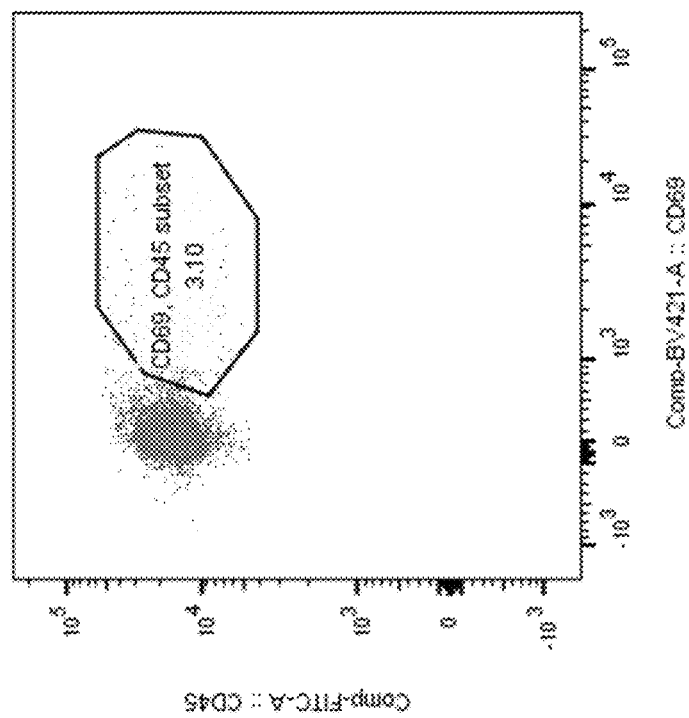

FIGS. 42A to 42C are flow cytometry plots showing MDA-231 (target) cells treated with normal human CD8 T (effector) cells at 1:5 T to E ratio.

Figure 43A:
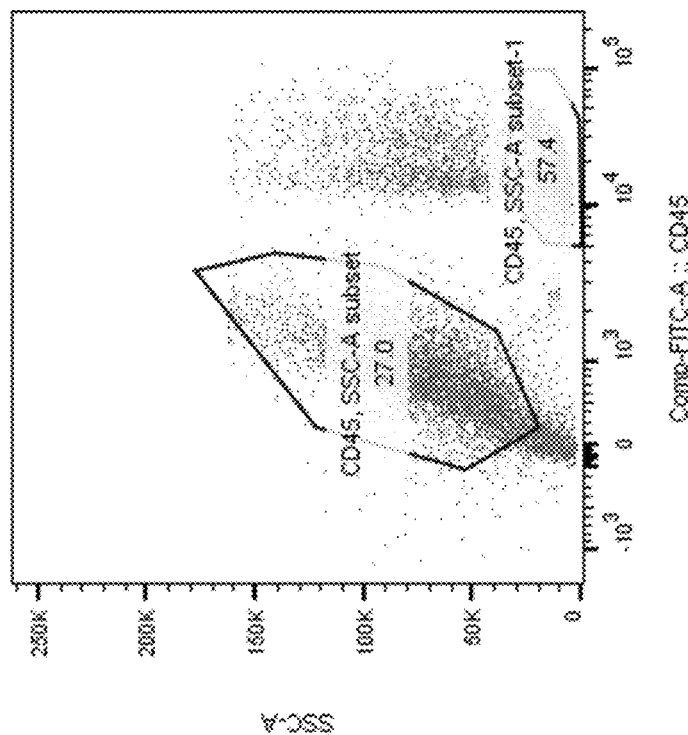
Figure 43C:
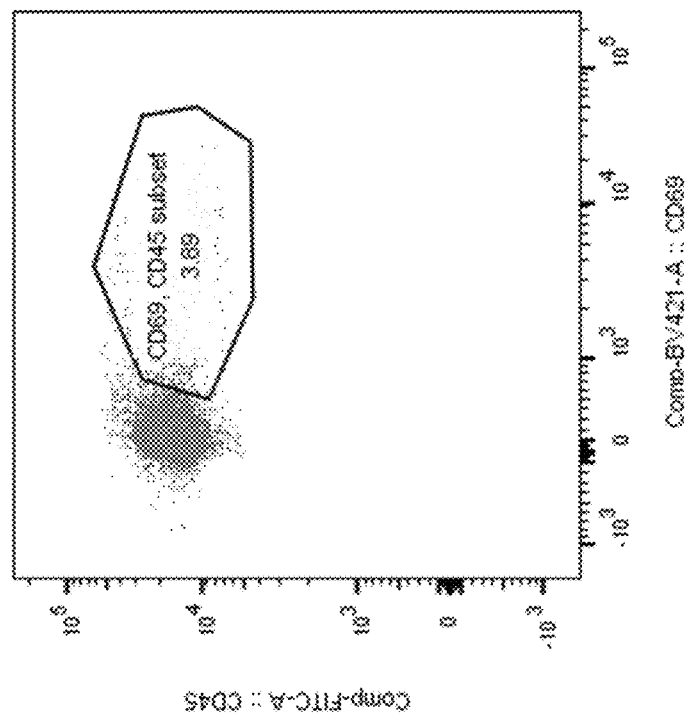
Figure 43B:
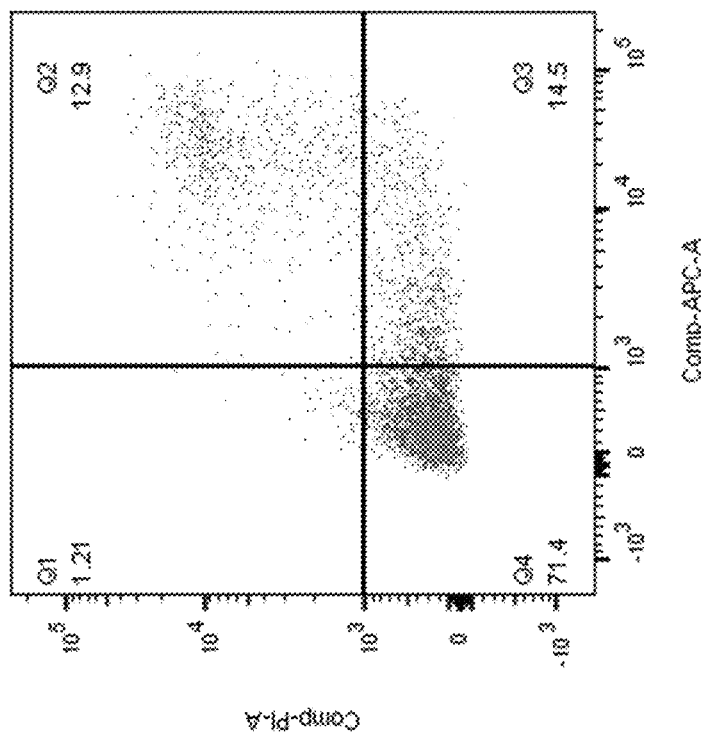

FIGS. 43A to 43C are flow cytometry plots showing MDA-231 (target) cells treated with normal human CD8 T (effector) cells at 1:5 of T to E ratio+Pembro (μM).

Figure 44B:
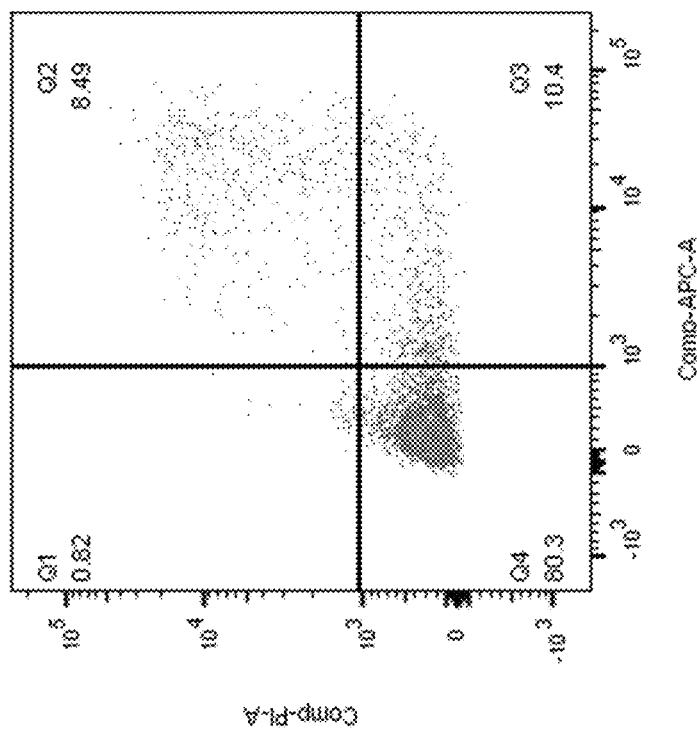
Figure 44A:
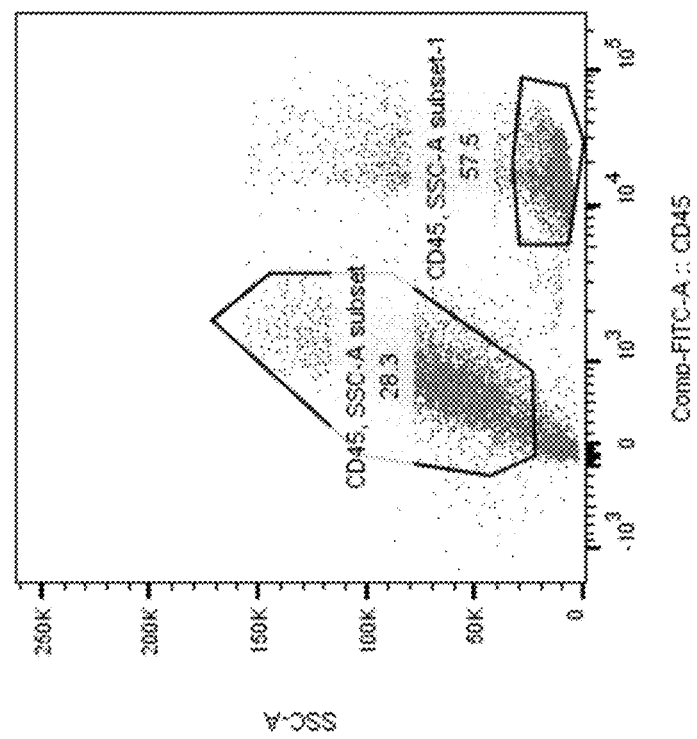
Figure 44C:
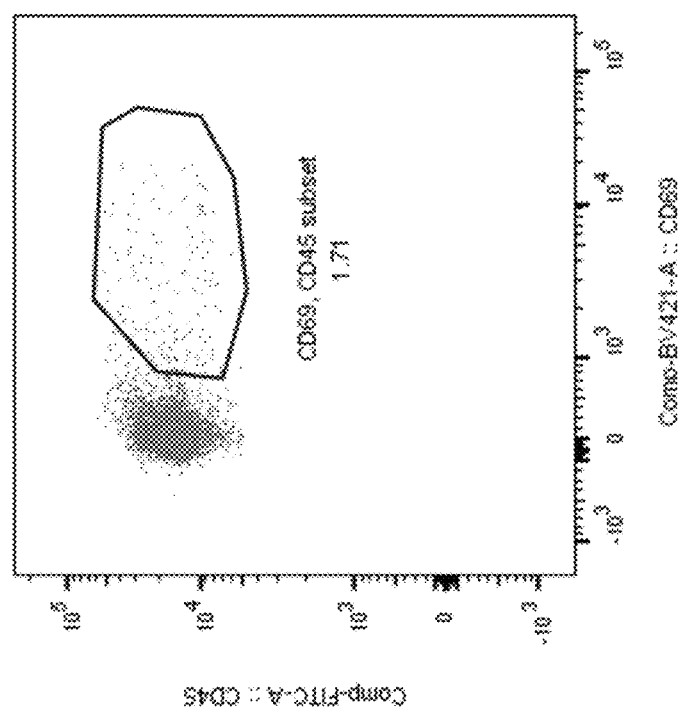

FIGS. 44A to 44C are flow cytometry plots showing MDA-231 (target) cells treated with normal human CD8 T (effector) cells at 1:5 T to E ratio+Nivo (μM).

Figure 45A:
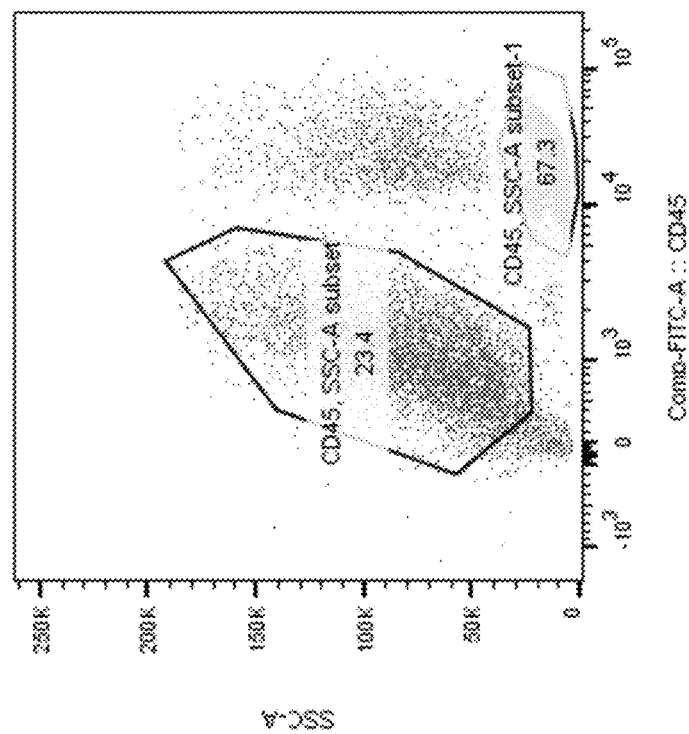
Figure 45C:
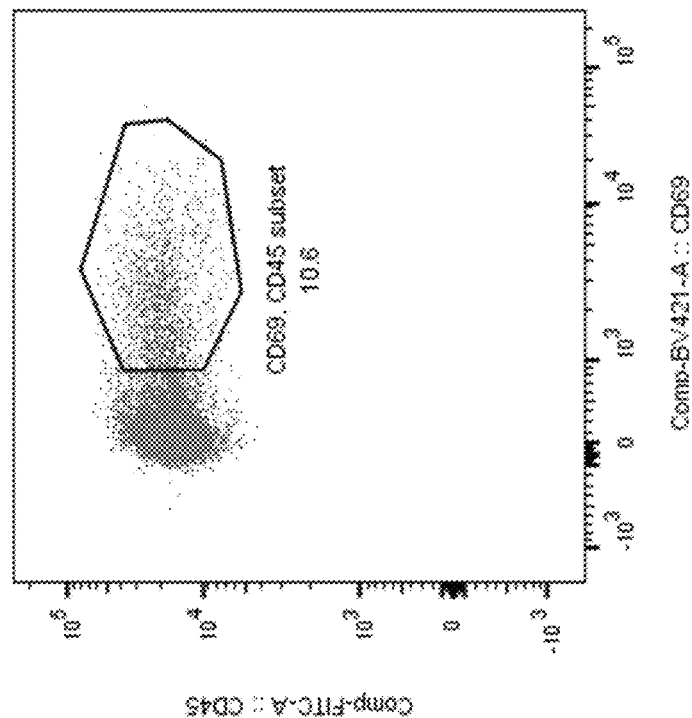
Figure 45B:
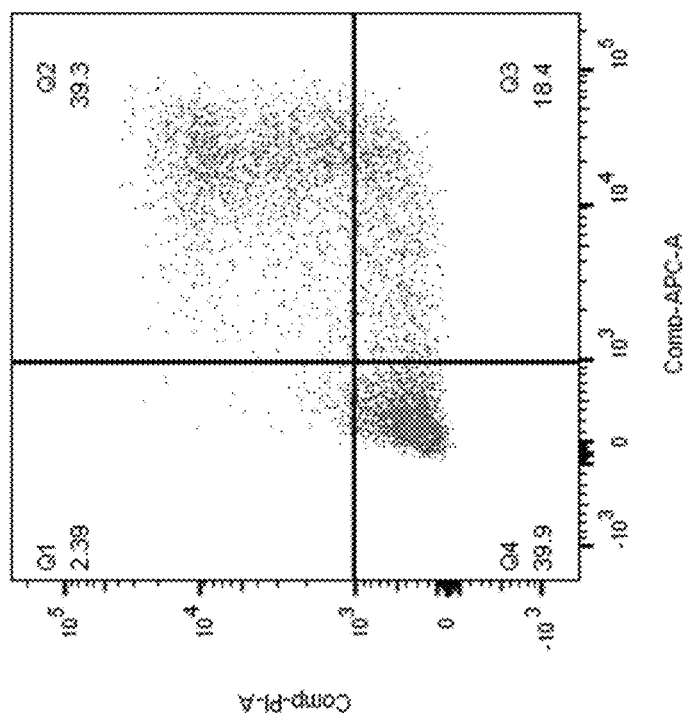

FIGS. 45A to 45C are flow cytometry plots showing MDA-231 (target) cells treated with normal human CD8 T (effector) cells at 1:5 of T to E ratio+bispecific antibody at conc of 5 ug/ml.

Figure 46B:
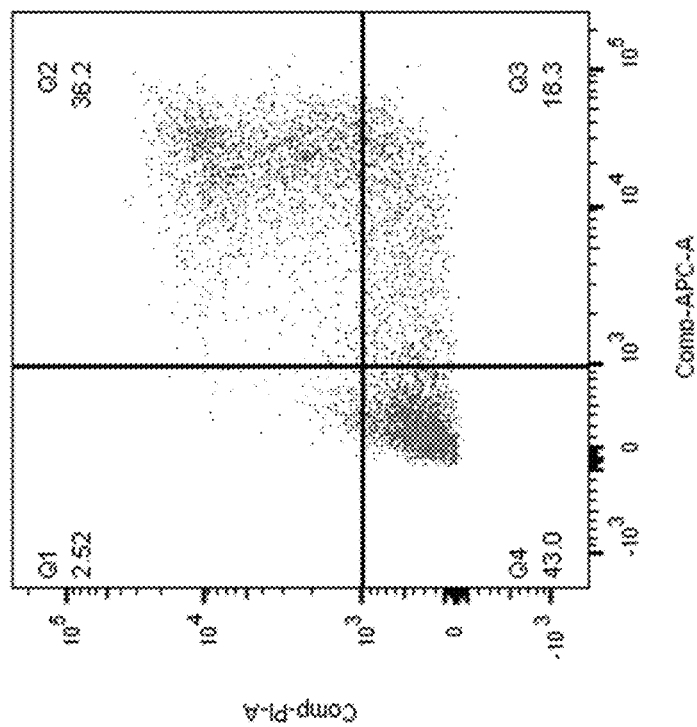
Figure 46A:
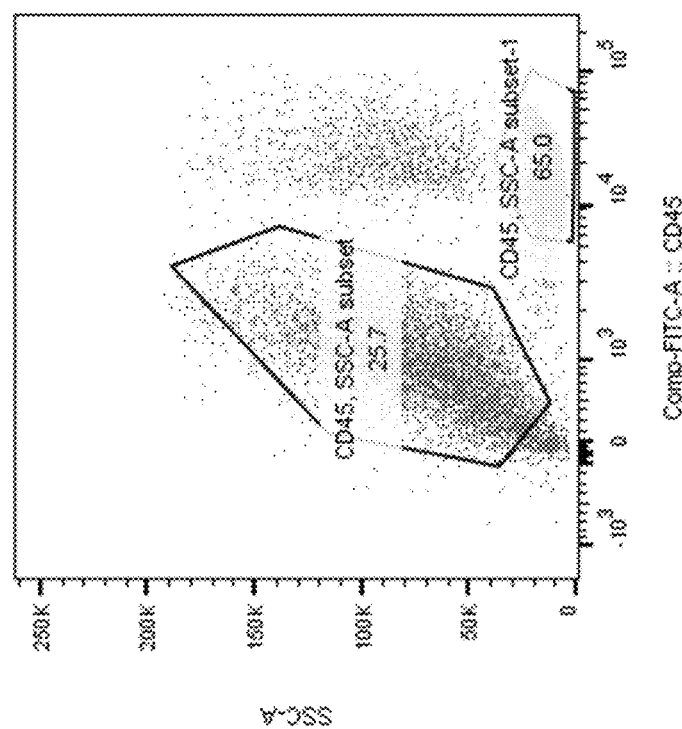
Figure 46C:
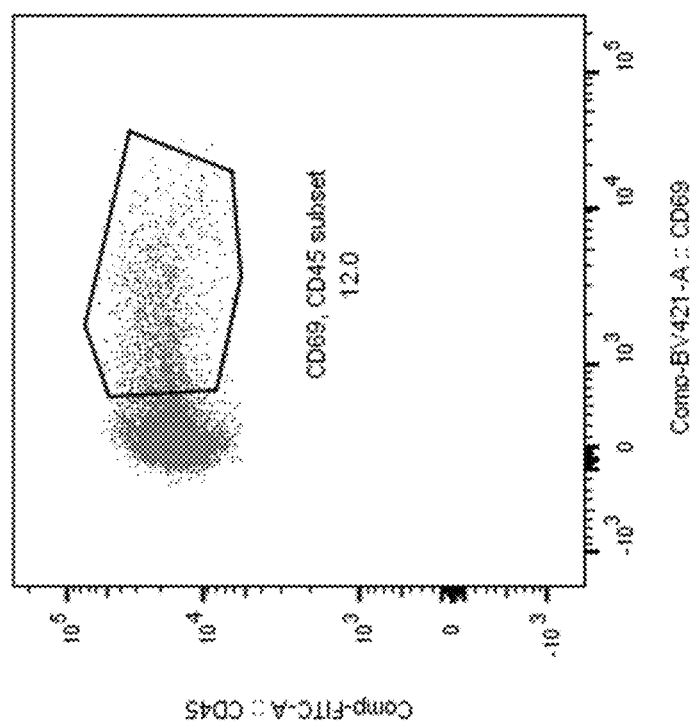

FIGS. 46A to 46C are flow cytometry plots showing MDA-231 (target) cells treated with normal human CD8 T (effector) cells at 1:5 of T to E ratio+bispecific antibody at conc of 5 ug/ml+Pembro (5 μM).

Figure 47A:
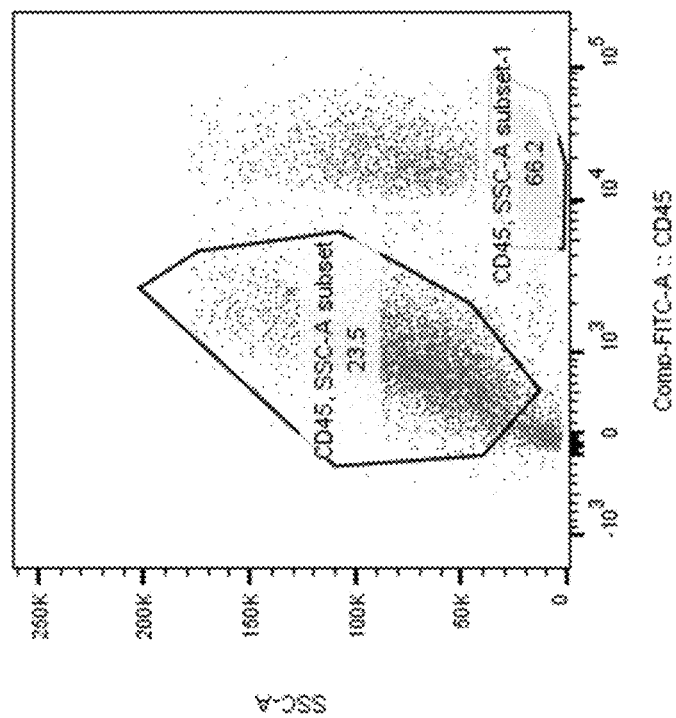
Figure 47C:
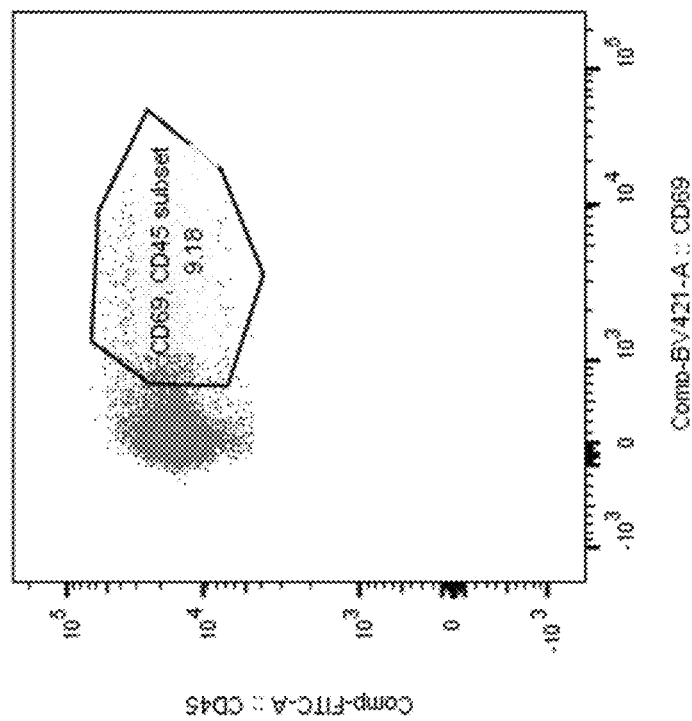
Figure 47B:
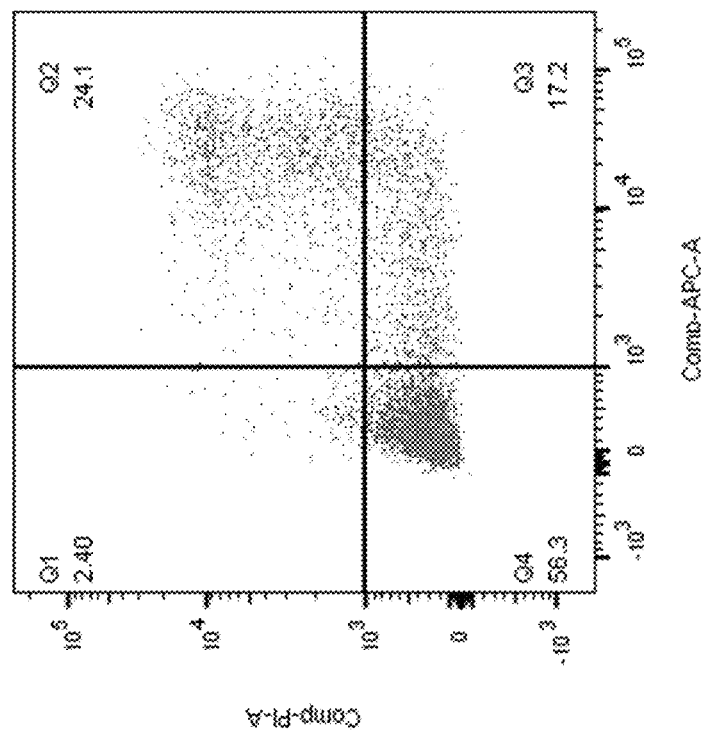

FIGS. 47A to 47C are flow cytometry plots showing MDA-231 (target) cells treated with normal human CD8 T (effector) cells at 1:5 of T to E ratio+bispecific antibody at conc of 5 ug/ml+Nivo (5 μM).

Figure 48:
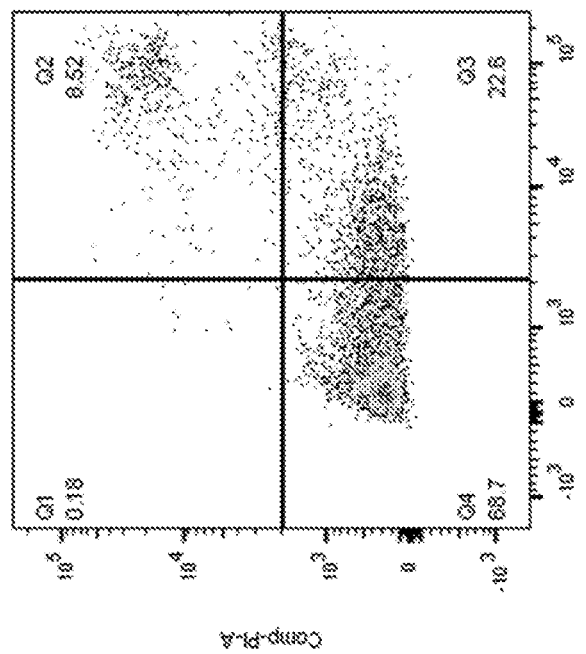

FIG. 48 is a flow cytometry plot showing untreated MDA-175VII (target) cells as negative control.

Figure 49:
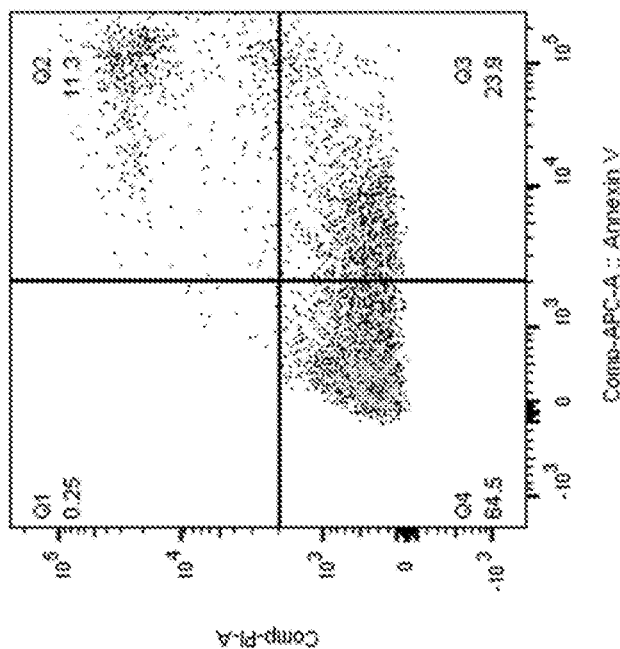

FIG. 49 is a flow cytometry plot showing MDA-175VII cells treated with bispecific antibody (pilot) at conc of 5 μg/ml.

Figure 50B:
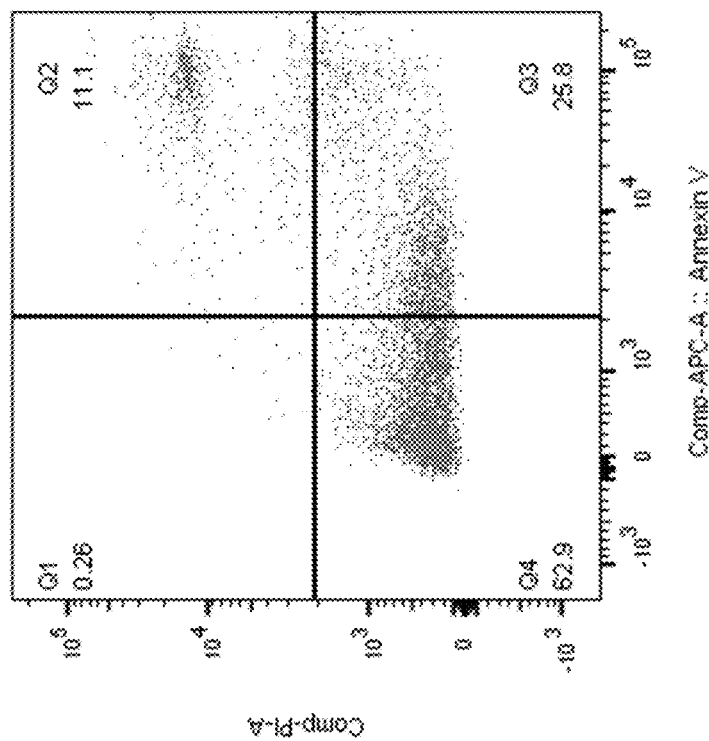
Figure 50A:
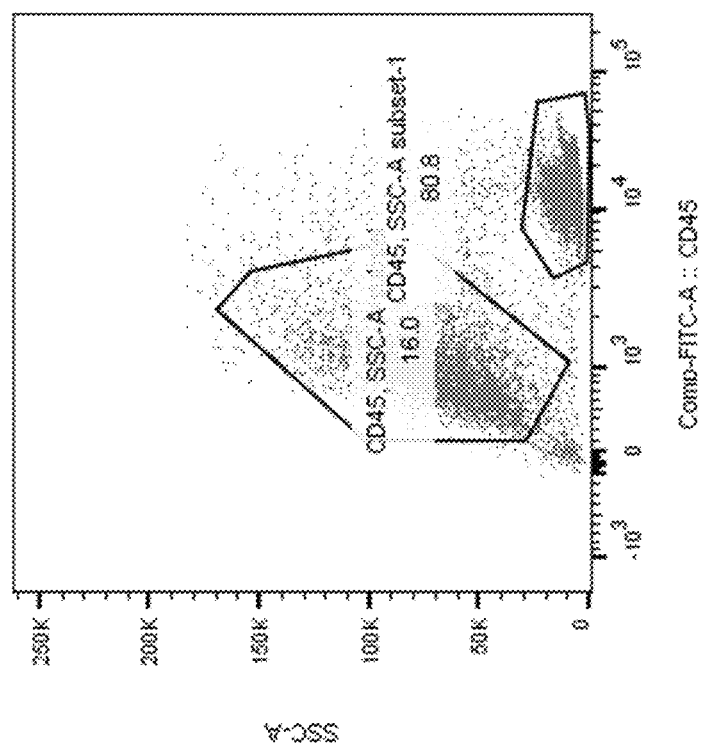
Figure 50C:
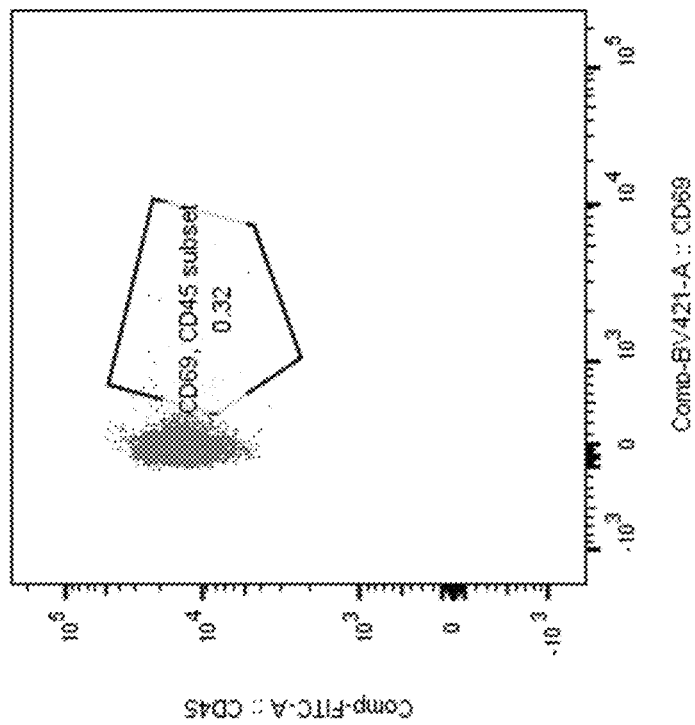

FIGS. 50A to 50C are flow cytometry plots showing MDA-175VII (target) cells treated with normal human CD8 T (effector) cells at 1:5 T to E ratio.

Figure 51A:
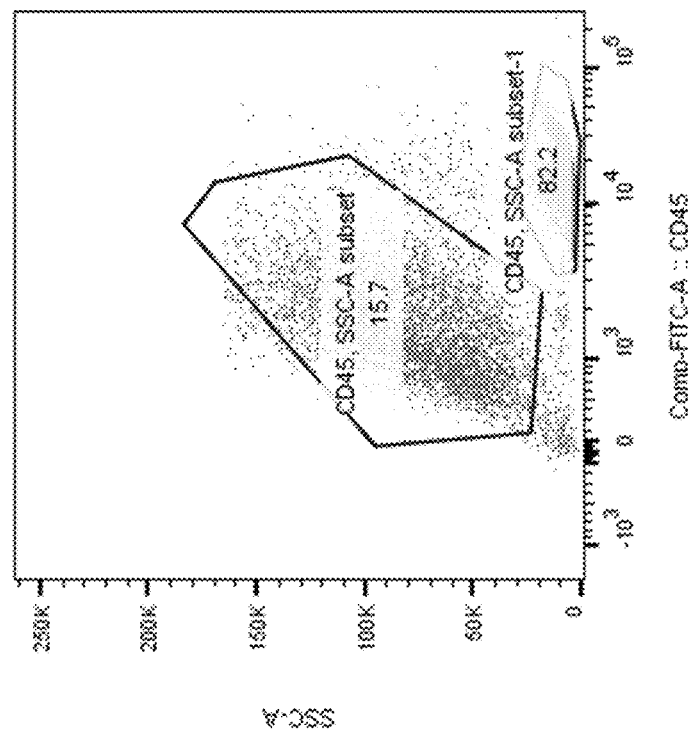
Figure 51C:
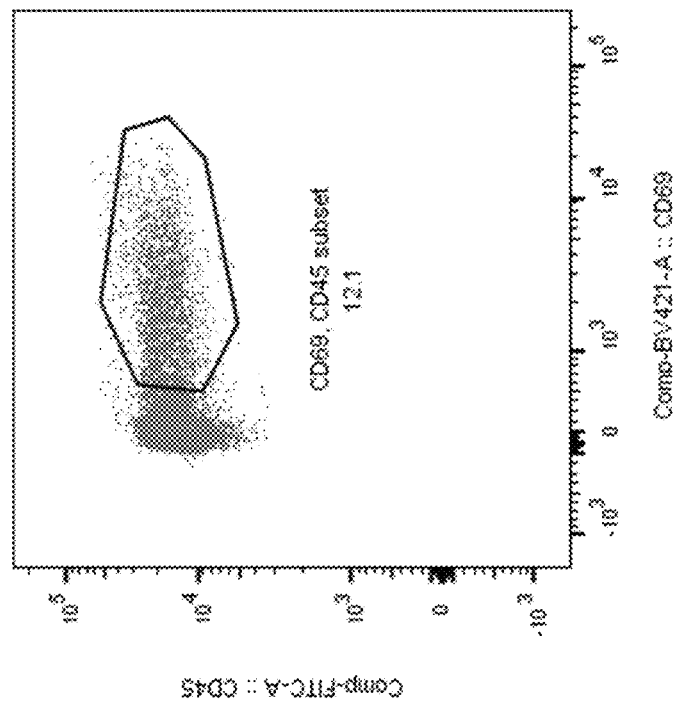
Figure 51B:
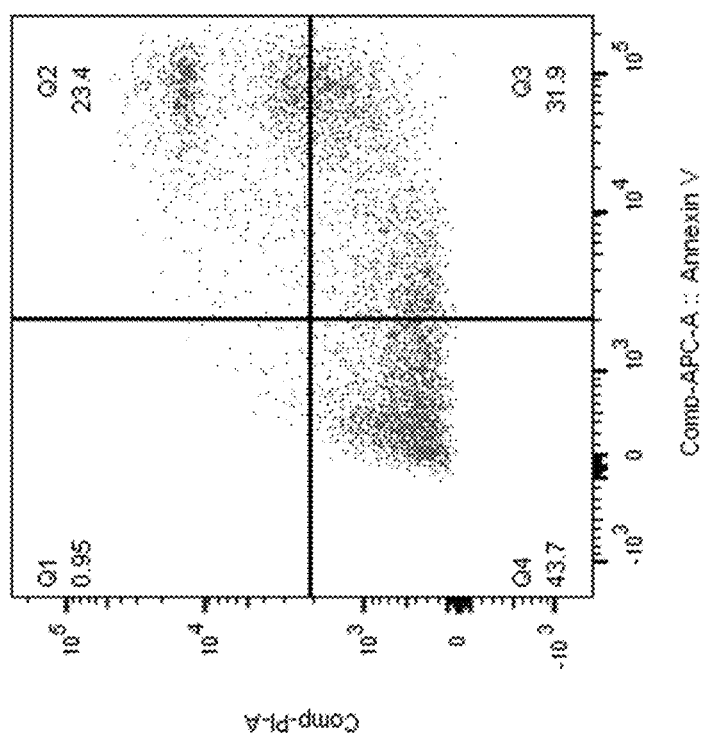

FIGS. 51A to 51C are flow cytometry plots showing MDA-175VII (target) cells treated with normal human CD8 T (effector) cells at 1:5 of T to E ratio+bispecific antibody (pilot) at conc of 5 ug/ml.

Figure 52:
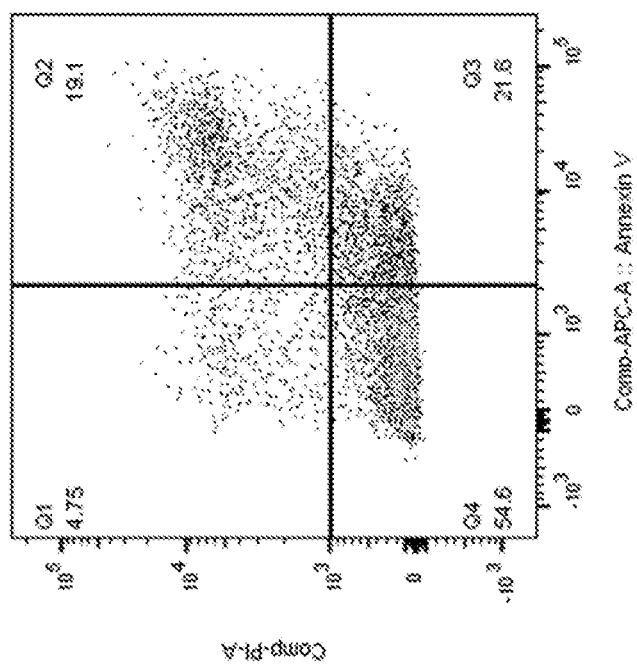

FIG. 52 is a flow cytometry plot showing Untreated Ls-174T (target) cells as negative control.

Figure 53:
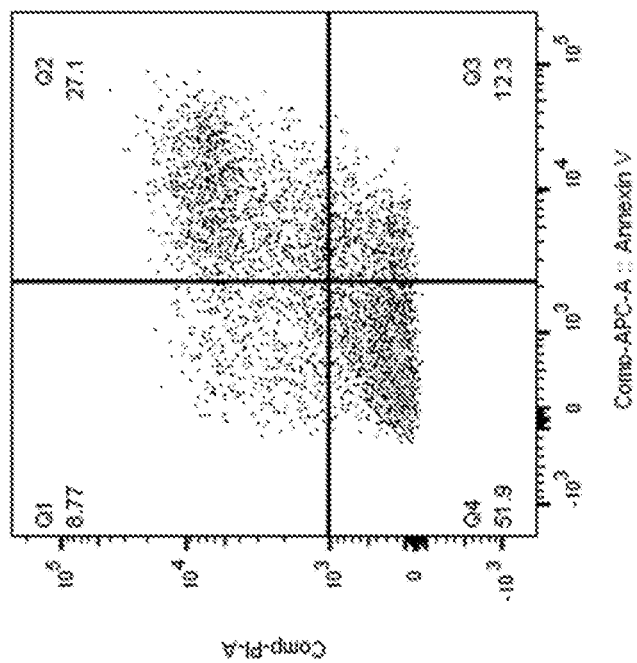

FIG. 53 is a flow cytometry plot showing Ls-174T cells treated with bispecific antibody (pilot) at conc of 5 μg/ml.

Figure 54B:
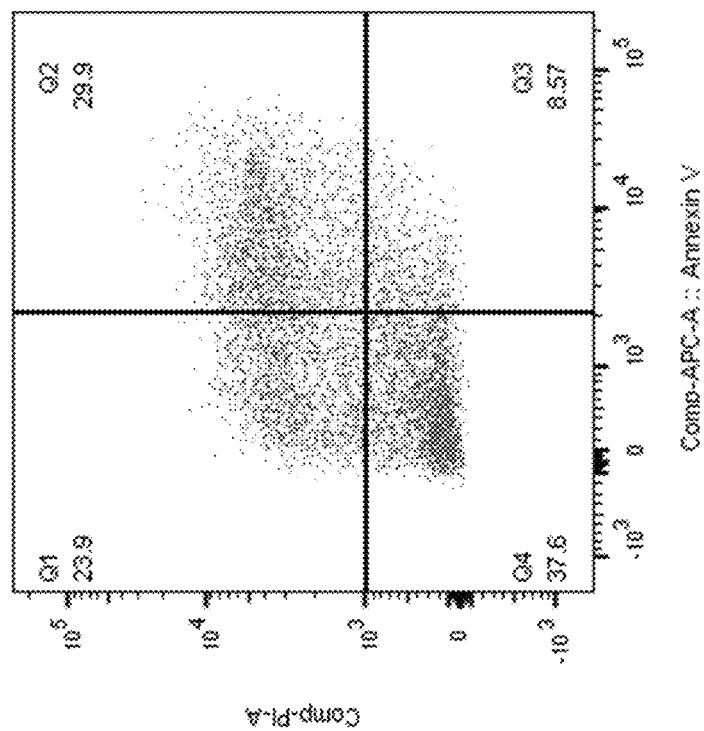
Figure 54A:
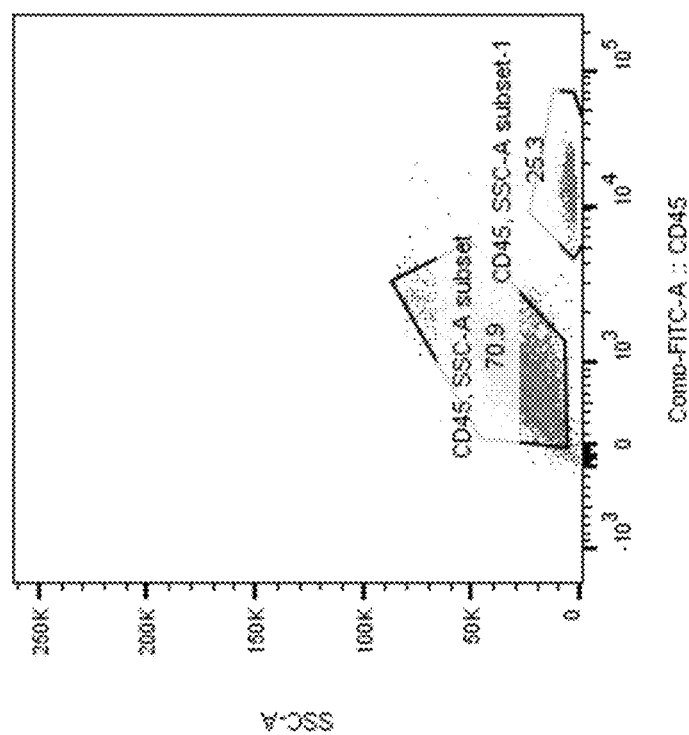
Figure 54C:
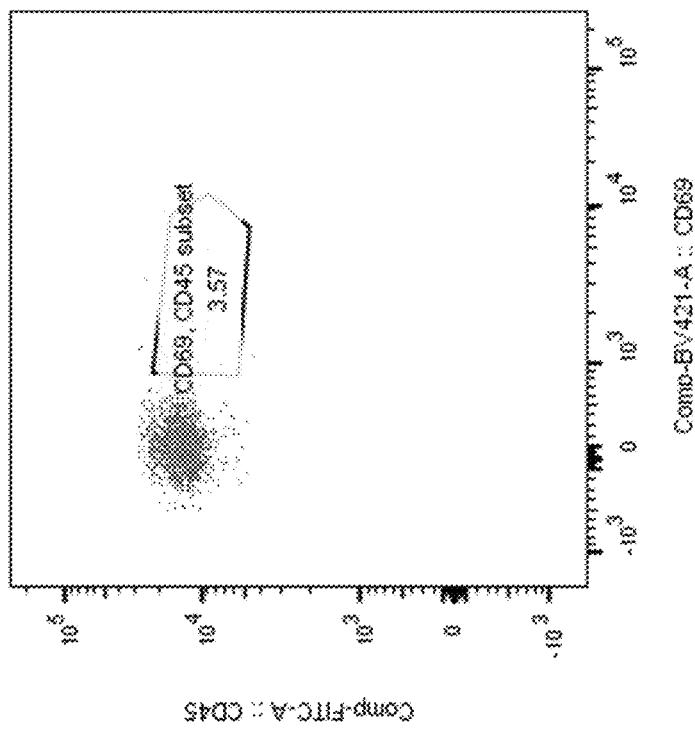

FIGS. 54A to 54C are flow cytometry plots showing Ls-174T (target) cells treated with normal human CD8 T (effector) cells at 1:5 T to E ratio.

Figure 55A:
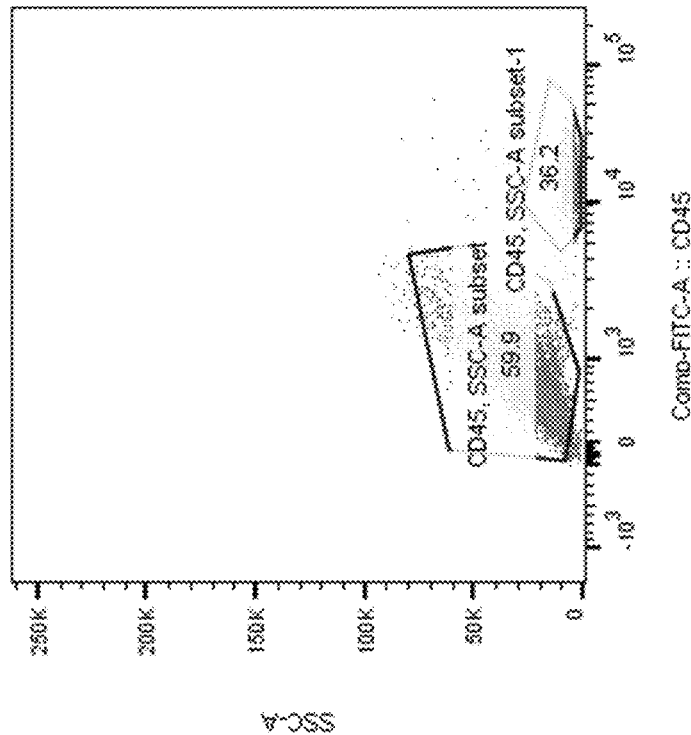
Figure 55C:
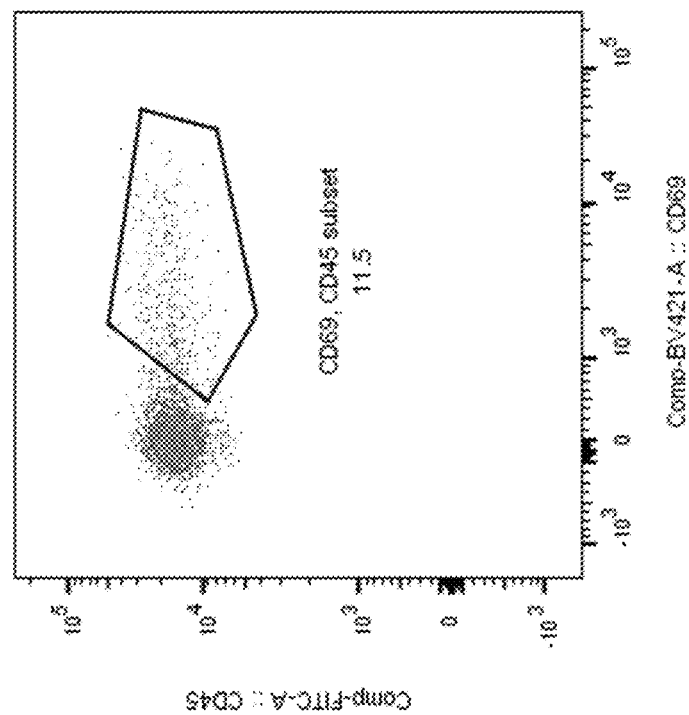
Figure 55B:
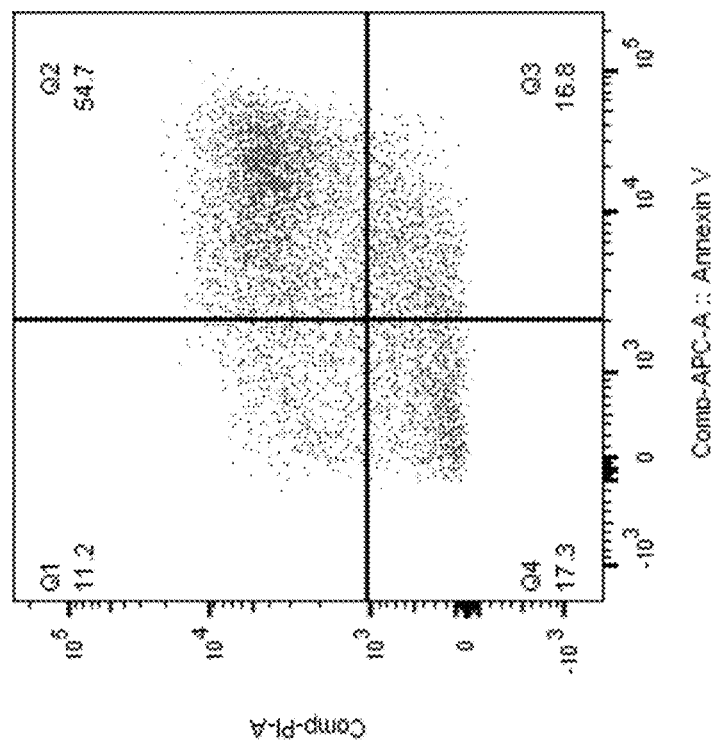

FIGS. 55A to 55C are flow cytometry plots showing Ls-174T (target) cells treated with normal human CD8 T (effector) cells at 1:5 of T to E ratio+bispecific antibody (pilot) at conc of 5 ug/ml.

Figure 56:
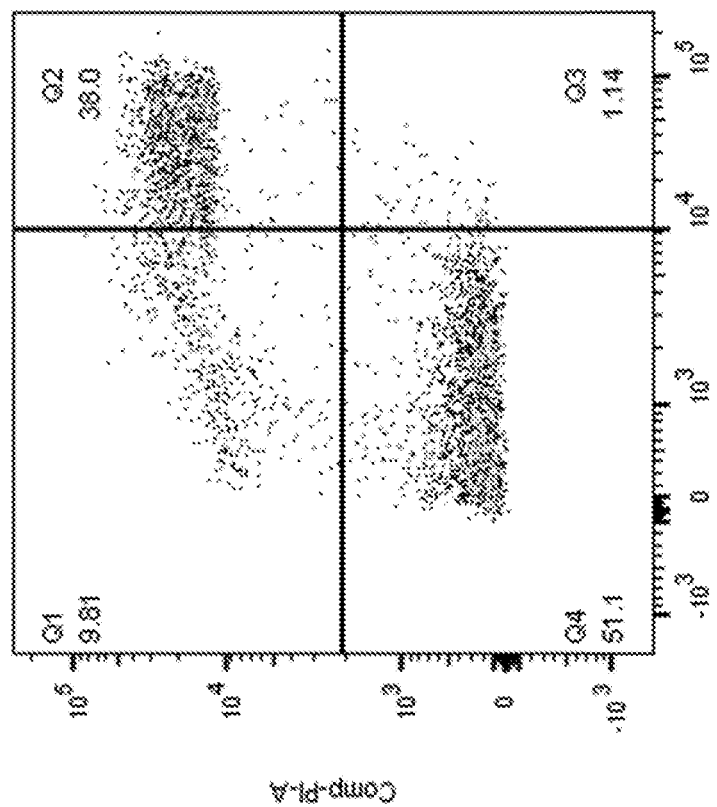

FIG. 56 is a flow cytometry plot showing untreated MCF-7 (target) cells as negative control.

Figure 57:
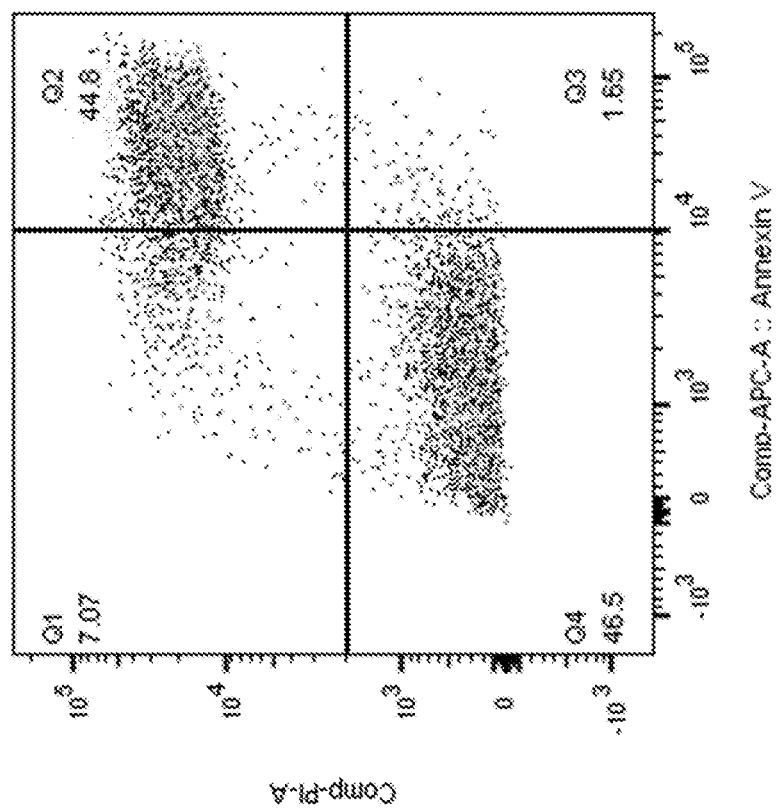

FIG. 57 is a flow cytometry plot showing MCF-7 cells treated with bispecific antibody at conc of 5 μg/ml.

Figure 58:
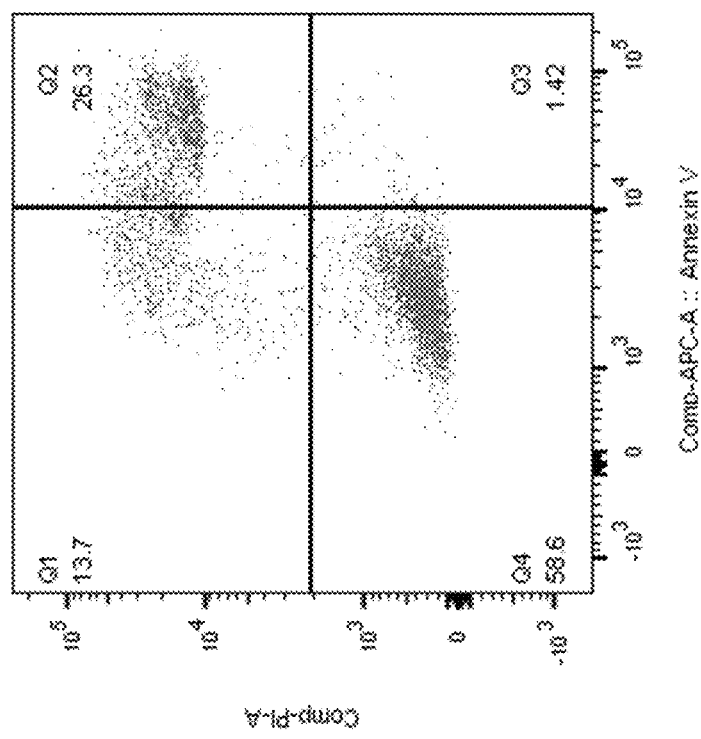

FIG. 58 is a flow cytometry plot showing MCF-7 (target) cells treated with visudyne (1 μM).

Figure 59:
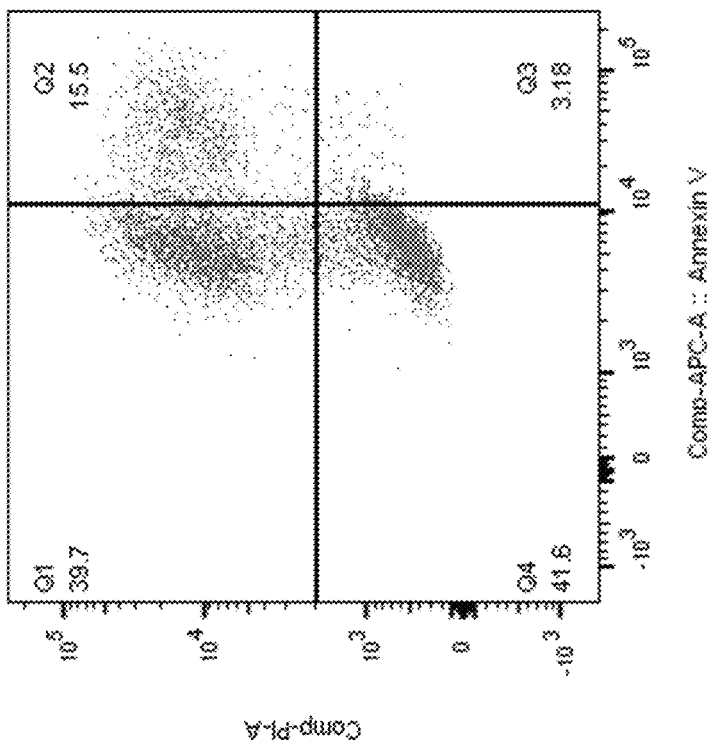

FIG. 59 is a flow cytometry plot showing MCF-7 (target) cells treated with visudyne (2 μM).

Figure 60:
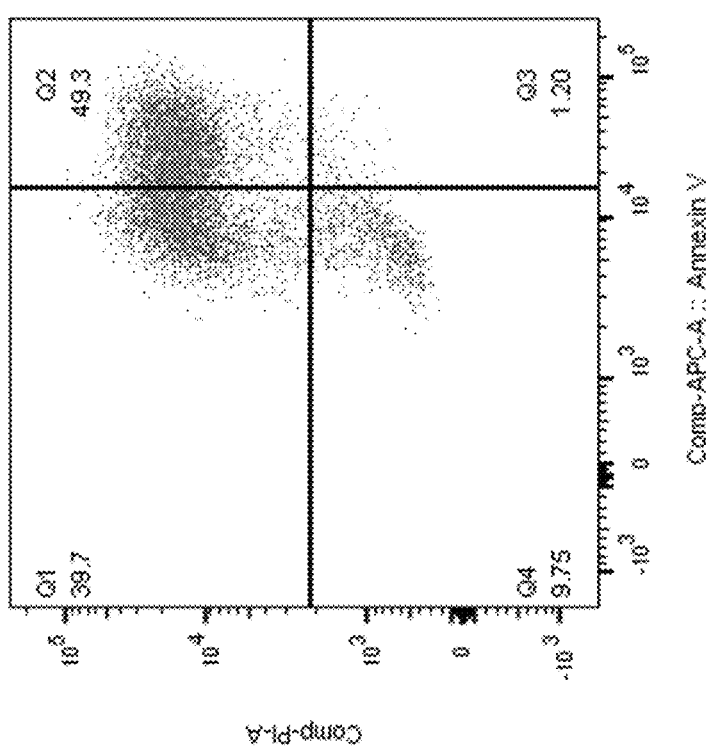

FIG. 60 is a flow cytometry plot showing MCF-7 (target) cells treated with visudyne (5 μM).

Figure 61A:
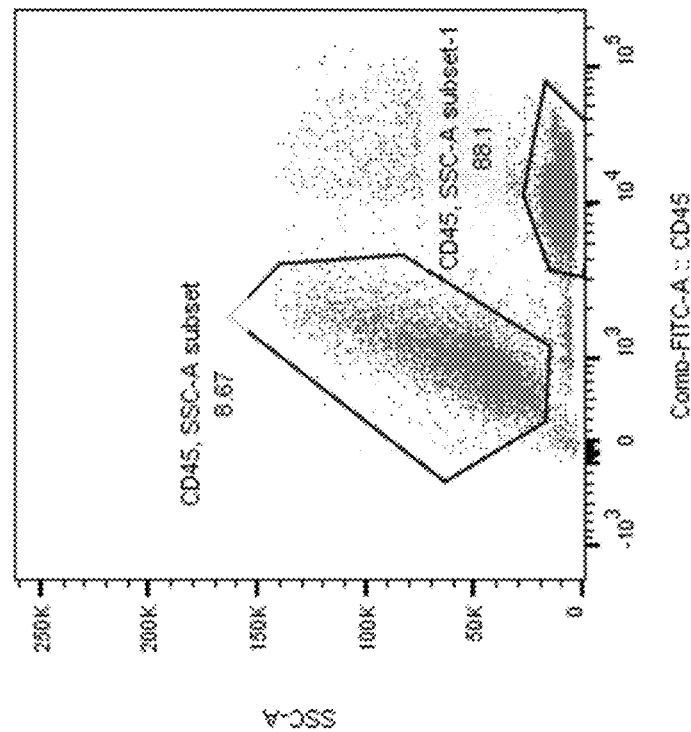
Figure 61C:
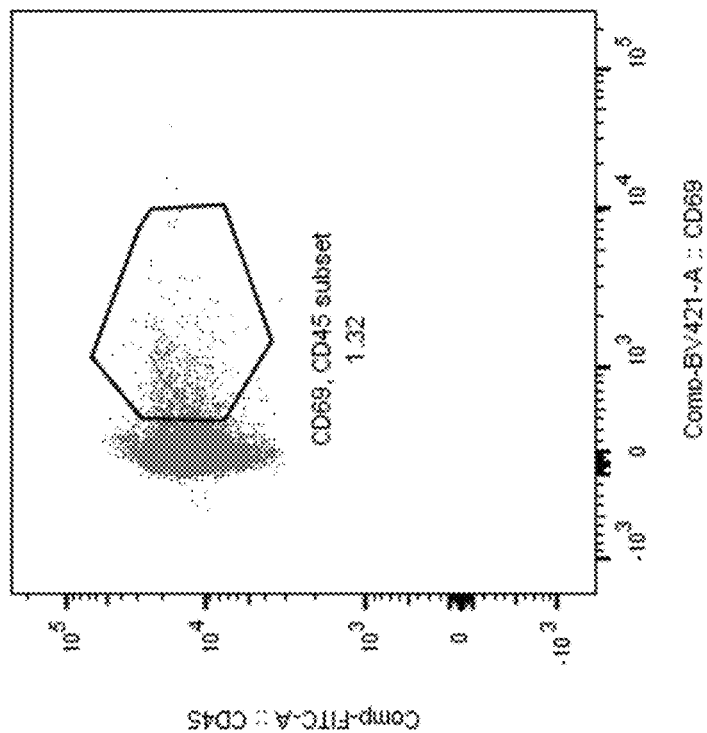
Figure 61B:
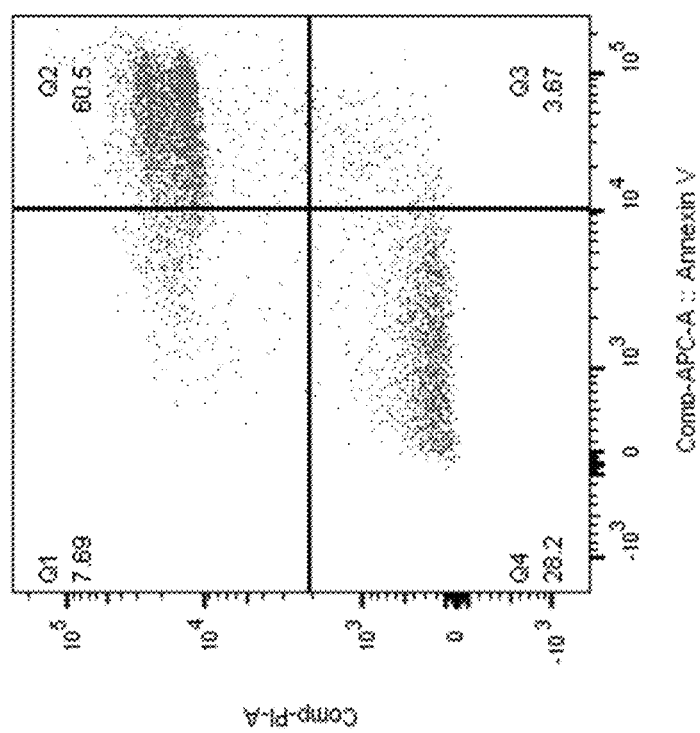

FIGS. 61A to 61C are flow cytometry plots showing MCF-7 (target) cells treated with normal human CD8 T (effector) cells at 1:5 T to E ratio.

Figure 62B:
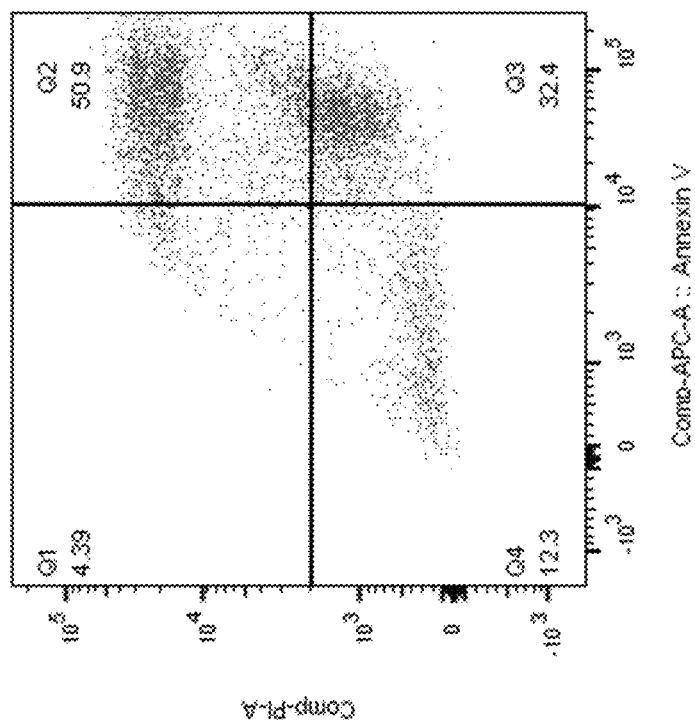
Figure 62A:
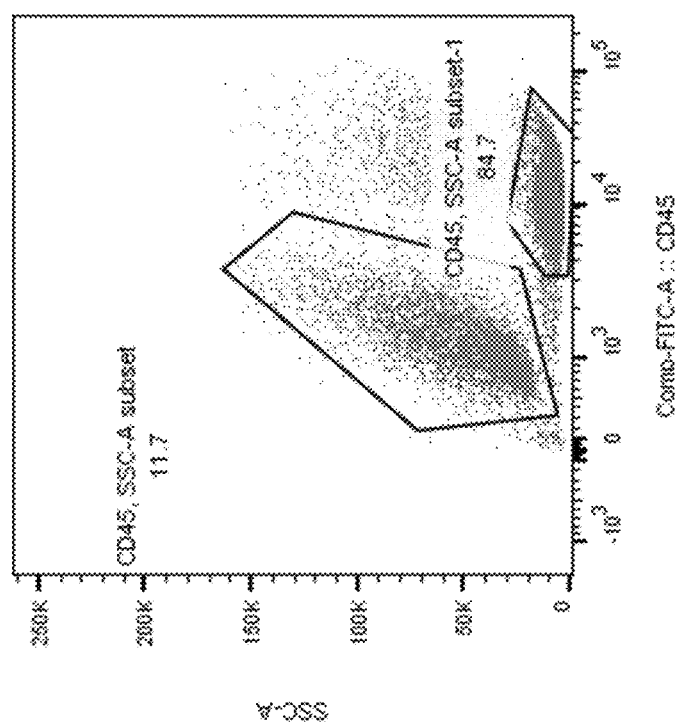
Figure 62C:
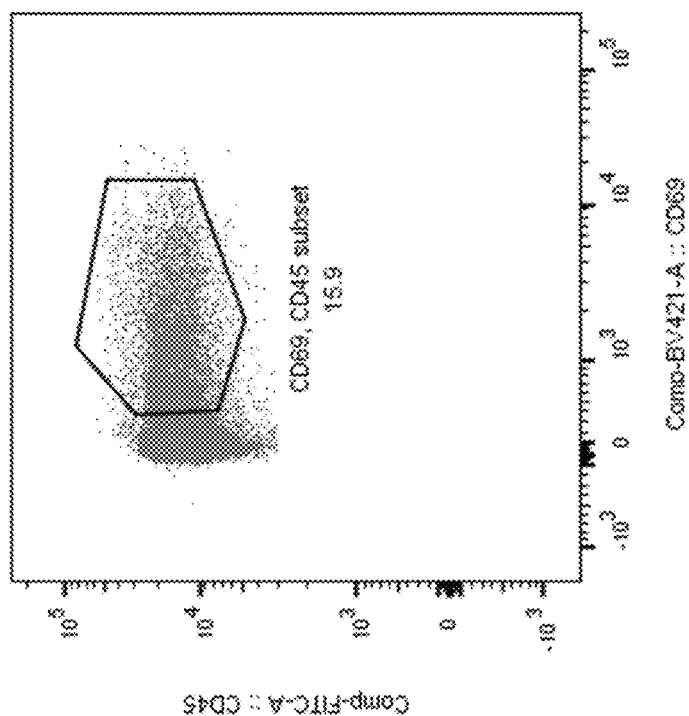

FIGS. 62A to 62C are flow cytometry plots showing MCF-7 (target) cells treated with normal human CD8 T (effector) cells at 1:5 of T to E ratio+bispecific antibody (pilot) at conc of 5 ug/ml.

Figure 63A:
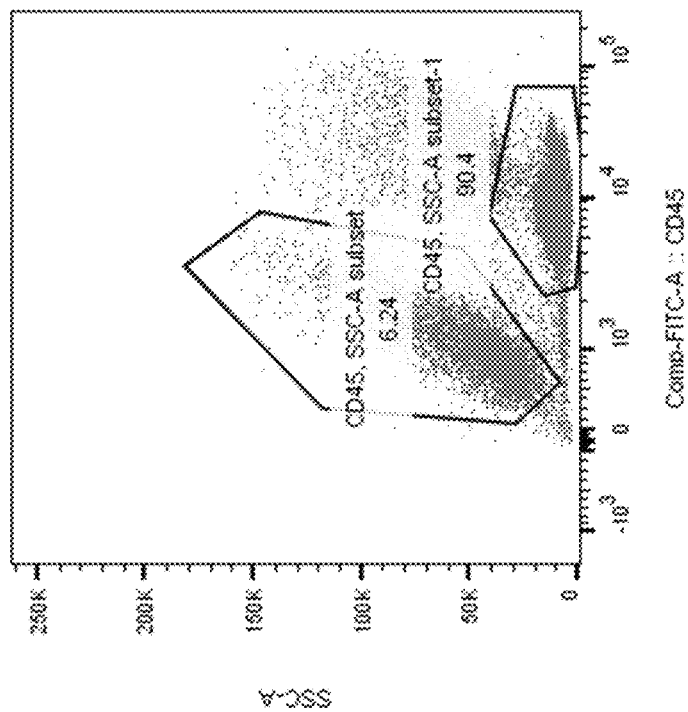
Figure 63C:
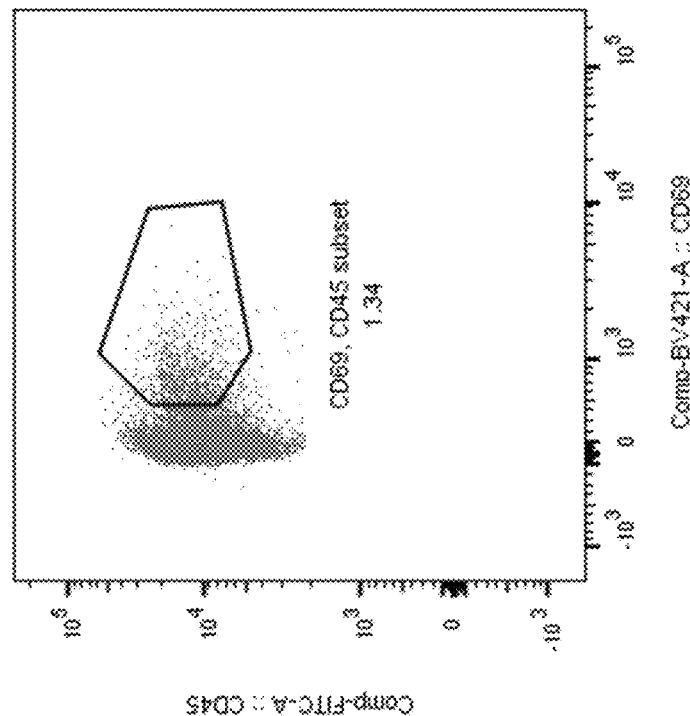
Figure 63B:
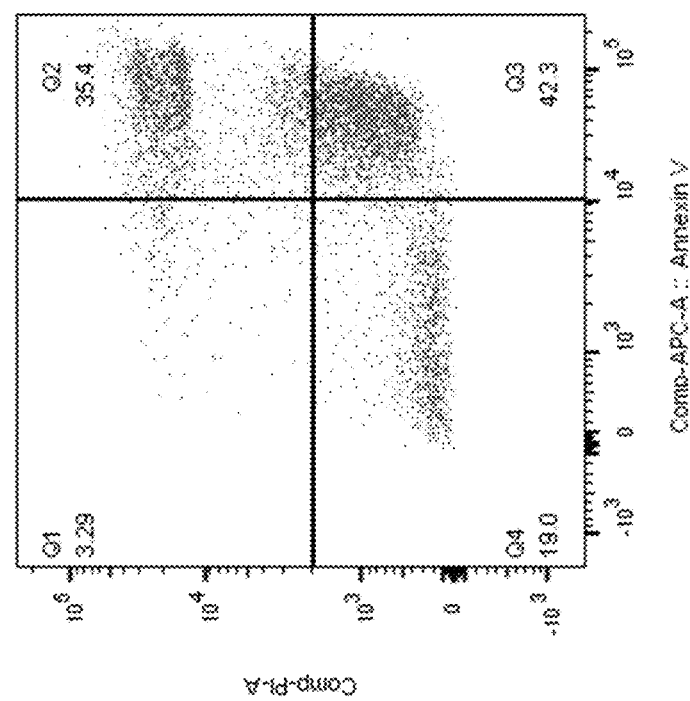

FIGS. 63A to 63C are flow cytometry plots showing MCF-7 (target) cells treated with normal human CD8 T (effector) cells+visudyne (1 μM).

Figure 64B:
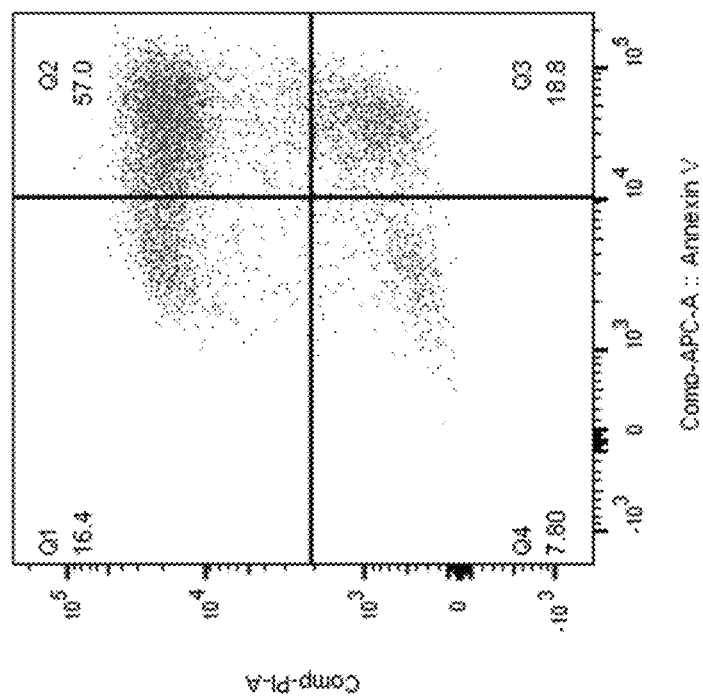
Figure 64A:
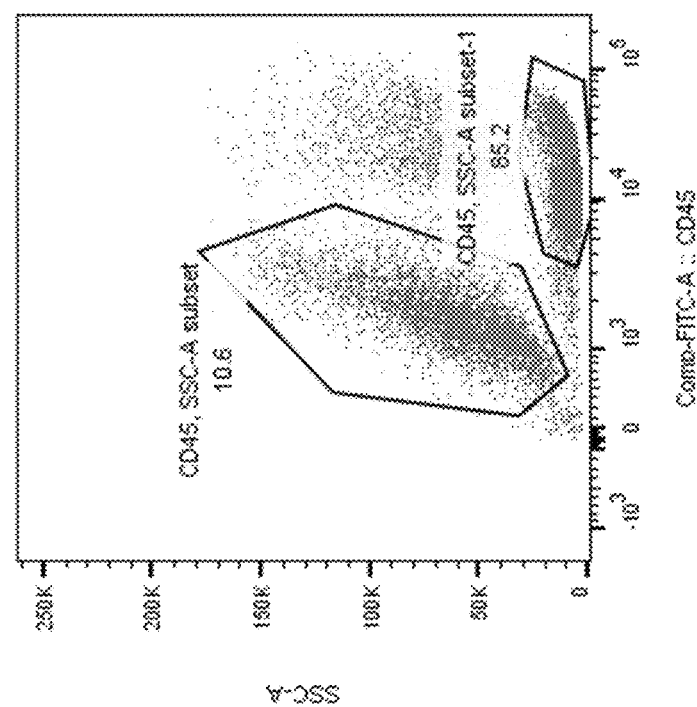
Figure 64C:
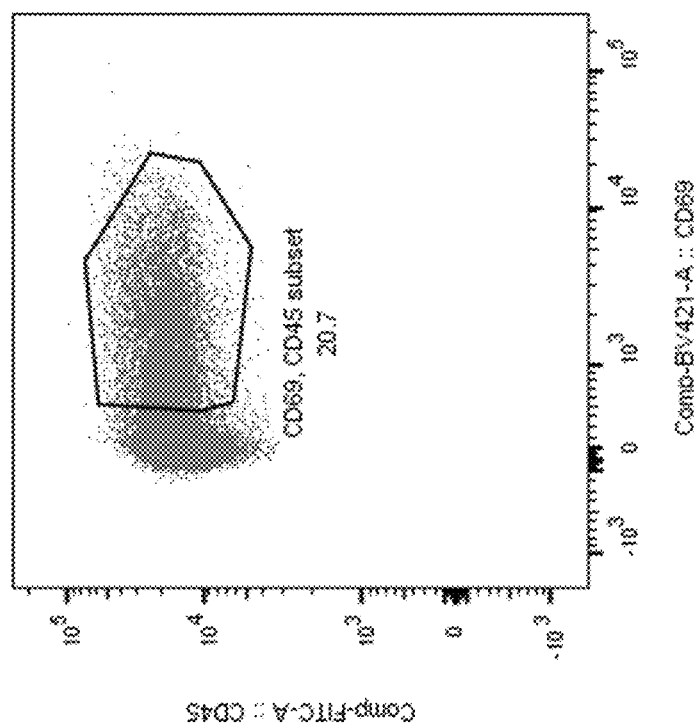

FIGS. 64A to 64C are flow cytometry plots showing MCF-7 (target) cells treated with normal human CD8 T (effector) cells at 1:5 of T to E ratio+bispecific antibody (pilot) at conc of 5 ug/ml+visudyne (11 μM).

Figure 65A:
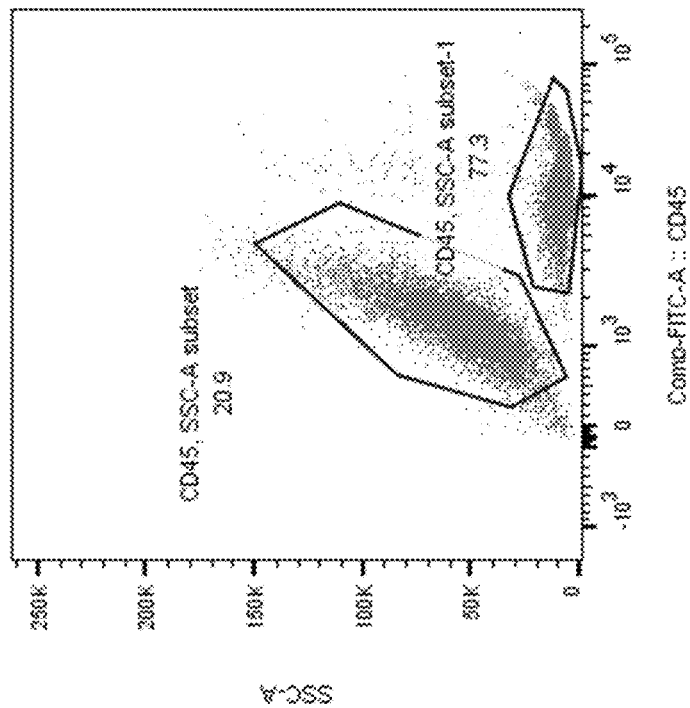
Figure 65C:
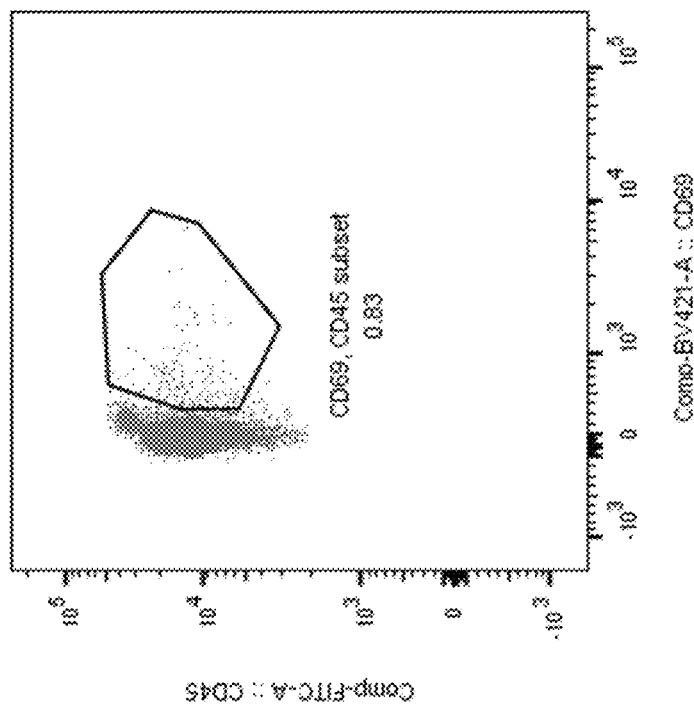
Figure 65B:
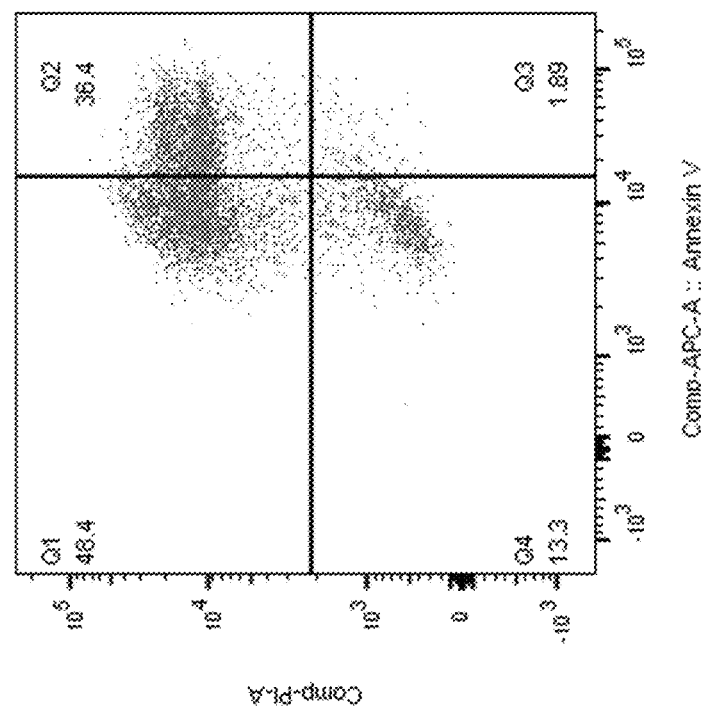

FIGS. 65A to 65C are flow cytometry plots showing MCF-7 (target) cells treated with normal human CD8 T (effector) cells+visudyne (2 μM).

Figure 66B:
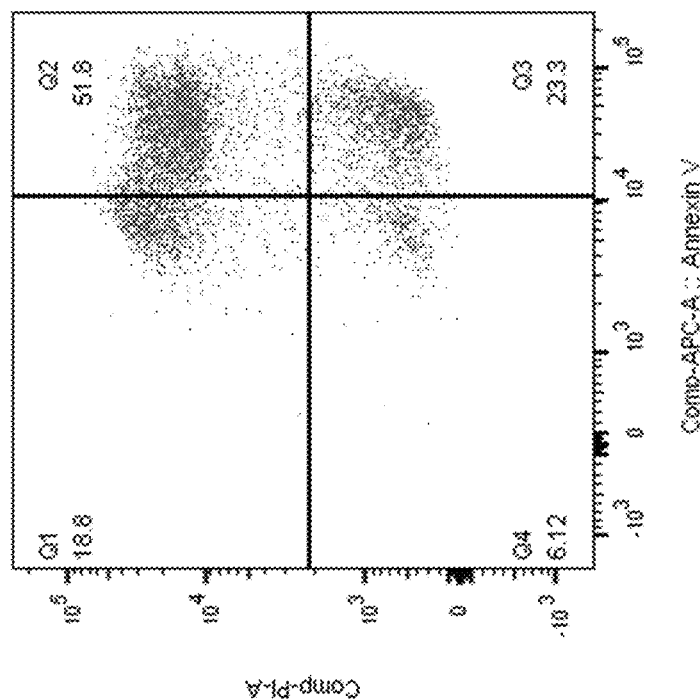
Figure 66A:
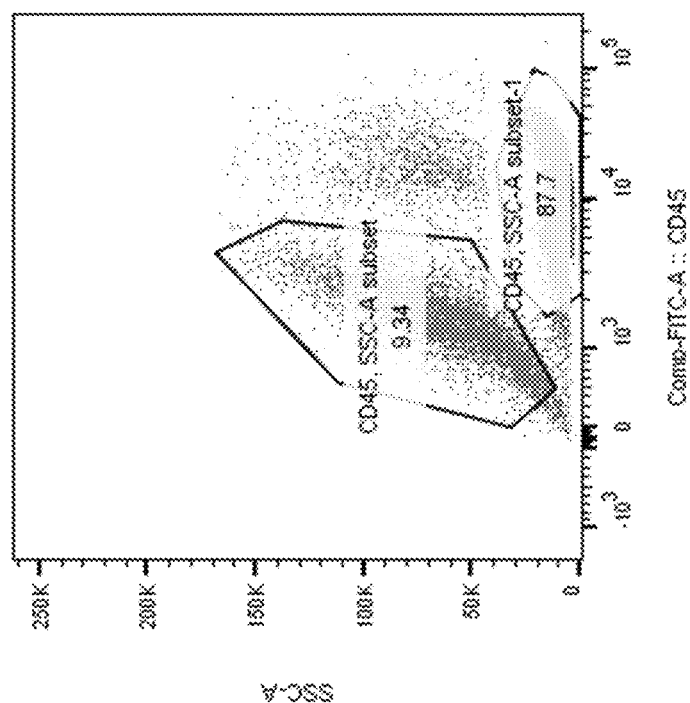
Figure 66C:
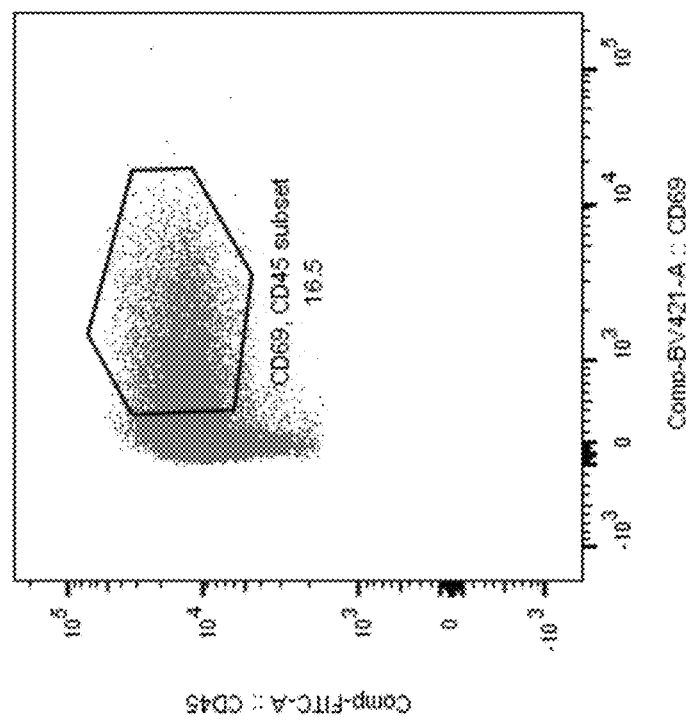

FIGS. 66A to 66C are flow cytometry plots showing MCF-7 (target) cells treated with normal human CD8 T (effector) cells at 1:5 of T to E ratio+bispecific antibody (pilot) at conc of 5 ug/ml+visudyne (2 μM).

Figure 67A:
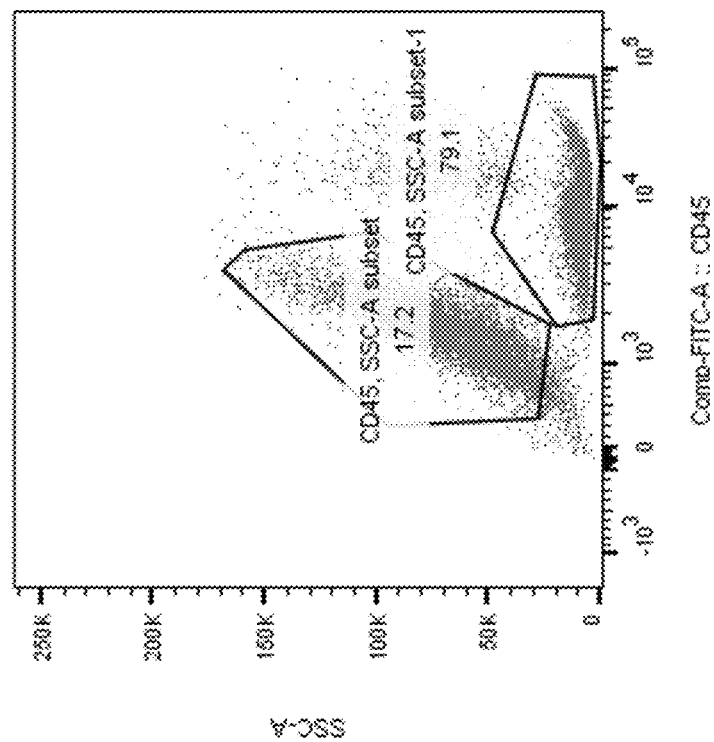
Figure 67C:
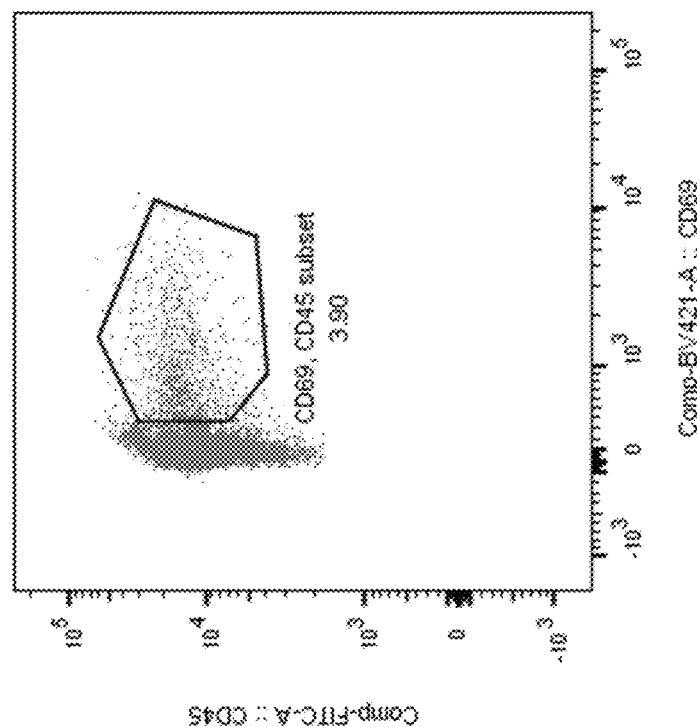
Figure 67B:
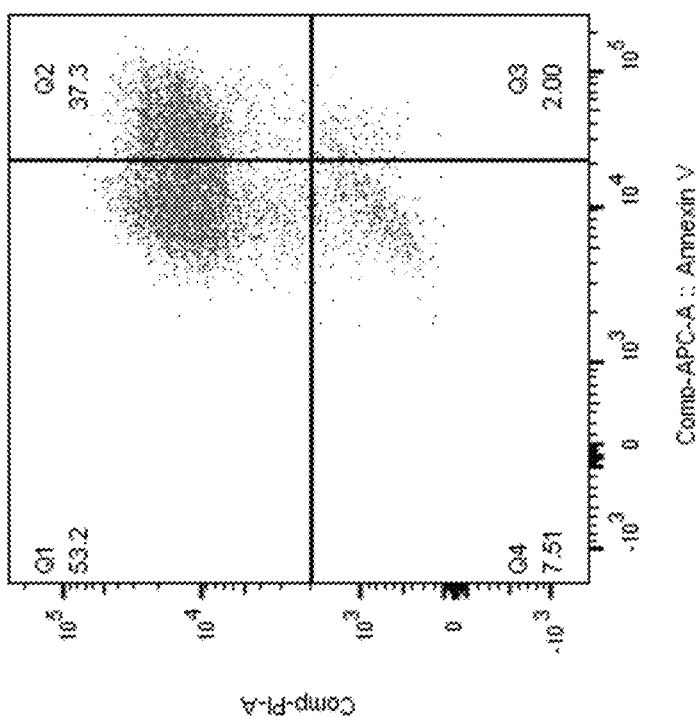

FIGS. 67A to 67C are flow cytometry plots showing MCF-7 (target) cells treated with normal human CD8 T (effector) cells at 1:5 of T to E ratio+visudyne (5 μM).

Figure 68B:
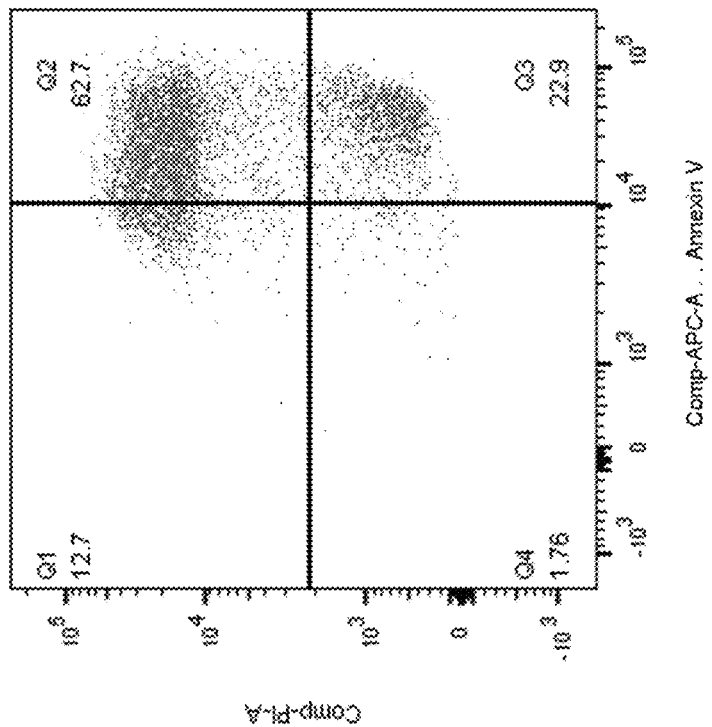
Figure 68A:
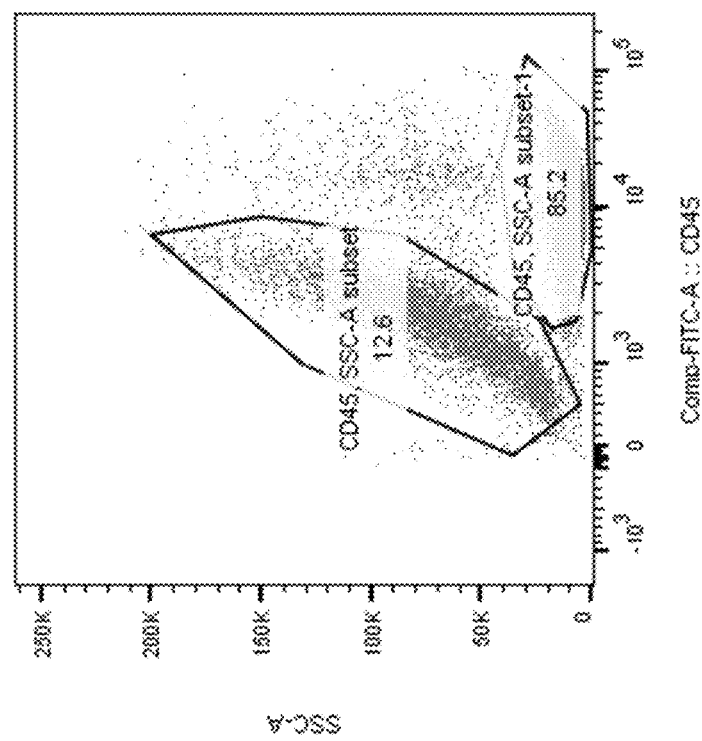
Figure 68C:
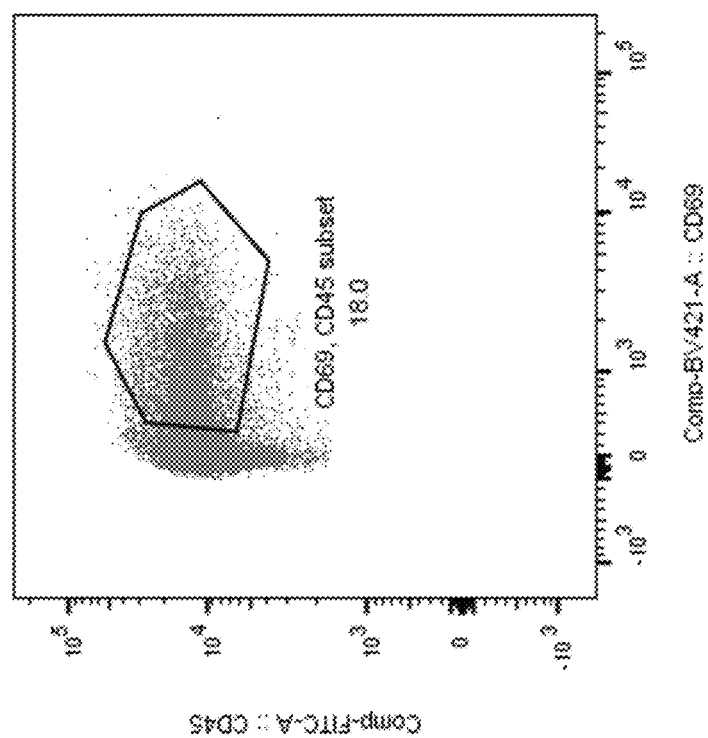

FIGS. 68A to 68C are flow cytometry plots showing MCF-7 (target) cells treated with normal human CD8 T (effector) cells at 1:5 of T to E ratio+bispecific antibody (pilot) at conc of 5 ug/ml+visudyne (5 μM).

Figure 70:
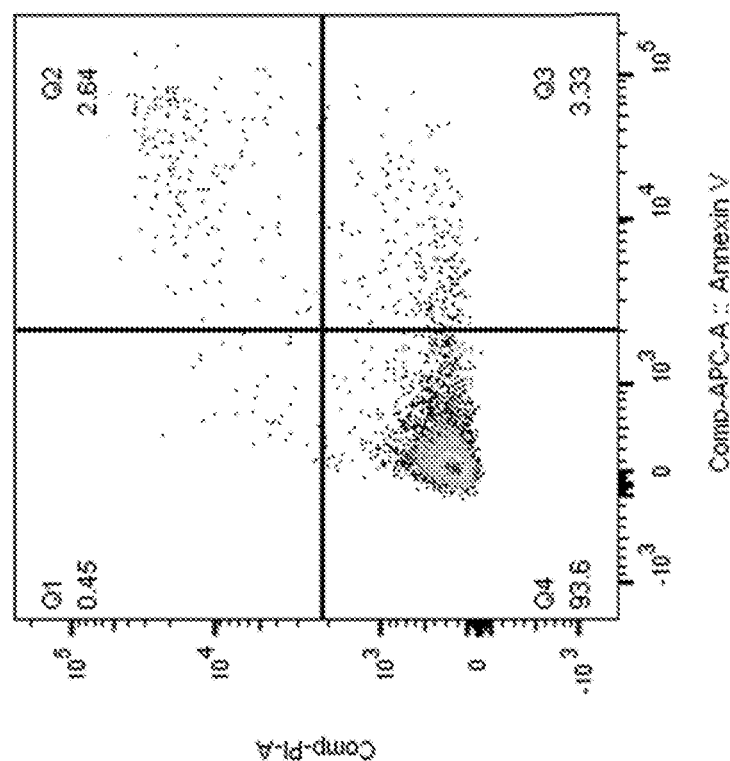
Figure 69:
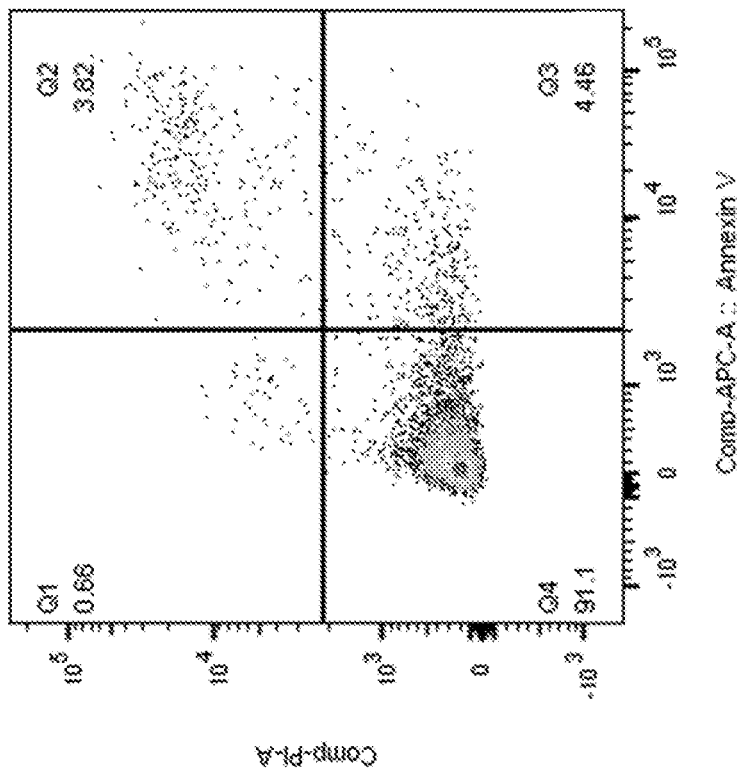

FIG. 69 is a flow cytometry plot showing untreated MDA-231 (target) cells as negative control FIG. 70 is a flow cytometry plot showing MDA-231 cells treated with bispecific antibody at conc of 5 µg/ml.

Figures 71, 72:
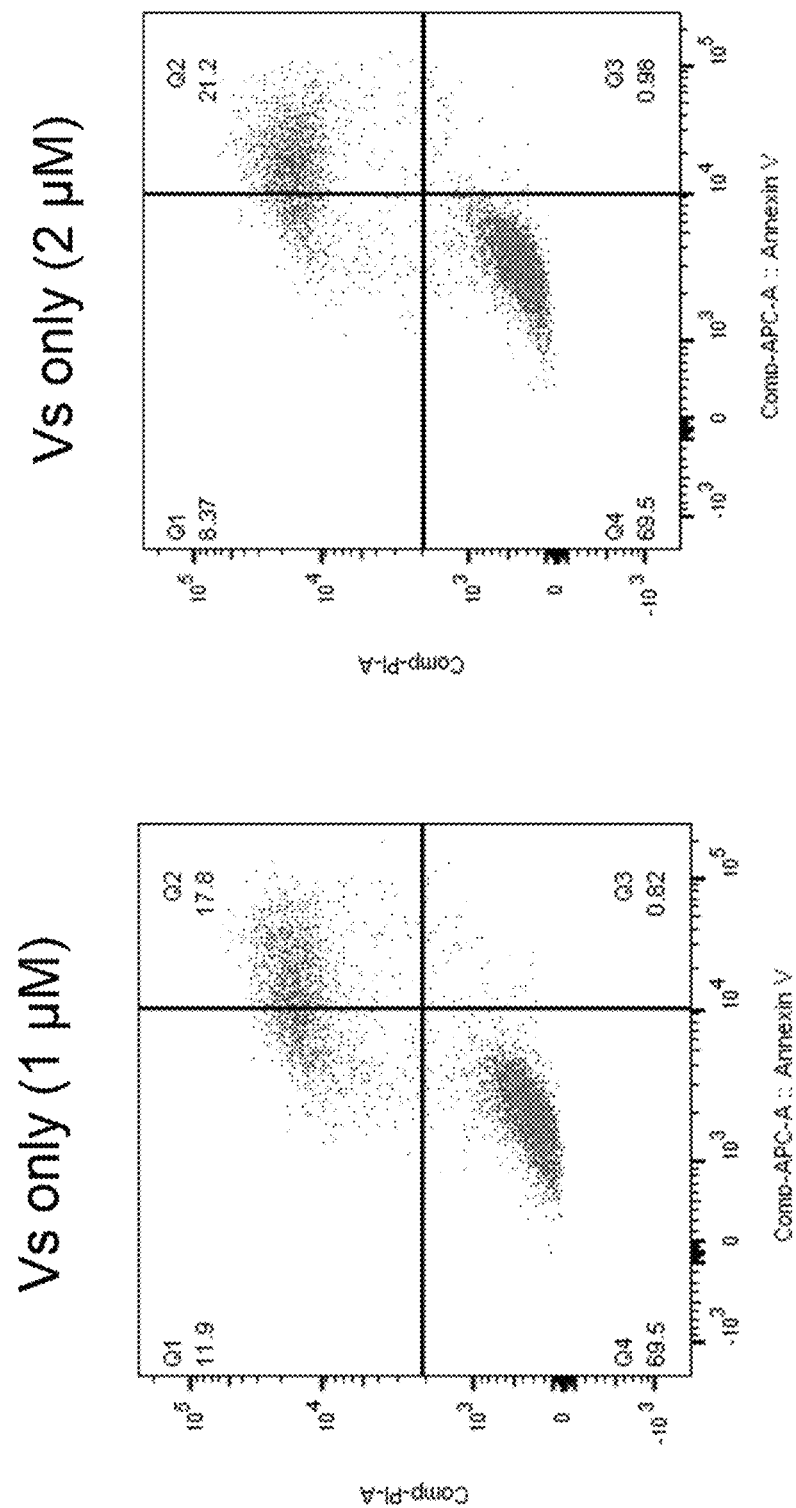

FIG. 71 is a flow cytometry plot showing MDA-231 (target) cells treated with visudyne (1 µM).

FIG. 72 is a flow cytometry plot showing MDA-231 (target) cells treated with visudyne (2 µM).

Figures 73, 74A:
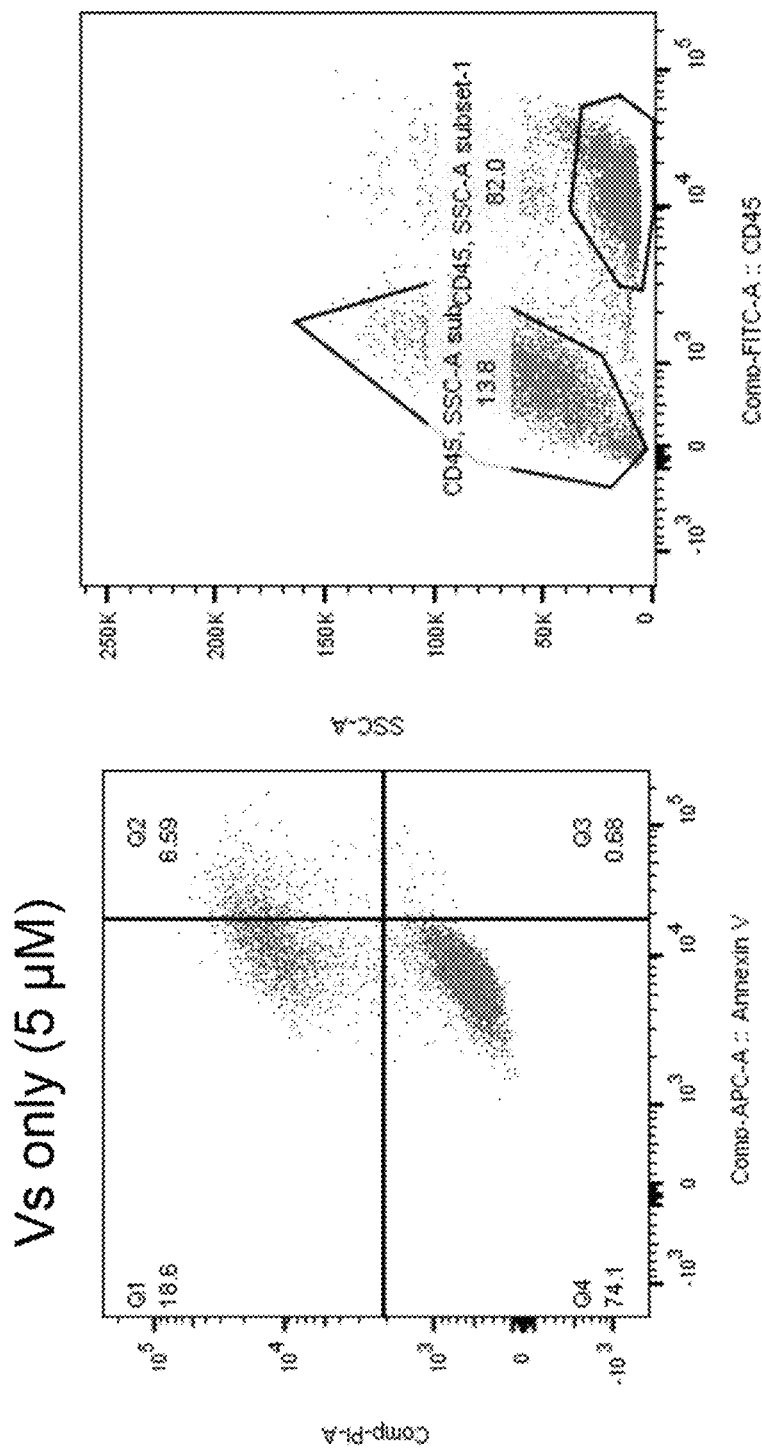

FIG. 73 is a flow cytometry plot showing MDA-231 (target) cells treated with visudyne (5 µM).

Figure 74C:
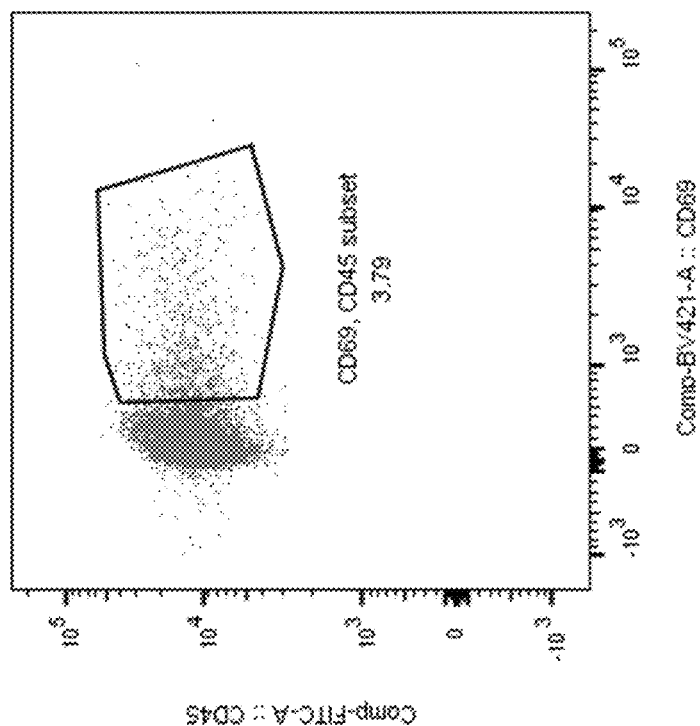
Figure 74B:
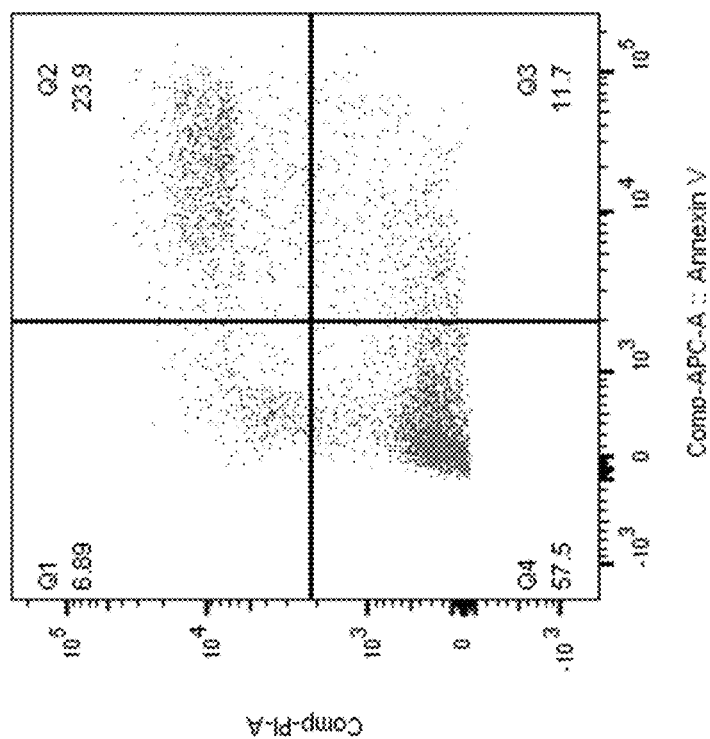

FIGS. 74A to 74C are flow cytometry plots showing MDA-231 (target) cells treated with normal human CD8 T (effector) cells at 1:5 T to E ratio.

Figure 75B:
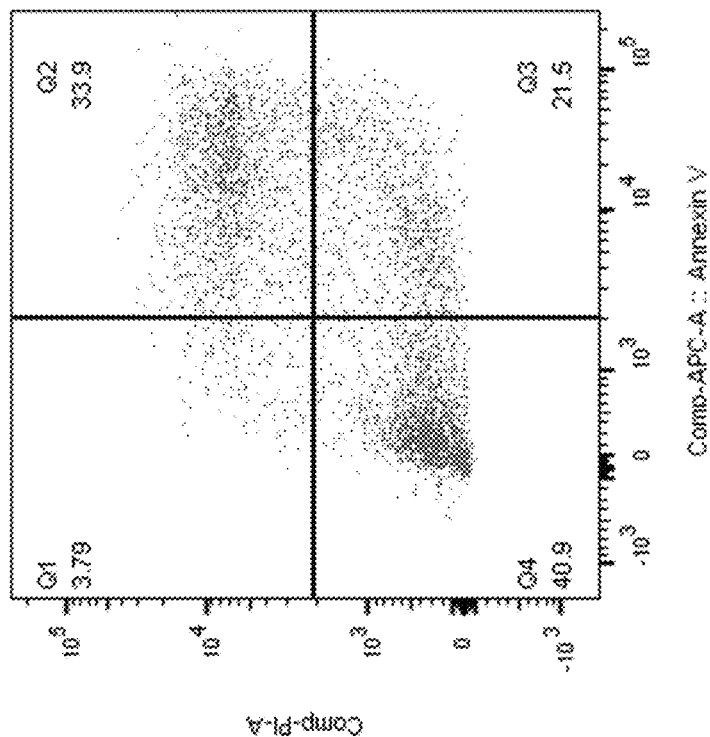
Figure 75A:
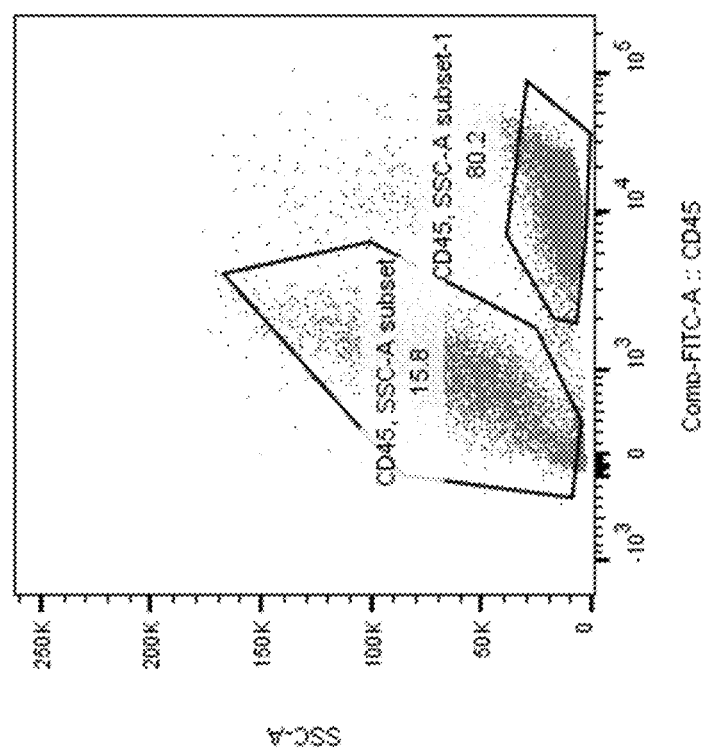
Figure 75C:
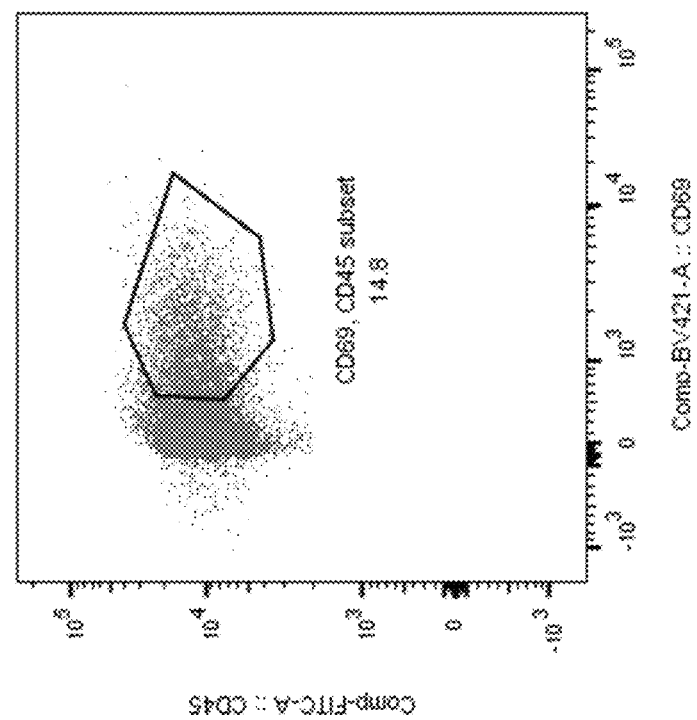

FIGS. 75A to 75C are flow cytometry plots showing MDA-231 (target) cells treated with normal human CD8 T (effector) cells at 1:5 of T to E ratio+bispecific antibody (pilot) at conc of 5 ug/ml.

Figure 76A:
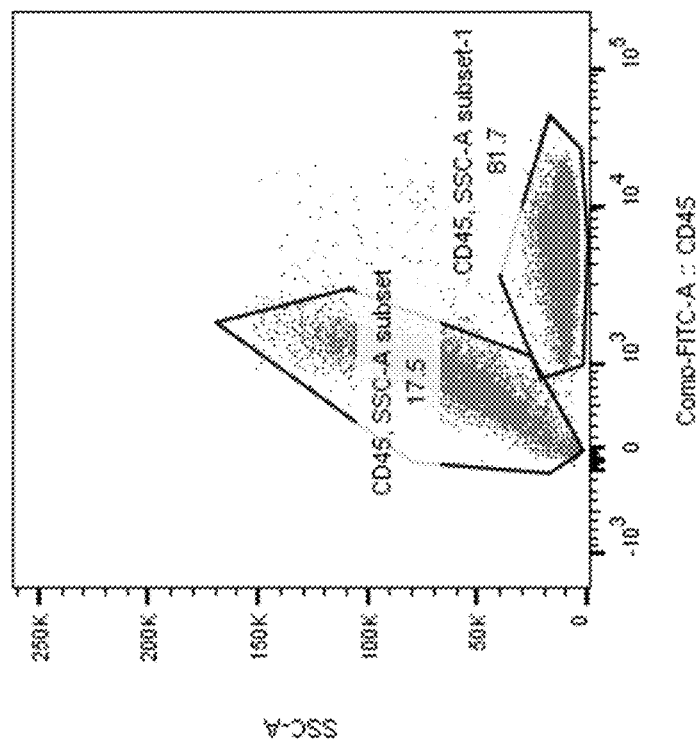
Figure 76C:
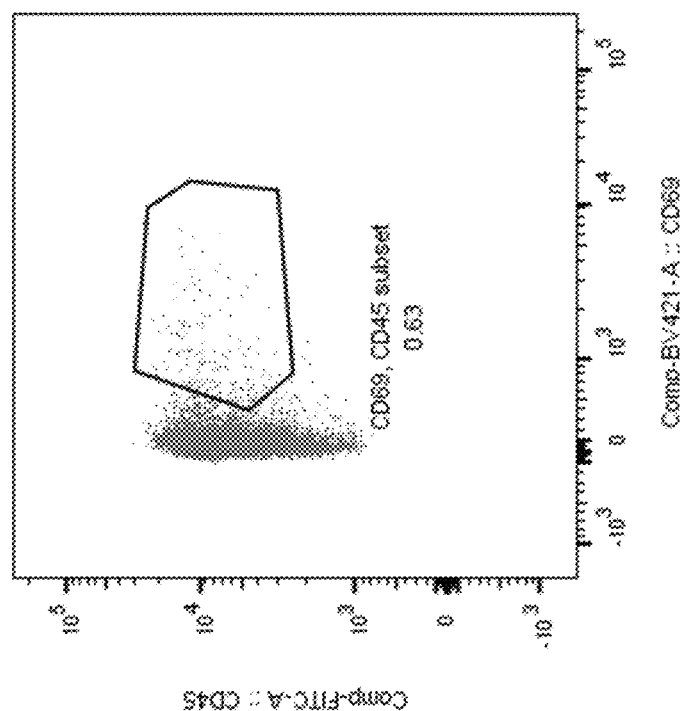
Figure 76B:
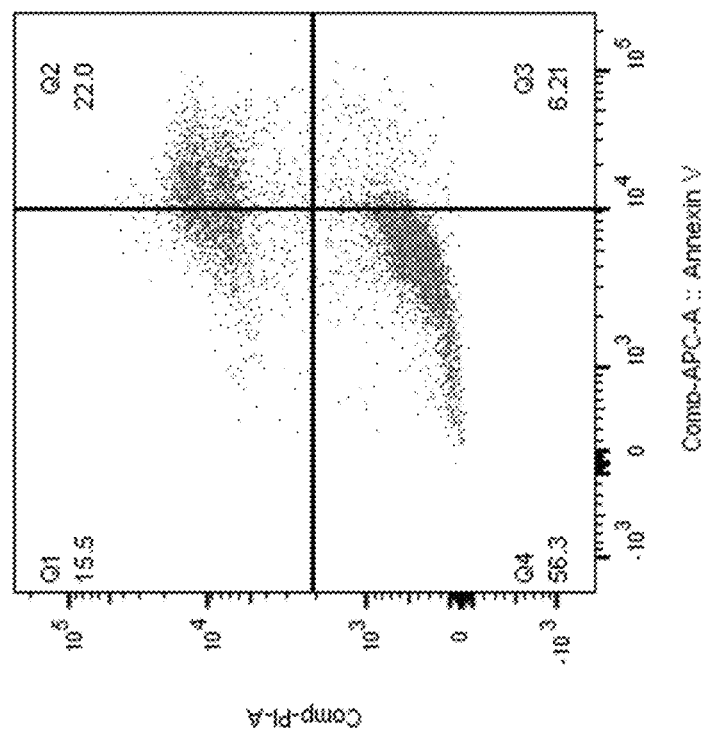

FIGS. 76A to 76C are flow cytometry plots showing MDA-231 (target) cells treated with normal human CD8 T (effector) cells+visudyne (1 µM).

Figure 77B:
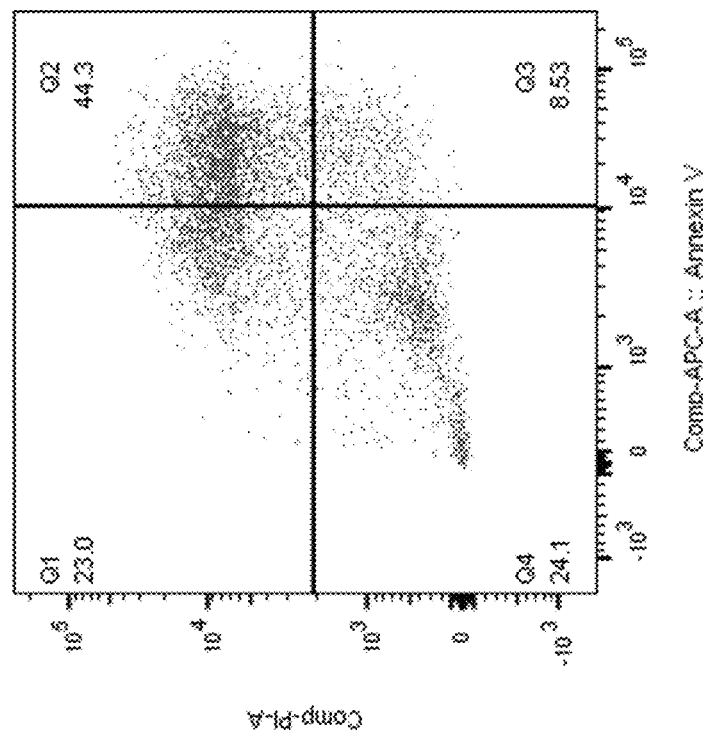
Figure 77A:
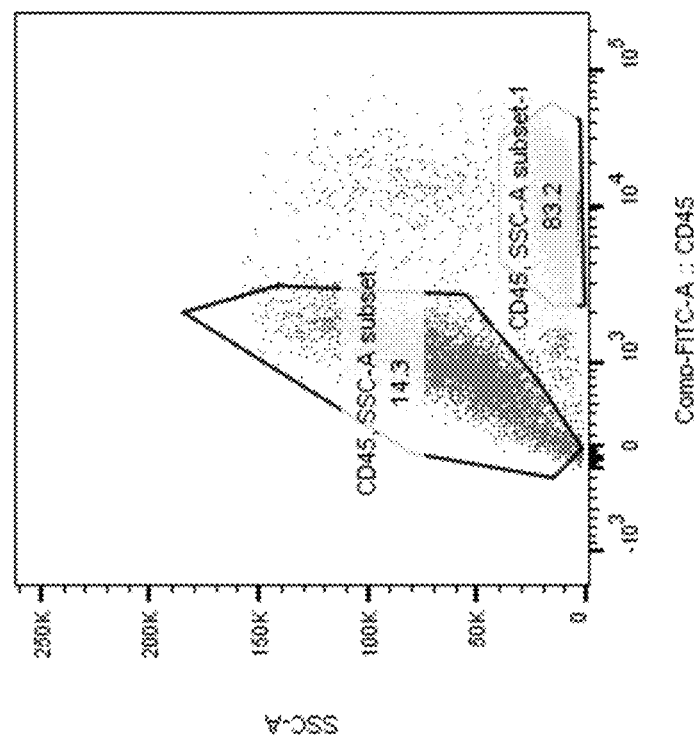
Figure 77C:
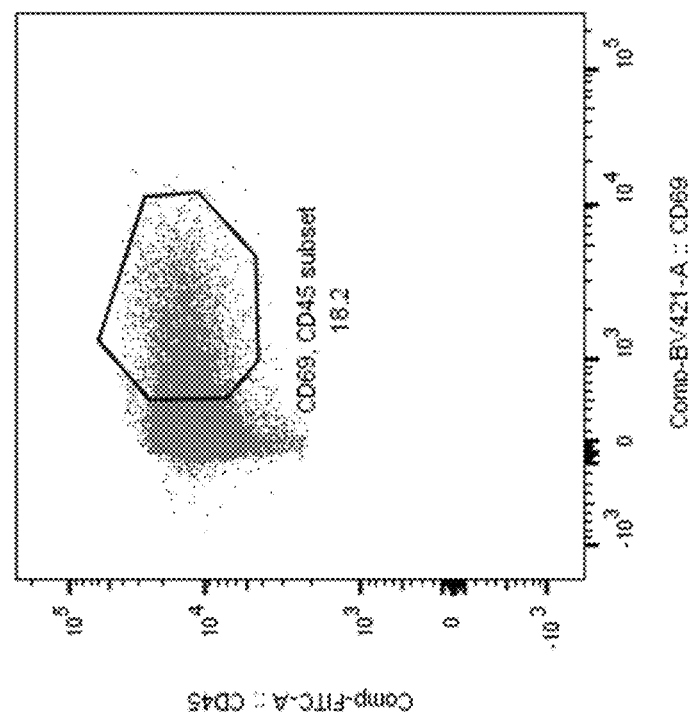

FIGS. 77A to 77C are flow cytometry plots showing MDA-231 (target) cells treated with normal human CD8 T (effector) cells at 1:5 of T to E ratio+bispecific antibody (pilot) at conc of 5 ug/ml+visudyne (1 µM).

Figure 78A:
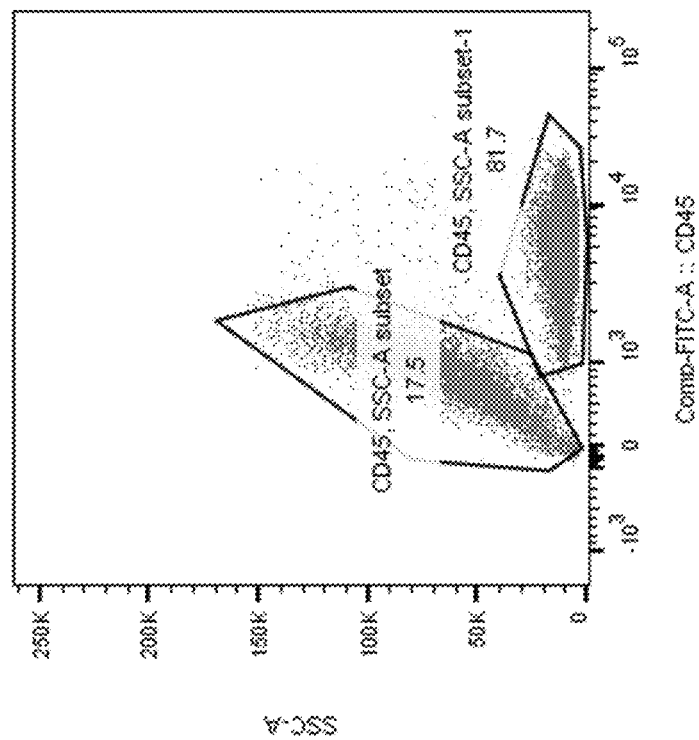
Figure 78C:
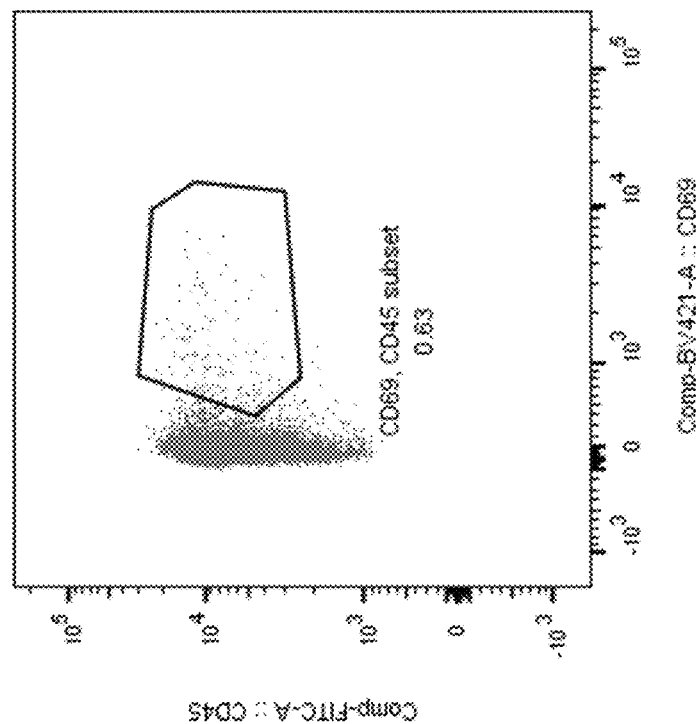
Figure 78B:
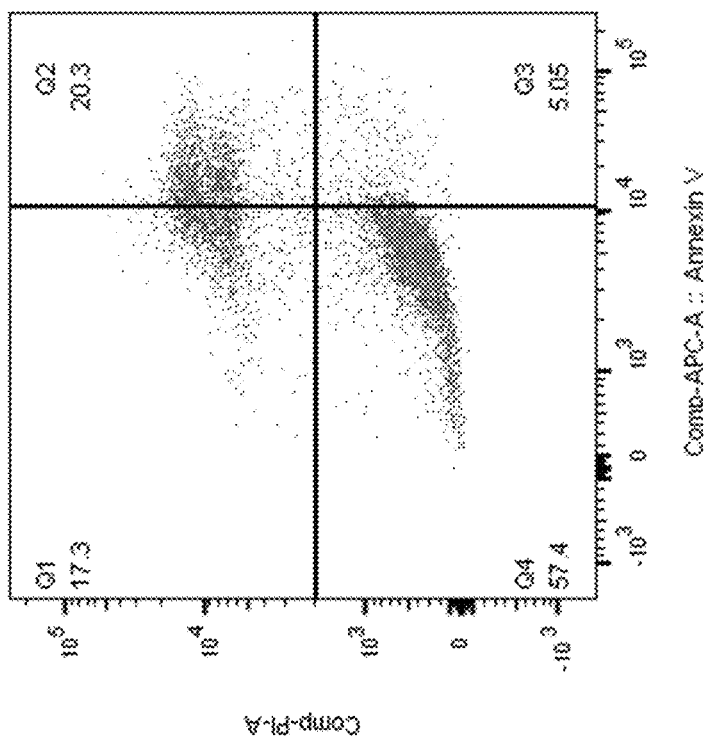

FIGS. 78A to 78C are flow cytometry plots showing MDA-231 (target) cells treated with normal human CD8 T (effector) cells+visudyne (2 µM).

Figure 79B:
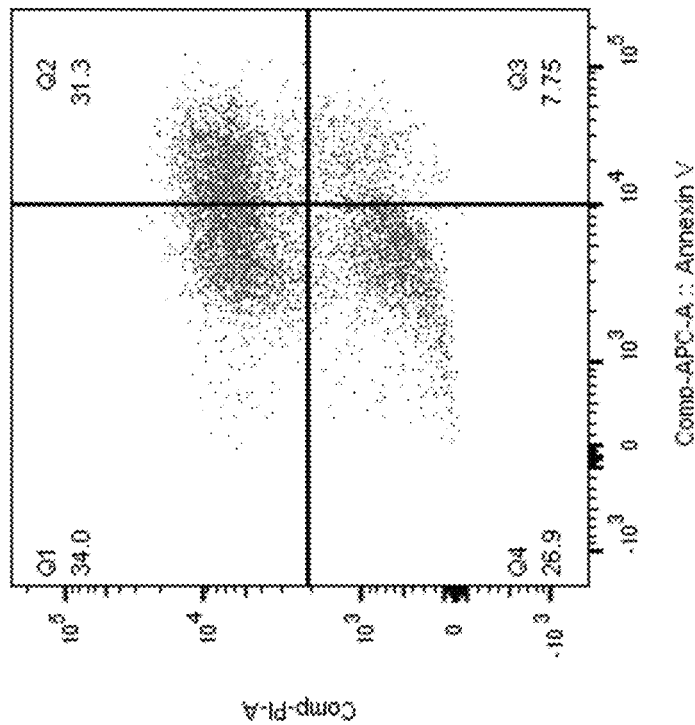
Figure 79A:
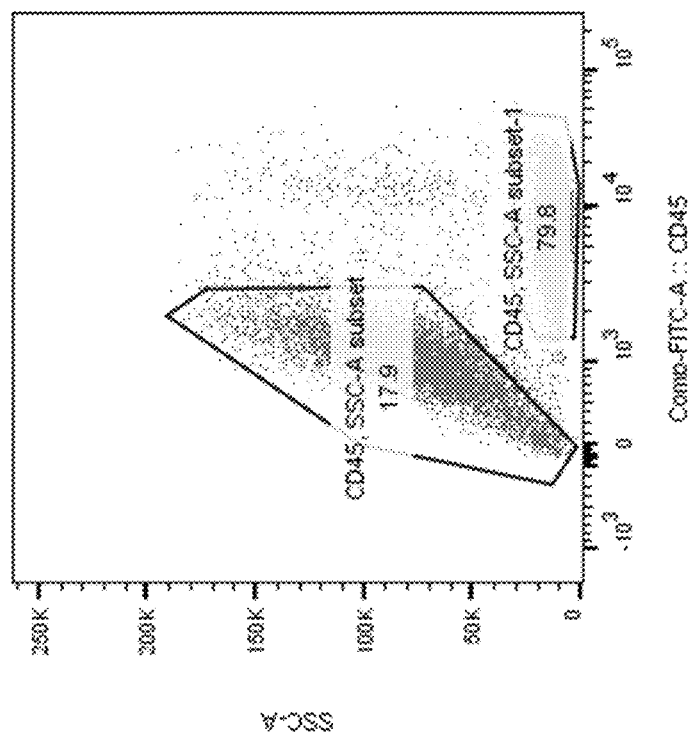
Figure 79C:
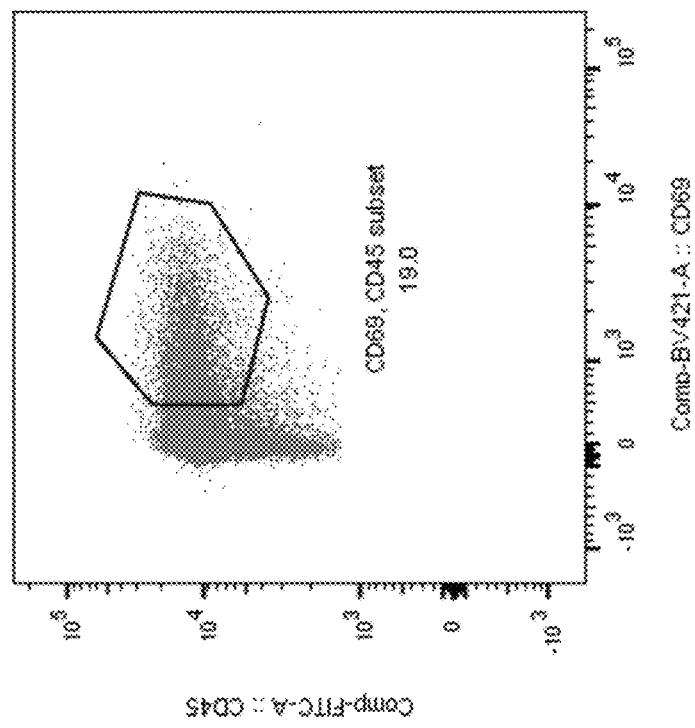

FIGS. 79A to 79C are flow cytometry plots showing MDA-231 (target) cells treated with normal human CD8 T (effector) cells at 1:5 of T to E ratio+bispecific antibody (pilot) at conc of 5 ug/ml+visudyne (2 µM).

Figure 80A:
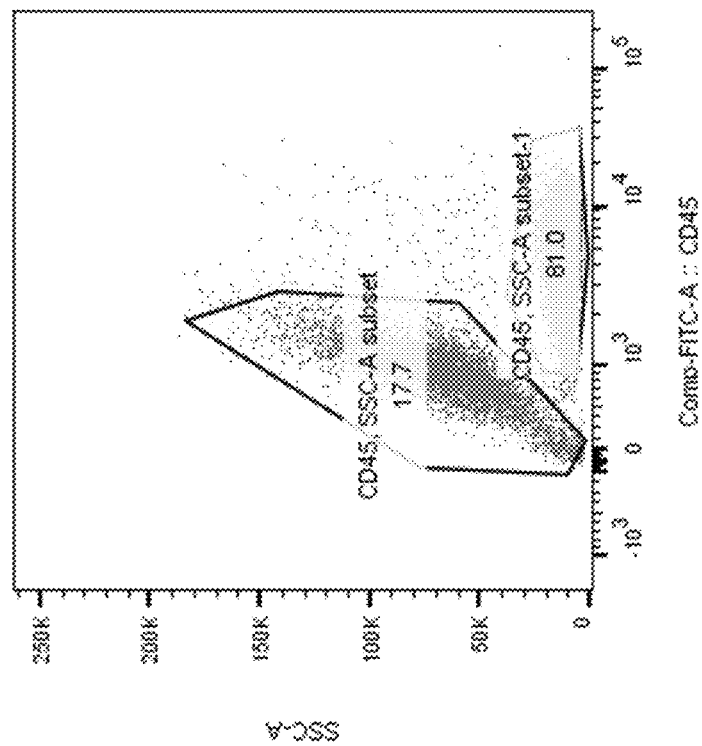
Figure 80C:
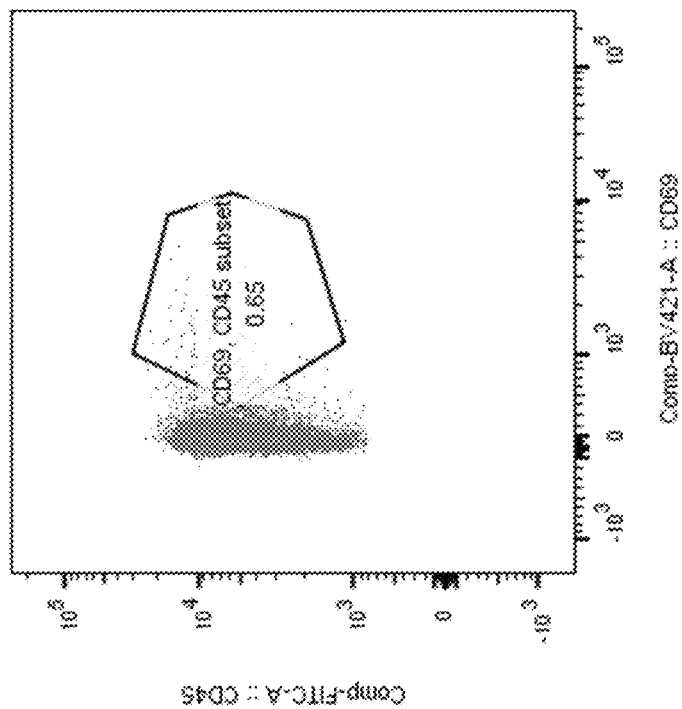
Figure 80B:
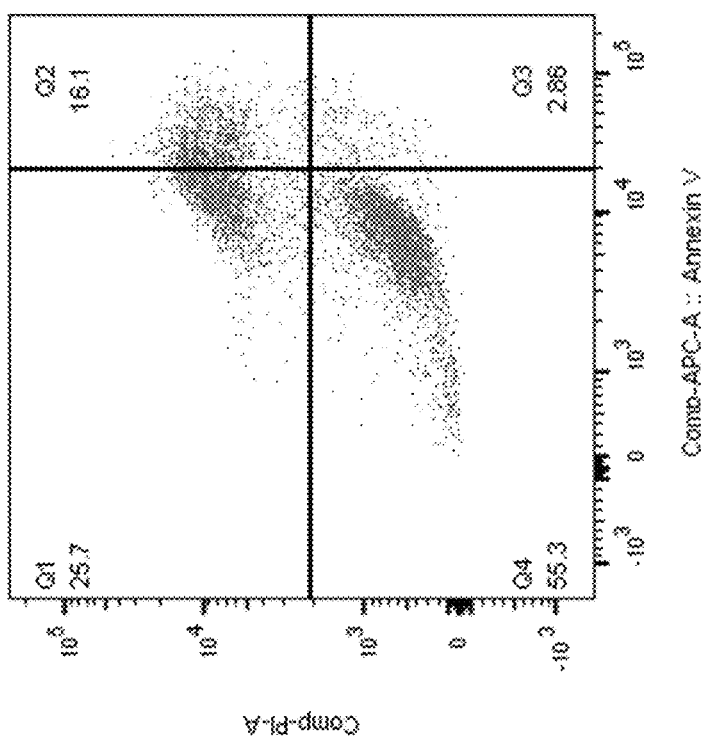

FIGS. 80A to 80C are flow cytometry plots showing MDA-231 (target) cells treated with normal human CD8 T (effector) cells at 1:5 of T to E ratio+visudyne (5 µM).

Figure 81B:
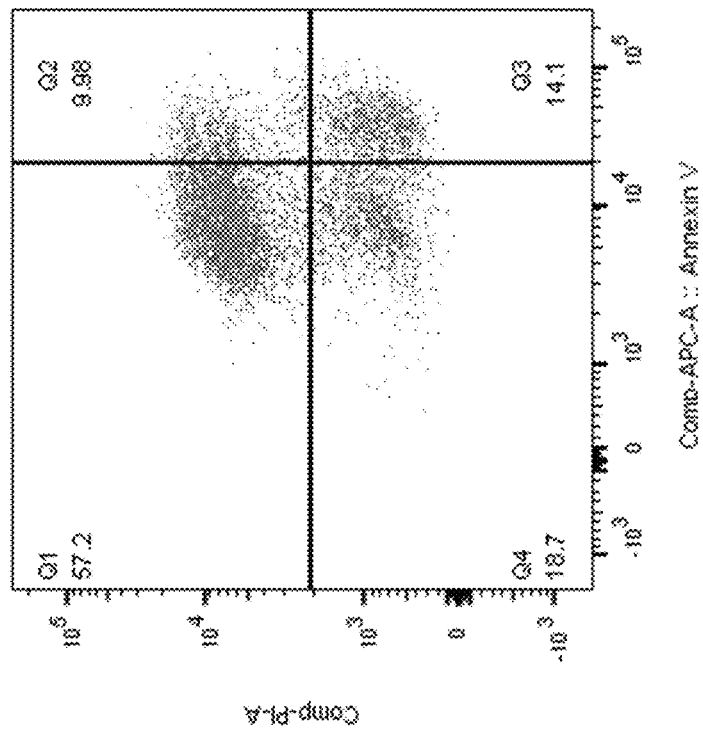
Figure 81A:
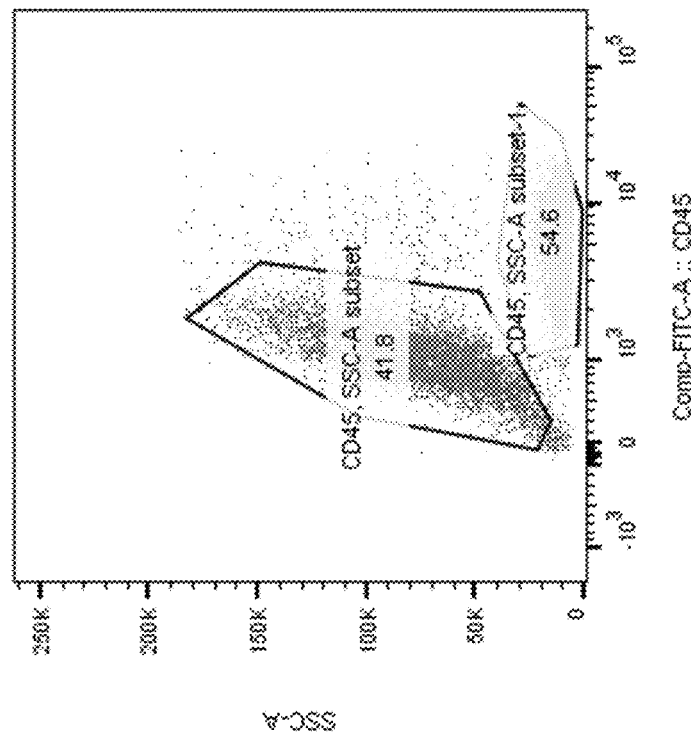
Figure 81C:
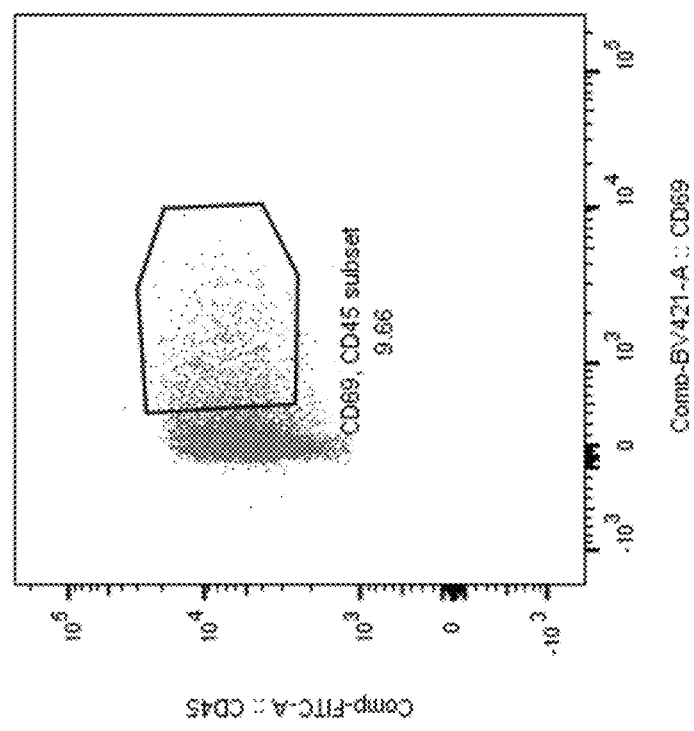

FIGS. 81A to 81C are flow cytometry plots showing MDA-231 (target) cells treated with normal human CD8 T (effector) cells at 1:5 of T to E ratio+bispecific antibody (pilot) at conc of 5 ug/ml+visudyne (5 µM).

Figure 82A:
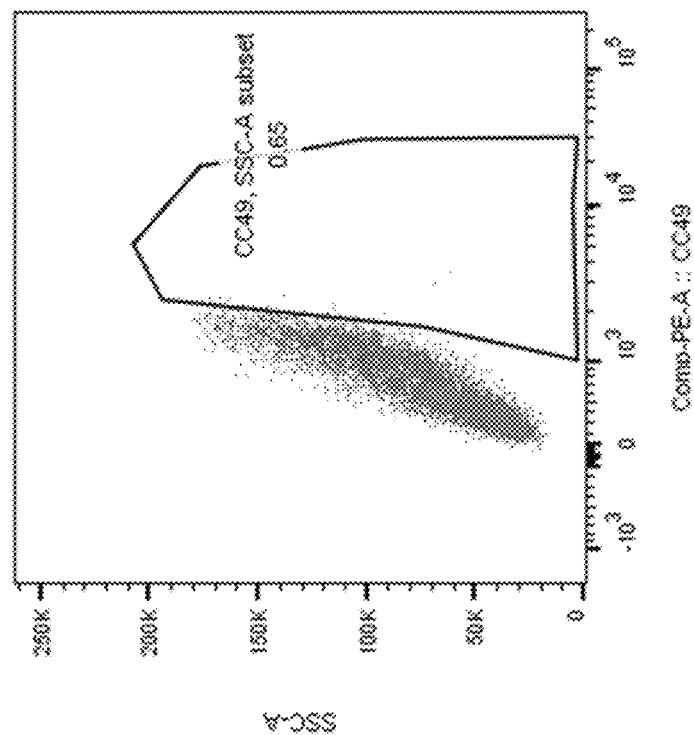
Figure 82C:
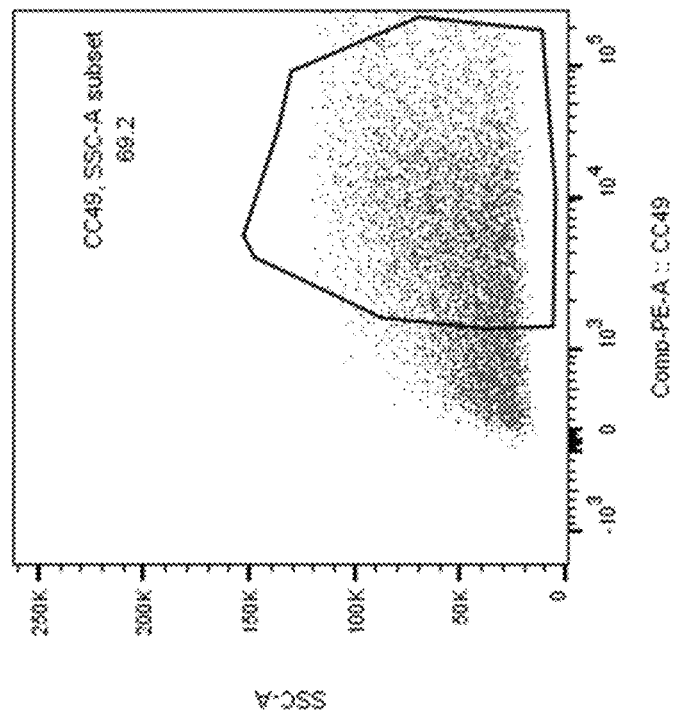
Figure 82B:
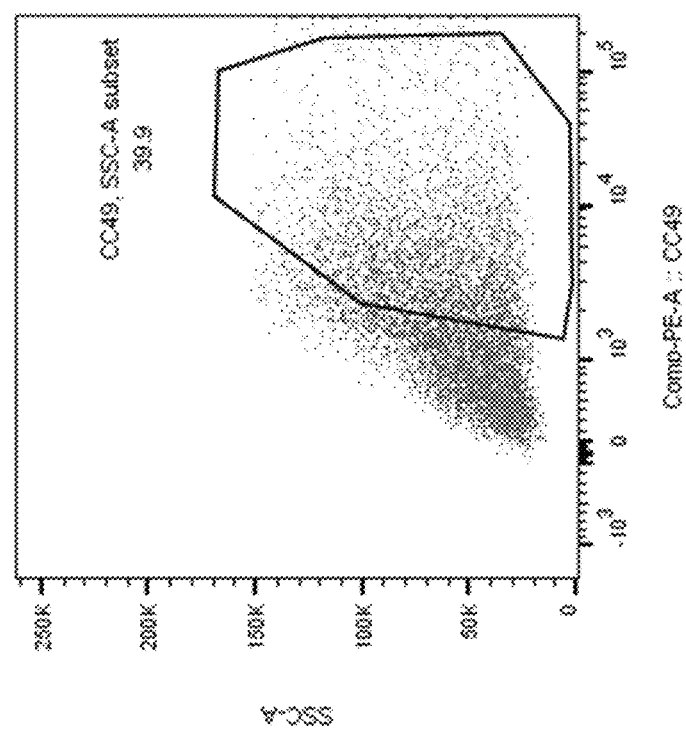

FIGS. 82A to 82C are flow cytometry plots showing CC49 expression in MCF-7 cells untreated as isotype control (FIG. 82A), stained (FIG. 82B), or FACS sorted for CC49 expression and passaged over time (FIG. 82C).

Figure 83B:
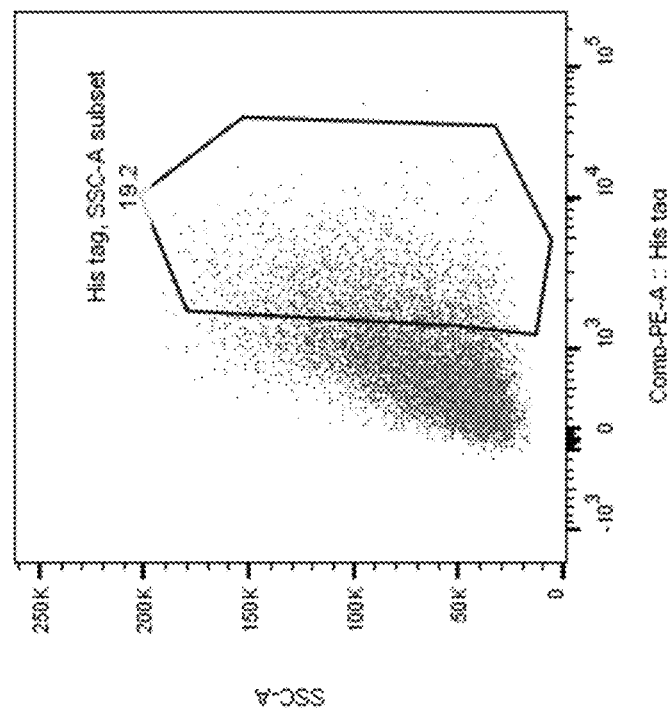
Figure 83A:
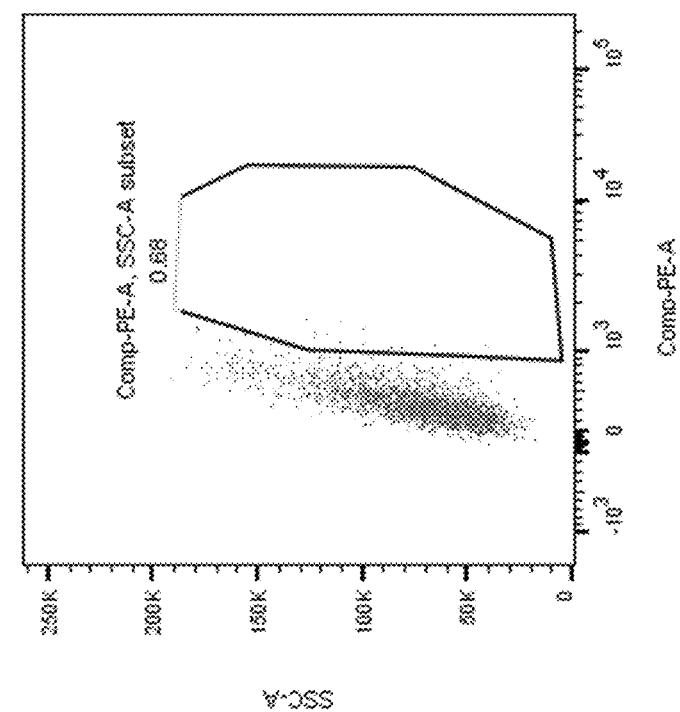
Figure 83D:
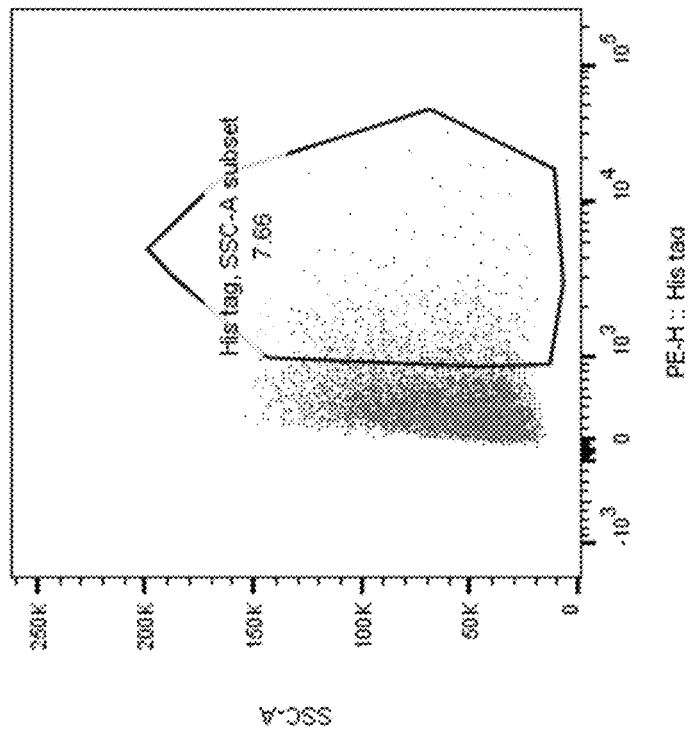
Figure 83C:
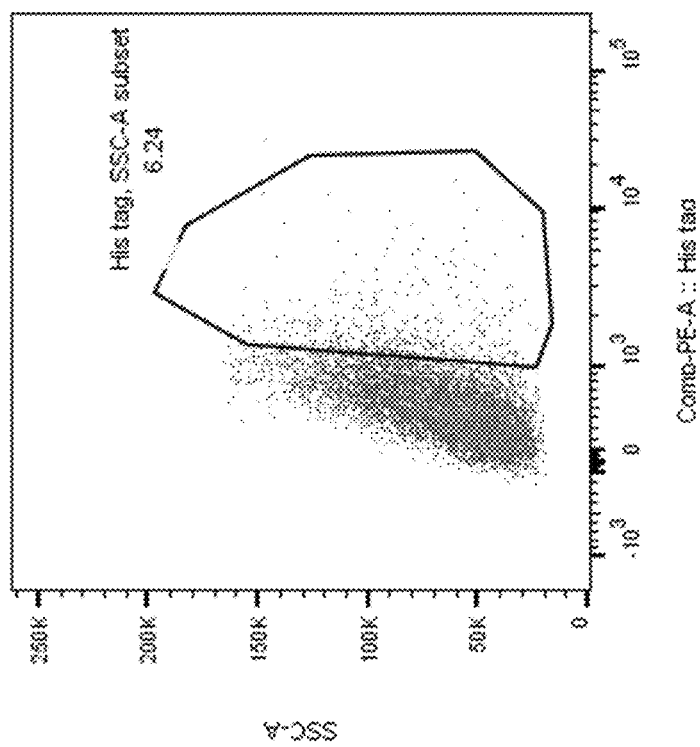
Figure 83F:
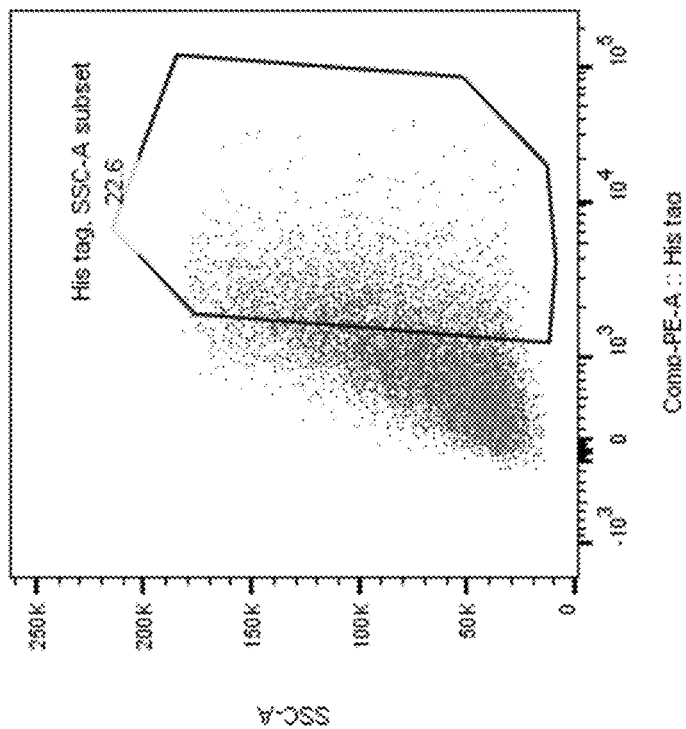
Figure 83E:
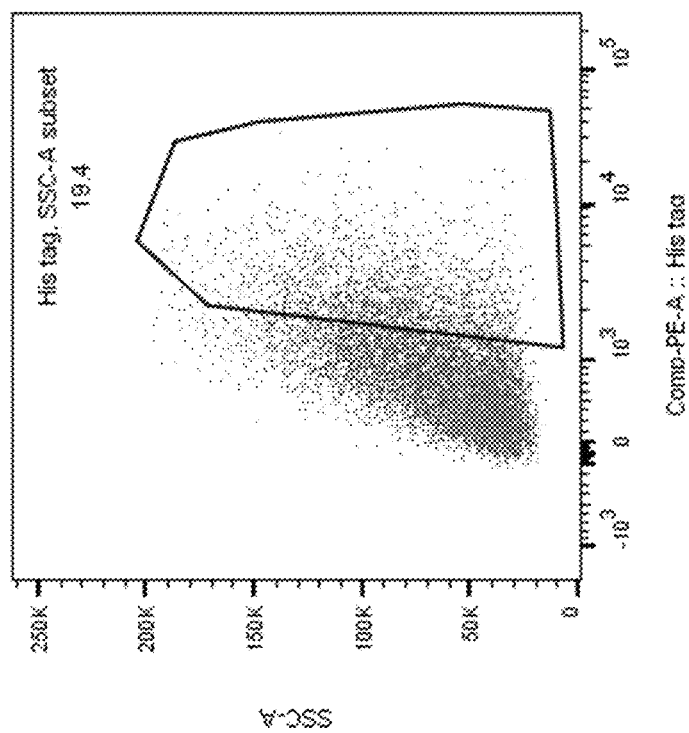

FIGS. 83A to 83F are flow cytometry plots showing 6×His tag expression for BiTe antibody binding to MCF-7 (CC49+ve) cells untreated as isotype control (FIG. 83A), treated with bispecific antibody old pilot (FIG. 83B), clone Ab4116 (FIG. 83C), clone Ab4117 (FIG. 83D), clone Ab4118 (FIG. 83E), and clone Ab3891 (FIG. 83F).

Figure 84B:
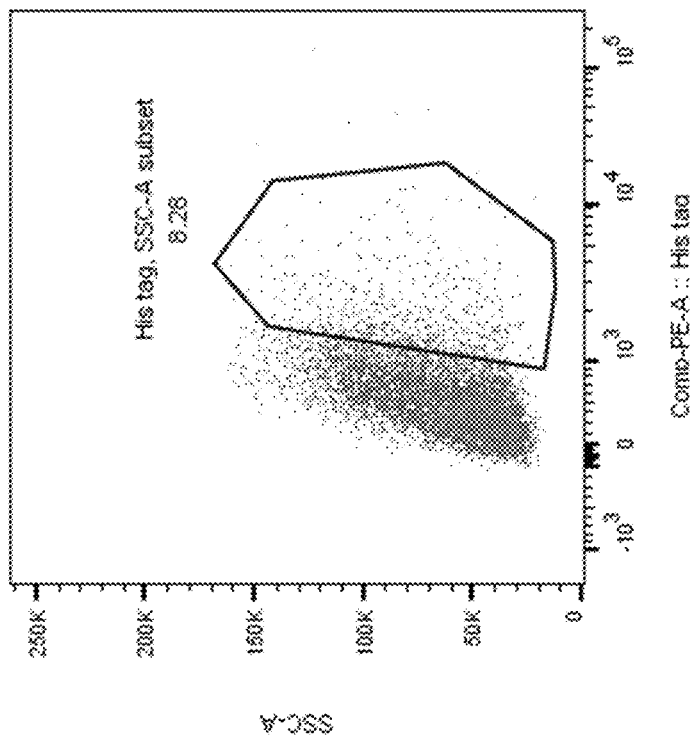
Figure 84A:
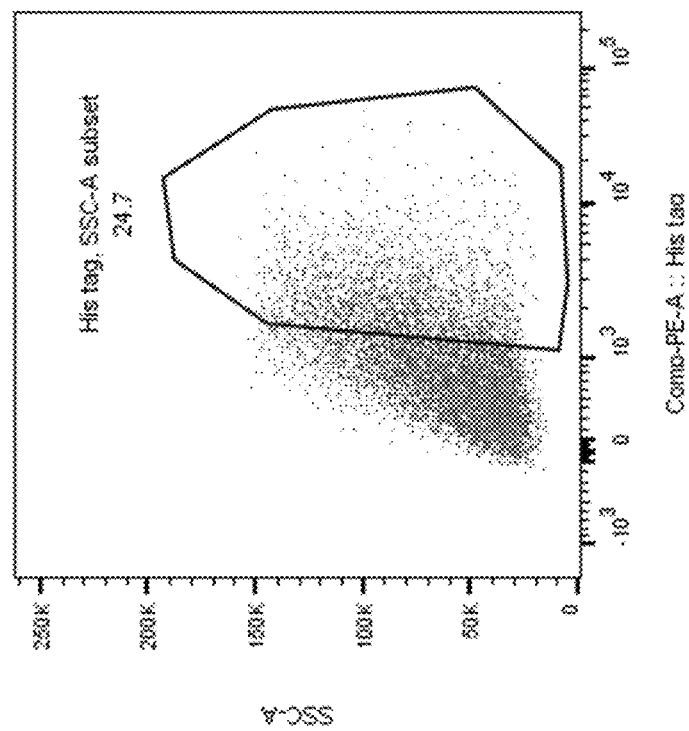

FIGS. 84A to 84E are flow cytometry plots showing 6×His tag expression for BiTe antibody binding to MCF-7 (CC49+ve FACS sorted) cells treated with bispecific antibody old pilot (FIG. 84A), clone Ab4116 (FIG. 84B), clone Ab4117 (FIG. 84C), clone Ab4118 (FIG. 84D), and clone Ab3891 (FIG. 84E).

Figures 84C, 85:
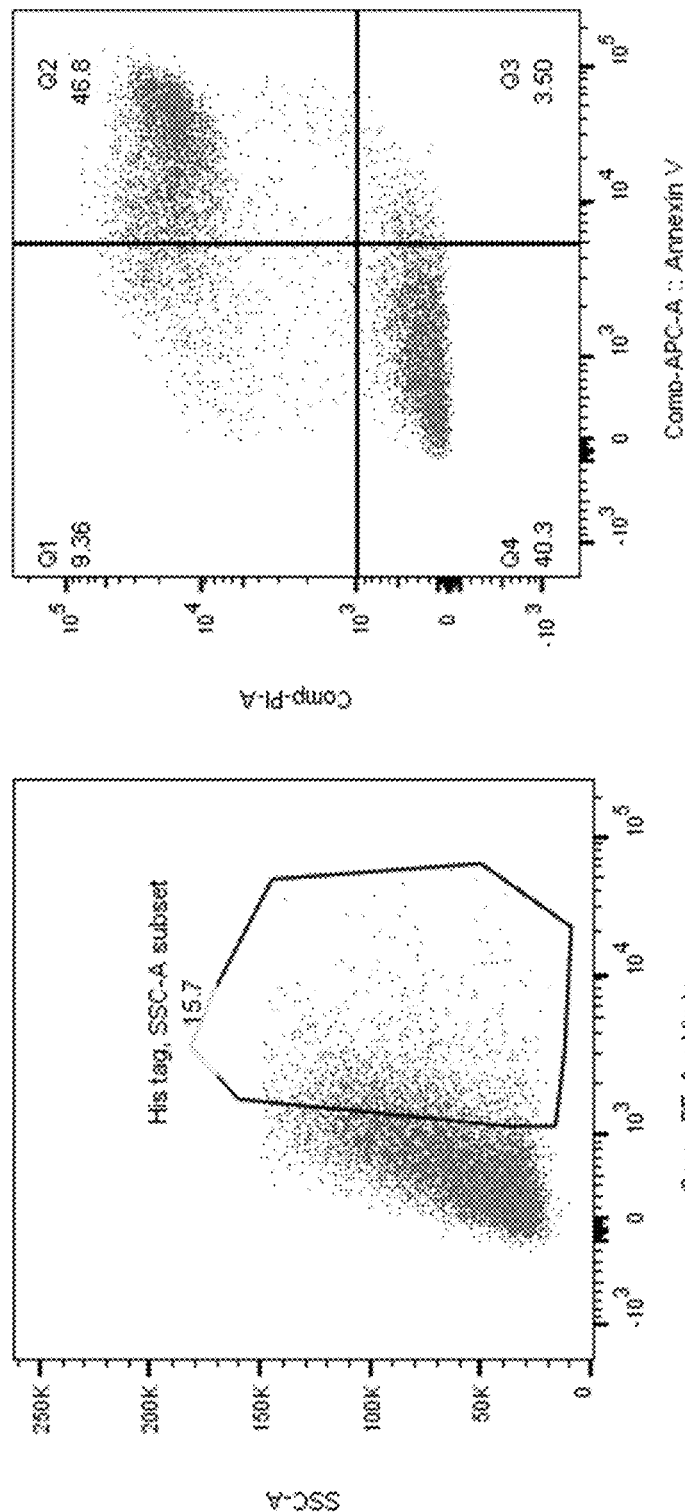

FIG. 85 is a flow cytometry plot showing untreated MCF-7 (target) cells as negative control.

Figure 86:
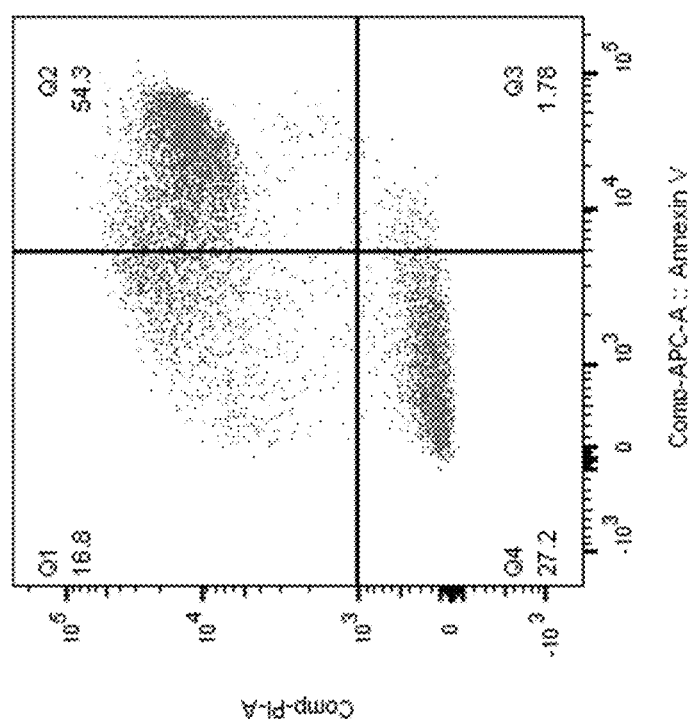

FIG. 86 is a flow cytometry plot showing MCF-7 (target) cells treated with bispecific antibody (old pilot) at conc of 5 µg/ml.

Figure 87:
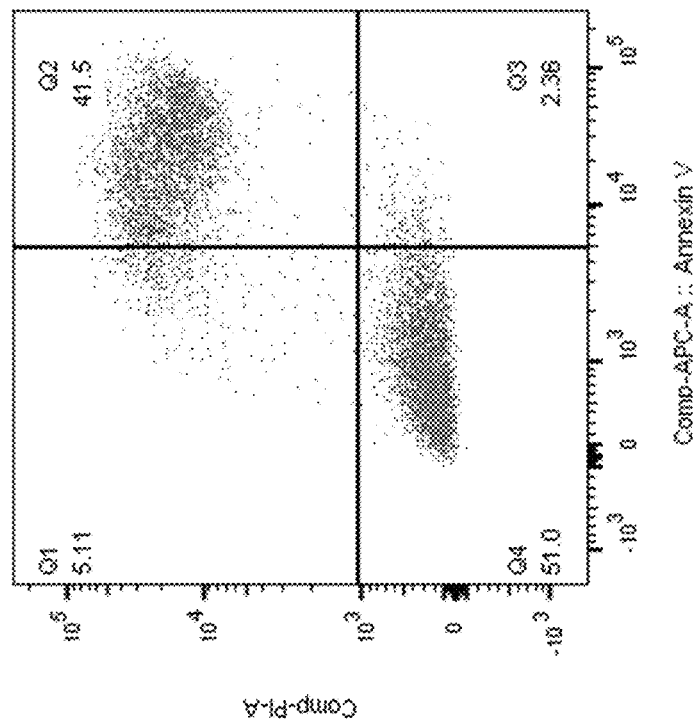

FIG. 87 is a flow cytometry plot showing MCF-7 (target) cells treated with bispecific antibody (clone Ab4116) at conc of 5 µg/ml.

Figure 88:
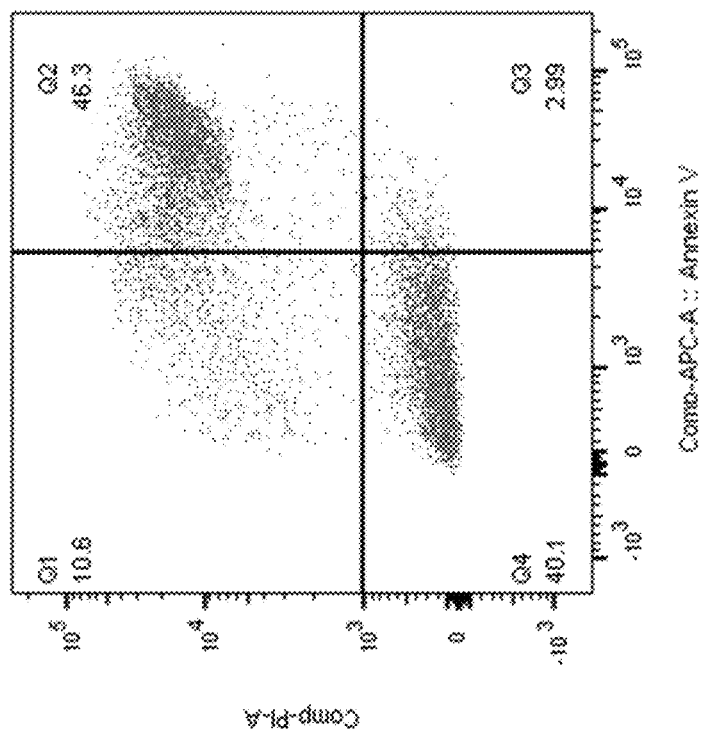
Figure 91A:
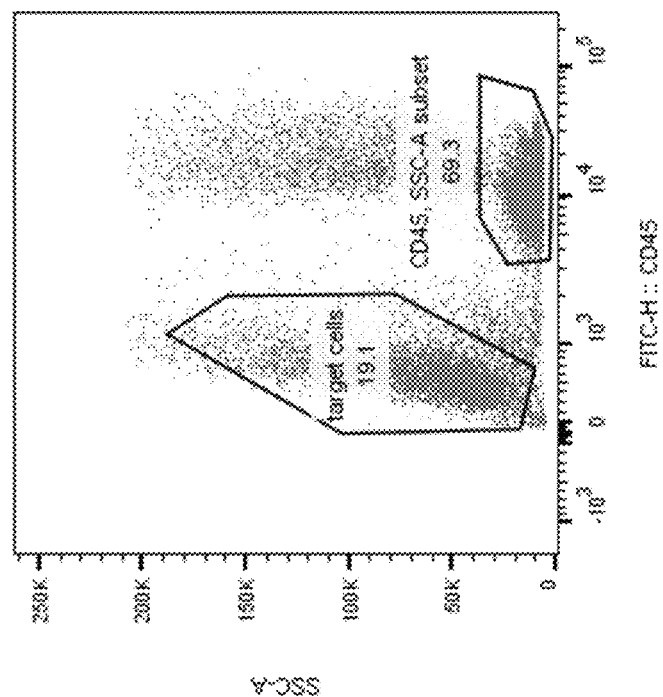

FIG. 88 is a flow cytometry plot showing MCF-7 (target) cells treated with bispecific antibody (clone Ab4117) at conc of 5 µg/ml.

Figure 89:
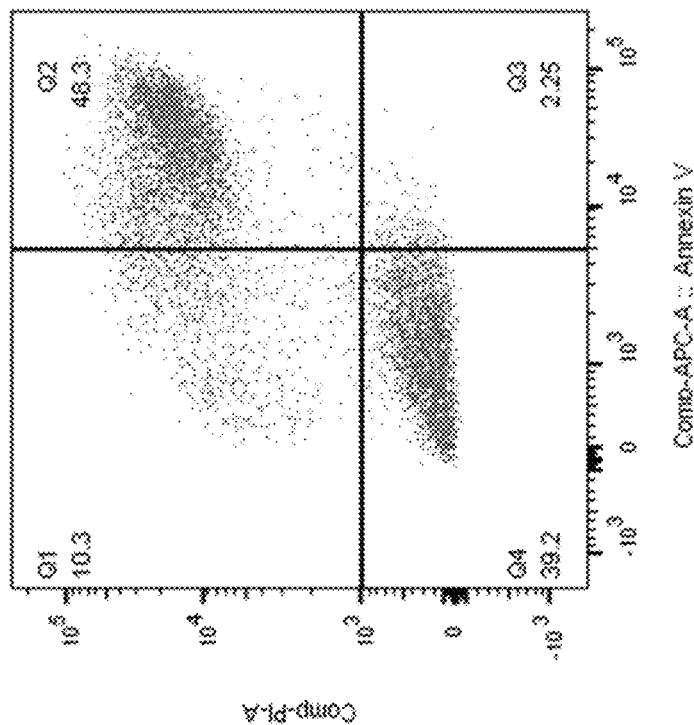

FIG. 89 is a flow cytometry plot showing MCF-7 (target) cells treated with bispecific antibody (clone Ab4118) at conc of 5 µg/ml.

Figure 90:
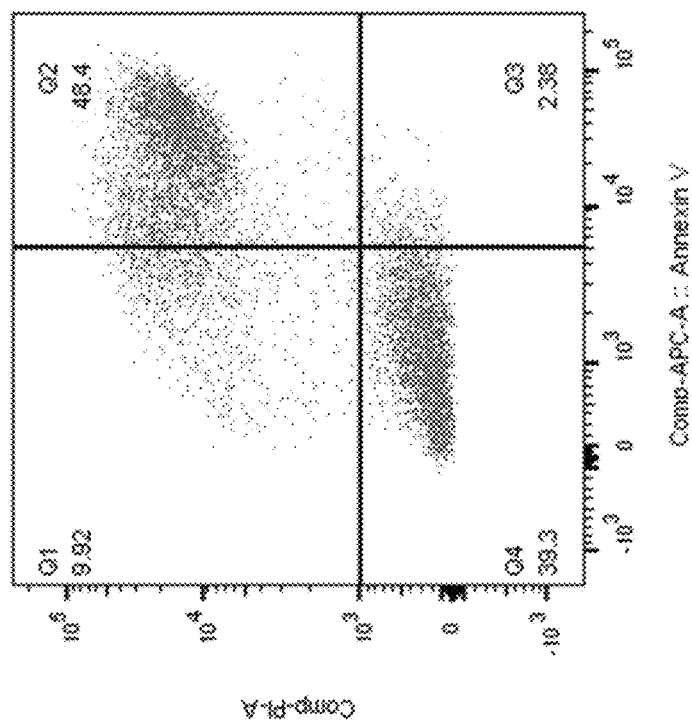
Figure 91C:
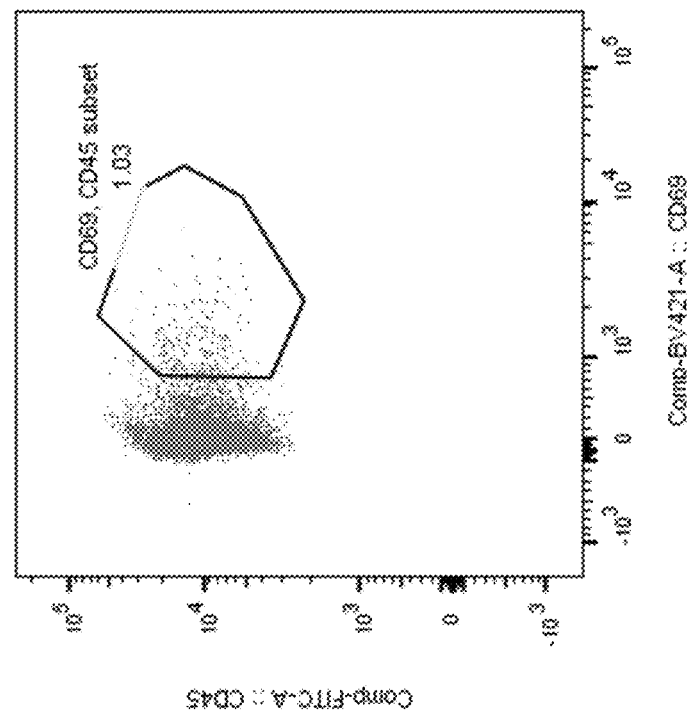
Figure 91B:
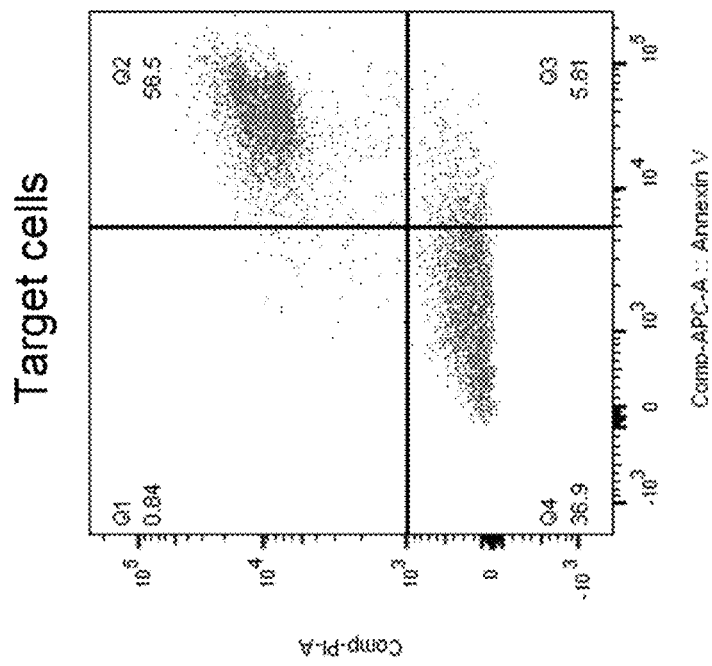
Figures 91D, 92A:
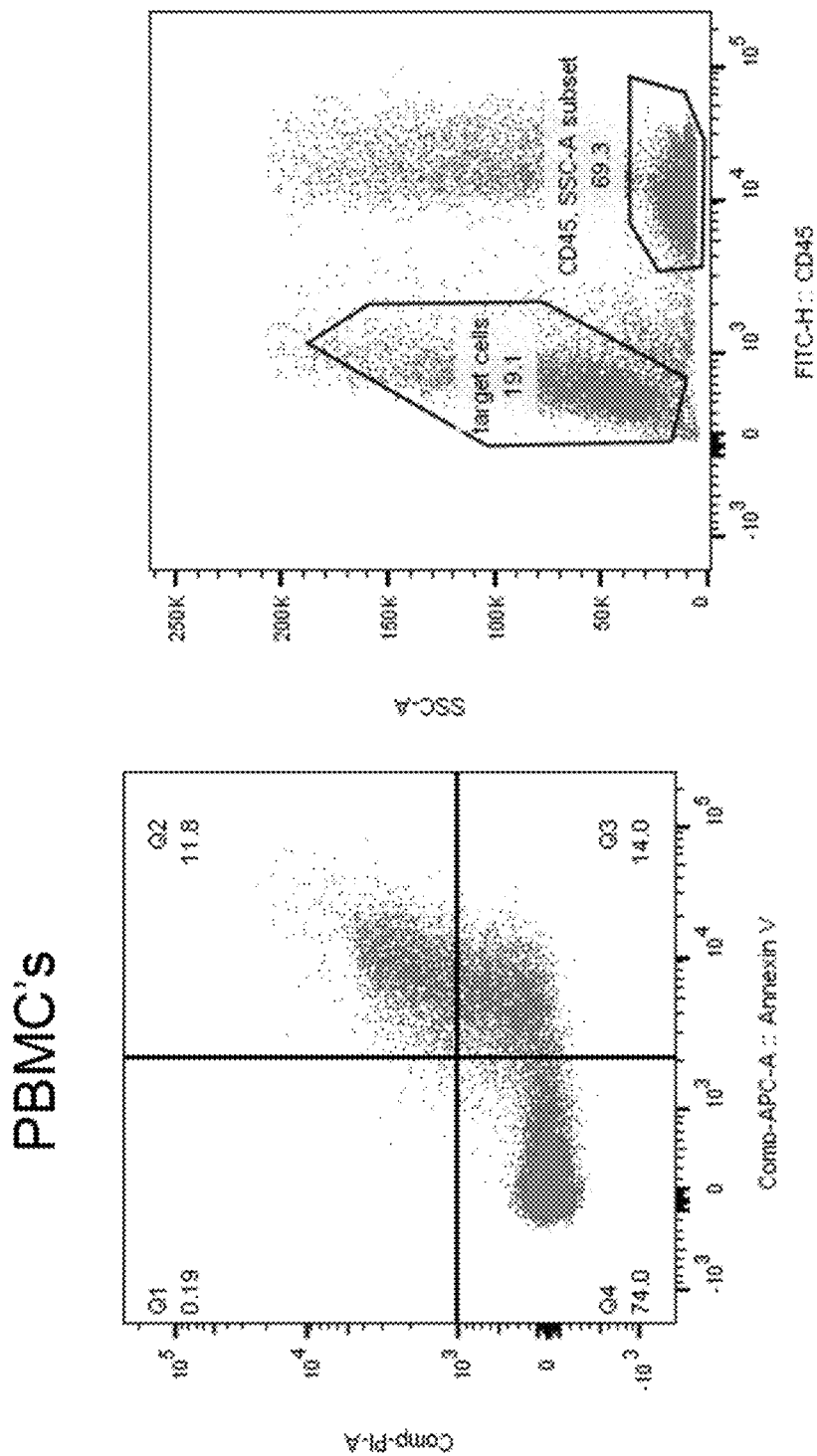
Figure 92C:
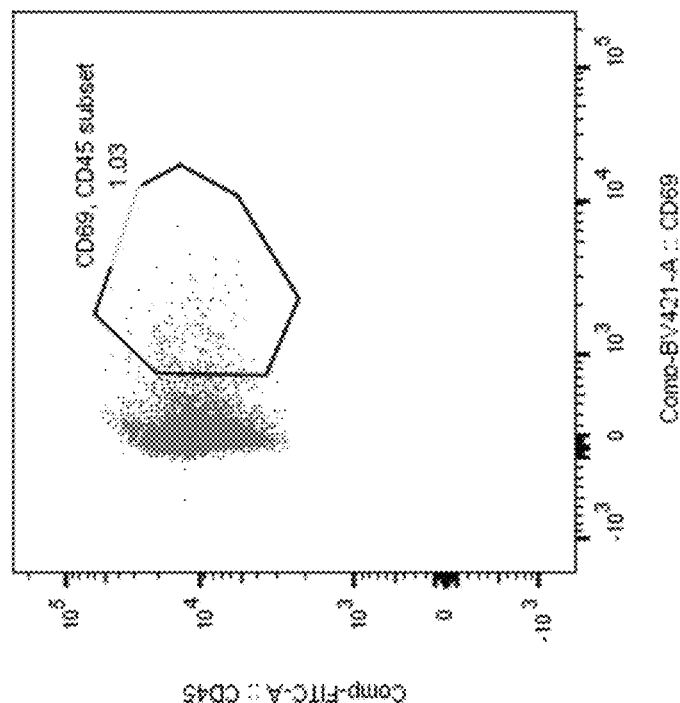
Figure 92B:
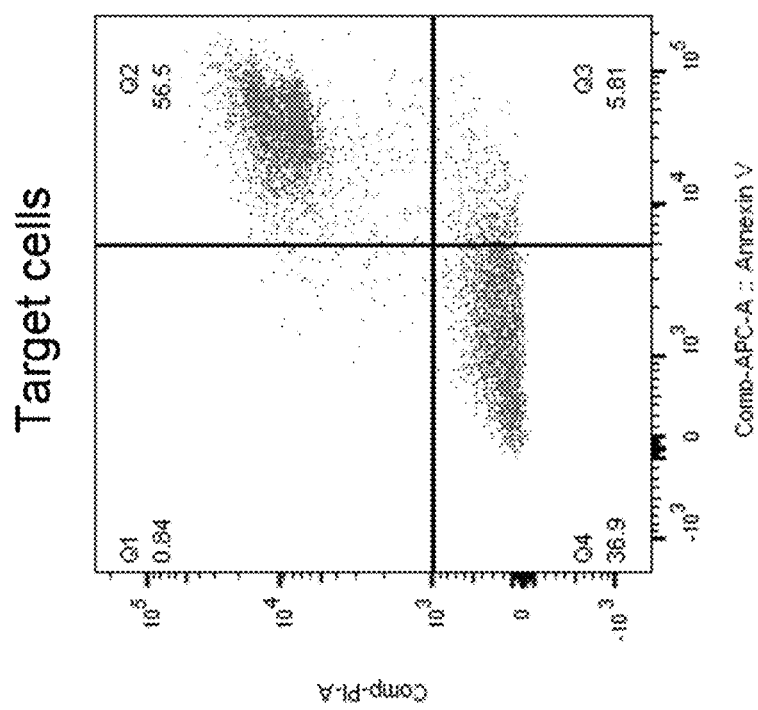
Figure 93A:
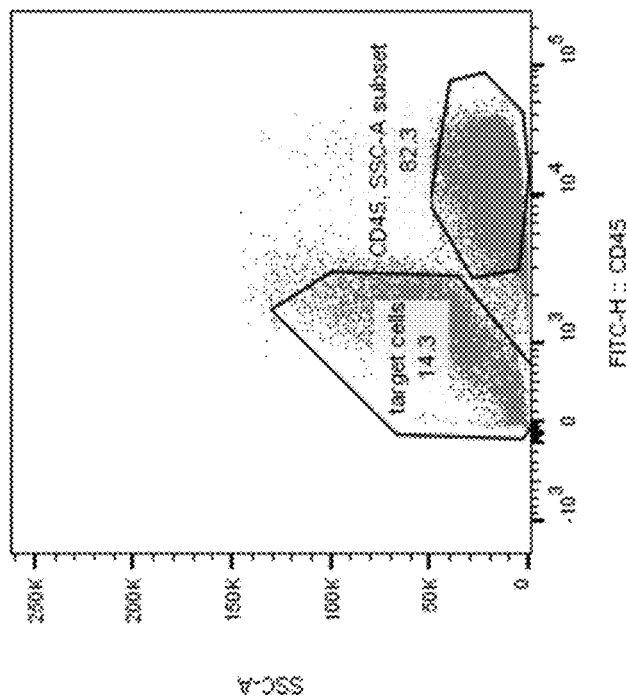
Figure 92D:
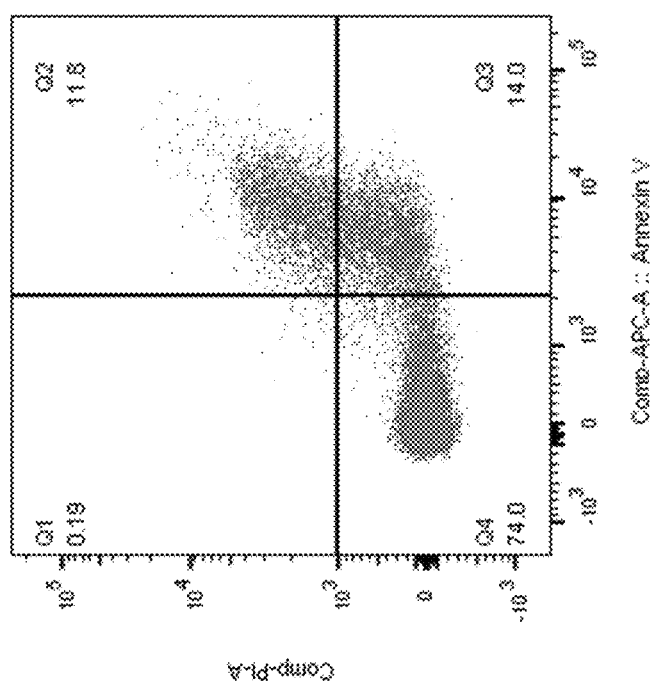
Figure 93C:
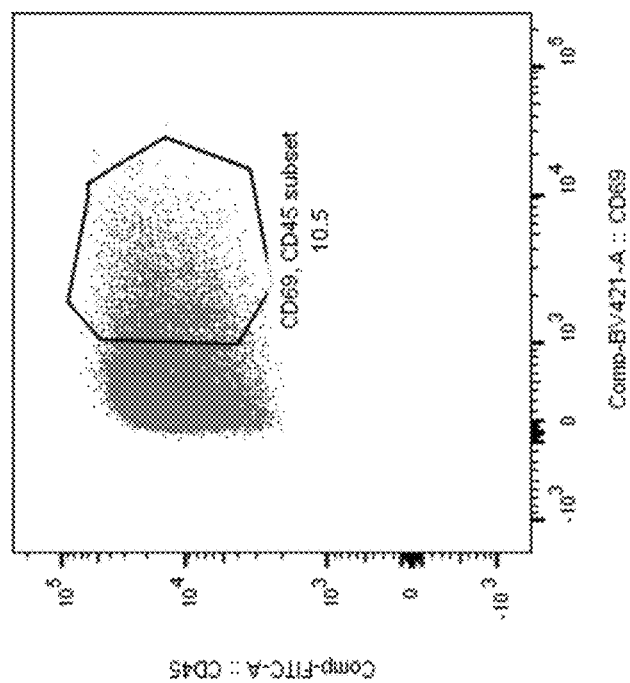
Figure 93B:
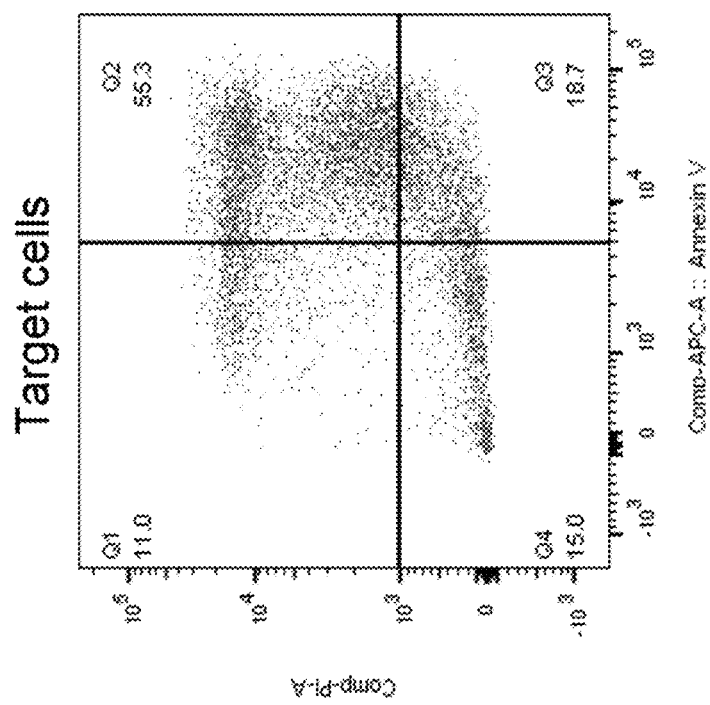
Figure 94A:
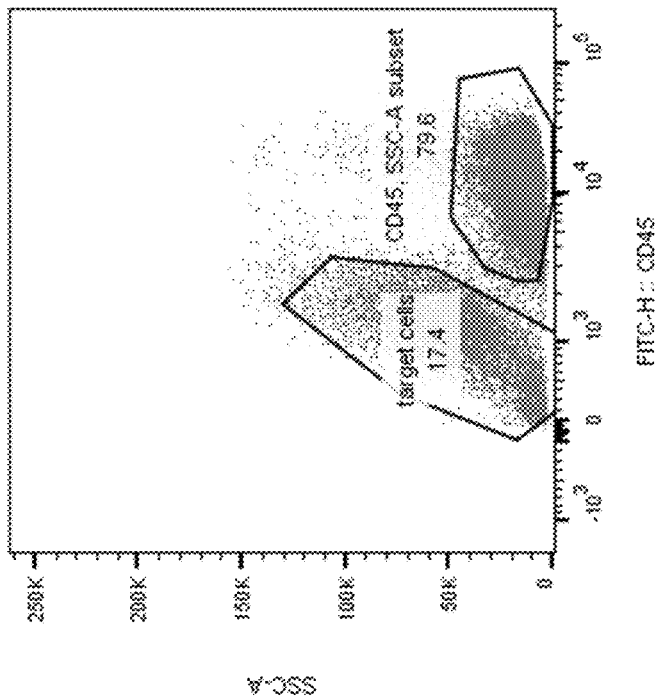
Figure 93D:
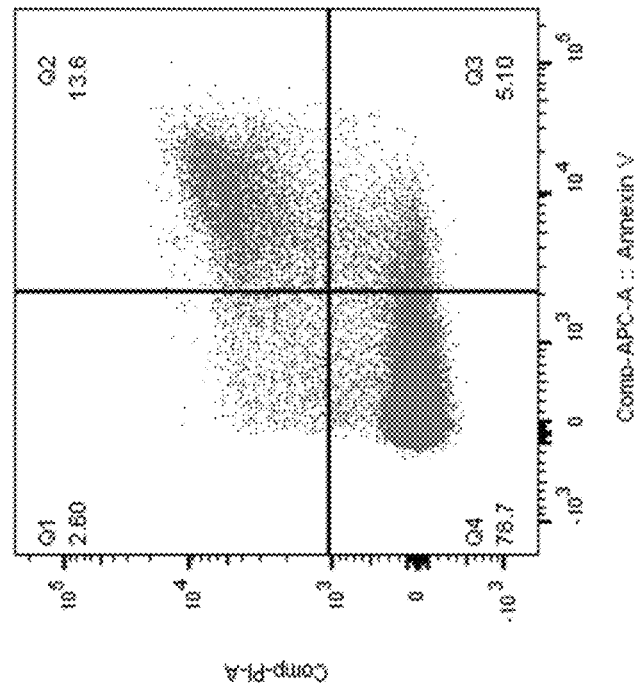
Figure 94C:
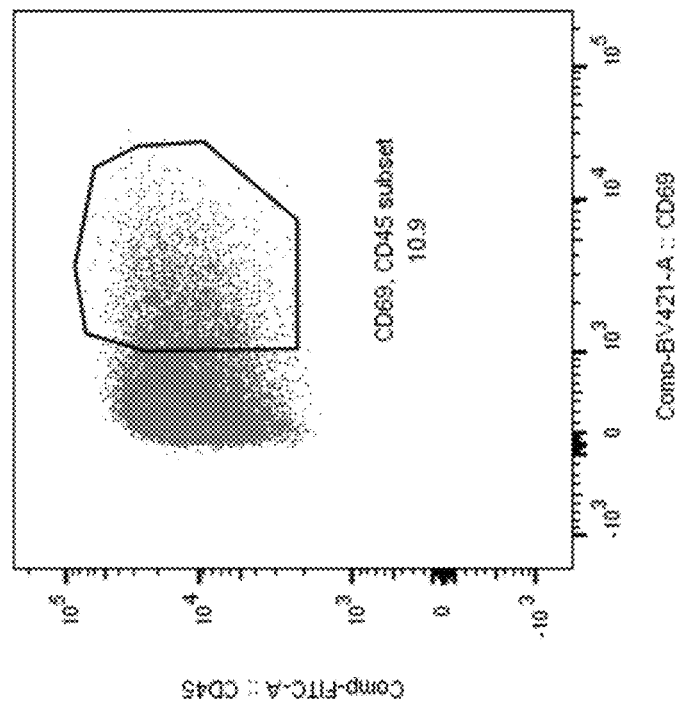
Figure 94B:
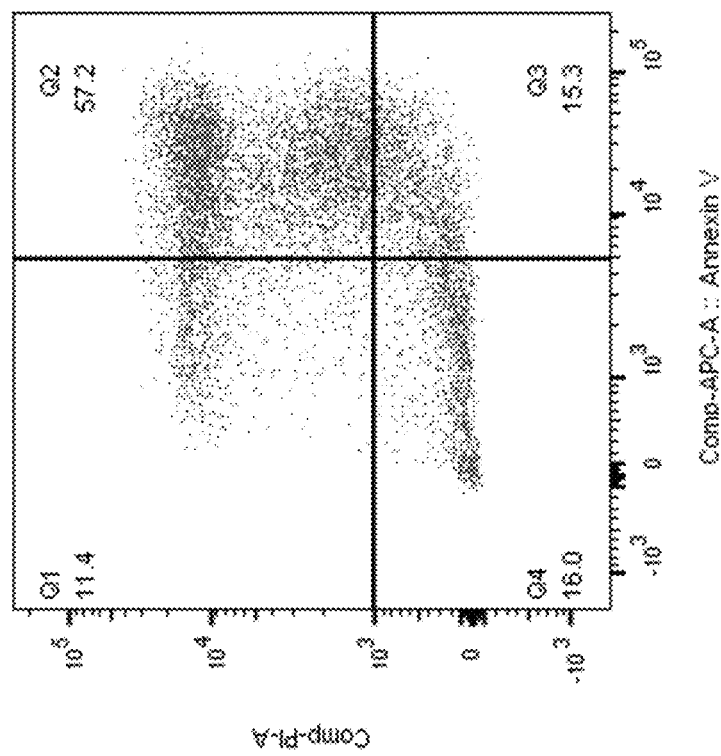
Figure 95A:
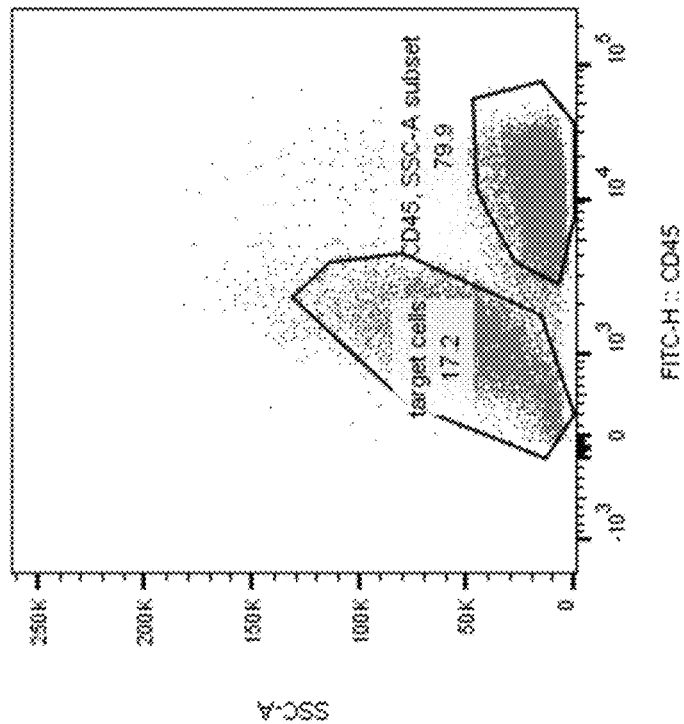
Figure 94D:
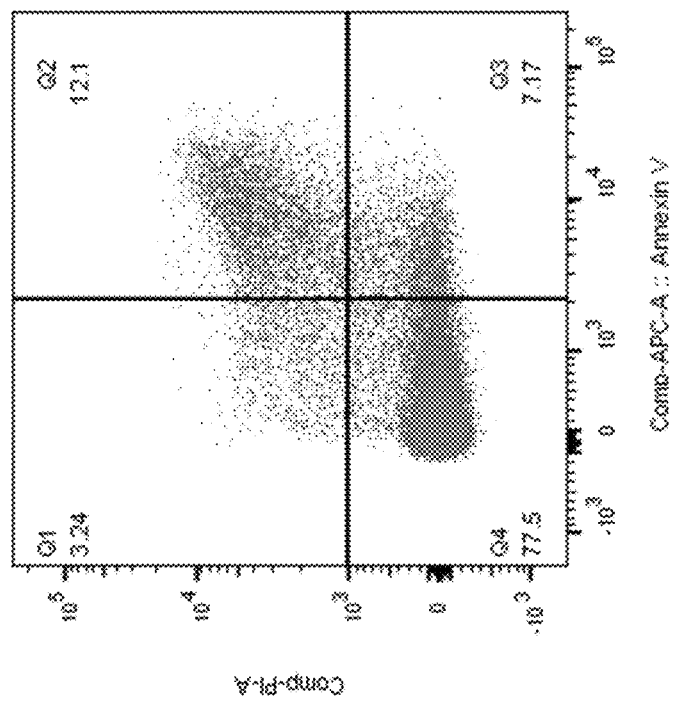
Figure 95C:
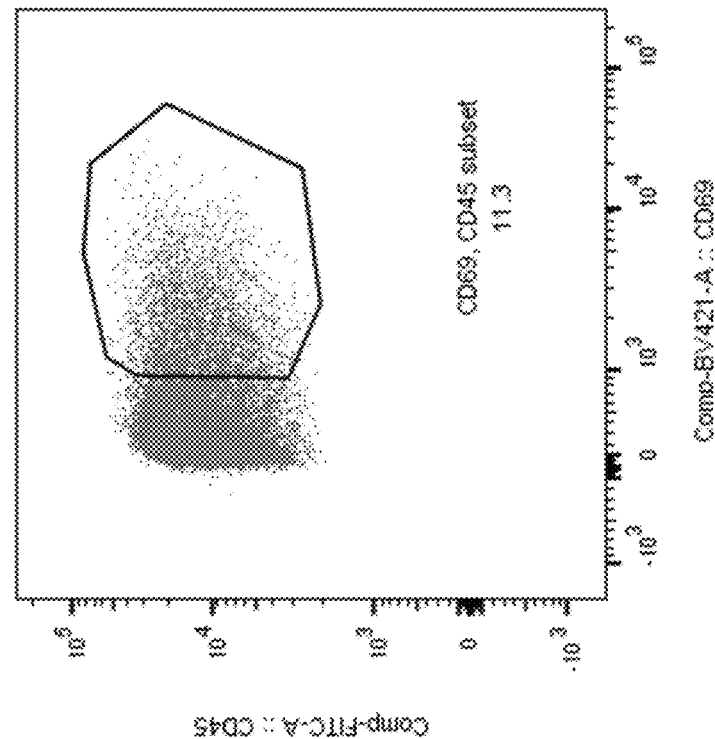
Figure 95B:
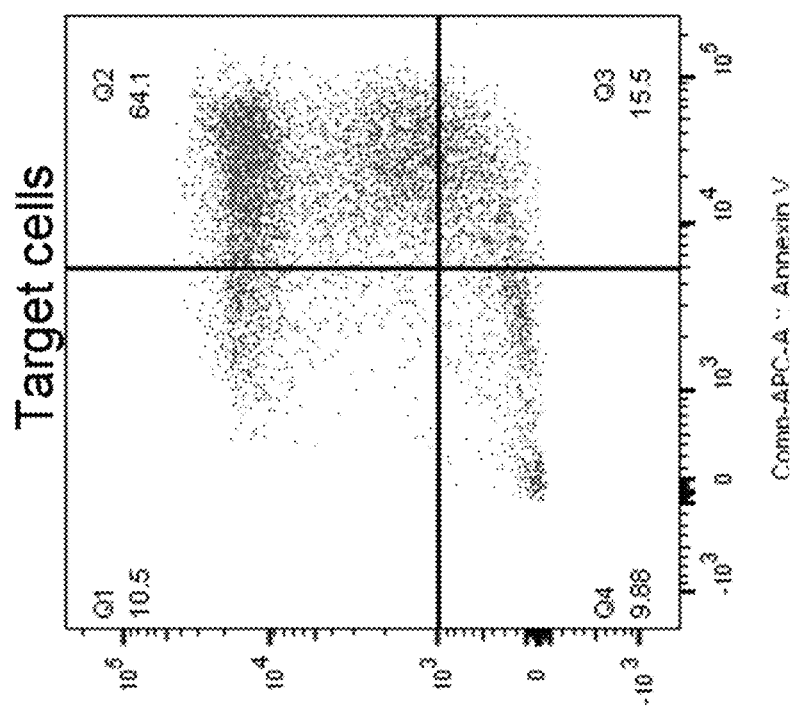
Figure 96A:
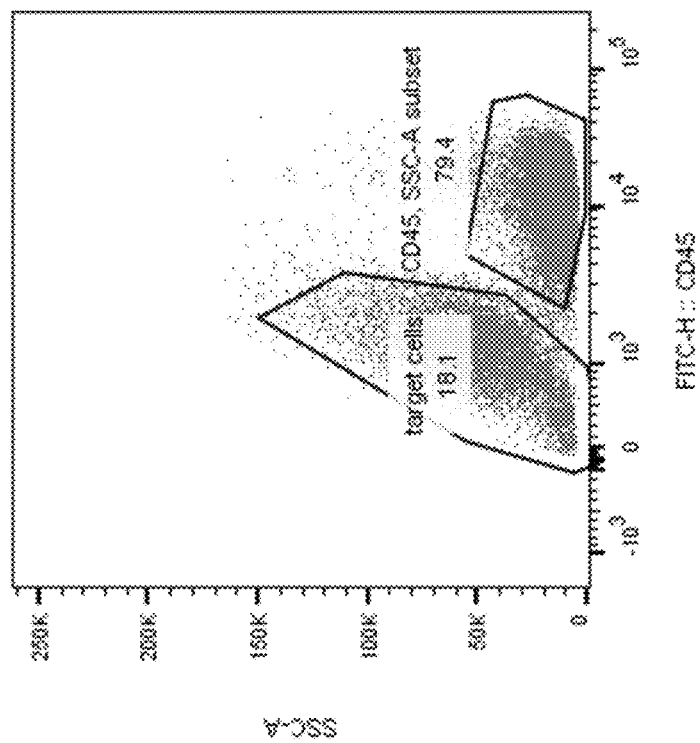
Figure 95D:
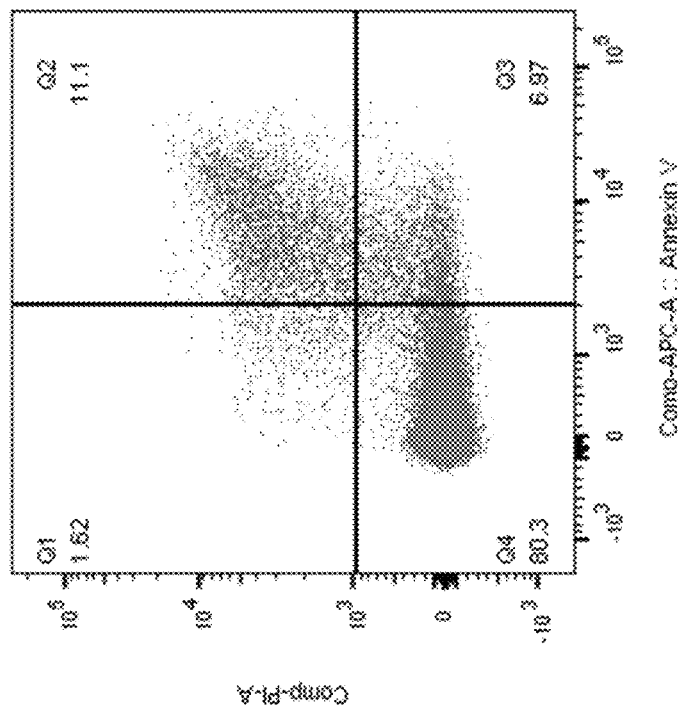
Figure 96C:
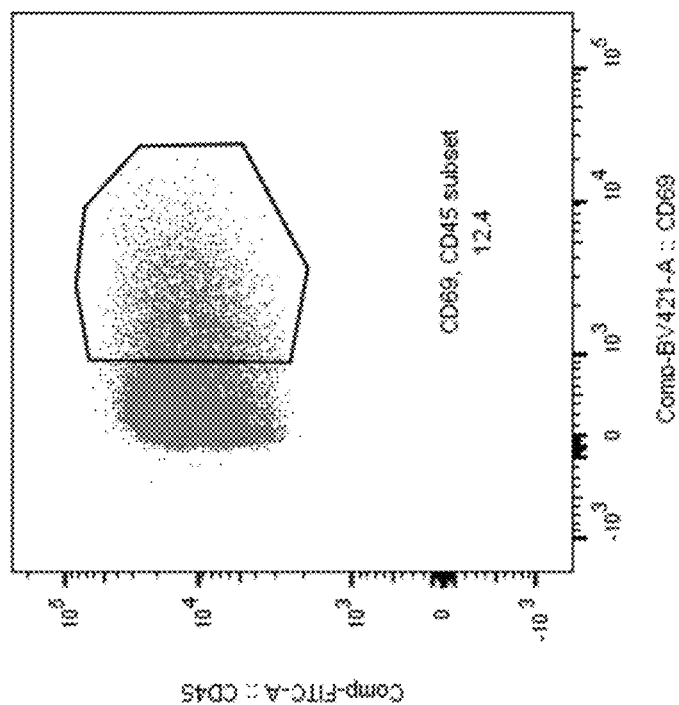
Figure 96B:
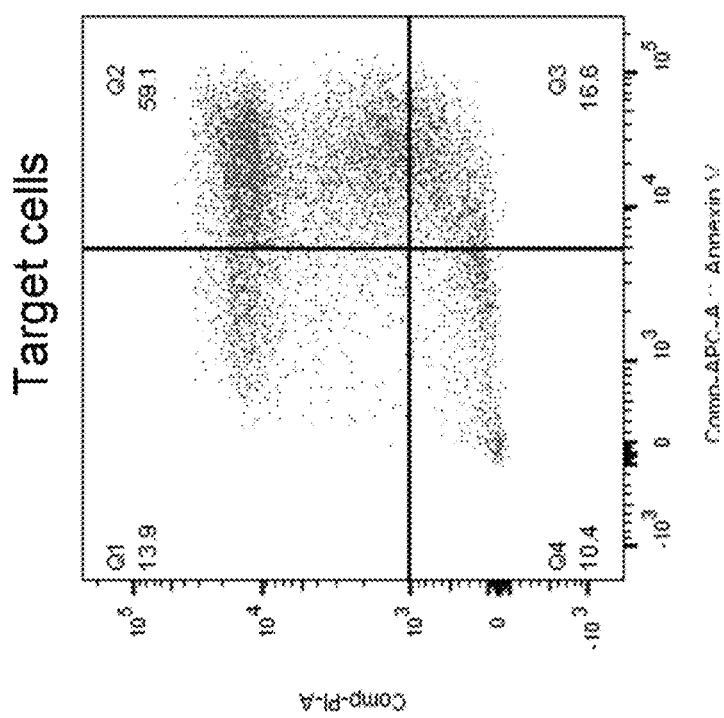
Figure 96D:
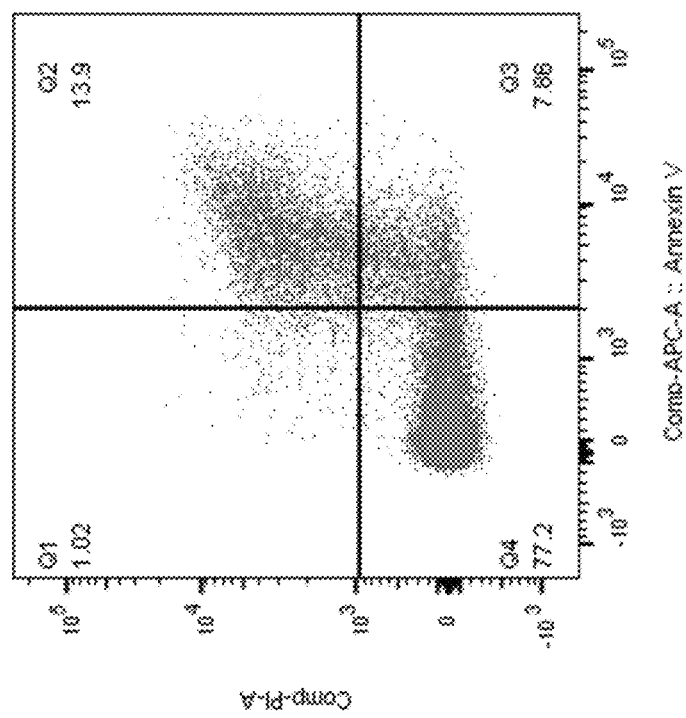

FIG. 90 is a flow cytometry plot showing MCF-7 (target) cells treated with bispecific antibody (clone Ab3891) at conc of 5 µg/ml.

FIGS. 91A to 91D are flow cytometry plots showing MCF-7 (target) cells treated with normal human CD8 T (effector) cells at 1:5 T to E ratio.

FIGS. 92A to 92D are flow cytometry plots showing MCF-7 (target) cells treated with normal human CD8 T (effector) cells at 1:5 of T to E ratio+bispecific antibody (old pilot) at conc of 5 ug/ml.

FIGS. 93A to 93D are flow cytometry plots showing MCF-7 (target) cells treated with normal human CD8 T (effector) cells at 1:5 of T to E ratio+bispecific antibody (clone Ab4116) at conc of 5 ug/ml.

FIGS. 94A to 94D are flow cytometry plots showing MCF-7 (target) cells treated with normal human CD8 T (effector) cells at 1:5 of T to E ratio+bispecific antibody (clone Ab4117) at conc of 5 ug/ml.

FIGS. 95A to 95D are flow cytometry plots showing MCF-7 (target) cells treated with normal human CD8 T (effector) cells at 1:5 of T to E ratio+bispecific antibody (clone Ab4118) at conc of 5 ug/ml.

FIGS. 96A to 96D are flow cytometry plots showing MCF-7 (target) cells treated with normal human CD8 T (effector) cells at 1:5 of T to E ratio+bispecific antibody (clone Ab3891) at conc of 5 ug/ml.

DETAILED DESCRIPTION

Disclosed are compositions and methods for targeted treatment of TAG-72-expressing cancers. In particular, disclosed herein are affinity maturated single chain variable fragment (scFv) antibodies that bind TAG-72 on cancer cells with higher affinity than prior TAG-72 scFv antibodies. These antibodies can be used alone. However, in some cases, the disclosed antibodies are conjugated to a therapeutic moiety for selective killing of TAG-72 expressing cancer cells.

Antibody-Drug Conjugates

Immunotoxins and antibody-drug conjugates are protein-based drugs combining a target-specific binding domain with a cytotoxic domain. Such compounds are potentially therapeutic against diseases including cancer, and several clinical trials have shown encouraging results.

Immunotoxins

Immunotoxins are protein-based therapeutics comprising at least two functional domains, one allowing them to bind specific target cells, and one that kills the cells following internalization.

Plants and fungi produce a number of molecules with defensive functions, to protect themselves against pathogens, such as microorganisms, and predators, such as insects. These defense proteins include ribosome-inactivating proteins, which are capable of inhibiting RNA translation. A broad spectrum of activities, encompassing antiproliferative, antitumor, immunomodulatory, antiviral, antifungal and anti-insect activities, have been attributed to these proteins.

These include, for example, holotoxins (RIPs type II) composed of a catalytic "A-chain" disulfide-bonded to binding "B-chains", and "hemitoxins" (RIPs type I), such as gelonin, saporin, etc., containing only a catalytic chain. The bacterial toxins *Pseudomonas* exotoxin (PE) and difteria toxin (DT) are single-chain proteins, containing both binding and catalytic domains. Both plant and bacterial toxins are able to bind to the cell surface, and can internalize into endosomes, translocate into the cytosol, and catalytically inhibit ribosomes, which kills the cell by apoptosis.

Type II RIPs have been isolated from plants belonging to the Asteridae, Liliidae, Magnoliidae and Rosidae, the bulk belonging to the Asteridae. They are divided into toxic type II RIPs and non-toxic type II RIPs. The toxic ones include ricin from *Ricinus communis*, abrin from *Abrus precatorius*, volkensin from *Adenia volkensii*, and modeccin from *Adenia digitata*. Nigrins from *Sambus nigra*, and ebulin from *S. ebulus* are non-toxic RIPs. Nigrin b has much higher cell-free translation inhibitory potency, but much lower in vitro cytotoxicity and in vivo toxicity, than does ricin, due to the replacement of Tyr 249 in ricin by Phe in ebulin 1. Agglutinin-I from *Abrus precatorius* seeds is a type II RIP, with greatly attenuated toxicity compared with abrin, another type II RIP isolated from the same seeds, due to replacement of Asn-200 in abrin with Pro-199 in agglutinin I.

Type I RIPs have been isolated, most often from seeds and sometimes from leaves and roots of plants belonging to the Asteridae, Caryophyllidae, Liliidae, Magnoliidae, and Rosidae, the greatest number being isolated from the Rosidae, which comprises Cucurbitacea, Euphorbiaceae and Fabaceae.

In the last twenty years, RIPs of new structure have been isolated from flowering plants and mushrooms. Some of these RIPs possess a molecular mass in the vicinity of 20 kDa and an N-terminal amino acid sequence that is distinctly different from those of the 30-kDa type I RIPs, which often demonstrate remarkable homology to one another. Small RIPs with a molecular mass of 10 kDa or below have been purified from the seeds of several gourds, which are members of the Cucurbitaceae. These are characterized by an abundance of arginine and glutamate or glutamine residues. Mushrooms produce RIPs with various molecular masses. The N-terminal sequences of some of the mushroom RIPs isolated to date are similar to one another, but others are widely dissimilar. These new RIPs generally exhibit biological activities similar to those of type I RIPs.

Type I RIPs with small molecular mass have been isolated from plants both in the Cucurbitaceae family and outside it. Mushrooms and other fungi also produce type I RIPs. The N-terminal amino acid sequences of these low-molecular-mass single-chained plant type I RIPs and mushroom type I RIPs, are distinct from those of classical type I and type II RIPs from plants. The biological activities of these low-molecular-mass type I RIPs, which include, alongside translation-inhibitory, also N-glycosidase and antifungal activities, await full elucidation. The active site residues of RIPs are distinct from the antigenic site residues, and RIPs with fully-preserved biological activities, but with decreased immunogenicity, have been produced. Other modern anticancer approaches concerning toxins are based on transcriptional targeting and protease specific targeting (Protease activated toxins).

Antibody Drug Conjugates

Antibody-drug conjugates (ADCs) are anticancer treatment agents that combines the selectivity of targeted treatment with the cytotoxic potency of chemotherapy drugs. In some cases, the disclosed scFv antibodies that bind TAG-72 are combined with one or more therapeutic moieties, such a chemotherapy drugs that are capable of killing TAG-72 expressing cancer cells.

Optimal chemotherapy drugs for ADC should be extremely potent, being effective at picomolar or nanomolar concentrations. There are two main categories of cytotoxic drugs used in ADC development: microtubule inhibitors and DNA-damaging drugs. Auristatins block tubulin assembly and cause G2/M phase cell cycle arrest. Monomethyl auristatin E (MMAE) is the cytotoxic payload of brentuximab vendotin and has a free drug $IC_{50}$: $10^{-11}$-$10^{-9}$ allowing it to be effective in the low nanomolar range. Maytansinoids, another class of tubulin inhibitors, have also been used successfully in the ADC development. The cytotoxic payload of trastuzumab emtansine (T-DM1) DM1 is a highly potent maytansinoid, developed by Immunogen, with a free drug $IC_{50}$: $10^{-11}$-$10^{-9}$. Another maytansinoid drug, DM4 incorporated on SAR3419, is being investigated in phase II trials exhibiting significant 'bystander effect' as the ADC's metabolites have lipophilic properties allowing crossing of the cellular membrane. Tubulysins are a promising new class of tubulin inhibitors. Tubulisin analogues were successfully conjugated to trastuzumab forming a stable and potent ADC. The DNA-damaging agents have the ability to be active throughout the different cell cycle phases. Duocarmycin is a powerful cytotoxic alkylating compound that binds to the minor groove of DNA and has shown activity against various multidrug-resistant models. Duocarmycin-based ADCs are currently under investigation in a phase 1 trial setting conjugated to the anti-HER-2 antibody, trastuzumab.

Calicheamicin is a potent anti-tumor antibiotic that causes double-strand DNA breaks and rapid cell death by binding to the DNA's minor groove. It is less dependent on cell cycle progression making it potentially useful against TICs who have lower rates of proliferation. Gemtuzumab ozogamicin and other ADCs such as inotuzumab ozogamicin in non-Hodgkin lymphoma and MDX-1203 in renal cancer are using these agents.

A potential new drug under investigation is a-amanitin, an RNA polymerase II inhibitor in the picomolar range, derived from the mushroom, Amanita phalloides. Other topoisomerase inhibitors under investigation is the SN38, the active metabolite of irinotecan. Another new category is the pyrrolobenzodiazepines (PBDs) that bind to discrete DNA sequences causing lethal lesions and have interestingly not been found to have cross-resistance with common chemotherapeutic agents.

In some cases, the drug conjugate comprises calicheamicin, Monomethyl auristatin E (MMAE), Monomethyl auristatin F (MMAF), DM1, DM3, DM4, doxorubicin, maytansine, a camptothecin analog (e.g. SN-38), PBD dimer, auristatin, duocarmycin, or maytansine.

A different approach, but in line with ADC principles, are the radioimmunoconjugates where radionuclides are the cytotoxic payloads linked to monoclonal antibodies. Two radioimmunoconjugates targeting CD20 have been approved for treatment of refractory HodHL, (Yttdum-90-ibritumomab tiuxetan and iodine-131-tositumomab). Despite its efficacy due to under-utilisation tositumomab manufacturer has discontinued its production. In solid tumours, radioimmunoconjugates are being investigated, particularly in treating minimal residual disease in prostate and Bispecific Antibodies In some embodiments, the disclosed composition is a bi-specific T-cell engager (BiTE) that is able to direct cytotoxic T-cells to TAG-72-expressing cancers. For example, in some cases, the disclosed scFv antibodies that bind TAG-72 are incorporated into bispecific antibodies, e.g., to engage T-cells that can kill the cancer cells. Also provided are fusion polypeptides capable of forming a bispecific engineered antibody that is able to engage T-cells to destroy TAG-72 expressing malignant cells. The engineered antibody may comprise for example, at least one scFv, at least one Fab fragment, at least one Fv fragment, etc. It may be bivalent, trivalent, tetravalent, etc. The multivalent antibodies is multispecific, e.g., bispecific, trispecific, tetraspecific, etc. The multivalent antibodies may be in any form, such as a diabody, triabody, tetrabody, etc.

Bispecific antibodies may contain a heavy chain comprising one or more variable regions and/or a light chain comprising one or more variable regions. Bispecific antibodies can be constructed using only antibody variable domains. A fairly efficient and relatively simple method is to make the linker sequence between the $V_H$ and $V_L$ domains so short that they cannot fold over and bind one another. Reduction of the linker length to 3-12 residues prevents the monomeric configuration of the scFv molecule and favors intermolecular VH-VL pairings with formation of a 60 kDa non-covalent scFv dimer "diabody". The diabody format can also be used for generation of recombinant bis-pecific antibodies, which are obtained by the noncovalent association of two single-chain fusion products, consisting of the VH domain from one antibody connected by a short linker to the VL domain of another antibody. Reducing the linker length still further below three residues can result in the formation of trimers (triabody, about 90 kDa) or tetramers ('tetrabody', about 120 kDa). For a review of engineered antibodies, particularly single domain fragments, see Holliger and Hudson, 2005, Nature Biotechnology, 23:1126-1136. All of such engineered antibodies may be used in the fusion polypeptides provided herein.

Peptide linkers (-) suitable for production of scFv antibodies are described in Kumada Y, et al. Biochemical Engineering Journal. 2007 35(2):158-165; Albrecht H, et al. J Immunol Methods. 2006 310(1-2):100-16; Feng J, et al. J Immunol Methods. 2003 282(1-2):33-43; Griffiths A D, et al. Curr Opin Biotechnol. 1998 9(1):102-8; Huston J S, et al. Methods Enzymol. 1991 203:46-88; Bird R E, et al. Science. 1988 242(4877):423-6; Takkinen K, et al. Protein Eng. 1991 4(7):837-41; Smallshaw J E, et al. Protein Eng. 1999 12(7):623-30; Argos P. J Mol Biol. 1990 211(4):943-58; and Whitlow M, et al. Protein Eng. 1993 6(8):989-95, which are hereby incorporated by reference for the teachings of these linkers and methods of producing scFv antibodies against different targets using various linkers.

Tetravalent Tandab® may be prepared substantially as described in WO 1999057150 A3 or US20060233787, which are incorporated by reference for the teaching of methods of making Tandab® molecules.

The antigen recognition sites or entire variable regions of the engineered antibodies may be derived from one or more parental antibodies directed against any antigen of interest. The parental antibodies can include naturally occurring antibodies or antibody fragments, antibodies or antibody fragments adapted from naturally occurring antibodies, antibodies constructed de novo using sequences of antibodies or antibody fragments known to be specific for an antigen of interest. Sequences that may be derived from parental antibodies include heavy and/or light chain variable regions and/or CDRs, framework regions or other portions thereof.

The particular length of the peptide linker (--) used to join the scFv molecules together is important in determining half-life, immunogenicity, and activity of the overall construct. In some embodiments, the linker sequence (--) is 4, 5, 6, 7, 8, 9, 10, 11, 12, 13, 14, 15, 16, 17, 18, 19, 20, 21, 22, 23, 24, 25 or more amino acids in length. In some embodiments, the linker sequence (--) comprises GGGGS (SEQ ID NO:19). In some cases, the linker comprises 2, 3, 4, 5, or more GGGGS sequences. The linker is preferably long enough to not interfere with proper folding and association of the $V_H$-$V_L$ chains but not so long as to cause added immunogenicity.

Most variations occur in the CDR3 regions therefore it is predicted that much of the specificity is dictated by sequence changes in these regions. Affinity maturation using site directed mutagenesis and phage library experiments can be used to determine high affinity TAG72 sequences. This would focus on mutations in these key regions (particularly CDR3). In some cases, the $V_H$T and $V_L$T sequences comprise one or more amino acid substitutions within the above described CDR1, CDR2, and/or CDR3 sequences, including 1, 2, or 3 amino acid substitutions. These substitutions can be assayed using routine immunoassay techniques to evaluate changes in affinity for TAG-72.

In some cases, the $V_H$I-$V_L$I scFv sequence comprises the amino acid sequence DIKLQQSGAELARP-GASVKMSCKTSGYTFTRYTMHWVKQRPGQGLEWI-GYINPSR GYTNYNQKFKDKATLTTDKSSSTAYMQLSSLTSED-SAVYYCARYYDDHYCLDYWG QGTTLTVSSVEG-GSGGSGGSGGSGGVDDIQLTQSPAIM-SASPGEKVTMTCRASSS VSYMNWYQQKSGTSPKRWIYDTSK-VASGVPYRFSGSGSGTSYSLTISSM EAE-DAATYYCQQWSSNPLTFGAGTKLELKHHHHHH (SEQ ID NO:20, OKT3-H6), or a fragment or variant thereof able to bind CD-3. This is a commonly used sequence of T cell activating antibodies which work through binding of a set of narrow sequences on the CD3 epsilon subunit (AAs 34, 46, 48, and 79-85). The poly histidine tag at the end of the sequence allows for purification of the artificial construct and use of his tagged fluorescence antibodies for detection.

Candidate engineered antibodies for inclusion in the fusion polypeptides, or the fusion polypeptides themselves, may be screened for activity using a variety of known assays. For example, screening assays to determine binding specificity are well known and routinely practiced in the art. For a comprehensive discussion of such assays, see Harlow et al. (Eds.), ANTIBODIES: A LABORATORY MANUAL; Cold Spring Harbor Laboratory; Cold Spring Harbor, N.Y., 1988, Chapter 6.

In some embodiments, the bispecific antibody may be subjected to an alteration to render it less immunogenic when administered to a human. Such an alteration may comprise one or more of the techniques commonly known as chimerization, humanization, CDR-grafting, deimmunization and/or mutation of framework region amino acids to correspond to the closest human germline sequence (germlining). Bispecific antibodies which have been altered will therefore remain administrable for a longer period of time with reduced or no immune response-related side effects than corresponding bispecific antibodies which have not undergone any such alteration(s). One of ordinary skill in the art will understand how to determine whether, and to what degree an antibody must be altered in order to prevent it from eliciting an unwanted host immune response.

Pharmaceutical Composition

Also disclosed is a pharmaceutical composition comprising a disclosed molecule in a pharmaceutically acceptable carrier. Pharmaceutical carriers are known to those skilled in the art. These most typically would be standard carriers for administration of drugs to humans, including solutions such as sterile water, saline, and buffered solutions at physiological pH. For example, suitable carriers and their formulations are described in Remington: The Science and Practice of Pharmacy (21 ed.) ed. PP. Gerbino, Lippincott Williams & Wilkins, Philadelphia, Pa. 2005. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. The solution should be RNAse free. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutically acceptable carriers include any and all suitable solvents, dispersion media, coatings, antibacterial and antifungal agents, isotonicity agents, antioxidants and absorption delaying agents, and the like that are physiologically compatible with a bispecific antibody of the present invention. Examples of suitable aqueous and nonaqueous carriers which may be employed in the pharmaceutical compositions of the present invention include water, saline, phosphate buffered saline, ethanol, dextrose, polyols (such as glycerol, propylene glycol, polyethylene glycol, and the like), and suitable mixtures thereof, vegetable oils, carboxymethyl cellulose colloidal solutions, tragacanth gum and injectable organic esters, such as ethyl oleate, and/or various buffers. Pharmaceutically acceptable carriers include sterile aqueous solutions or dispersions and sterile powders for the extemporaneous preparation of sterile injectable solutions or dispersion. Proper fluidity may be maintained, for example, by the use of coating materials, such as lecithin, by the maintenance of the required particle size in the case of dispersions, and by the use of surfactants.

Pharmaceutical antibodies may also comprise pharmaceutically acceptable antioxidants for instance (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole, butylated hydroxytoluene, lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Pharmaceutical bispecific antibodies may also comprise isotonicity agents, such as sugars, polyalcohols, such as mannitol, sorbitol, glycerol or sodium chloride in the compositions.

The pharmaceutical bispecific antibodies may also contain one or more adjuvants appropriate for the chosen route of administration such as preservatives, wetting agents, emulsifying agents, dispersing agents, preservatives or buffers, which may enhance the shelf life or effectiveness of the pharmaceutical composition. The bispecific antibodies may be prepared with carriers that will protect the bispecific antibody against rapid release, such as a controlled release formulation, including implants, transdermal patches, and microencapsulated delivery systems. Such carriers may include gelatin, glyceryl monostearate, glyceryl distearate, biodegradable, biocompatible polymers such as ethylene vinyl acetate, polyanhydrides, polyglycolic acid, collagen, polyorthoesters, and polylactic acid alone or with a wax, or other materials well known in the art. Methods for the preparation of such formulations are generally known to those skilled in the art.

Sterile injectable solutions may be prepared by incorporating the active compound in the required amount in an appropriate solvent with one or a combination of ingredients e.g. as enumerated above, as required, followed by sterilization microfiltration. Generally, dispersions are prepared by incorporating the active compound into a sterile vehicle that contains a basic dispersion medium and the required other ingredients e.g. from those enumerated above. In the case of sterile powders for the preparation of sterile injectable solutions, examples of methods of preparation are vacuum drying and freeze-drying (lyophilization) that yield a powder of the active ingredient plus any additional desired ingredient from a previously sterile-filtered solution thereof.

Also disclosed is the use of a disclosed bispecific antibody for use as a medicament for the treatment of various forms of cancer, including metastatic cancer and refractory cancer.

Methods of Treatment

Also disclosed is a method for treating a TAG-72-expressing cancer in a subject by administering to the subject a therapeutically effective amount of the disclosed pharmaceutical composition.

The disclosed compositions, including pharmaceutical composition, may be administered in a number of ways depending on whether local or systemic treatment is desired, and on the area to be treated. For example, the disclosed compositions can be administered intravenously, intraperitoneally, intramuscularly, subcutaneously, intracavity, or transdermally. The compositions may be administered orally, parenterally (e.g., intravenously), by intramuscular injection, by intraperitoneal injection, transdermally, extracorporeally, ophthalmically, vaginally, rectally, intranasally, topically or the like, including topical intranasal administration or administration by inhalant.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

The compositions disclosed herein may be administered prophylactically to patients or subjects who are at risk for a TAG-72-expressing cancer. Thus, the method can further comprise identifying a subject at risk for a TAG-72-expressing cancer prior to administration of the herein disclosed compositions.

The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein. For example, effective dosages and schedules for administering the compositions may be determined empirically, and making such determinations is within the skill in the art. The dosage ranges for the administration of the compositions are those large enough to produce the desired effect in which the symptoms disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. A typical daily dosage of the disclosed composition used alone might range from about 1 µg/kg to up to 100 mg/kg of body weight or more per day, depending on the factors mentioned above.

In some embodiments, the molecule is administered in a dose equivalent to parenteral administration of about 0.1 ng to about 100 g per kg of body weight, about 10 ng to about 50 g per kg of body weight, about 100 ng to about 1 g per kg of body weight, from about 1 µg to about 100 mg per kg of body weight, from about 1 µg to about 50 mg per kg of body weight, from about 1 mg to about 500 mg per kg of body weight; and from about 1 mg to about 50 mg per kg of body weight. Alternatively, the amount of molecule administered to achieve a therapeutic effective dose is about 0.1 ng, 1 ng, 10 ng, 100 ng, 1 µg, 10 µg, 100 µg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

The cancer of the disclosed methods can be any TAG-72-expressing cell in a subject undergoing unregulated growth, invasion, or metastasis. Cancers that express TAG-72 include prostate cancer, ovarian cancer, adenocarcinoma of the lung, breast cancer, endometrial cancer, gastric cancer, colon cancer, and pancreatic cancer. TAG-72 has also been found on Jurkat cells. In some aspects, the cancer is a gallbladder cancer, exocrine adenocarcinoma, or apocrine adenocarcinomas.

In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, endometrial cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

An antibody disclosed herein may also be administered prophylactically in order to reduce the risk of developing cancer, delay the onset of the occurrence of an event in cancer progression, and/or reduce the risk of recurrence when a cancer is in remission.

The disclosed antibodies may also be administered in combination therapy, i.e., combined with other therapeutic agents relevant for the disease or condition to be treated. Accordingly, in one embodiment, the antibody-containing medicament is for combination with one or more further therapeutic agent, such as a cytotoxic, chemotherapeutic, or anti-angiogenic agent. For example, the method can further involve administering to the subject lenalidomide, or an analogue or derivative thereof.

The disclosed antibodies can be used in combination with any compound, moiety or group which has a cytotoxic or cytostatic effect. Drug moieties include chemotherapeutic agents, which may function as microtubulin inhibitors, mitosis inhibitors, topoisomerase inhibitors, or DNA intercalators, and particularly those which are used for cancer therapy.

The disclosed antibodies can be used in combination with a checkpoint inhibitor. The two known inhibitory checkpoint pathways involve signaling through the cytotoxic T-lymphocyte antigen-4 (CTLA-4) and programmed-death 1 (PD-1) receptors. These proteins are members of the CD28-B7 family of cosignaling molecules that play important roles throughout all stages of T cell function. The PD-1 receptor (also known as CD279) is expressed on the surface of activated T cells. Its ligands, PD-L1 (B7-HI; CD274) and PD-L2 (B7-DC; CD273), are expressed on the surface of APCs such as dendritic cells or macrophages. PD-L1 is the predominant ligand, while PD-L2 has a much more restricted expression pattern. When the ligands bind to PD-1, an inhibitory signal is transmitted into the T cell, which reduces cytokine production and suppresses T-cell proliferation. Checkpoint inhibitors include, but are not limited to antibodies that block PD-1 (Nivolumab (BMS-936558 or MDX1106), CT-011, MK-3475), PD-L1 (MDX-1105 (BMS-936559), MPDL3280A, MSB0010718C), PD-L2 (rHIgM12B7), CTLA-4 (Ipilimumab (MDX-010), Tremelimumab (CP-675,206)), IDO, B7-H3 (MGA271), B7-H4, TIM3, LAG-3 (BMS-986016).

Human monoclonal antibodies to programmed death I (PD-1) and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

In some embodiments, the PDL1 inhibitor comprises an antibody that specifically binds PDL1, such as BMS-936559 (Bristol-Myers Squibb) or MPDL3280A (Roche). In some embodiments, the PD1 inhibitor comprises an antibody that specifically binds PD1, such as lambrolizumab (Merck), nivolumab (Bristol-Myers Squibb), or MED14736 (AstraZeneca). Human monoclonal antibodies to PD-1 and methods for treating cancer using anti-PD-1 antibodies alone or in combination with other immunotherapeutics are described in U.S. Pat. No. 8,008,449, which is incorporated by reference for these antibodies. Anti-PD-L1 antibodies and uses therefor are described in U.S. Pat. No. 8,552,154, which is incorporated by reference for these antibodies. Anticancer agent comprising anti-PD-1 antibody or anti-PD-L1 antibody are described in U.S. Pat. No. 8,617,546, which is incorporated by reference for these antibodies.

The disclosed antibodies can be used in combination with other cancer immunotherapies. There are two distinct types of immunotherapy: passive immunotherapy uses components of the immune system to direct targeted cytotoxic activity against cancer cells, without necessarily initiating an immune response in the patient, while active immunotherapy actively triggers an endogenous immune response. Passive strategies include the use of the monoclonal antibodies (mAbs) produced by B cells in response to a specific antigen. The development of hybridoma technology in the 1970s and the identification of tumor-specific antigens permitted the pharmaceutical development of mAbs that could specifically target tumor cells for destruction by the immune system. Thus far, mAbs have been the biggest success story for immunotherapy; the top three best-selling anticancer drugs in 2012 were mAbs. Among them is rituximab (Rituxan, Genentech), which binds to the CD20 protein that is highly expressed on the surface of B cell malignancies such as non-Hodgkin's lymphoma (NHL). Rituximab is approved by the FDA for the treatment of NHL and chronic lymphocytic leukemia (CLL) in combination with chemotherapy. Another important mAb is trastuzumab (Herceptin; Genentech), which revolutionized the treatment of HER2 (human epidermal growth factor receptor 2)-positive breast cancer by targeting the expression of HER2.

Generating optimal "killer" CD8 T cell responses also requires T cell receptor activation plus co-stimulation, which can be provided through ligation of tumor necrosis factor receptor family members, including OX40 (CD134) and 4-1 BB (CD137). OX40 is of particular interest as treatment with an activating (agonist) anti-OX40 mAb augments T cell differentiation and cytolytic function leading to enhanced anti-tumor immunity against a variety of tumors.

In some embodiments, such an additional therapeutic agent may be selected from an antimetabolite, such as methotrexate, 6-mercaptopurine, 6-thioguanine, cytarabine, fludarabine, 5-fluorouracil, decarbazine, hydroxyurea, asparaginase, gemcitabine or cladribine.

In some embodiments, such an additional therapeutic agent may be selected from an alkylating agent, such as mechlorethamine, thioepa, chlorambucil, melphalan, carmustine (BSNU), lomustine (CCNU), cyclophosphamide, busulfan, dibromomannitol, streptozotocin, dacarbazine (DTIC), procarbazine, mitomycin C, cisplatin and other platinum derivatives, such as carboplatin.

In some embodiments, such an additional therapeutic agent may be selected from an anti-mitotic agent, such as taxanes, for instance docetaxel, and paclitaxel, and vinca alkaloids, for instance vindesine, vincristine, vinblastine, and vinorelbine.

In some embodiments, such an additional therapeutic agent may be selected from a topoisomerase inhibitor, such as topotecan or irinotecan, or a cytostatic drug, such as etoposide and teniposide.

In some embodiments, such an additional therapeutic agent may be selected from a growth factor inhibitor, such as an inhibitor of ErbBI (EGFR) (such as an EGFR antibody, e.g. zalutumumab, cetuximab, panitumumab or nimotuzumab or other EGFR inhibitors, such as gefitinib or erlotinib), another inhibitor of ErbB2 (HER2/neu) (such as a HER2 antibody, e.g. trastuzumab, trastuzumab-DM I or pertuzumab) or an inhibitor of both EGFR and HER2, such as lapatinib).

In some embodiments, such an additional therapeutic agent may be selected from a tyrosine kinase inhibitor, such as imatinib (Glivec, Gleevec ST1571) or lapatinib.

Therefore, in some embodiments, a disclosed antibody is used in combination with ofatumumab, zanolimumab, daratumumab, ranibizumab, nimotuzumab, panitumumab, hu806, daclizumab (Zenapax), basiliximab (Simulect), infliximab (Remicade), adalimumab (Humira), natalizumab (Tysabnr), omalizumab (Xolair), efalizumab (Raptiva), and/or rituximab.

In some embodiments, a therapeutic agent for use in combination with a bispecific antibody for treating the disorders as described above may be an anti-cancer immunogen, such as a cancer antigen/tumor-associated antigen (e.g., epithelial cell adhesion molecule (EpCAM/TAC-STDI), mucin 1 (MUC1), carcinoembryonic antigen (CEA), tumor-associated glycoprotein 72 (TAG-72), gplOO, Melan-A, MART-1, KDR, RCASI, MDA7, cancer-associated viral vaccines (e.g., human papillomavirus vaccines) or tumor-derived heat shock proteins.

In some embodiments, a therapeutic agent for use in combination with a bispecific antibody for treating the disorders as described above may be an anti-cancer cytokine, chemokine, or combination thereof. Examples of suitable cytokines and growth factors include IFNy, IL-2, IL-4, IL-6, IL-7, IL-10, IL-12, IL-13, IL-15, IL-18, IL-23, IL-24, IL-27, IL-28a, IL-28b, IL-29, KGF, IFNa (e.g., INFa2b), IFN, GM-CSF, CD40L, Flt3 ligand, stem cell factor, ancestim, and TNFa. Suitable chemokines may include Glu-Leu-Arg (ELR)-negative chemokines such as IP-10, MCP-3, MIG, and SDF-la from the human CXC and C—C chemokine families. Suitable cytokines include cytokine derivatives, cytokine variants, cytokine fragments, and cytokine fusion proteins.

In some embodiments, a therapeutic agent for use in combination with a bispecific antibody for treating the disorders as described above may be a cell cycle control/apoptosis regulator (or "regulating agent"). A cell cycle control/apoptosis regulator may include molecules that target and modulate cell cycle control/apoptosis regulators such as (i) cdc-25 (such as NSC 663284), (ii) cyclin-dependent kinases that overstimulate the cell cycle (such as flavopiridol (L868275, HMR1275), 7-hydroxystaurosporine (UCN-01, KW-2401), and roscovitine (R-roscovitine, CYC202)), and (iii) telomerase modulators (such as BIBR1532, SOT-095, GRN163 and compositions described in for instance U.S. Pat. Nos. 6,440,735 and 6,713,055). Non-limiting examples of molecules that interfere with apoptotic pathways include TNF-related apoptosis-inducing ligand (TRAIL)/apoptosis-2 ligand (Apo-2L), antibodies that activate TRAIL receptors, IFNs, and anti-sense Bcl-2.

In some embodiments, a therapeutic agent for use in combination with a bispecific antibody for treating the disorders as described above may be a hormonal regulating agent, such as agents useful for anti-androgen and anti-estrogen therapy. Examples of such hormonal regulating agents are tamoxifen, idoxifene, fulvestrant, droloxifene, toremifene, raloxifene, diethylstilbestrol, ethinyl estradiol/estinyl, an antiandrogene (such as flutaminde/eulexin), a progestin (such as such as hydroxyprogesterone caproate, medroxy-progesterone/provera, megestrol acepate/megace), an adrenocorticosteroid (such as hydrocortisone, prednisone), luteinizing hormone-releasing hormone (and analogs thereof and other LHRH agonists such as buserelin and goserelin), an aromatase inhibitor (such as anastrazole/arimidex, aminoglutethimide/cytraden, exemestane) or a hormone inhibitor (such as octreotide/sandostatin).

In some embodiments, a therapeutic agent for use in combination with an antibody for treating the disorders as described above may be an anti-cancer nucleic acid or an anti-cancer inhibitory RNA molecule.

Combined administration, as described above, may be simultaneous, separate, or sequential. For simultaneous administration the agents may be administered as one composition or as separate compositions, as appropriate.

In some embodiments, the disclosed bispecific is administered in combination with radiotherapy. Radiotherapy may comprise radiation or associated administration of radiopharmaceuticals to a patient is provided. The source of radiation may be either external or internal to the patient being treated (radiation treatment may, for example, be in the form of external beam radiation therapy (EBRT) or brachytherapy (BT)). Radioactive elements that may be used in practicing such methods include, e.g., radium, cesium-137, iridium-192, americium-241, gold-198, cobalt-57, copper-67, technetium-99, iodide-123, iodide-131, and indium-111.

In some embodiments, the disclosed bispecific antibody is administered in combination with surgery.

Definitions

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "bispecific antibody" refers to an antibody having two different antigen-binding regions defined by different antibody sequences. This can be understood as different target binding but includes as well binding to different epitopes in one target.

The term "carrier" means a compound, composition, substance, or structure that, when in combination with a compound or composition, aids or facilitates preparation, storage, administration, delivery, effectiveness, selectivity, or any other feature of the compound or composition for its intended use or purpose. For example, a carrier can be selected to minimize any degradation of the active ingredient and to minimize any adverse side effects in the subject.

The term "engineered antibody" refers to a recombinant molecule that comprises at least an antibody fragment comprising an antigen binding site derived from the variable domain of the heavy chain and/or light chain of an antibody and may optionally comprise the entire or part of the variable and/or constant domains of an antibody from any of the Ig classes (for example IgA, IgD, IgE, IgG, IgM and IgY).

The term "epitope" refers to the region of an antigen to which an antibody binds preferentially and specifically. A monoclonal antibody binds preferentially to a single specific epitope of a molecule that can be molecularly defined. In the present invention, multiple epitopes can be recognized by a multispecific antibody.

A "fusion protein" or "fusion polypeptide" refers to a hybrid polypeptide which comprises polypeptide portions from at least two different polypeptides. The portions may be from proteins of the same organism, in which case the fusion protein is said to be "intraspecies", "intragenic", etc. In various embodiments, the fusion polypeptide may comprise one or more amino acid sequences linked to a first polypeptide. In the case where more than one amino acid sequence is fused to a first polypeptide, the fusion sequences may be multiple copies of the same sequence, or alternatively, may be different amino acid sequences. A first polypeptide may be fused to the N-terminus, the C-terminus, or the N- and C-terminus of a second polypeptide. Furthermore, a first polypeptide may be inserted within the sequence of a second polypeptide.

The term "Fab fragment" refers to a fragment of an antibody comprising an antigen-binding site generated by cleavage of the antibody with the enzyme papain, which cuts at the hinge region N-terminally to the inter-H-chain disulfide bond and generates two Fab fragments from one antibody molecule.

The term "F(ab')2 fragment" refers to a fragment of an antibody containing two antigen-binding sites, generated by cleavage of the antibody molecule with the enzyme pepsin which cuts at the hinge region C-terminally to the inter-H-chain disulfide bond.

The term "Fc fragment" refers to the fragment of an antibody comprising the constant domain of its heavy chain.

The term "Fv fragment" refers to the fragment of an antibody comprising the variable domains of its heavy chain and light chain.

"Gene construct" refers to a nucleic acid, such as a vector, plasmid, viral genome or the like which includes a "coding sequence" for a polypeptide or which is otherwise transcribable to a biologically active RNA (e.g., antisense, decoy, ribozyme, etc), may be transfected into cells, e.g. in certain embodiments mammalian cells, and may cause expression of the coding sequence in cells transfected with the construct. The gene construct may include one or more regulatory elements operably linked to the coding sequence, as well as intronic sequences, polyadenylation sites, origins of replication, marker genes, etc.

The term "isolated polypeptide" refers to a polypeptide, which may be prepared from recombinant DNA or RNA, or be of synthetic origin, some combination thereof, or which may be a naturally-occurring polypeptide, which (1) is not associated with proteins with which it is normally associated in nature, (2) is isolated from the cell in which it normally occurs, (3) is essentially free of other proteins from the same cellular source, (4) is expressed by a cell from a different species, or (5) does not occur in nature.

The term "isolated nucleic acid" refers to a polynucleotide of genomic, cDNA, synthetic, or natural origin or some combination thereof, which (1) is not associated with the cell in which the "isolated nucleic acid" is found in nature, or (2) is operably linked to a polynucleotide to which it is not linked in nature.

The term "linker" is art-recognized and refers to a molecule or group of molecules connecting two compounds, such as two polypeptides. The linker may be comprised of a single linking molecule or may comprise a linking molecule and a spacer molecule, intended to separate the linking molecule and a compound by a specific distance.

The term "multivalent antibody" refers to an antibody or engineered antibody comprising more than one antigen recognition site. For example, a "bivalent" antibody has two antigen recognition sites, whereas a "tetravalent" antibody has four antigen recognition sites. The terms "monospecific", "bispecific", "trispecific", "tetraspecific", etc. refer to the number of different antigen recognition site specificities (as opposed to the number of antigen recognition sites) present in a multivalent antibody. For example, a "monospecific" antibody's antigen recognition sites all bind the same epitope. A "bispecific" antibody has at least one antigen recognition site that binds a first epitope and at least one antigen recognition site that binds a second epitope that is different from the first epitope. A "multivalent monospecific" antibody has multiple antigen recognition sites that all bind the same epitope. A "multivalent bispecific" antibody has multiple antigen recognition sites, some number of which bind a first epitope and some number of which bind a second epitope that is different from the first epitope.

The term "nucleic acid" refers to a polymeric form of nucleotides, either ribonucleotides or deoxynucleotides or a modified form of either type of nucleotide. The terms should also be understood to include, as equivalents, analogs of either RNA or DNA made from nucleotide analogs, and, as applicable to the embodiment being described, single-stranded (such as sense or antisense) and double-stranded polynucleotides.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

As used herein, "peptidomimetic" means a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. One embodiment of the present invention is a peptidomimetic wherein the compound has a bond, a peptide backbone or an amino acid component replaced with a suitable mimic. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

The term "protein" (if single-chain), "polypeptide" and "peptide" are used interchangeably herein when referring to a gene product, e.g., as may be encoded by a coding sequence. When referring to "polypeptide" herein, a person of skill in the art will recognize that a protein can be used instead, unless the context clearly indicates otherwise. A "protein" may also refer to an association of one or more polypeptides. By "gene product" is meant a molecule that is produced as a result of transcription of a gene. Gene products include RNA molecules transcribed from a gene, as well as proteins translated from such transcripts.

The terms "polypeptide fragment" or "fragment", when used in reference to a particular polypeptide, refers to a polypeptide in which amino acid residues are deleted as compared to the reference polypeptide itself, but where the remaining amino acid sequence is usually identical to that of the reference polypeptide. Such deletions may occur at the amino-terminus or carboxy-terminus of the reference polypeptide, or alternatively both. Fragments typically are at least about 5, 6, 8 or 10 amino acids long, at least about 14 amino acids long, at least about 20, 30, 40 or 50 amino acids long, at least about 75 amino acids long, or at least about 100, 150, 200, 300, 500 or more amino acids long. A fragment can retain one or more of the biological activities of the reference polypeptide. In various embodiments, a fragment may comprise an enzymatic activity and/or an interaction site of the reference polypeptide. In another embodiment, a fragment may have immunogenic properties.

The term "single chain variable fragment or scFv" refers to an Fv fragment in which the heavy chain domain and the light chain domain are linked. One or more scFv fragments may be linked to other antibody fragments (such as the constant domain of a heavy chain or a light chain) to form antibody constructs having one or more antigen recognition sites.

The term "specifically binds", as used herein, when referring to a polypeptide (including antibodies) or receptor, refers to a binding reaction which is determinative of the presence of the protein or polypeptide or receptor in a heterogeneous population of proteins and other biologics. Thus, under designated conditions (e.g. immunoassay conditions in the case of an antibody), a specified ligand or antibody "specifically binds" to its particular "target" (e.g. an antibody specifically binds to an endothelial antigen) when it does not bind in a significant amount to other proteins present in the sample or to other proteins to which the ligand or antibody may come in contact in an organism. Generally, a first molecule that "specifically binds" a second molecule has an affinity constant (Ka) greater than about $10^5$ $M^{-1}$ (e.g., $10^6$ $M^{-1}$, $10^7$ $M^{-1}$, $10^8$ $M^{-1}$, $10^9$ $M^{-1}$, $10^{10}$ $M^{-1}$, $10^{11}$ $M^{-1}$, and $10^{12}$ $M^{-1}$ or more) with that second molecule.

The term "specifically deliver" as used herein refers to the preferential association of a molecule with a cell or tissue bearing a particular target molecule or marker and not to cells or tissues lacking that target molecule. It is, of course, recognized that a certain degree of non-specific interaction may occur between a molecule and a non-target cell or tissue. Nevertheless, specific delivery, may be distinguished as mediated through specific recognition of the target molecule. Typically specific delivery results in a much stronger association between the delivered molecule and cells bearing the target molecule than between the delivered molecule and cells lacking the target molecule.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder preventative treatment, that is, treatment directed to minimizing or partially or completely inhibiting the development of the associated disease, pathological condition, or disorder and supportive treatment, that is, treatment employed to supplement another specific therapy directed toward the improvement of the associated disease, pathological condition, or disorder.

A number of embodiments of the invention have been described. Nevertheless, it will be understood that various modifications may be made without departing from the spirit and scope of the invention. Accordingly, other embodiments are within the scope of the following claims.

A number of embodiments of the invention have been described. Nevertheless, it will be understood that various modifications may be made without departing from the spirit and scope of the invention. Accordingly, other embodiments are within the scope of the following claims.

A number of embodiments of the invention have been described. Nevertheless, it will be understood that various modifications may be made without departing from the spirit and scope of the invention. Accordingly, other embodiments are within the scope of the following claims.

EXAMPLES

Example 1: Affinity Maturation of TAG-72 scSv Antibody

Based on the sequence for TAG-72 antibody and a choice of linker, the following two scFv constructs were produced:

```
Ab3890 (VH-linker-VL) -
                                     (SEQ ID NO: 21)
QVQLQQSDAELVKPGASVKISCKASGYTFTDHAIHWVKQNPEQGLEWIGY

FSPGNDDFKYNERFKGKATLTADKSSSTAYVQLNSLTSEDSAVYFCTRSL

NMAYWGQGTSVTVSSLSADDAKKDAAKKDDAKKDDAKKDLDIVMSQSPSS

LPVSVGEKVTLSCKSSQSLLYSGNQKNYLAWYQQKPGQSPKLLIYWASAR

ESGVPDRFTGSGSGTDFTLSISSVKTEDLAVYYCQQYYSYPLTFGAGTKL

VLK;
and

Ab3890 (VL-linker-VH) -
                                     (SEQ ID NO: 22)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNDDFKYNE

RFKGKATLTADKSSSTAYVQLNSLTSEDSAVYFCTRSLNMAYWGQGTSVT

VSS.
``` scFvs were cloned into a vector and produced as purified protein and phage. Both scFvs were successfully purified.

Antigen S was re-suspended according to manufacturer's instructions. 1 mg of the Antigen S was biotinylated using amine coupling kit (EZ Link Biotinylation kit, Thermo, 21955). Protein was analyzed by TruHits assay (to evaluate biotinylation) and SDS-PAGE, and successful biotinylation was confirmed.

Figure 1A:
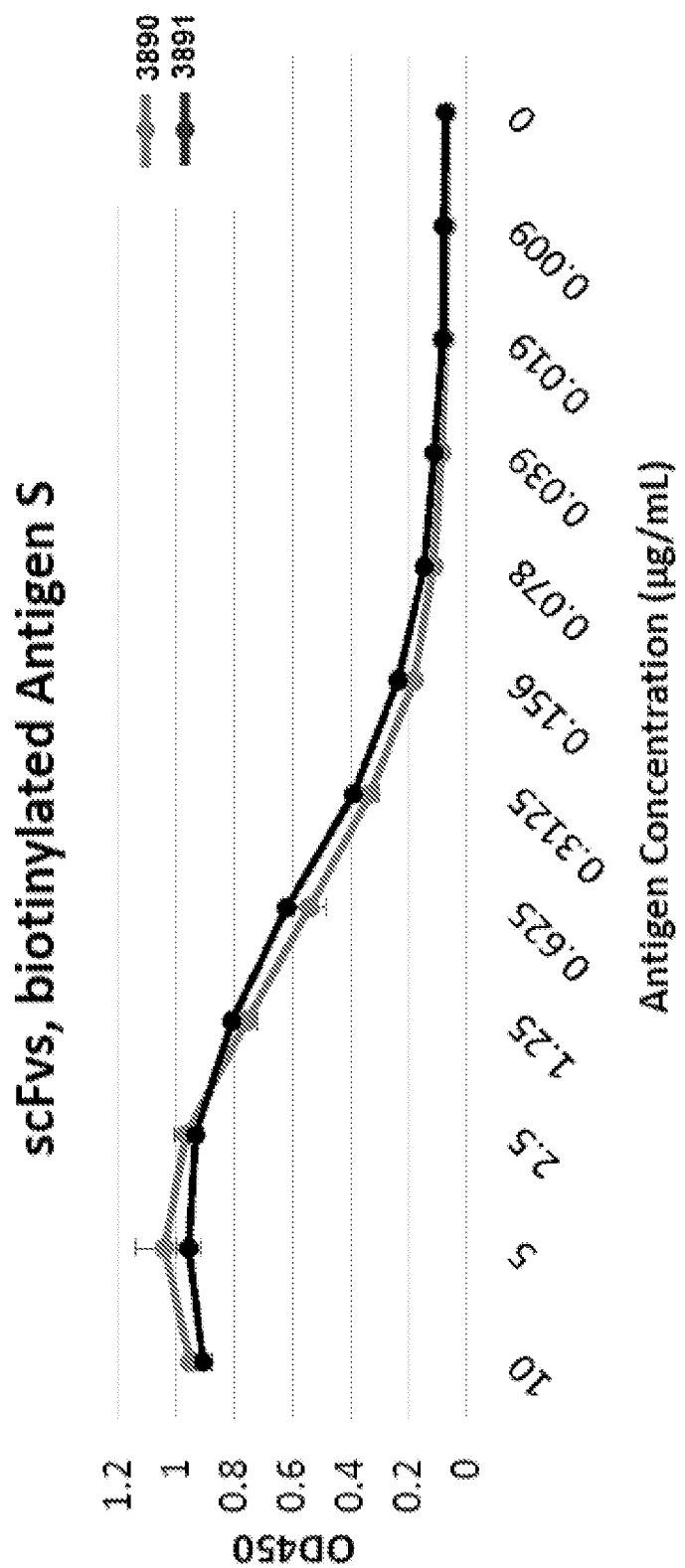
FIGS. 1A and 1B show binding of scFvs Ab3890 and Ab3891 to biotinylated antigen S FIG. 1A) and unmodified antigen S (FIG. 1B).
Figure 1B:
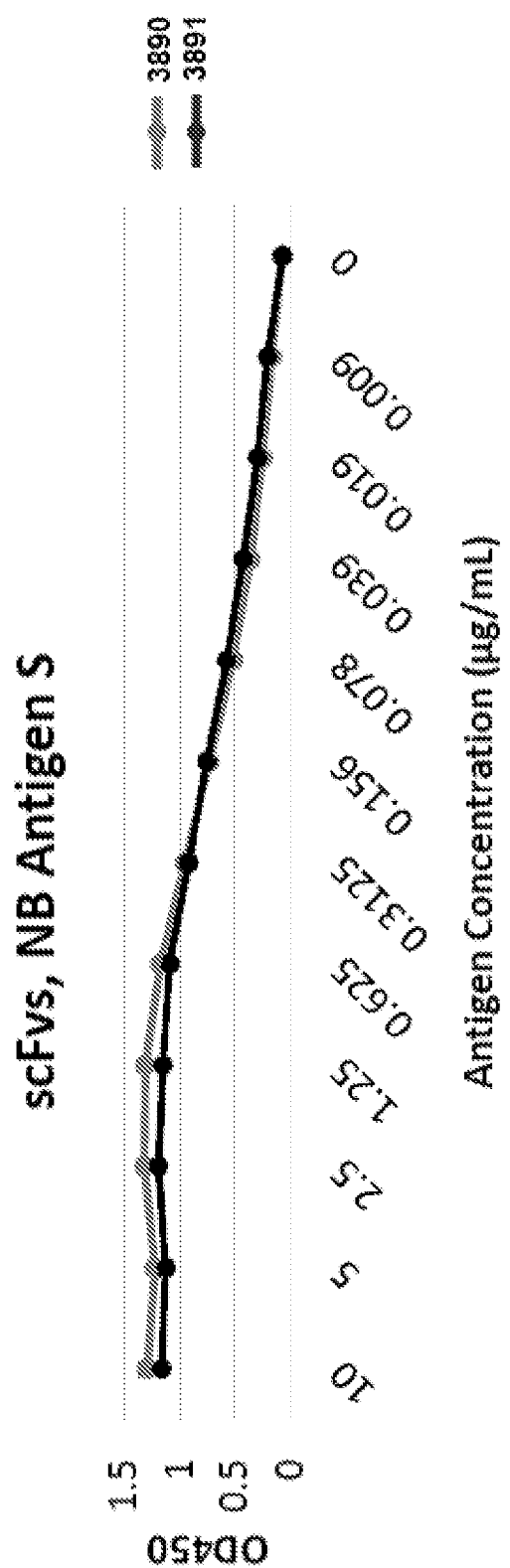

As shown in FIGS. 1A and 1B, both scFvs bound to biotinylated and unmodified antigen S. All scFvs were used at 1 µg/ml. The secondary antibody was anti-FLAG-HRP (Abcam, ab49763, 1:5000).

Figure 2A:
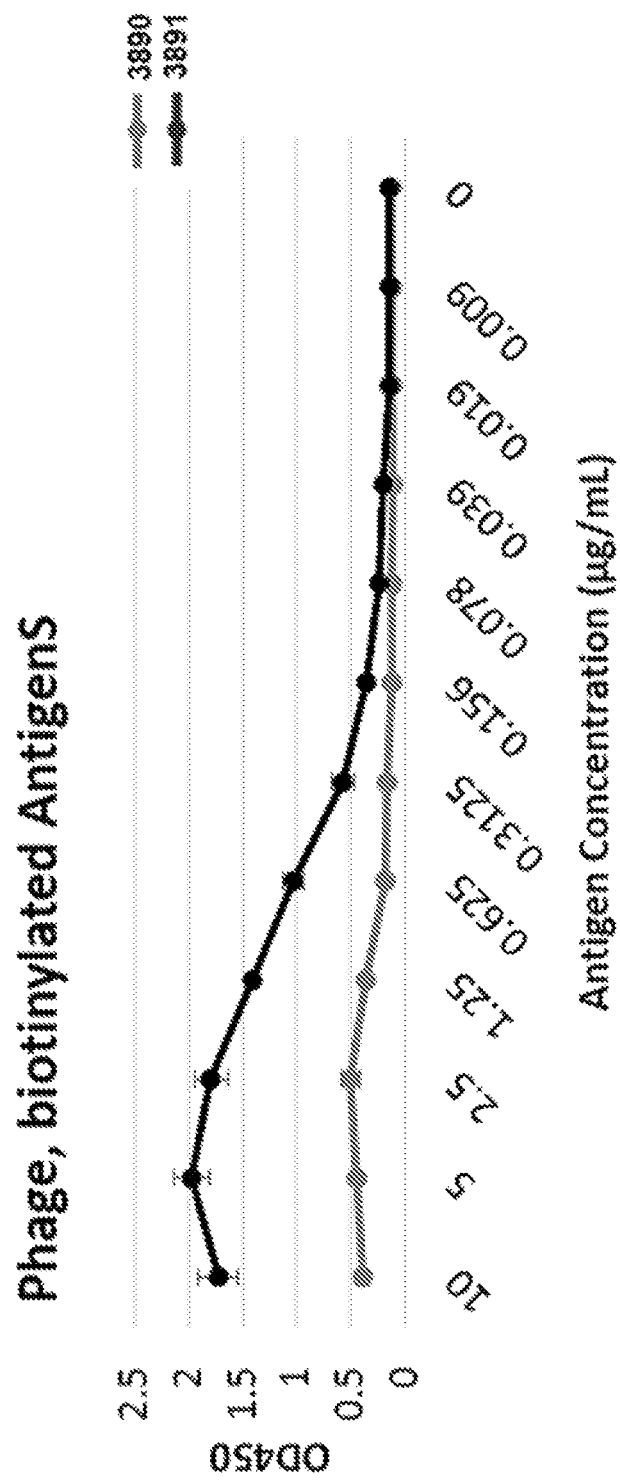
FIGS. 2A and 2B show phage binding of scFvs Ab3890 and Ab3891 to biotinylated antigen S FIG. 2A) and unmodified antigen S (FIG. 2B).
Figure 2B:
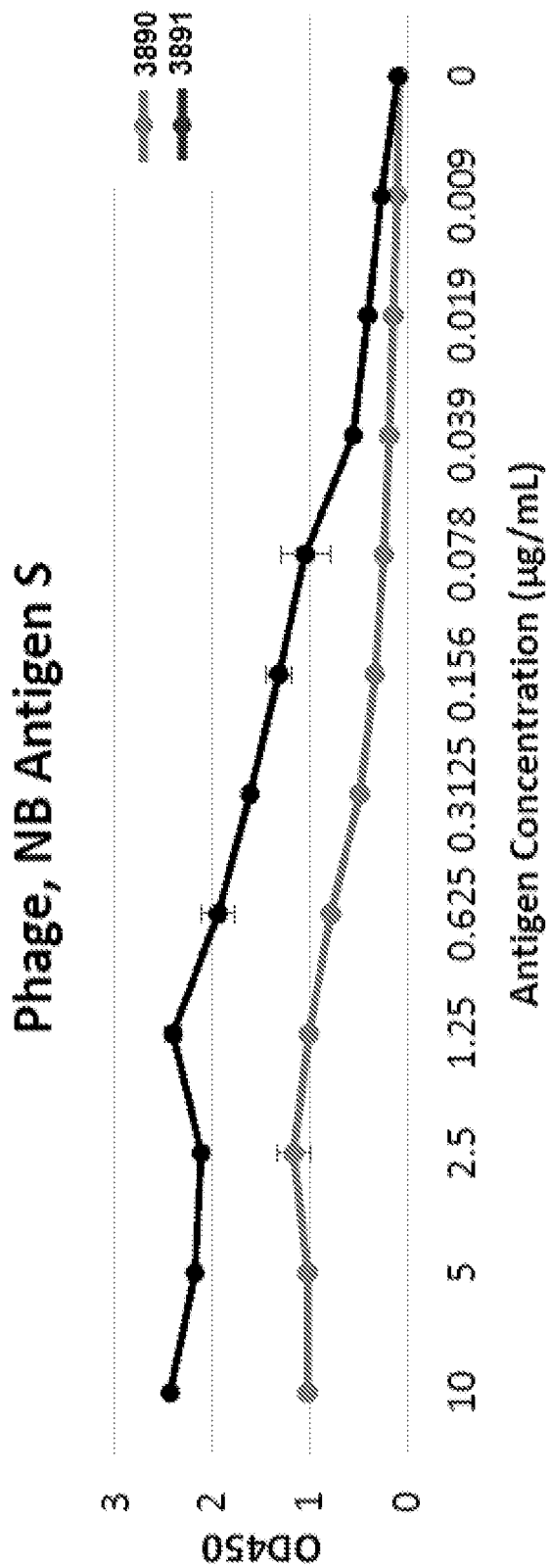

However, as shown in FIGS. 2A and 2B, Ab3891 had a better phage binding profile than Ab3890. The secondary antibody was anti-m13-HRP (GE Healthcare, 27-9521, 1:5000). Therefore, Ab3891 was selected for affinity maturation.

Standard mutagenesis library was prepared from Ab3891 and quality controlled by sequencing. The library was screened through 3 rounds of affinity maturation using standard protocol. Biotinylated Antigen S was used as the target. The following three unique clones with CDR mutations were identified:

```
Ab4116 -
                                     (SEQ ID NO: 16)
DIVMSQSPSSLPVSVGEKVTLSCKSSQSLLYSGNHKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNDDFRYNE

RFKGKATLTADKSSSTAYVQLNSLTSEDSAVYFCTRSLNMAYWGQGTSVT

VSS,

Ab4117 -
                                     (SEQ ID NO: 17)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKGLQVQLQQSDAELV

KPGASVKISCKASGYTFTDHAIHWVKQNPEQGLEWIGYFSPGNDDFKYNE

RYKGKATLTADKSSSTAYVQLNSLTSEDSAVYFCTRSLNMAYWGQGTSVT

VSS,

Ab4118 -
                                     (SEQ ID NO: 18)
DIVMSQSPSSLPVSVGEKVTLSCKSSQSLLYSGNQKNYLAWYQQKPGQSP

KLLIYWASARESGVPDRFTGSGSGTDFTLSISSVKTEDLAVYYCQQYYSY

PLTFGAGTKLVLKLSADDAKKDAAKKDDAKKDDAKKDLQVQLQQSDAELV

KPGASVKISCKASGYTFTDHAIHWVKQNPEQGLEWIGYFSPGNNDFKYNE

RFKGKATLTADKSSSTAYVQLNSLTSEDSAVYFCTRSLNMAYWGQGTSVT

VSS.
```

Figure 3A:
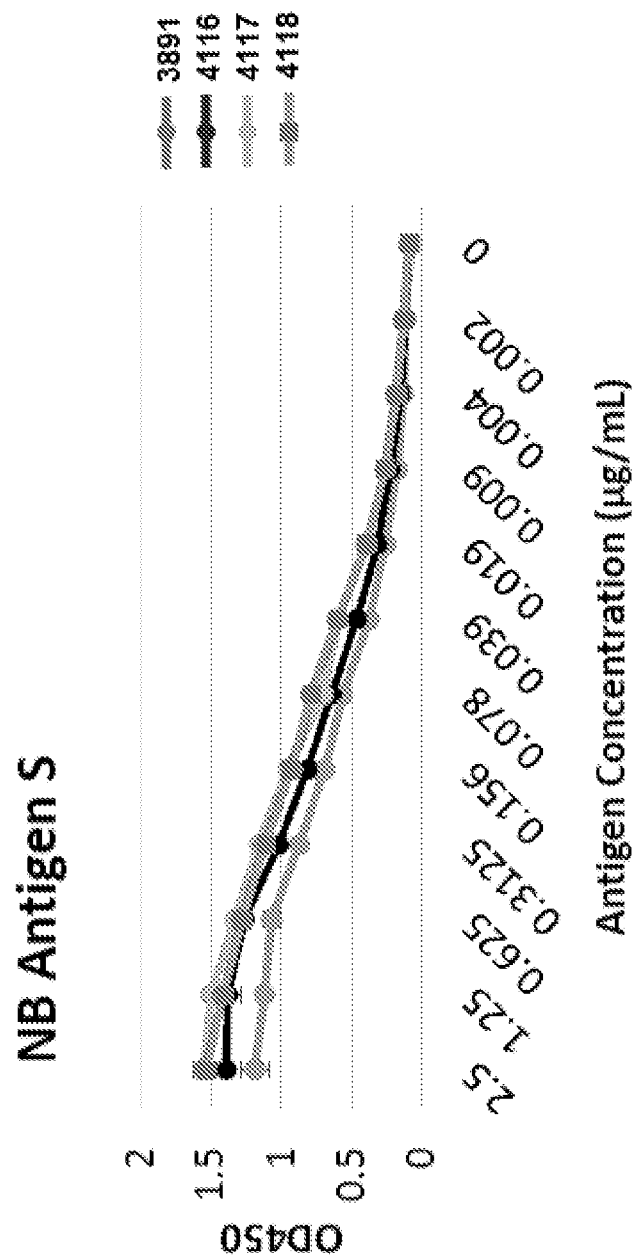
FIGS. 3A and 3B show binding of scFvs Ab3891, Ab4116, Ab4117, and Ab4118 to unmodified antigen S (FIG. 3A) and biotinylated antigen S (FIG. 3B).
Figure 3B:
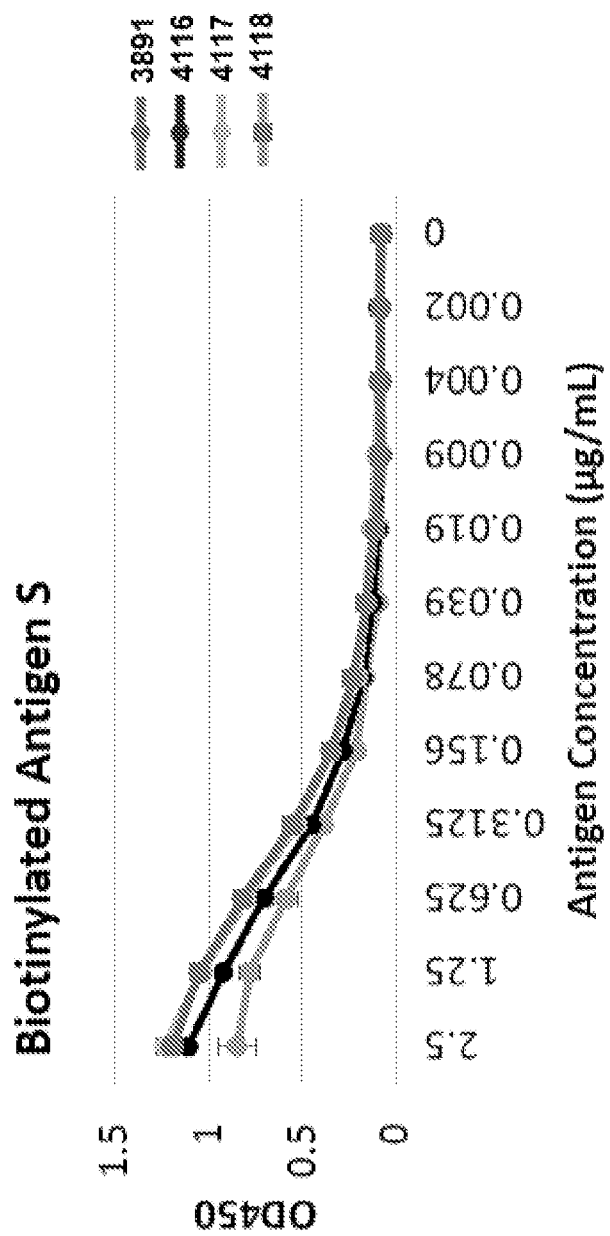
Figure 4B:
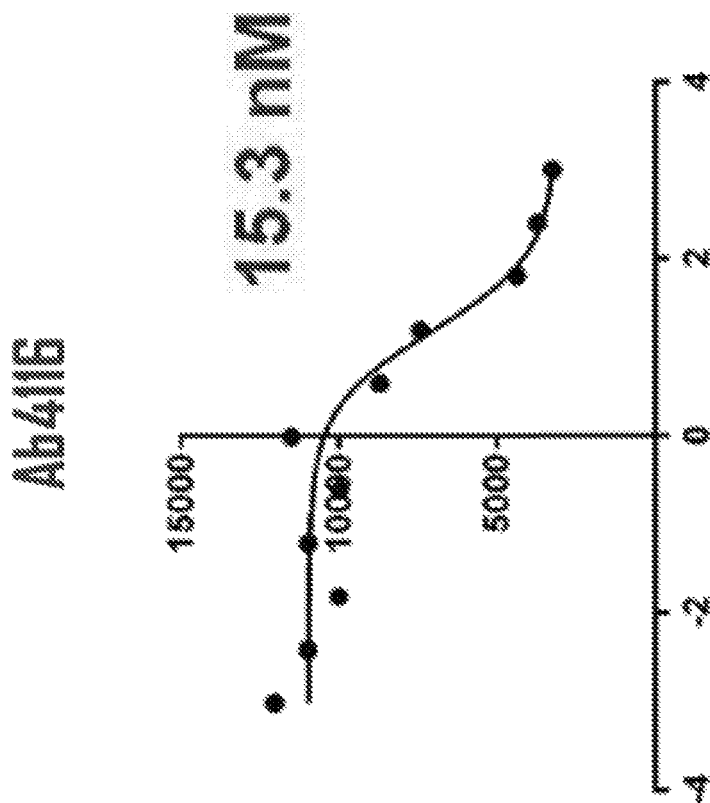
FIGS. 4A to 4D show dissociation constants (KD) for Ab3891 (FIG. 4A), Ab4116 (FIG. 4B), Ab4117 (FIG. 4C), and Ab4118 (FIG. 4D) as determined by Alpha Screen.
Figure 4A:
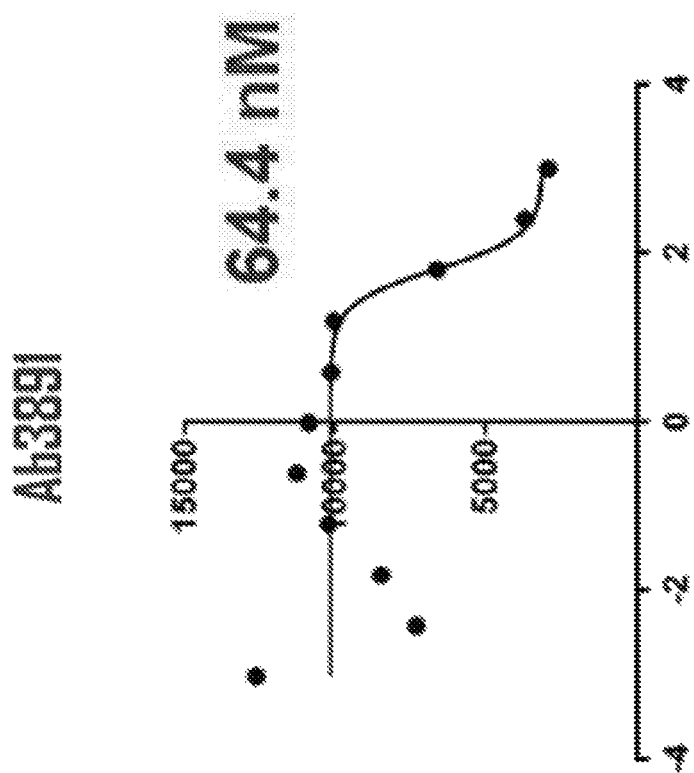
Figure 4D:
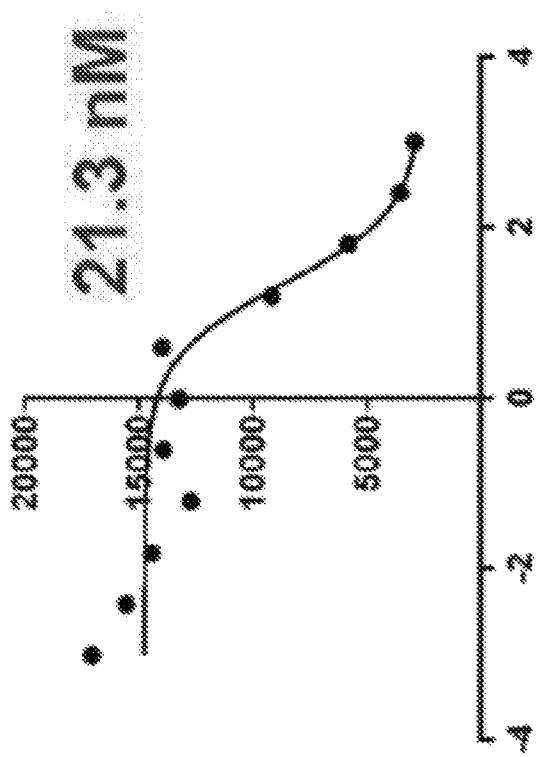
Figure 4C:
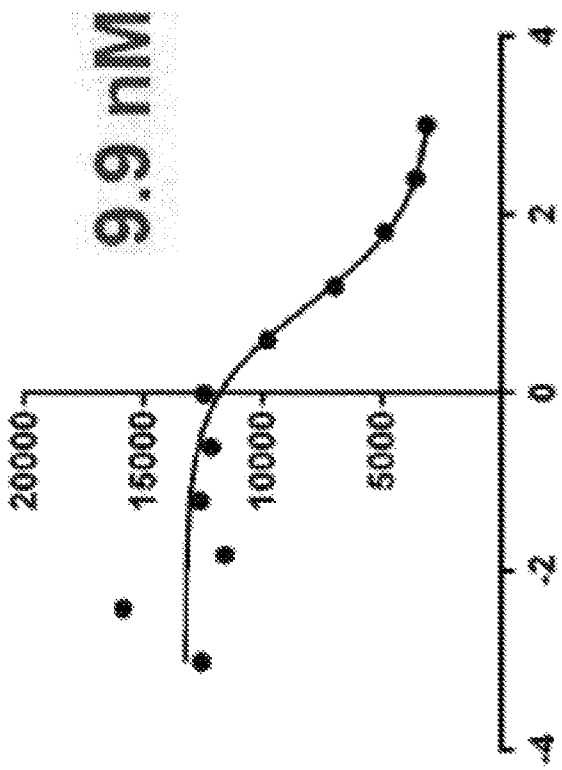
Figure 6:
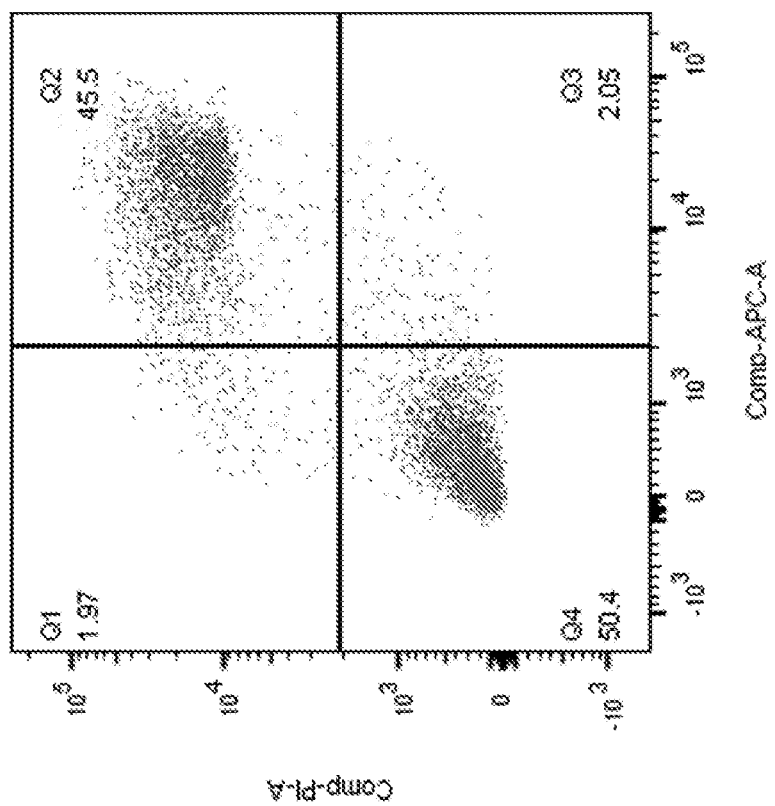
FIG. 6 is a flow cytometry plot showing MCF-7 cells treated with bispecific antibody (pilot) at conc of 10 μg/ml.

As shown in FIGS. 3A and 3B, all matured clones shows moderate improvement compared to Ab3891 when evaluated by traditional ELISA. All scFvs were used at 1 µg/ml. The secondary antibody was anti-FLAG-HRP (Abcam, ab49763, 1:5000).

FIGS. 4A to 4D show KD determination of the four scFvs by Alpha Screen. Based on this assay, there was a 3-6 fold improvement (FIG. 1A, Ab3891, 64.4 nM) (FIG. 1B, Ab4116, 15.3 nM) (FIG. 1C, Ab4117, 9.9 nM), (FIG. 1D, Ab4118, 21.3 nM). Therefore, the best clone was Ab4117 with a 6 fold affinity improvement achieved.

Example 2

Figure 5:
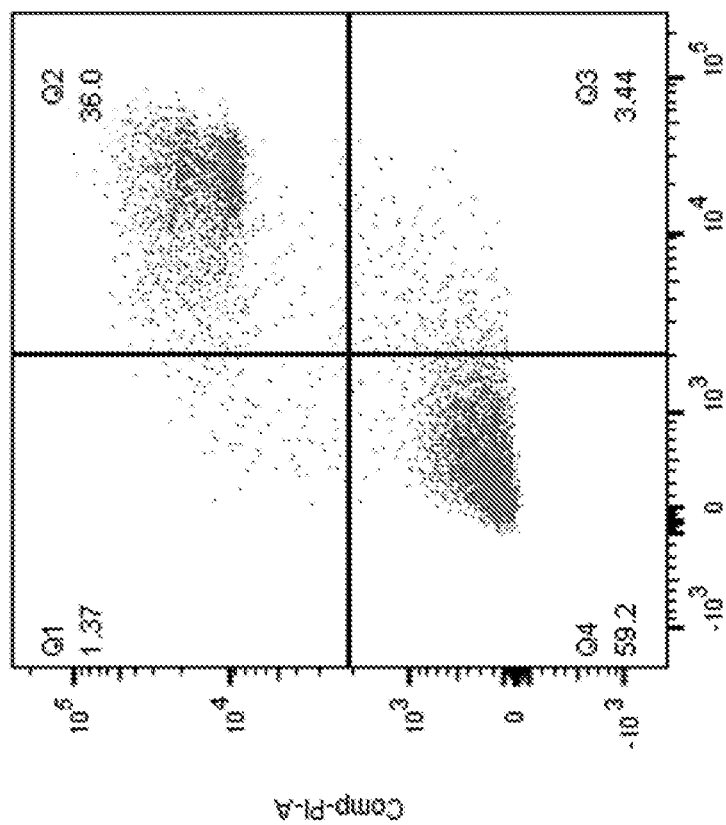
FIG. 5 is a flow cytometry plot showing untreated MCF-7 (target) cells as negative control.
Figure 7B:
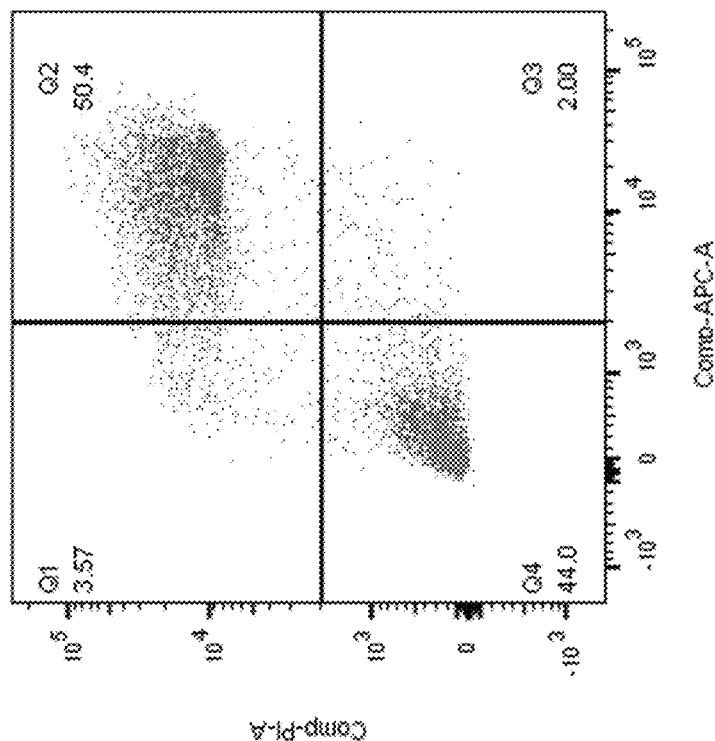
FIGS. 7A to 7C are flow cytometry plots showing MCF-7 (target) cells treated with normal human CD8 T (effector) cells at 1:5 T to E ratio.
Figure 7A:
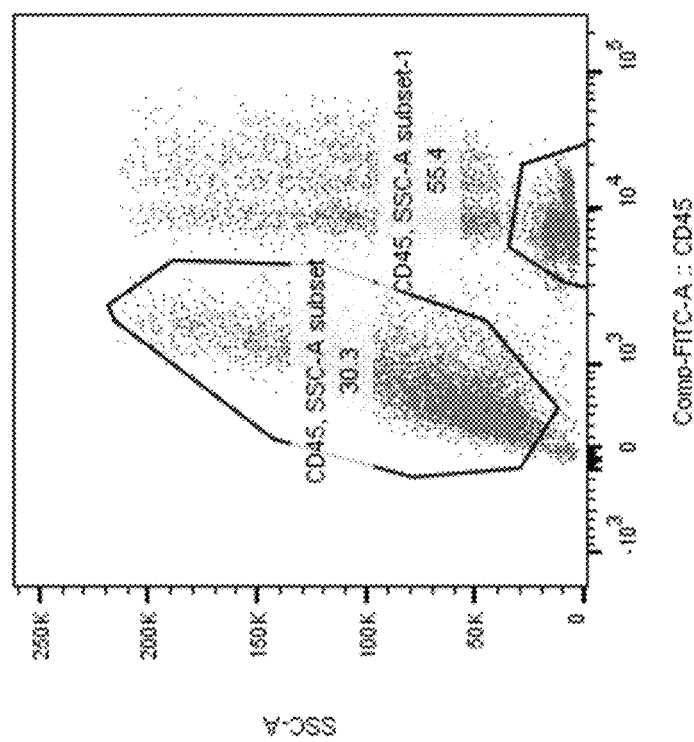
Figure 8A:
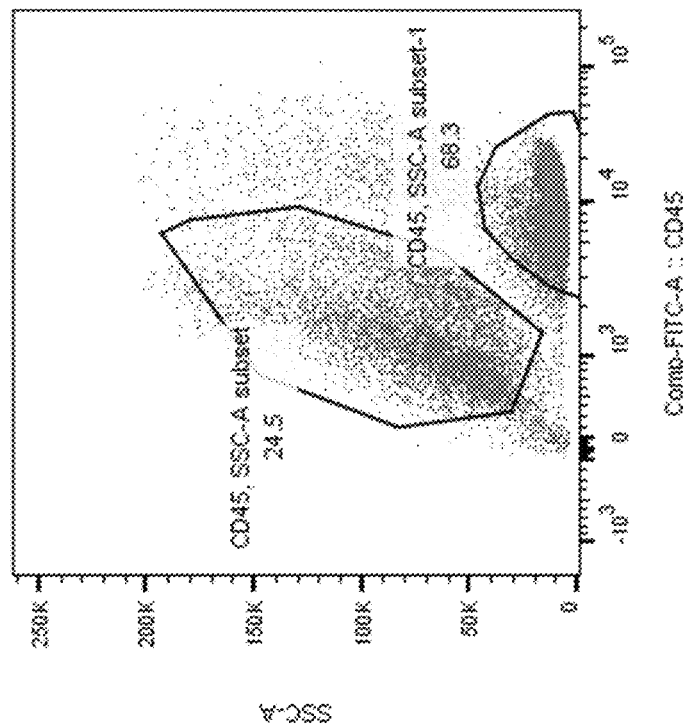
FIGS. 8A to 8C are flow cytometry plots showing MCF-7 (target) cells treated with normal human CD8 T (effector) cells at 1:5 of T to E ratio+bispecific antibody (pilot) at conc of 1 μg/ml.
Figure 7C:
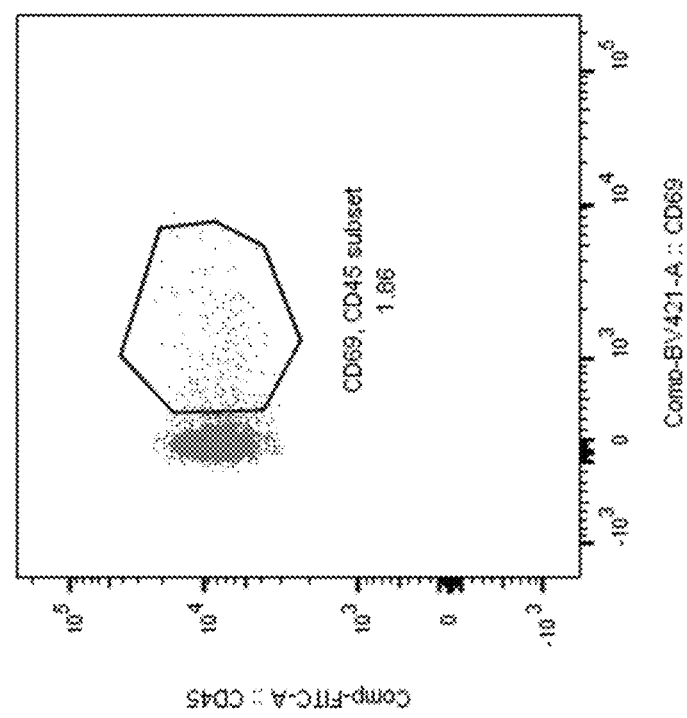
Figure 8C:
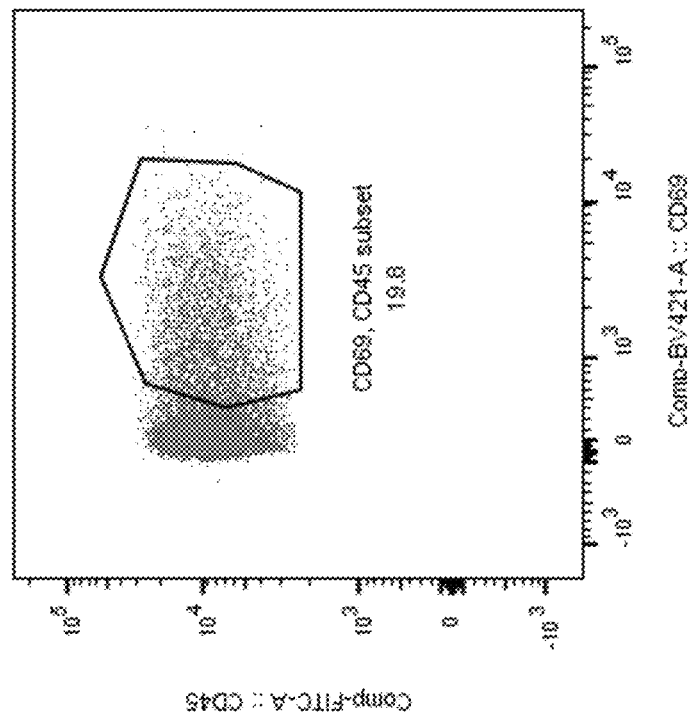
Figure 8B:
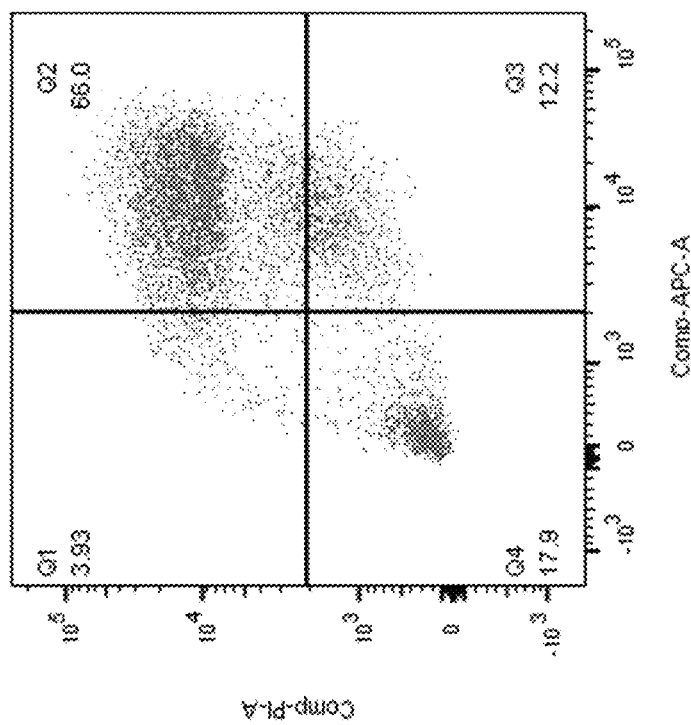
Figure 9B:
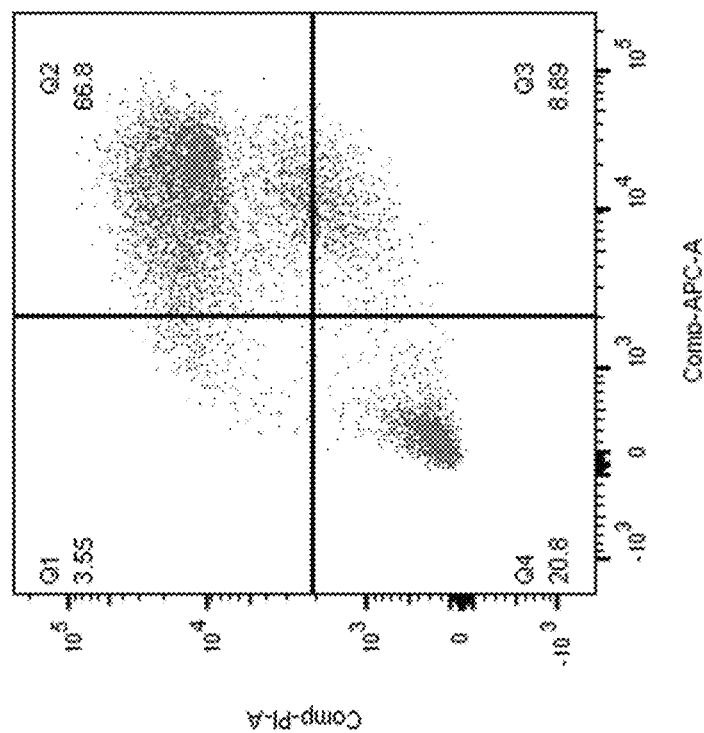
FIGS. 9A to 9C are flow cytometry plots showing MCF-7 (target) cells treated with normal human CD8 T (effector) cells at 1:5 of T to E ratio+bispecific antibody (pilot) at conc of 5 ug/ml.
Figure 9A:
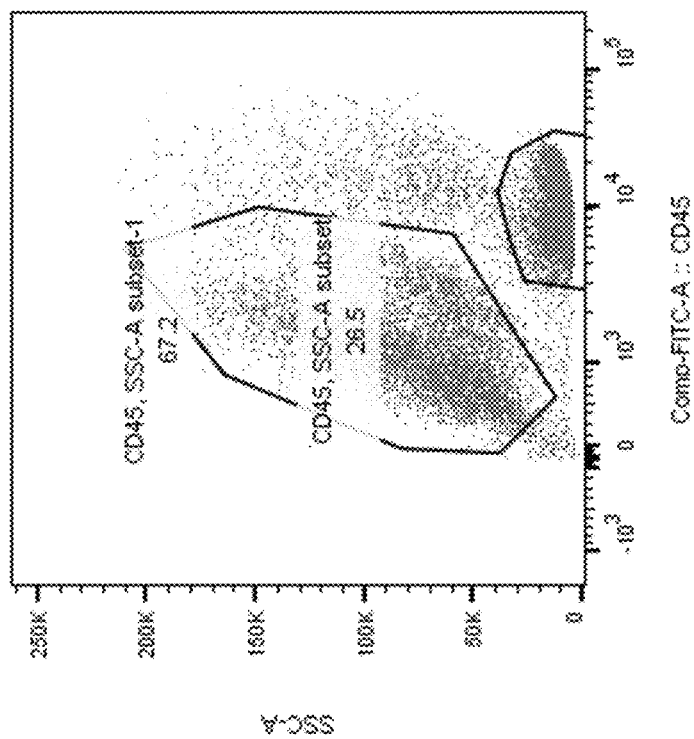
Figure 10A:
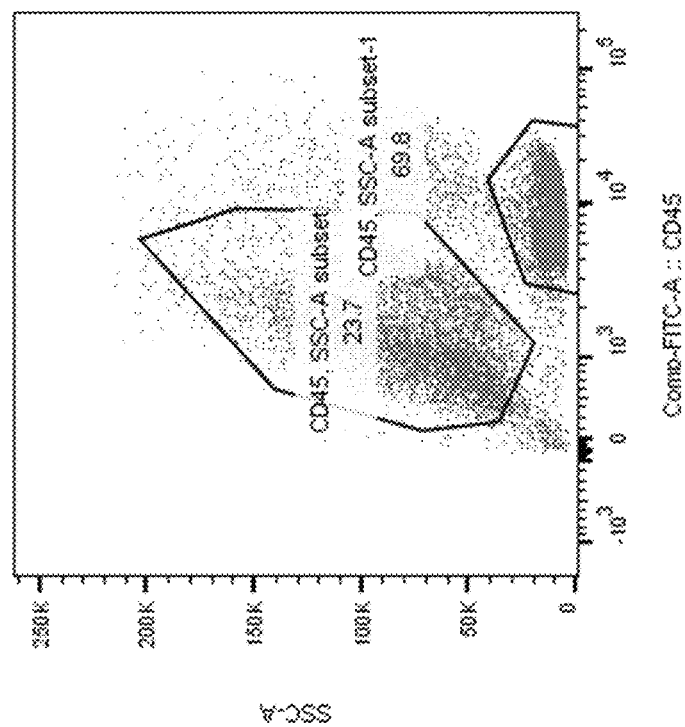
FIG. 10A to 10C are flow cytometry plots showing MCF-7 (target) cells treated with normal human CD8 T (effector) cells at 1:5 of T to E ratio+bispecific antibody (pilot) at conc of 10 ug/ml.
Figure 9C:
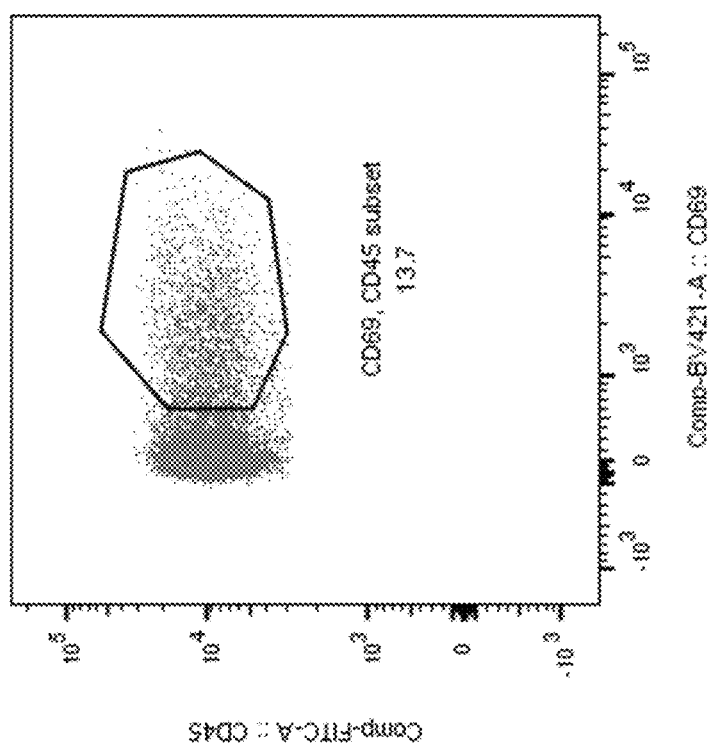
Figure 10C:
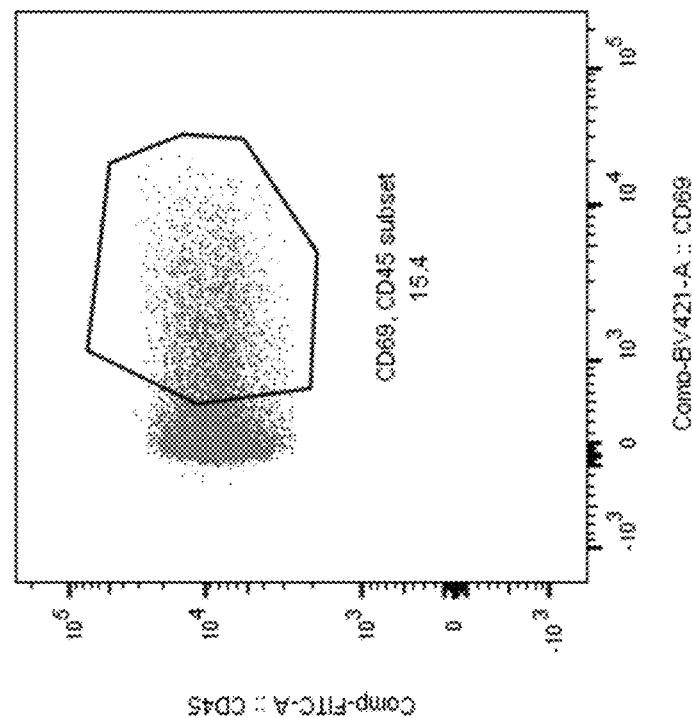
Figure 10B:
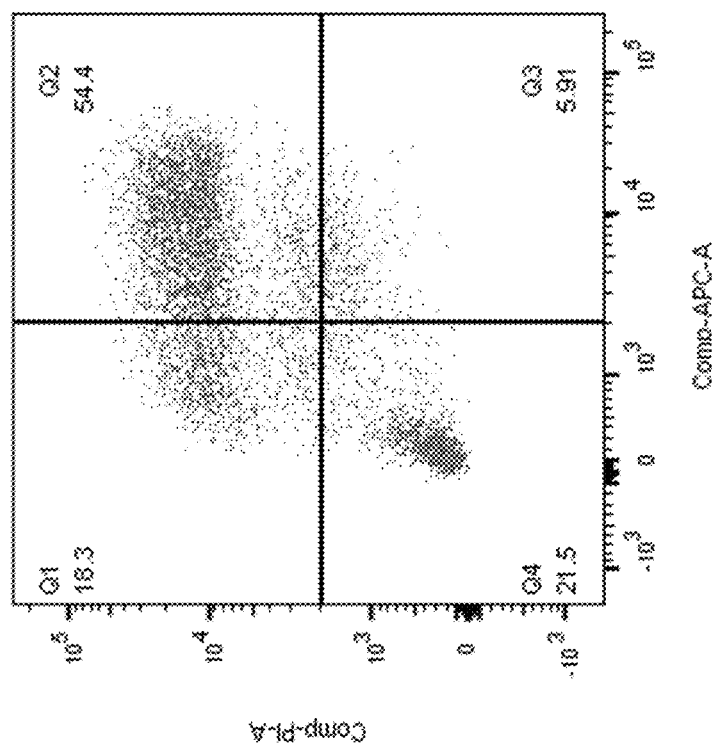
Figure 12:
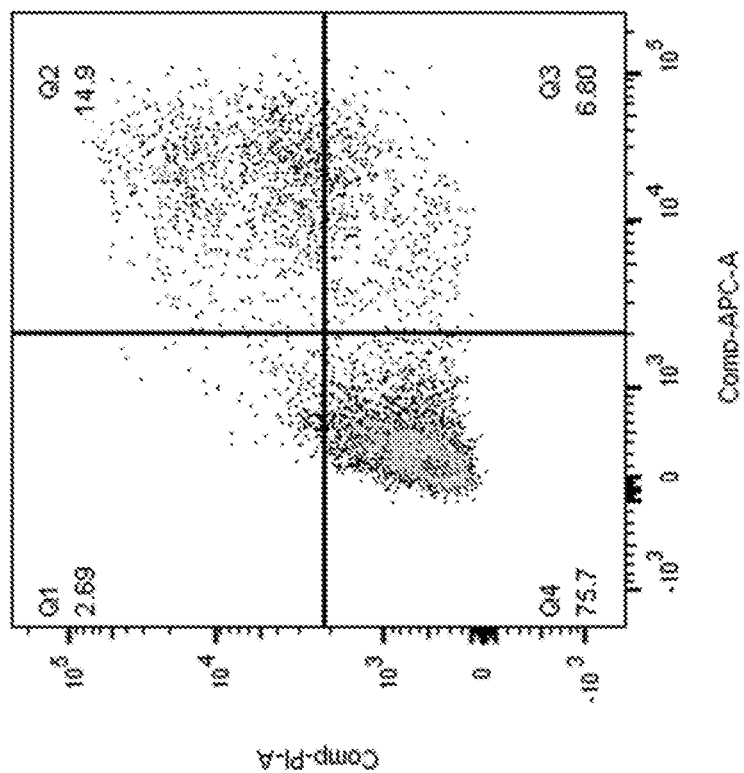
FIG. 12 is a flow cytometry plot showing KLE (target) cells treated with bispecific antibody (pilot) at conc of 10 μg/ml.
Figure 11:
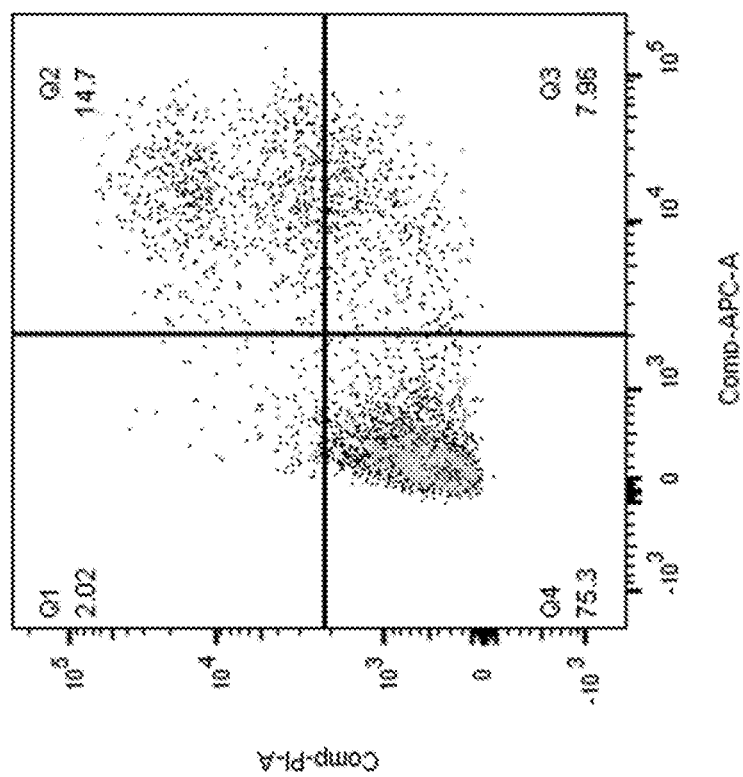
FIG. 11 is a flow cytometry plot showing untreated KLE (target) cells as negative control.
Figure 13B:
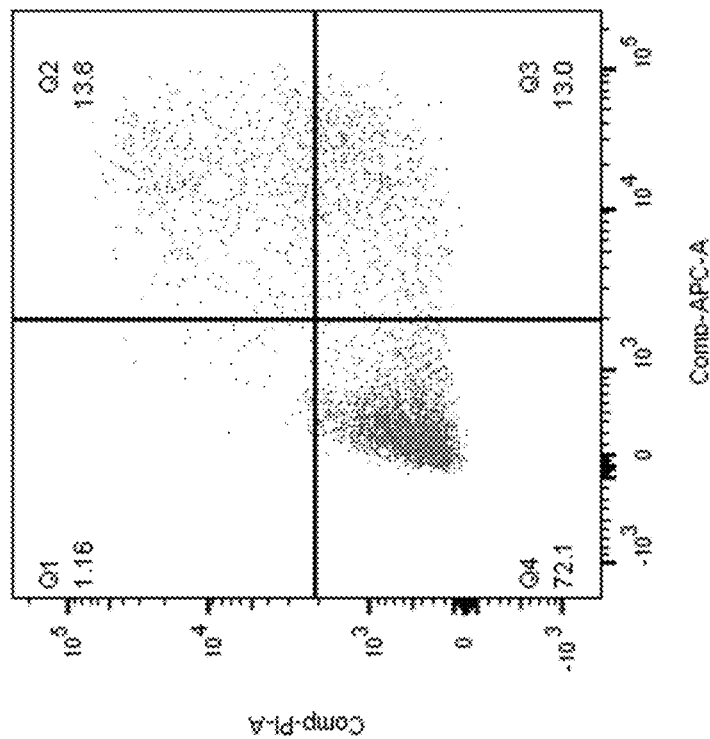
FIGS. 13A to 13C are flow cytometry plots showing KLE (target) cells treated with normal human CD8 T (effector) cells at 1:5 T to E ratio.
Figure 13A:
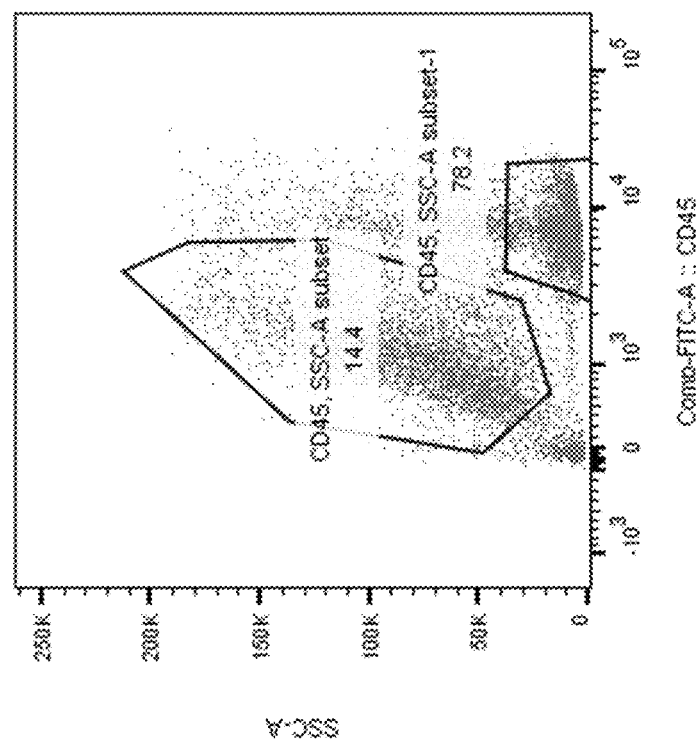
Figure 14A:
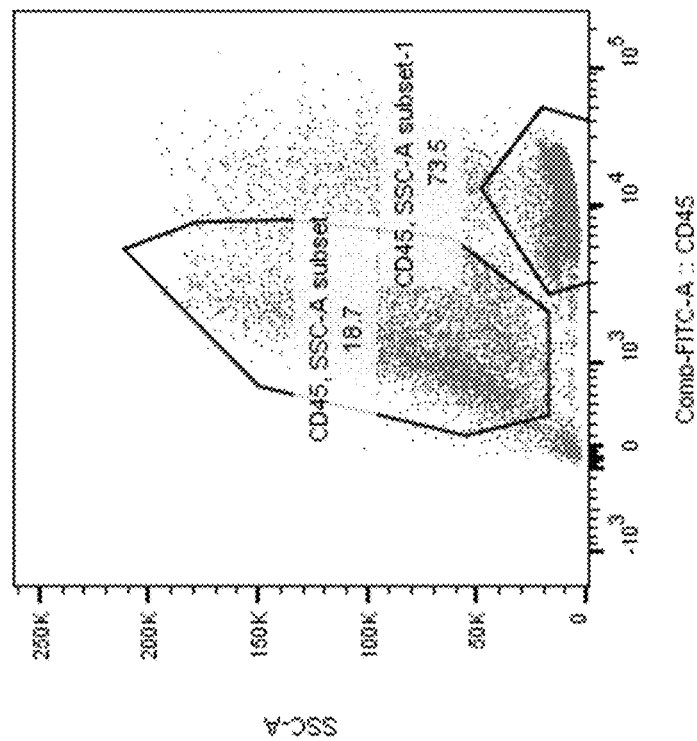
FIGS. 14A to 14C are flow cytometry plots showing KLE (target) cells treated with normal human CD8 T (effector) cells at 1:5 of T to E ratio+bispecific antibody (pilot) at conc of 5 ug/ml.
Figure 13C:
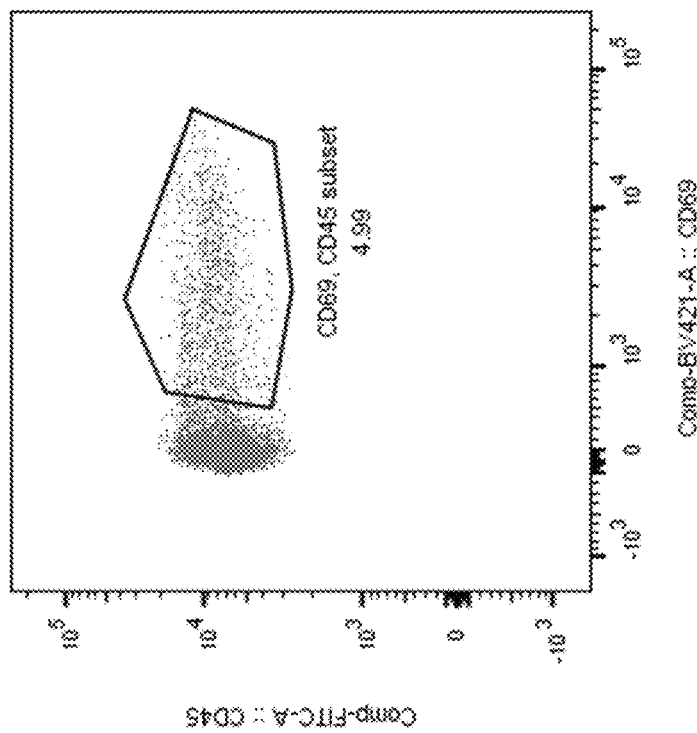
Figure 14C:
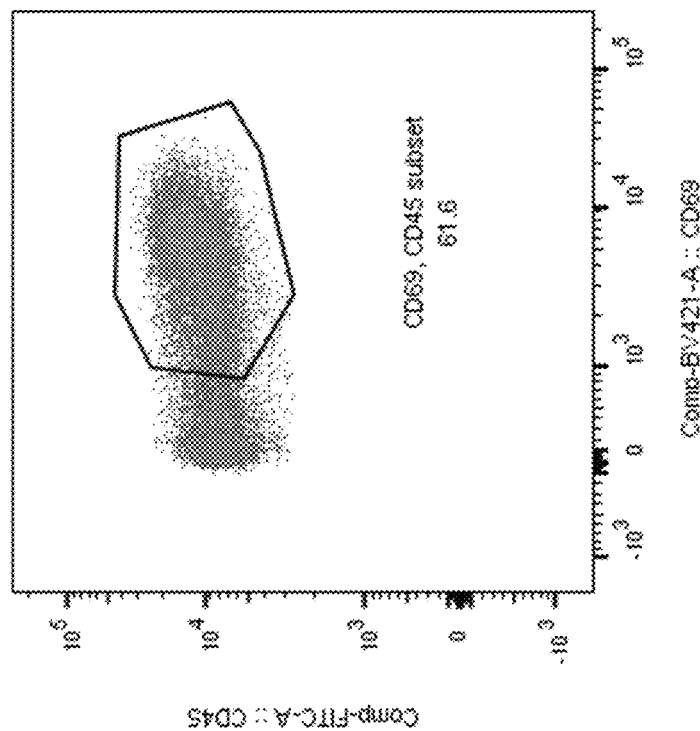
Figure 14B:
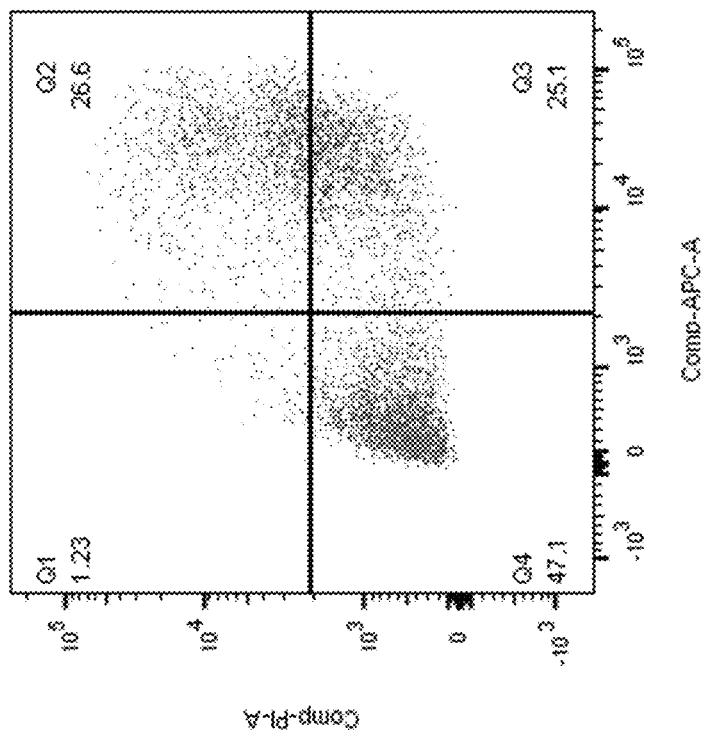
Figure 15B:
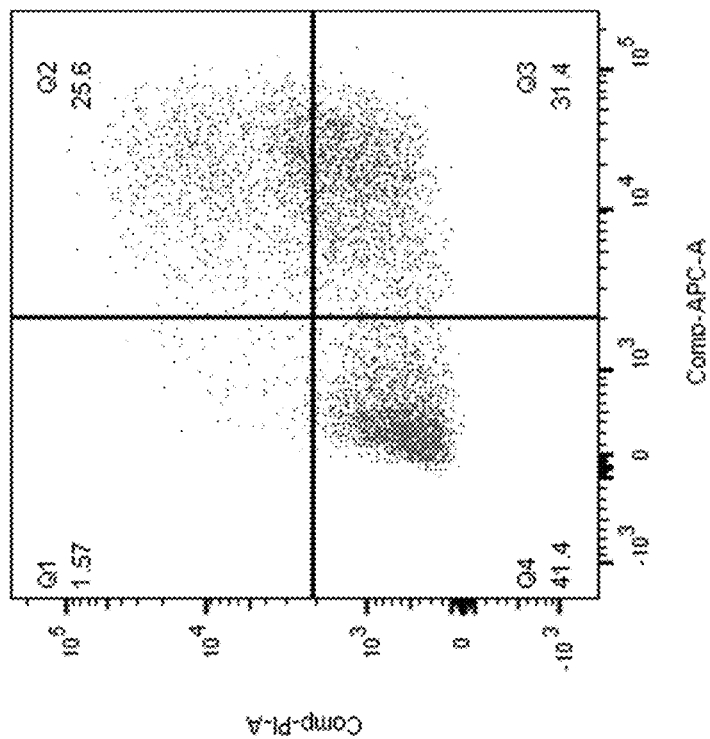
FIGS. 15A to 15C are flow cytometry plots showing KLE (target) cells treated with normal human CD8 T (effector) cells at 1:5 of T to E ratio+bispecific antibody (pilot) at conc of 10 ug/ml.
Figure 15A:
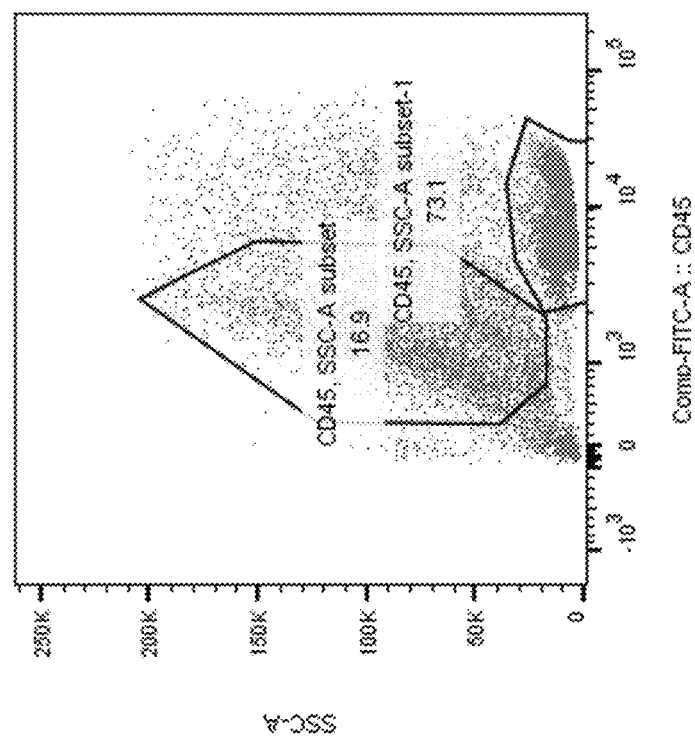
Figure 15C:
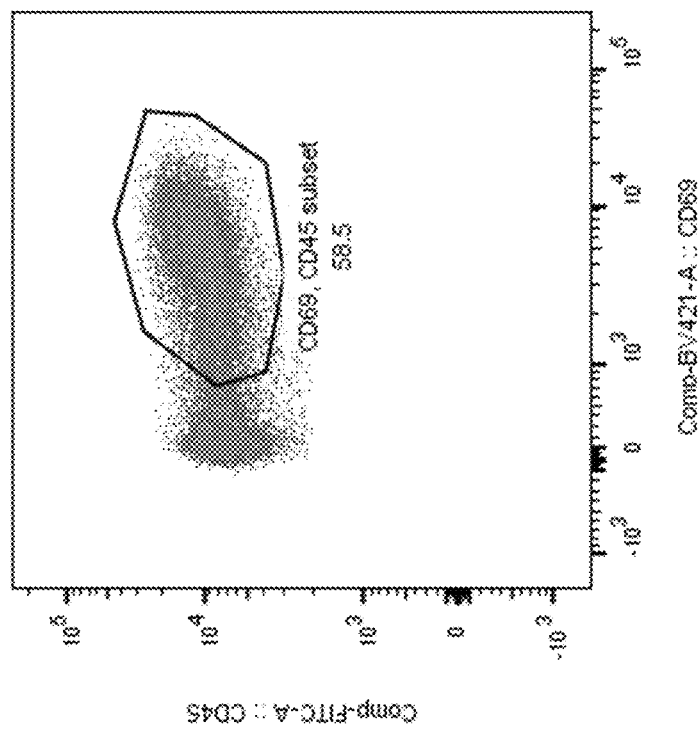
Figure 17:
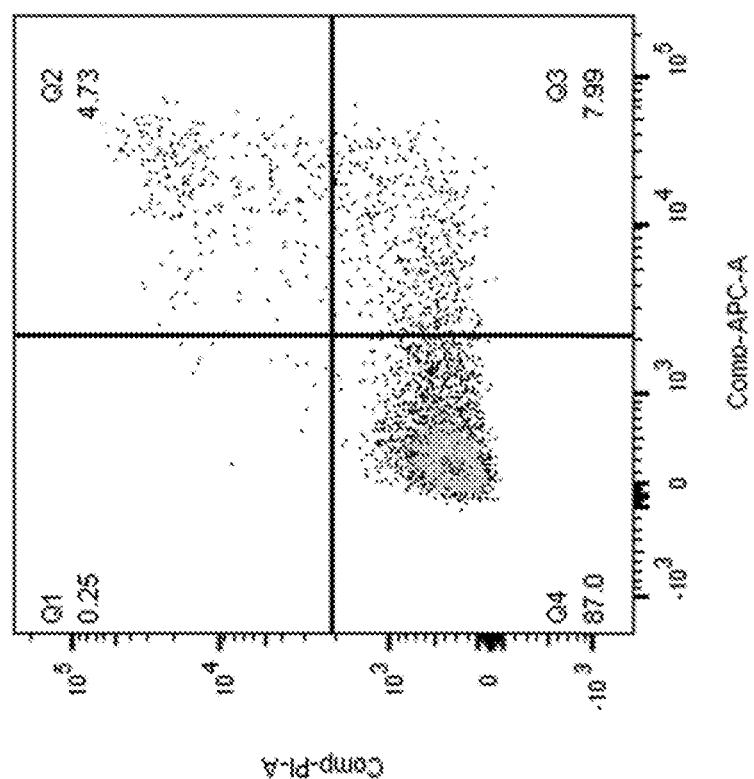
FIG. 17 is a flow cytometry plot showing MDA-231 cells treated with bispecific antibody (pilot) at conc of 10 μg/ml.
Figure 16:
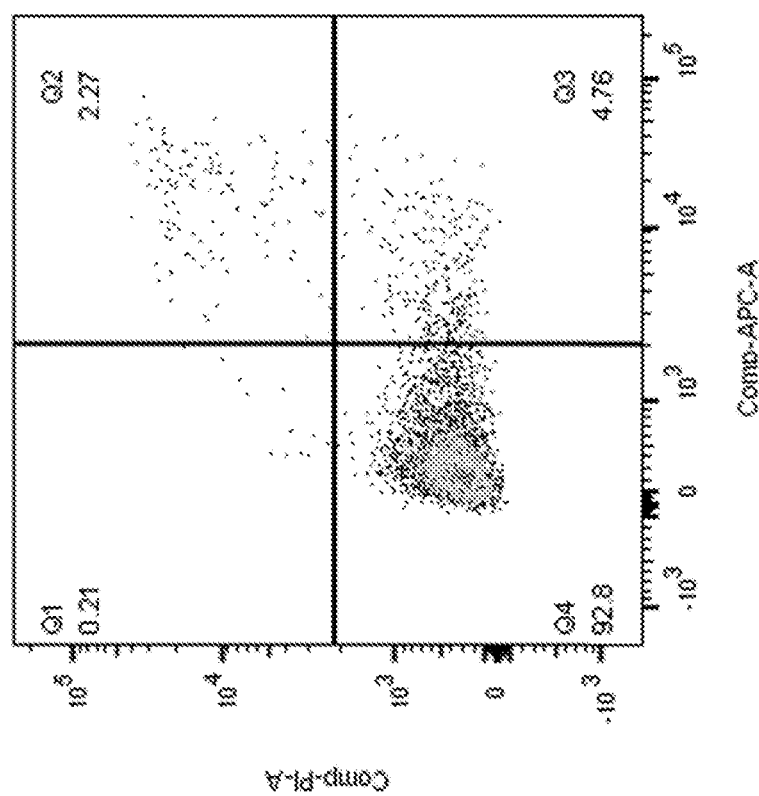
FIG. 16 is a flow cytometry plot showing untreated MDA-231 (target) cells as negative control.
Figure 18B:
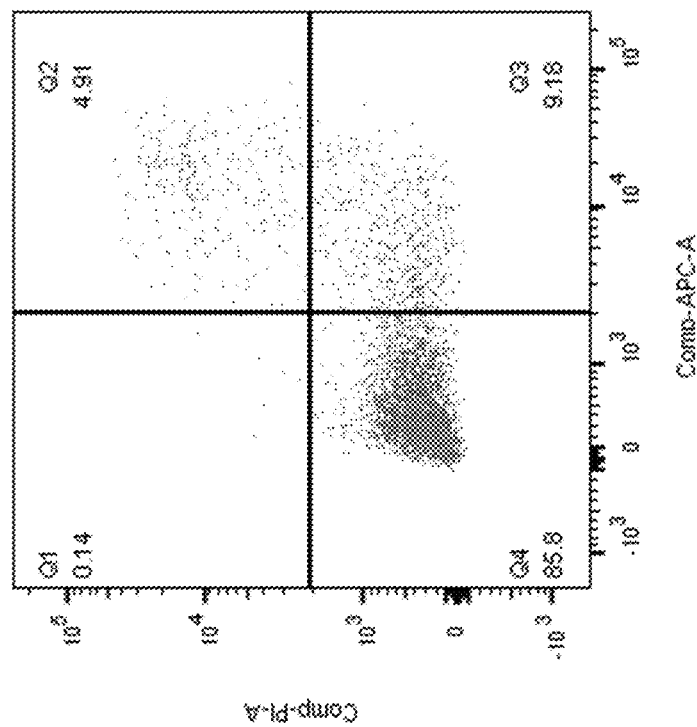
FIGS. 18A to 18C are flow cytometry plots showing MDA-231 (target) cells treated with normal human CD8 T (effector) cells at 1:5 T to E ratio.
Figure 18A:
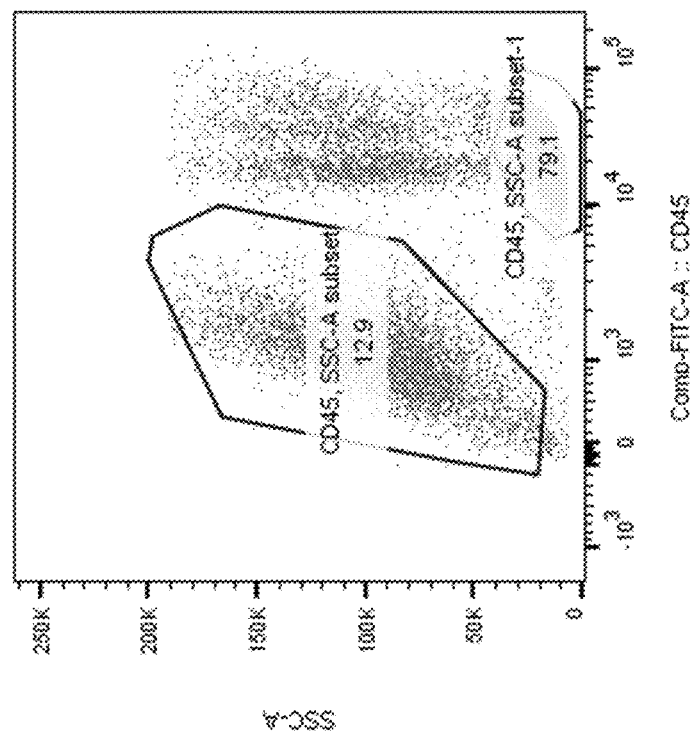
Figure 19A:
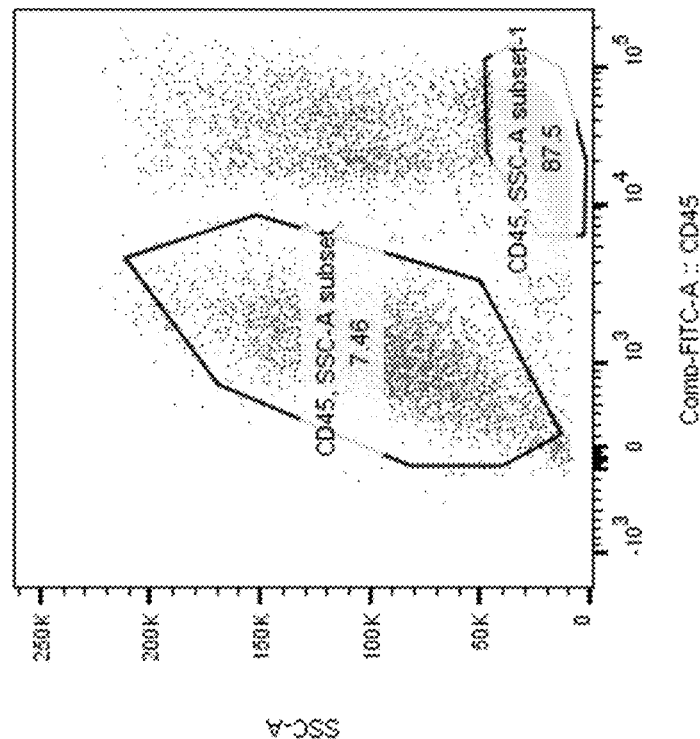
FIGS. 19A to 19C are flow cytometry plots showing MDA-231 (target) cells treated with normal human CD8 T (effector) cells at 1:5 of T to E ratio+bispecific antibody (pilot) at conc of 1 ug/ml.
Figure 18C:
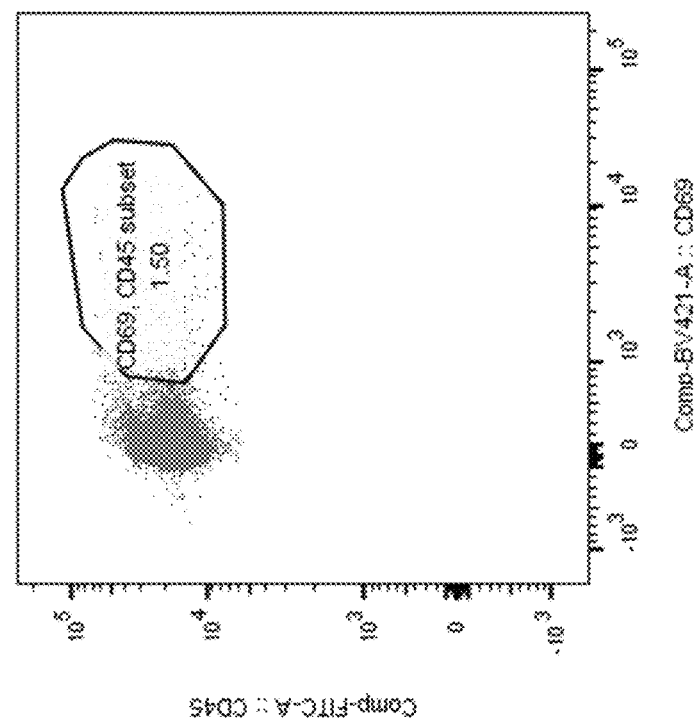
Figure 19C:
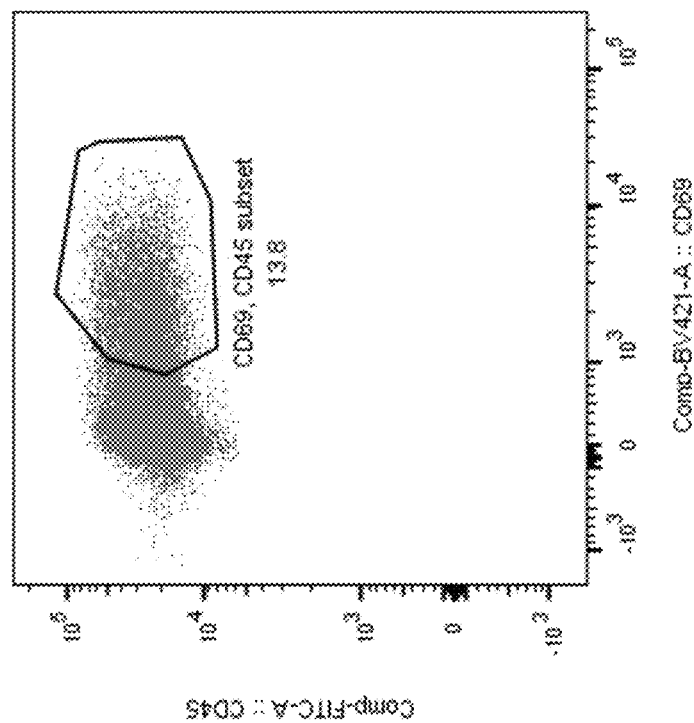
Figure 19B:
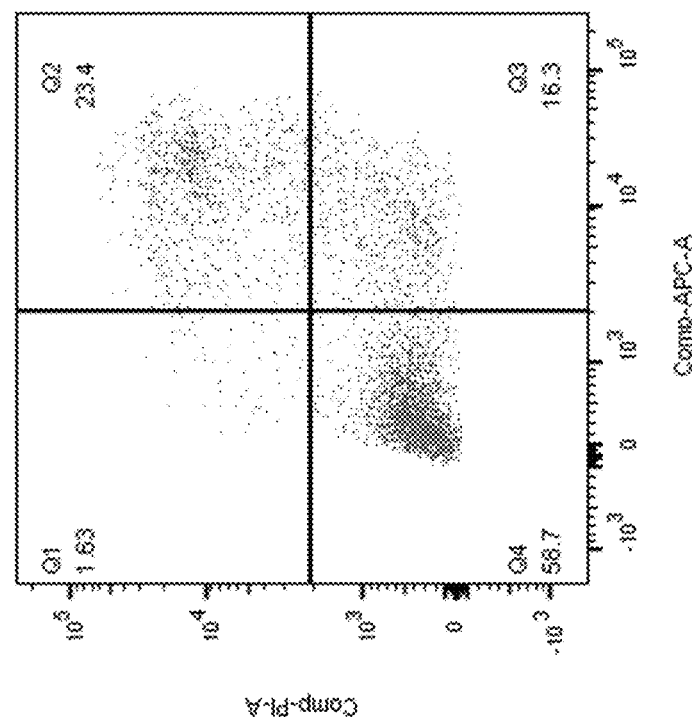
Figure 20B:
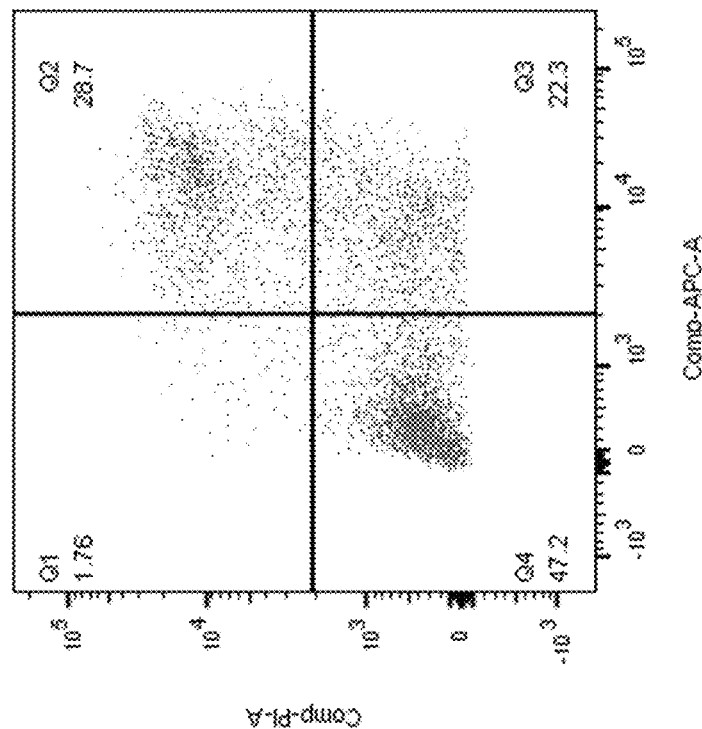
FIGS. 20A to 20C are flow cytometry plots showing MDA-231 (target) cells treated with normal human CD8 T (effector) cells at 1:5 of T to E ratio+bispecific antibody (pilot) at conc of 5 ug/ml.
Figure 20A:
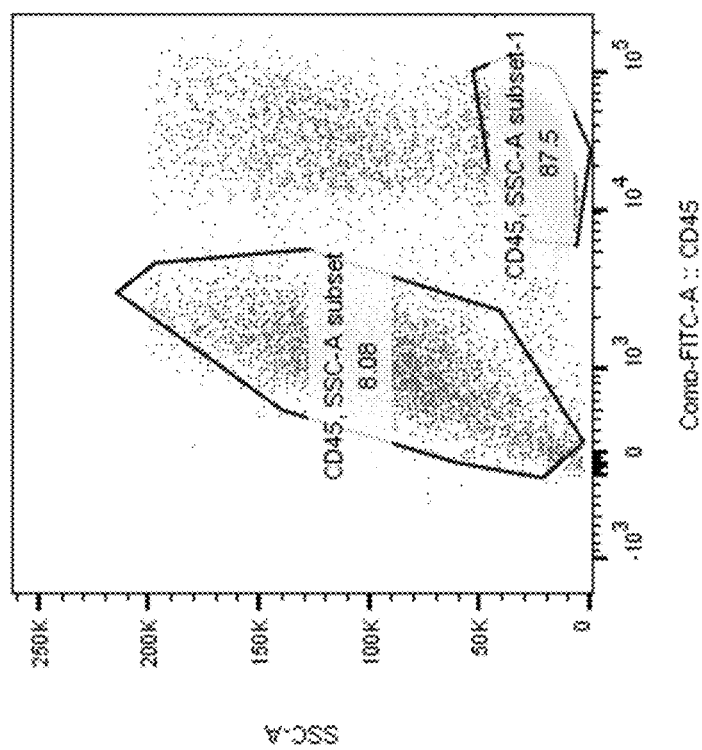
Figure 21A:
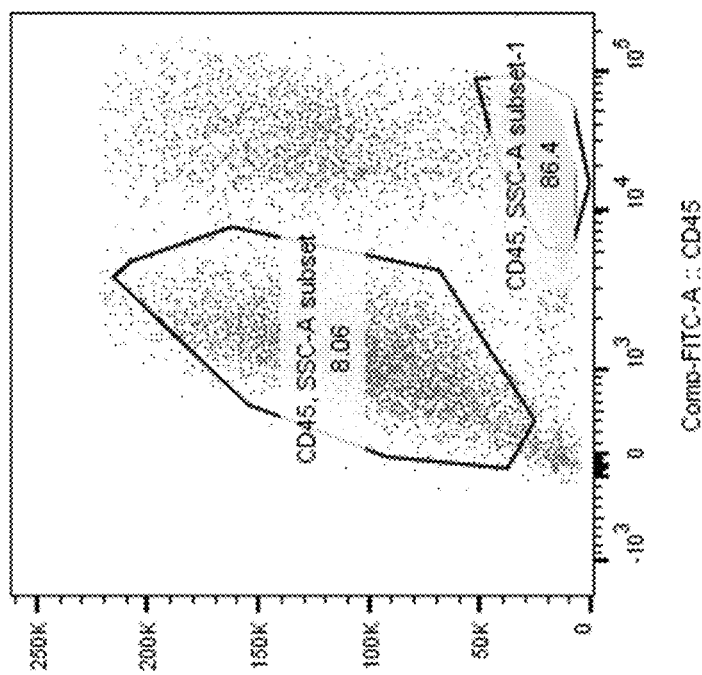
Figure 20C:
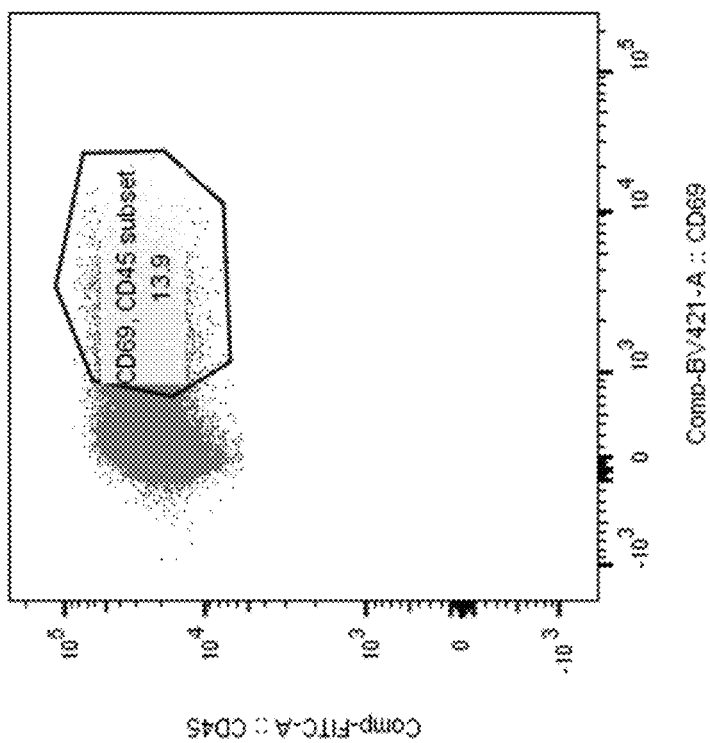
Figure 21C:
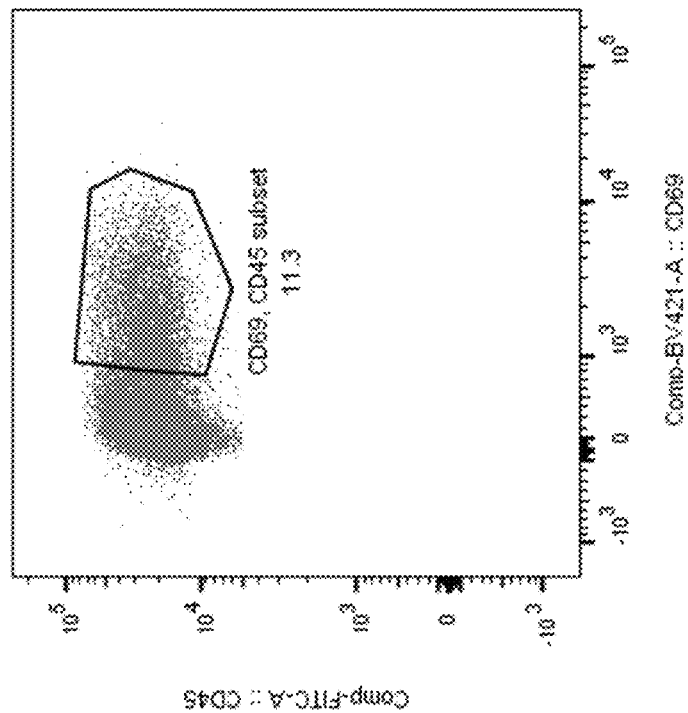
Figure 21B:
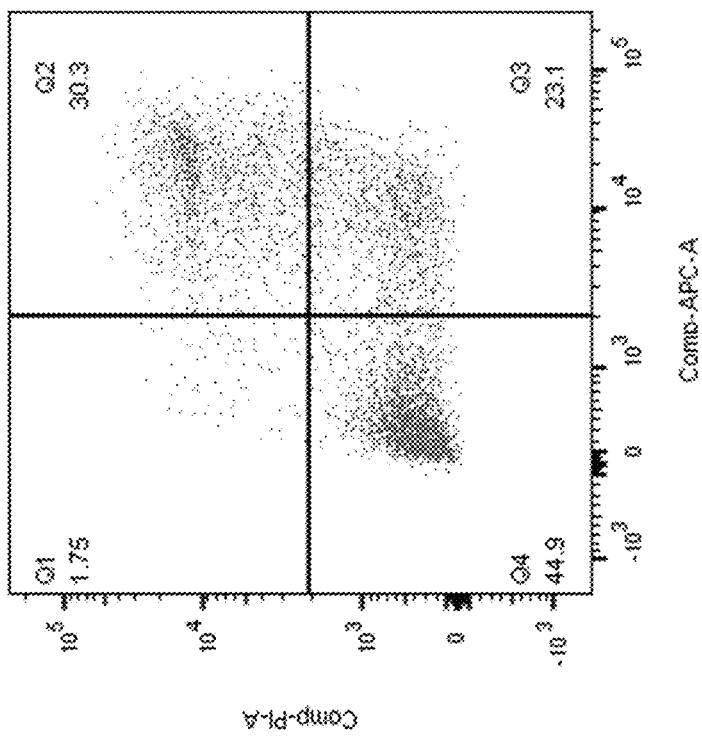
Figure 23:
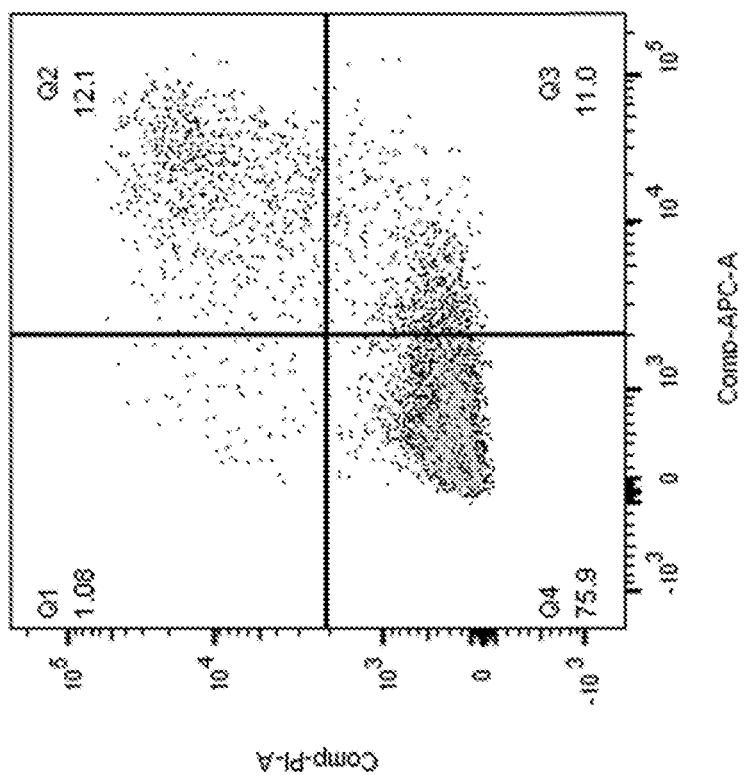
FIG. 23 is a flow cytometry plot showing SKBR3 cells treated with bispecific antibody at conc of 10 μg/ml.
Figure 22:
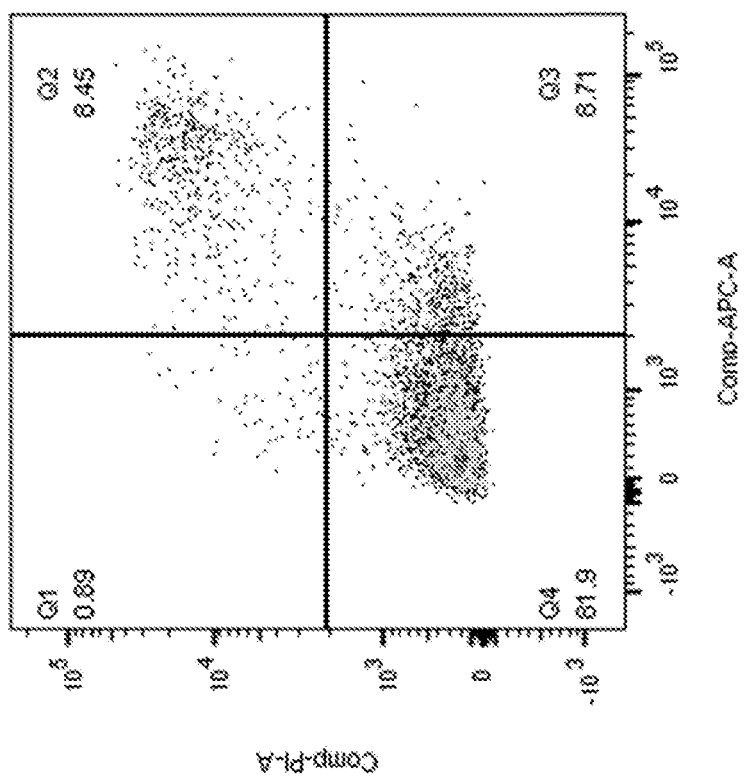
FIG. 22 is a flow cytometry plot showing untreated SKBR3 (target) cells as negative control.
Figure 24B:
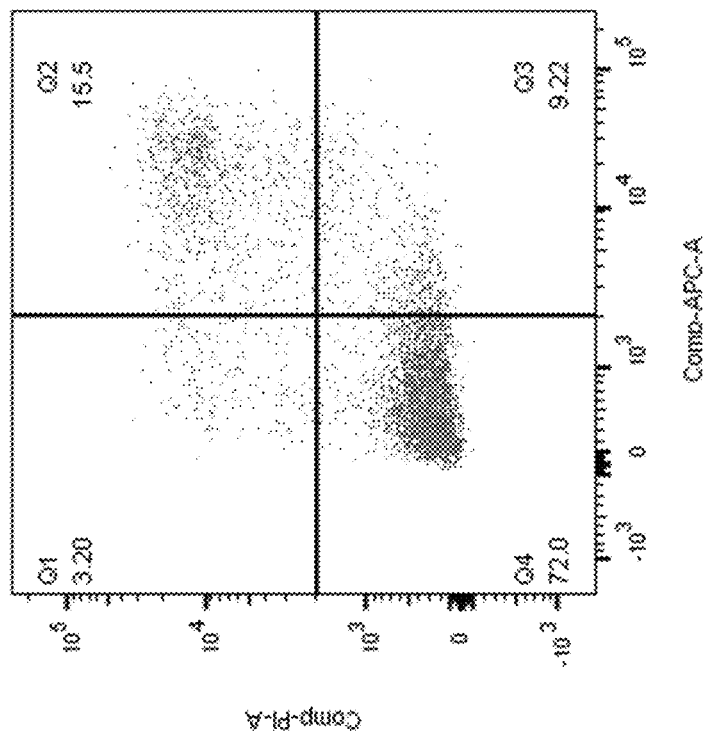
FIGS. 24A to 24C are flow cytometry plots showing SKBR3 (target) cells treated with normal human CD8 T (effector) cells at 1:5 T to E ratio.
Figure 24A:
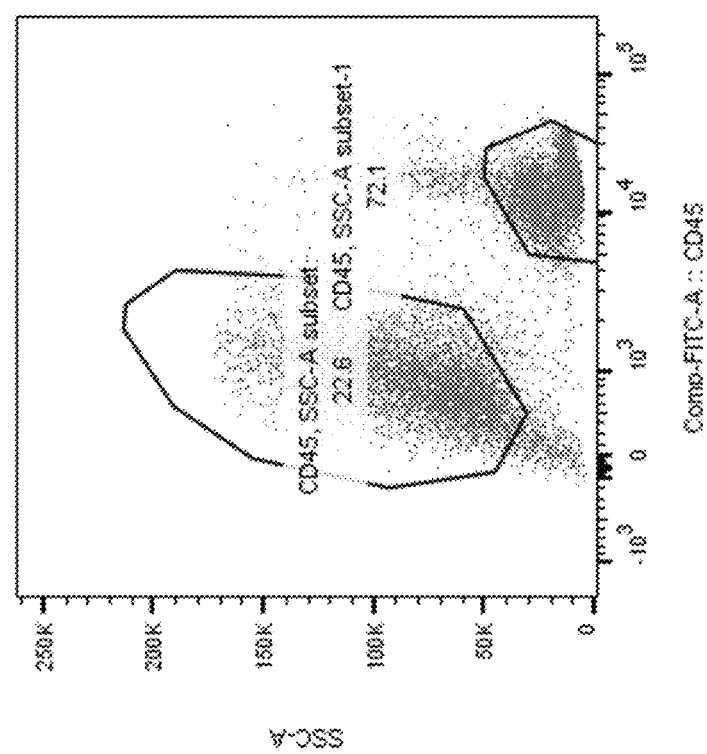
Figure 25A:
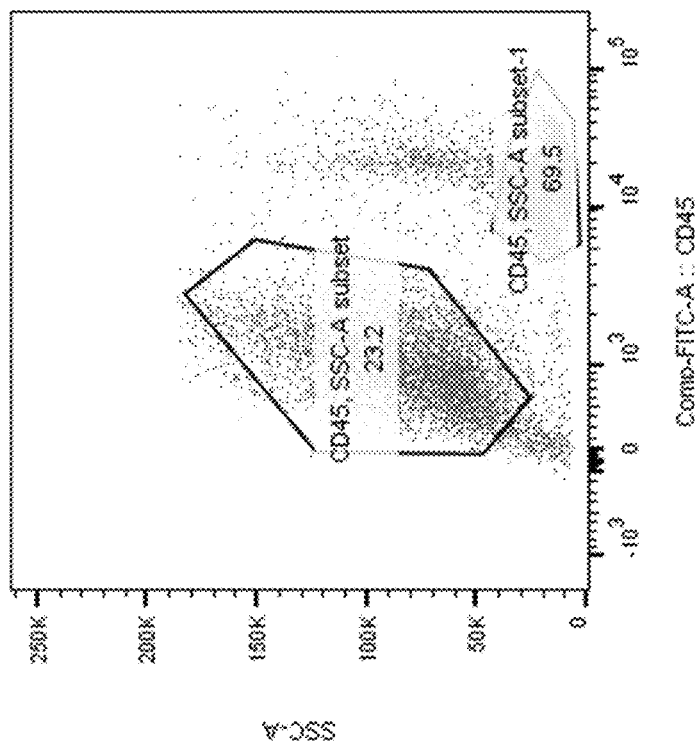
FIGS. 25A to 25C are flow cytometry plots showing SKBR3 (target) cells treated with normal human CD8 T (effector) cells at 1:5 of T to E ratio+bispecific antibody at conc of 1 ug/ml.
Figure 24C:
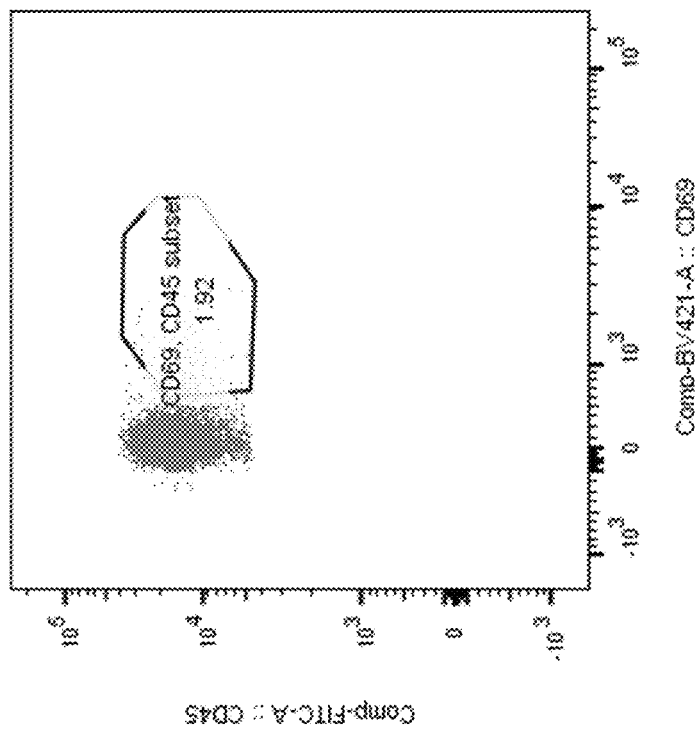
Figure 25C:
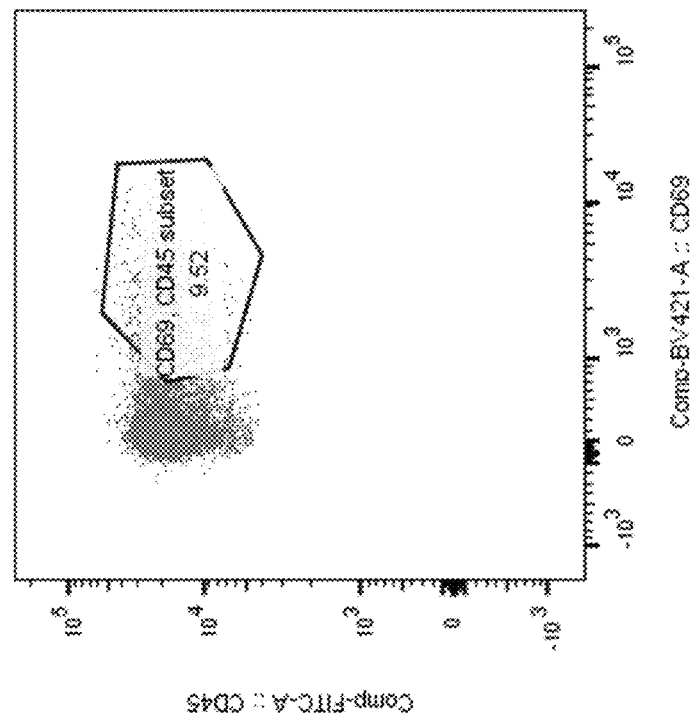
Figure 25B:
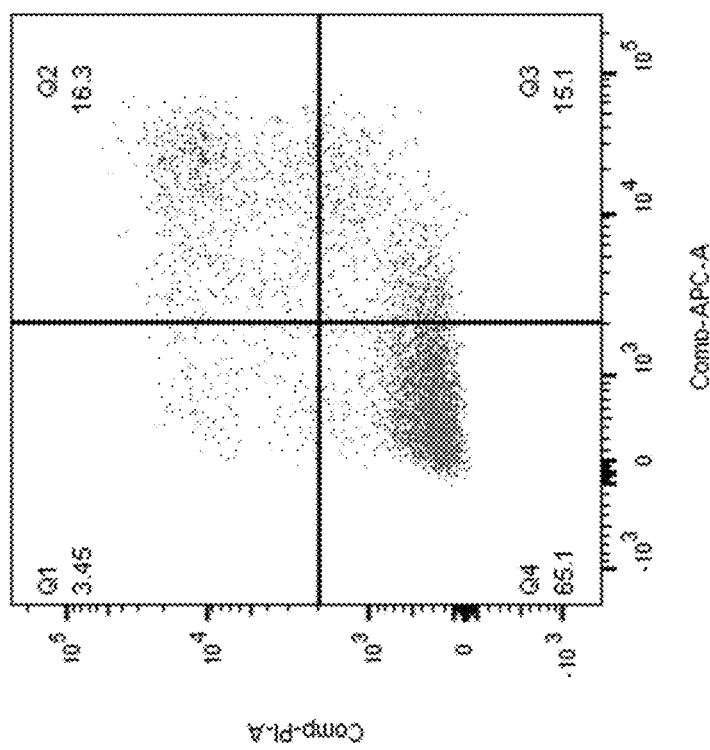
Figure 26B:
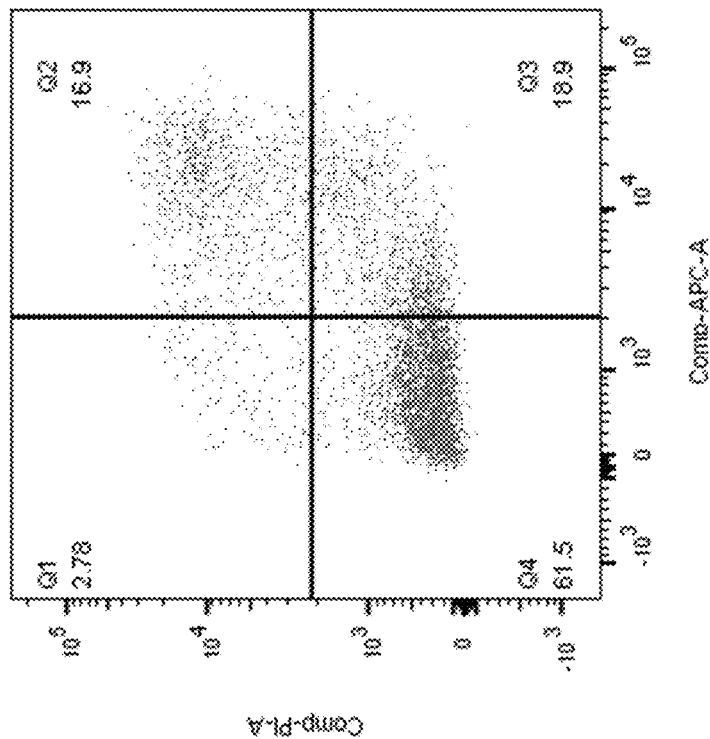
FIGS. 26A to 26C are flow cytometry plots showing SKBR3 (target) cells treated with normal human CD8 T (effector) cells at 1:5 of T to E ratio+bispecific antibody at conc of 5 ug/ml.
Figure 26A:
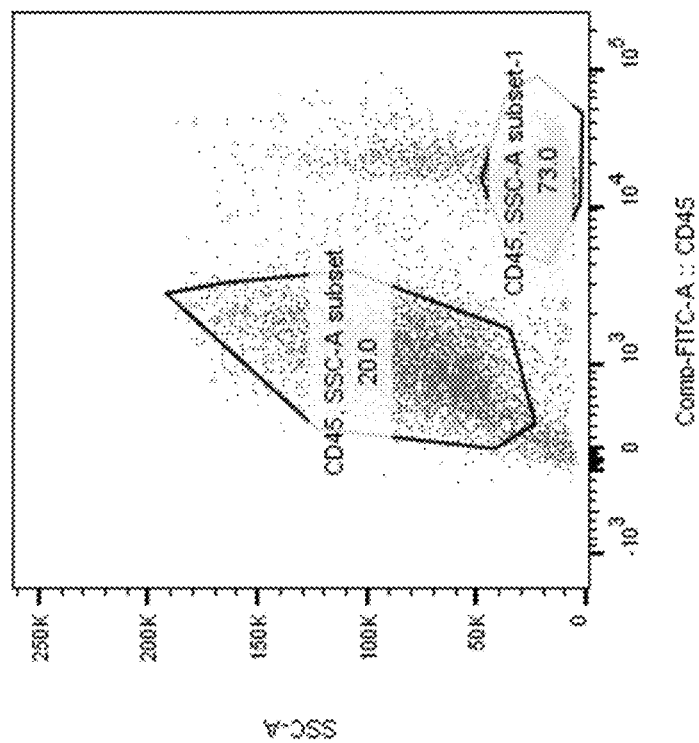
Figure 27A:
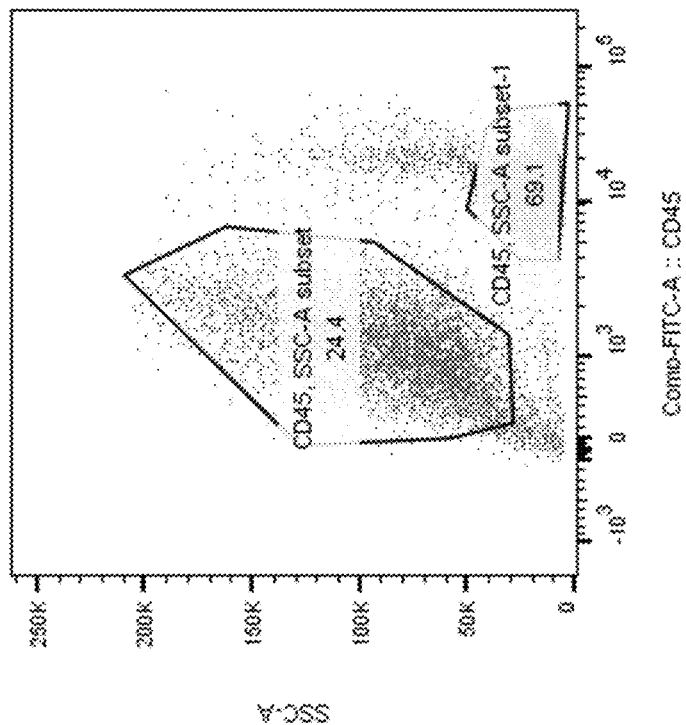
FIGS. 27A to 27C are flow cytometry plots showing SKBR3 (target) cells treated with normal human CD8 T (effector) cells at 1:5 of T to E ratio+bispecific antibody at conc of 10 ug/ml.
Figure 26C:
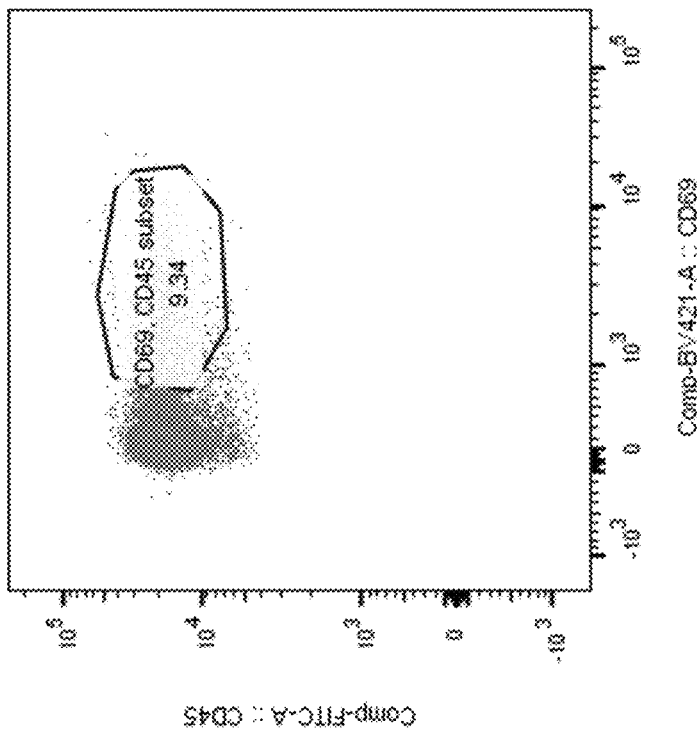
Figure 27C:
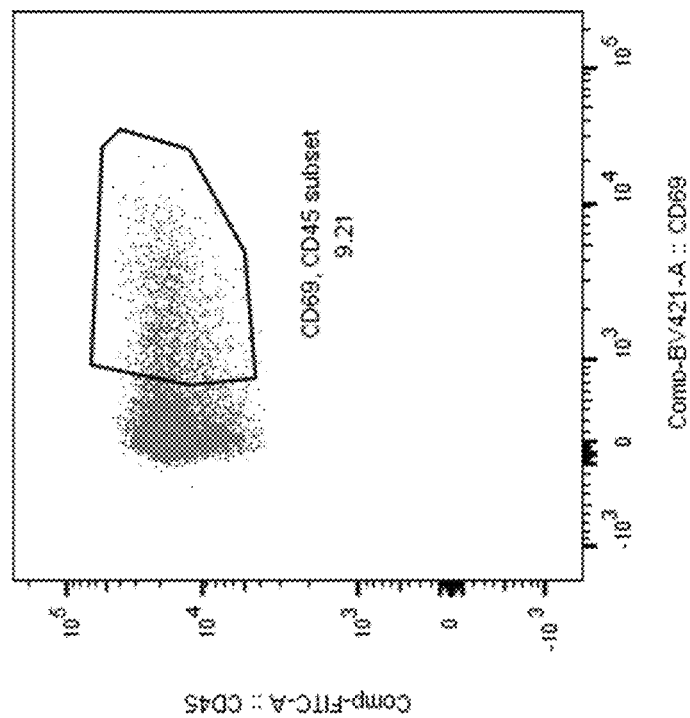
Figure 27B:
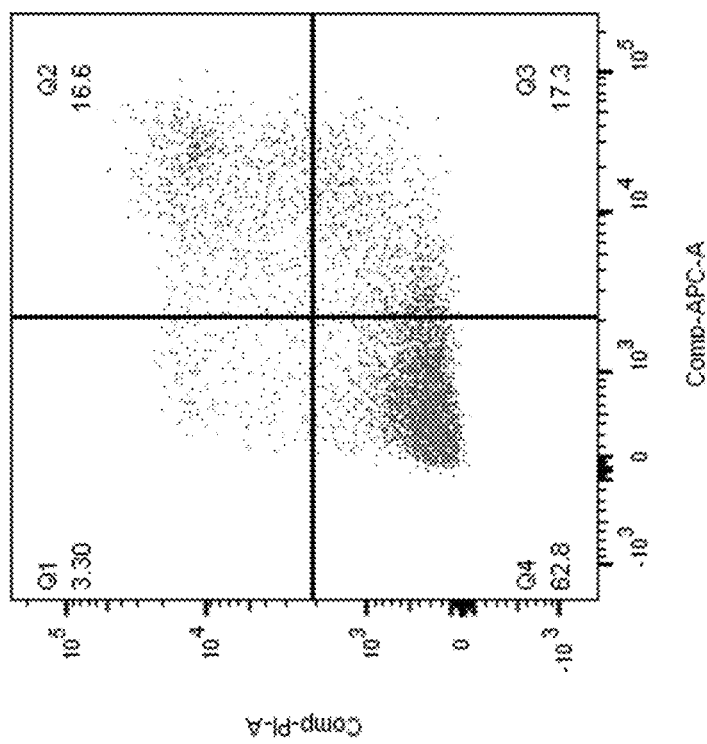
Figure 29:
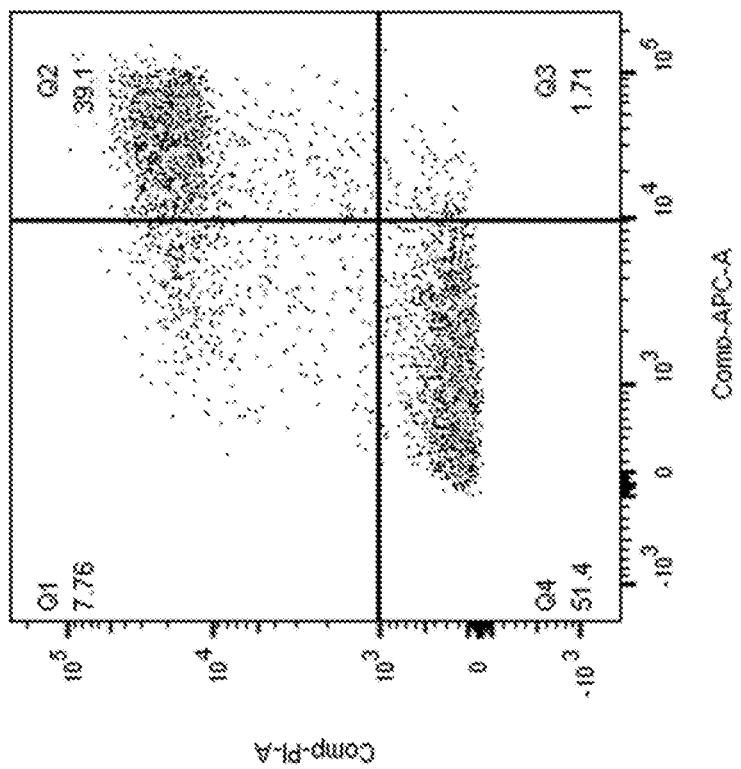
FIG. 29 are flow cytometry plots showing MCF-7 cells treated with bispecific antibody at conc of 5 μg/ml.
Figure 28:
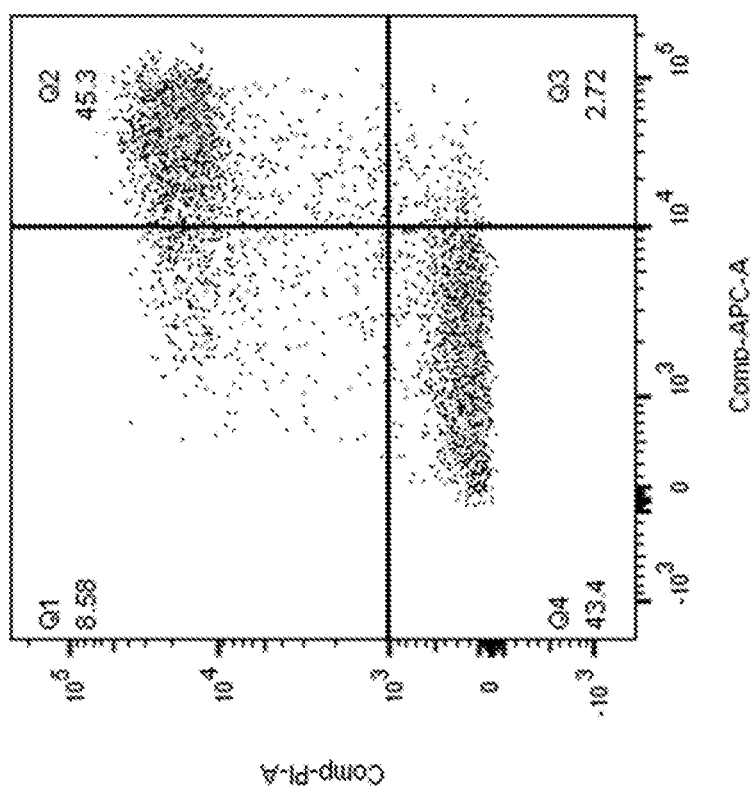
FIG. 28 are flow cytometry plots showing untreated MCF-7 (target) cells as negative control.
Figure 31:
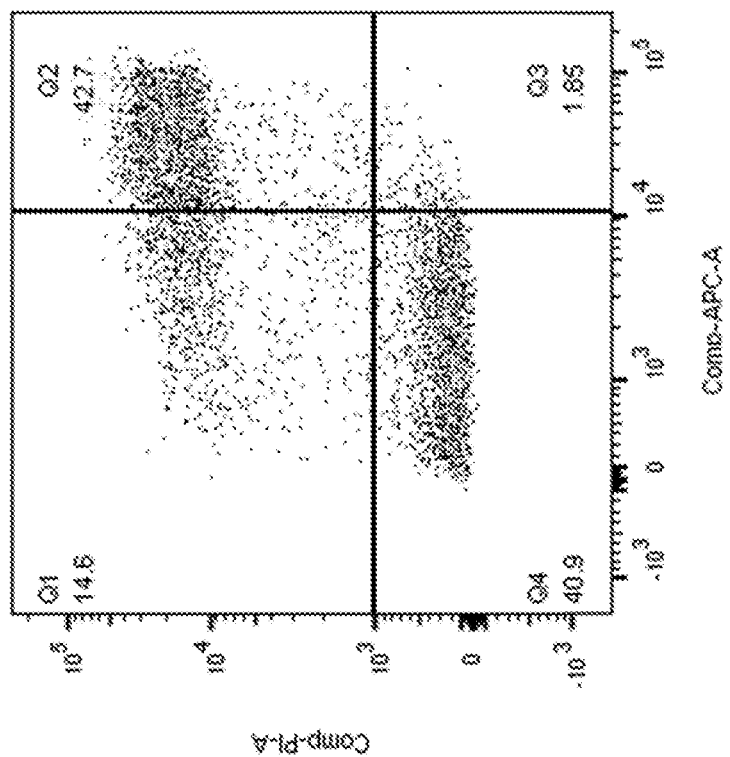
FIG. 31 are flow cytometry plots showing MCF-7 (target) cells treated with Nivo (5 μM).
Figure 30:
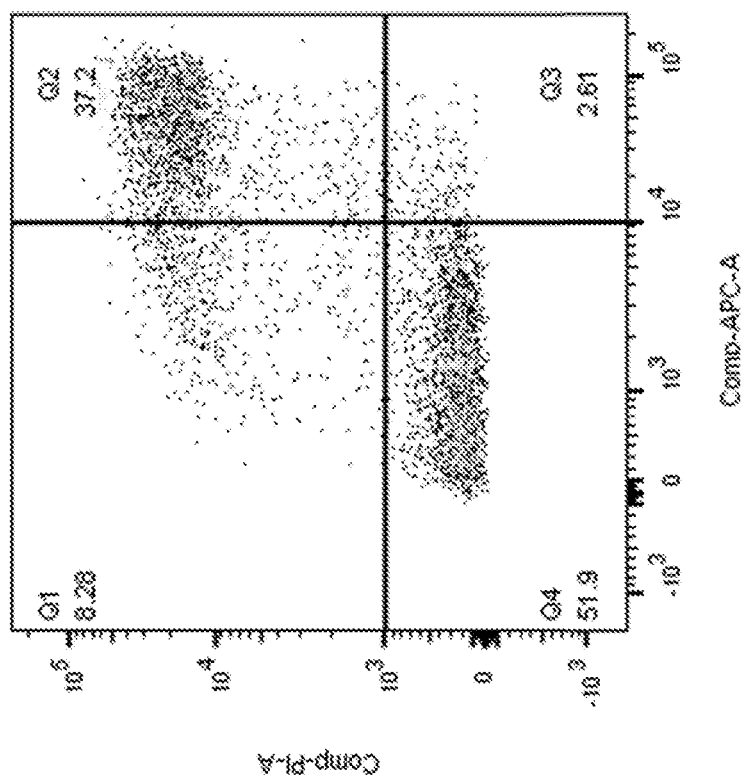
FIG. 30 are flow cytometry plots showing MCF-7 (target) cells treated with Pembro (5 μM).
Figure 32B:
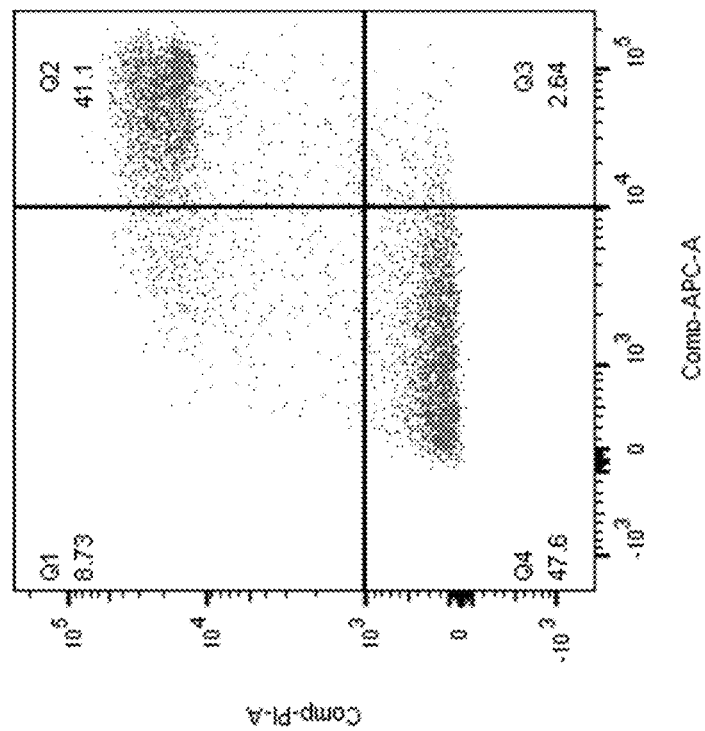
FIGS. 32A to 32C are flow cytometry plots showing MCF-7 (target) cells treated with normal human CD8 T (effector) cells at 1:5 T to E ratio.
Figure 32A:
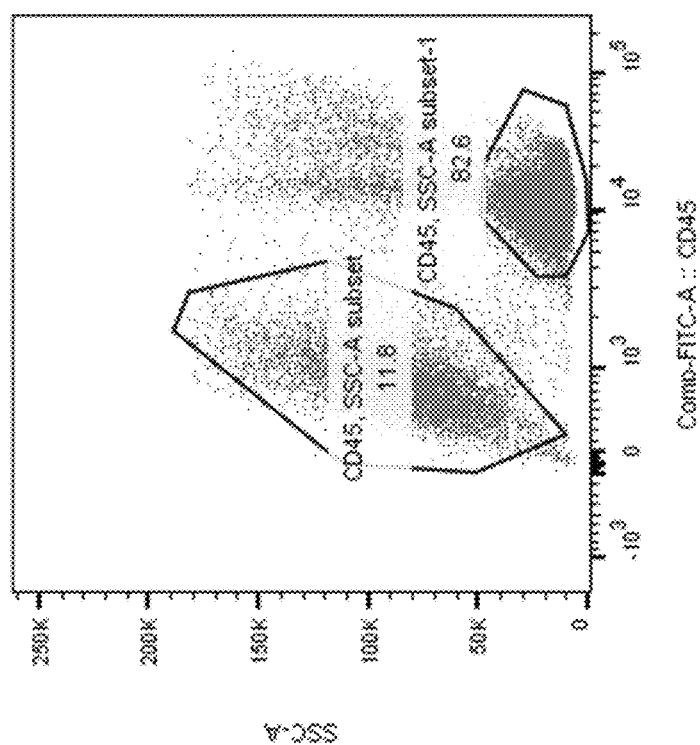
Figure 33A:
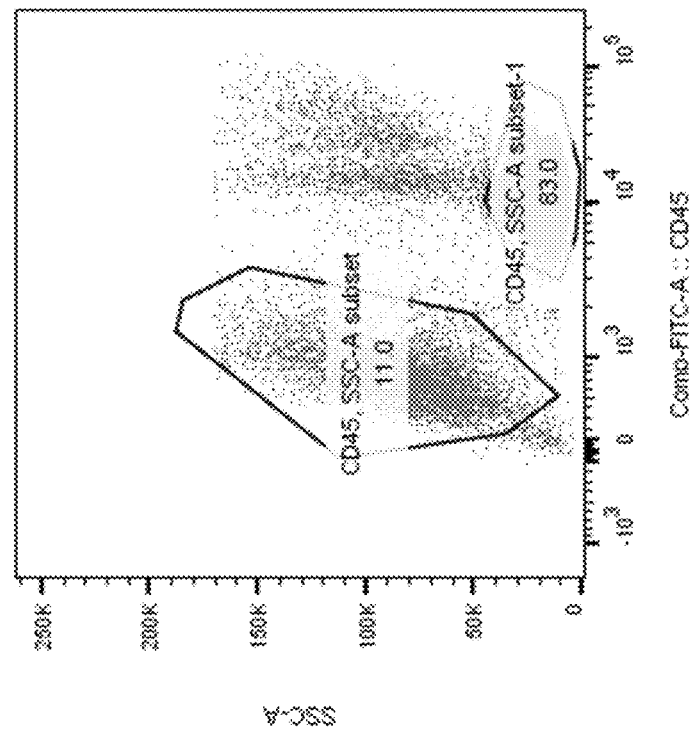
Figure 32C:
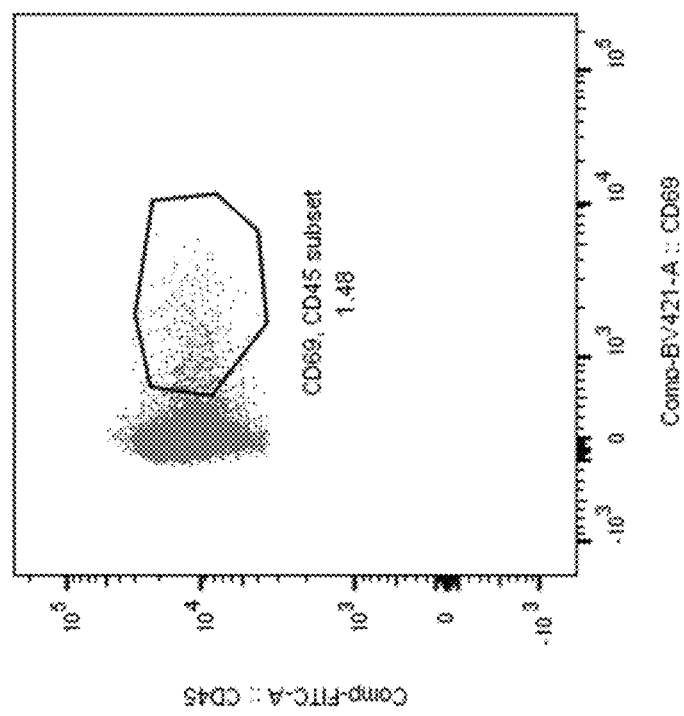
Figure 33C:
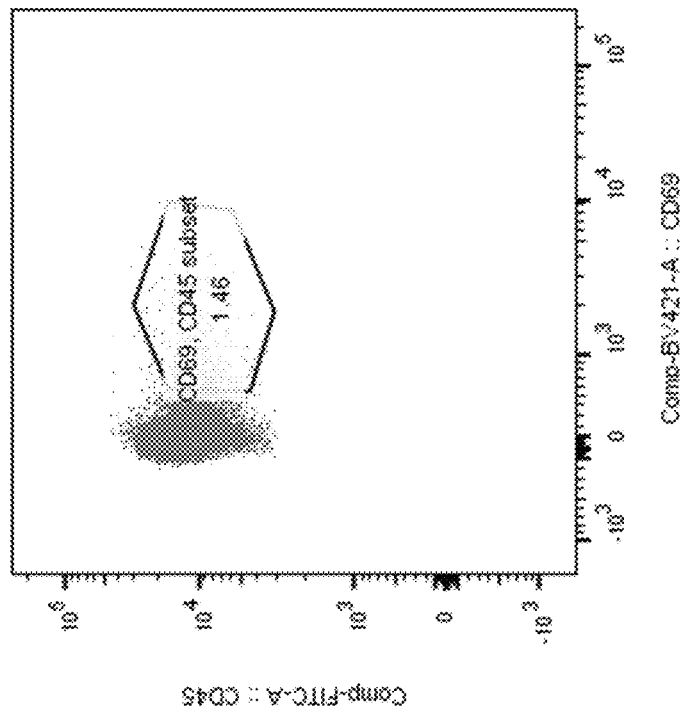
Figure 33B:
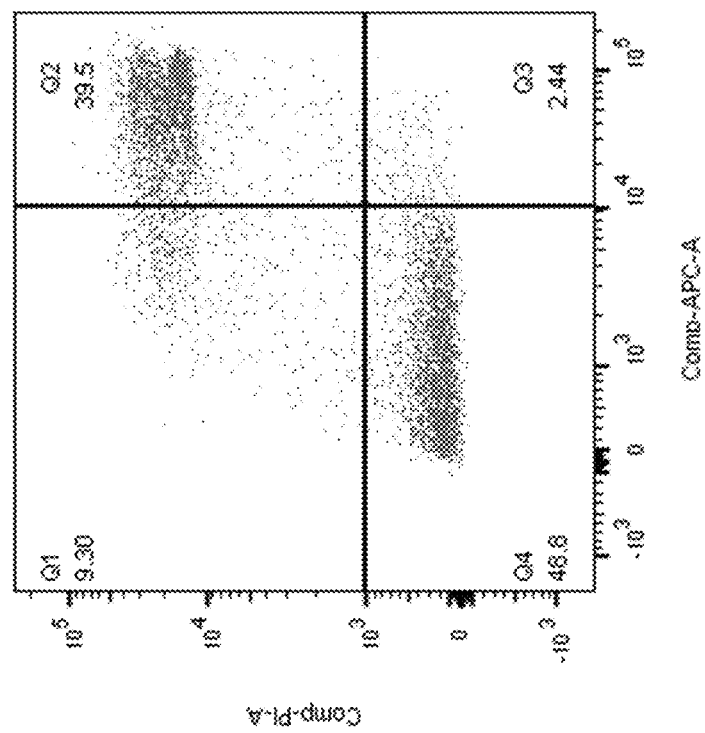

FIGS. 5 to 96 are flow cytometry plots testing the disclosed bispecific antibodies. Table 1 summarizes flow cytometry results measuring apoptosis with annexin V and PI in gated populations of MCF-7 and MDA-231 cells treated with human CD8 T cells with bi-specific antibodies plus or minus the photosensitizing compound verteporfin. Verteporfin was investigated as an immune stimulating agent to be used in conjunction with our bispecific antibody since it demonstrated an ability to reduce tumor cell programmed cell death ligand 1 (PDL1) surface expression. Table 2 shows ELISA validation results of antibody clones. Table 3 shows percentage of antibody binding to MCF-7 (CC49+ve facs sorted cells) using anti 6x-His-tag Ab by flow cytometry. Table 4 shows results of cytotoxicity assay in MCF-7 cells treated with human CD8 T cells with bi-specific antibodies.

TABLE 1

| Cell line | Control group (%) | Exp. group (%) | (%) decline in viable cells as compared to control group |
|---|---|---|---|
| MCF-7 | CD8 only (28.2) | CD8 + BiTe (5 µg/ml) (12.3) | 56.38 |
|  | CD8+ Vs (1 µM) (19) | CD8 + BiTe (5 µg/ml) + Vs (1 µM) (7.80) | 58.94 |
|  | CD8+ Vs (2 µM) (13.3) | CD8 + BiTe (5 µg/ml) + Vs (2 µM) (6.12) | 53.98 |
|  | CD8+ Vs (5 µM) (7.51) | CD8 + BiTe (5 µg/ml) + Vs (5 µM) (1.76) | 76.56 |
| MDA-231 | CD8 only (57.5) | CD8 + BiTe (5 µg/ml) (40.9) | 28.86 |
|  | CD8+ Vs (1 µM) (56.3) | CD8 + BiTe (5 µg/ml) + Vs (1 µM) (23.9) | 57.5 |
|  | CD8+ Vs (2 µM) (57.4) | CD8 + BiTe (5 µg/ml) + Vs (2 µM) (26.9) | 53.13 |
|  | CD8+ Vs (5 µM) (55.3) | CD8 + BiTe (5 µg/ml) + Vs (5 µM) (18.7) | 66.18 |

TABLE 2

ELISA validation of Ab clones

|  | Ab3891 | Ab4116 | Ab4117 | Ab4118 | Ab3891 | Ab4116 | Ab4117 | Ab4118 |
|---|---|---|---|---|---|---|---|---|
| 500 ng | 0.994 | 0.846 | 0.909 | 0.97 | 0.35 | 0.32 | 0.336 | 0.339 |
| 250 ng | 0.722 | 0.451 | 0.588 | 0.662 | 0.336 | 0.186 | 0.24 | 0.284 |
| 125 ng | 0.639 | 0.451 | 0.473 | 0.496 | 0.292 | 0.221 | 0.272 | 0.286 |
| 62.5 ng | 0.408 | 0.277 | 0.288 | 0.321 | 0.216 | 0.106 | 0.17 | 0.194 |
| 31.25 ng | 0.247 | 0.168 | 0.164 | 0.21 | 0.192 | 0.109 | 0.13 | 0.168 |
| 15.625 ng | 0.15 | 0.098 | 0.113 | 0.097 | 0.11 | 0.081 | 0.087 | 0.112 |
| 7.81 ng | 0.119 | 0.083 | 0.082 | 0.082 | 0.09 | 0.056 | 0.072 | 0.084 |
| NC | 0.065 | 0.047 | 0.05 | 0.047 | 0.042 | 0.033 | 0.035 | 0.032 |
|  | Mucin | | | | TAG-72 | | | |

TABLE 3

% of Ab binding to MCF-7 (CC49+ve facs sorted cells) using anti 6X-His-tag Ab by Flow

| Ab clones | % His-tag expression |
|---|---|
| CD8 + Ab (old pilot) (5 µg/ml) | 24.7 |
| CD8 + Ab4116 (new pilot) (5 µg/ml) | 8.28 |
| CD8 + Ab4117 (5 µg/ml) | 15.7 |
| CD8 + Ab4118 (5 µg/ml) | 28.9 |
| CD8 + Ab3891 (5 µg/ml) | 27.6 |

TABLE 4

Cytotoxicity assay by Flow

| Cell line | Control group (%) | Exp. group (%) | (%) decline in viable cells as compared to control (CD8 only) group |
|---|---|---|---|
| MCF-7 | CD8 only (35.46) | CD8 + Ab (old pilot) (5 µg/ml) (13.5) | 61.9 |
|  |  | CD8 + Ab4116 (new pilot) (5 µg/ml) (14.8) | 58.2 |
|  |  | CD8 + Ab4117 (5 µg/ml) (16.0) | 54.8 |
|  |  | CD8 + Ab4118 (5 µg/ml) (9.21) | 74.0 |
|  |  | CD8 + Ab3891 (5 µg/ml) (9.48) | 73.26 |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A single chain variable fragment (scFv) TAG-72 antibody, comprising a variable heavy (V$_H$) domain having CDR1, CDR2 and CDR3 sequences and a variable light (V$_L$) domain having CDR1, CDR2 and CDR3 sequences,
   wherein the CDR1 sequence of the V$_H$ domain comprises the amino acid sequence DHAIH (SEQ ID NO:1),
   wherein the CDR2 sequence of the V$_H$ domain has an amino acid sequence selected from the group consisting of WIGYFSPGNDDFRYNERFKG (SEQ ID NO:3), WIGYFSPGNDDFKYNERYKG (SEQ ID NO:4), and WIGYFSPGNNDFKYNERFKG (SEQ ID NO:5),
   wherein the CDR3 sequence of the V$_H$ domain comprises the amino acid sequence LNMAY (SEQ ID NO:2),
   wherein the CDR1 sequence of the V$_L$ domain has an amino acid sequence selected from the group consisting of KSSQSLLYSGNQKNYLA (SEQ ID NO:9) and KSSQSLLYSGNHKNYLA (SEQ ID NO:12),
   wherein the CDR2 sequence of the V$_L$ domain comprises the amino acid sequence WASARES (SEQ ID NO:10),
   wherein the CDR3 sequence of the V$_L$ domain comprises the amino acid sequence QQYYSYPLT (SEQ ID NO:11), and
   wherein when the CDR2 sequence of the V$_H$ domain has the amino acid sequence SEQ ID NO:3, the CDR1 sequence of the V$_L$ domain has the amino acid sequence SEQ ID NO:12.

2. The antibody of claim 1, wherein the V$_H$ domain comprises the amino acid sequence SEQ ID NO:6, SEQ ID NO:7, or SEQ ID NO:8.

3. The antibody of claim 1, wherein the V$_L$ domain comprises the amino acid sequence SEQ ID NO:13.

4. The antibody of claim 1, comprising a peptide linker between the V$_H$ and V$_L$ domains comprising the amino acid sequence SEQ ID NO:15.

5. The antibody of claim 1, comprising an amino acid sequence selected from the group consisting of SEQ ID NO:16, SEQ ID NO:17, and SEQ ID NO:18.

6. A bispecific antibody comprising a single polypeptide chain comprising a first antigen-binding region and a second antigen-binding region, wherein the first antigen-binding region is capable of recruiting the activity of a human immune effector cell by specifically binding to an immune cell antigen located on the human immune effector cell, and wherein the second antigen-binding region comprises the antibody of claim 1.

7. The bispecific antibody of claim 6, wherein the human effector cell is a member of the human lymphoid lineage.

8. The bispecific antibody of claim 6, wherein the effector cell is capable of exerting a cytotoxic or an apoptotic effect on a target cell.

9. The bispecific antibody of claim 8, wherein the immune cell antigen is selected from the group consisting of human CD3 antigen, the human CD16 antigen, the human NKG2D antigen, the human CD2 antigen, the human CD28 antigen and the human CD25 antigen.

10. The bispecific antibody of claim 6, wherein the human effector cell is a member of the human myeloid lineage.

11. The bispecific antibody of claim 10, wherein the human effector cell is capable of exerting a cytotoxic or an apoptotic effect on a target cell.

12. The bispecific antibody of claim 11, wherein the immune cell antigen is chosen from one or more of the human CD64 antigen or the human CD89 antigen.

13. A pharmaceutical composition comprising the antibody of claim 1 in a pharmaceutically acceptable carrier.

14. A method for treating cancer in a subject, comprising administering to the subject a therapeutically effective amount of the pharmaceutical composition of claim 13.

15. The method of claim 14, further comprising administering to the subject a checkpoint inhibitor.

16. The method of claim 15, wherein the checkpoint inhibitor comprises an anti-PD-1 antibody, anti-PD-L1 antibody, anti-CTLA-4 antibody, or a combination thereof.

17. An isolated nucleic acid encoding the antibody of claim 1.

* * * * *